United States Patent
Zhang et al.

(10) Patent No.: US 12,018,016 B2
(45) Date of Patent: Jun. 25, 2024

(54) ARYL SULFONYL (HYDROXY) PIPERIDINES AS CCR6 INHIBITORS

(71) Applicant: CHEMOCENTRYX, INC., San Carlos, CA (US)

(72) Inventors: Penglie Zhang, Foster City, CA (US); Daniel R. Marshall, San Mateo, CA (US); Howard S. Roth, Sunnyvale, CA (US); Aubrie Harland, Redwood City, CA (US); Ju Yang, Palo Alto, CA (US); Christopher W. Lange, Hayward, CA (US); Rebecca M. Lui, Mountain View, CA (US); Antoni Krasinski, Sunnyvale, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 17/820,271

(22) Filed: Aug. 17, 2022

(65) Prior Publication Data

US 2023/0133406 A1    May 4, 2023

Related U.S. Application Data

(60) Provisional application No. 63/354,906, filed on Jun. 23, 2022, provisional application No. 63/234,271, filed on Aug. 18, 2021.

(51) Int. Cl.
| | |
|---|---|
| *C07D 401/14* | (2006.01) |
| *C07D 401/12* | (2006.01) |
| *C07D 413/14* | (2006.01) |
| *C07D 417/14* | (2006.01) |
| *C07D 471/04* | (2006.01) |
| *C07D 487/10* | (2006.01) |
| *C07D 491/107* | (2006.01) |
| *C07D 491/20* | (2006.01) |

(52) U.S. Cl.
CPC ......... *C07D 401/14* (2013.01); *C07D 401/12* (2013.01); *C07D 413/14* (2013.01); *C07D 417/14* (2013.01); *C07D 471/04* (2013.01); *C07D 487/10* (2013.01); *C07D 491/107* (2013.01); *C07D 491/20* (2013.01)

(58) Field of Classification Search
CPC .. C07D 401/14; C07D 401/12; C07D 413/14; C07D 417/14; C07D 471/04; C07D 487/10; C07D 491/107; C07D 491/20
See application file for complete search history.

(56) References Cited

U.S. PATENT DOCUMENTS

| | | | |
|---|---|---|---|
| 8,153,793 B2 | 4/2012 | Kugimiya et al. | |
| 9,163,017 B2 | 10/2015 | Degoey et al. | |
| 2008/0255222 A1 | 10/2008 | Halazy et al. | |
| 2015/0175547 A1 | 6/2015 | Dairaghi et al. | |
| 2016/0206613 A1 | 7/2016 | Groppe | |
| 2016/0289212 A1* | 10/2016 | Qiu .................. | A61K 31/553 |
| 2020/0297710 A1 | 9/2020 | Axten et al. | |
| 2023/0125684 A1* | 4/2023 | Zhang ................. | C07D 491/20 |
| | | | 514/303 |

FOREIGN PATENT DOCUMENTS

| | | |
|---|---|---|
| CN | 113135896 A | 7/2021 |
| JP | 2005119987 A | 5/2005 |
| WO | 02/074761 A1 | 9/2002 |
| WO | 03/042174 A1 | 5/2003 |
| WO | 03/075929 A1 | 9/2003 |
| WO | 03/076395 A1 | 9/2003 |
| WO | 03/076400 A1 | 9/2003 |
| WO | 03/076401 A1 | 9/2003 |
| WO | 03/076421 A1 | 9/2003 |
| WO | 03/076430 A1 | 9/2003 |
| WO | 03/076438 A1 | 9/2003 |
| WO | 2004/033632 A2 | 4/2004 |
| WO | 2004/033632 A3 | 4/2004 |
| WO | 2005/014579 A1 | 2/2005 |
| WO | 2005/014593 A1 | 2/2005 |
| WO | 2006/034341 A2 | 3/2006 |
| WO | 2006/034341 A3 | 3/2006 |
| WO | 2007/037187 A1 | 4/2007 |
| WO | 2007/047431 A2 | 4/2007 |
| WO | 2007/047431 A3 | 4/2007 |
| WO | 2007/092435 A2 | 8/2007 |
| WO | 2007/092435 A3 | 8/2007 |
| WO | 2008/077057 A2 | 6/2008 |
| WO | 2008/077057 A3 | 6/2008 |
| WO | 2009/158587 A1 | 12/2009 |
| WO | 2010/065782 A1 | 6/2010 |
| WO | 2010/075376 A2 | 7/2010 |
| WO | 2010/075376 A3 | 7/2010 |
| WO | 2011/088192 A1 | 7/2011 |

(Continued)

OTHER PUBLICATIONS

National Center for Biotechnology Information. "PubChem Substance Record for SID 350049627, SID 350049627, Source: ChemBridge" PubChem, https://pubchem.ncbi.nlm.nih.gov/substance/350049627. Date available Dec. 20, 2017. (Year: 2017).*

(Continued)

*Primary Examiner* — Daniel R Carcanague
(74) *Attorney, Agent, or Firm* — Robert Bernstein

(57) ABSTRACT

Compounds of formula (A) are provided which are useful in the treatment of diseases or conditions modulated at least in part by CCR6:

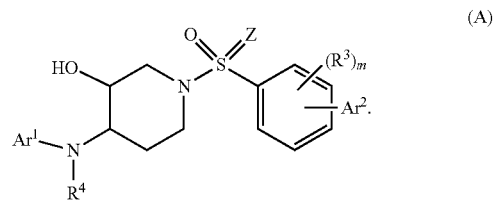

(A)

59 Claims, No Drawings

(56) References Cited

FOREIGN PATENT DOCUMENTS

| | | |
|---|---|---|
| WO | 2011078370 A1 | 7/2011 |
| WO | 2012/012282 A1 | 1/2012 |
| WO | 2012/015760 A1 | 2/2012 |
| WO | 2013/157021 A1 | 10/2013 |
| WO | 2014/127350 A1 | 8/2014 |
| WO | 2015/058163 A2 | 4/2015 |
| WO | 2015/058163 A3 | 4/2015 |
| WO | 2015/078374 A1 | 6/2015 |
| WO | 2015/123465 A1 | 8/2015 |
| WO | 2016/205633 A1 | 12/2016 |
| WO | 2016/210296 A1 | 12/2016 |
| WO | 2017/070320 A1 | 4/2017 |
| WO | 2017/172802 A1 | 10/2017 |
| WO | 2017/212425 A1 | 12/2017 |
| WO | 2018/098361 A1 | 5/2018 |
| WO | 2018/106818 A1 | 6/2018 |
| WO | 2019/204442 A1 | 10/2019 |
| WO | 2019/204505 A2 | 10/2019 |
| WO | 2019/204505 A3 | 10/2019 |
| WO | 2020/006497 A1 | 1/2020 |
| WO | 2020/014599 A1 | 1/2020 |
| WO | 2021/102361 A1 | 5/2021 |
| WO | 2022/173849 A1 | 8/2022 |

OTHER PUBLICATIONS

Martina, Maria Grazia et al., "Discovery of small-moelcules targeting the CCL20/CCR6 axis as first-in-class inhibitors for inflammatory bowel diseases," *European Journal of Medicinal Chemistry* (Aug. 29, 2022) 243:114703; 11 pages.

Tawaraishi, Taisuke et al., "Identification of a novel series of potent and selective CCR6 inhibitors as biological probes," *Bioorganic & Medicinal Chemistry Letters* (Jul. 30, 2018) 28:3067-3072.

International Search Report dated Feb. 23, 2023 corresponding to PCT/US2022/075047 filed Aug. 17, 2022; 11 pages.

International Search Report dated Mar. 2023 corresponding to PCT/US2022/075045 filed Aug. 17, 2022; 11 pages.

Pubchem, Substance Record for SID 160846779, Modify Date: Sep. 9, 2020 [retrieved on Dec. 1, 2022]; Retrieved from the Internet: <URL: https://pubchem.ncbi.nlm.nih.giv/substance/ 160846779>; 1 page.

* cited by examiner

ARYL SULFONYL (HYDROXY) PIPERIDINES AS CCR6 INHIBITORS

CROSS-REFERENCES TO RELATED APPLICATIONS

This application claims the benefit of priority under 35 U.S.C § 119(e) to U.S. Provisional Application Ser. No. 63/234,271 filed Aug. 18, 2021 and U.S. Provisional Application Ser. No. 63/354,906 filed Jun. 23, 2022, the disclosure of each are incorporated herein by reference in their entirety.

STATEMENT AS TO RIGHTS TO INVENTIONS MADE UNDER FEDERALLY SPONSORED RESEARCH AND DEVELOPMENT

Not Applicable.

REFERENCE TO A "SEQUENCE LISTING," A TABLE, OR A COMPUTER PROGRAM LISTING APPENDIX SUBMITTED ON A COMPACT DISK

Not Applicable.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr Opin. Immunol.* 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ([Ca2+]), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are two main classes of chemokines, CXC (alpha) and CC (beta), depending on whether the first two cysteines are separated by a single amino acid (C—X—C) or are adjacent (C—C). The alpha-chemokines, such as interleukin-8 (IL-8), neutrophil-activating protein-2 (NAP-2) and melanoma growth stimulatory activity protein (MGSA) are chemotactic primarily for neutrophils, whereas beta-chemokines, such as RANTES, MIP-1a, MIP-1b, monocyte chemotactic protein-1 (MCP-1), MCP-2, MCP-3 and eotaxin are chemotactic for macrophages, T-cells, eosinophils and basophils (Deng, et al., *Nature*, 381:661-666 (1996)). The chemokines bind specific cell-surface receptors belonging to the family of G-protein-coupled seven-transmembrane-domain proteins (reviewed in Horuk, *Trends Pharm. Sci.*, 15:159-165 (1994)) which are termed "chemokine receptors."

On binding their cognate ligands, chemokine receptors transduce an intracellular signal though the associated trimeric G protein, resulting in a rapid increase in intracellular calcium concentration. There are at least eleven human chemokine receptors that bind or respond to beta-chemokines and at least seven human chemokine receptors that bind to the alpha chemokines. Additionally CX3CR1 (fractalkine receptor) can bind to the fractalkine chemokine, which is distinguished by a series of three amino acids between the first two cysteines. Chemokine receptors, have been implicated as being important mediators of inflammatory and immunoregulatory disorders and diseases, including asthma and allergic diseases, as well as autoimmune pathologies such as rheumatoid arthritis and atherosclerosis.

CCR6 is known to be expressed primarily in B cells, IL17 secreting T cells, regulatory T cells and dendritic cells and shows strong binding to its cognate ligand CCL20 (MIP-3a). It is expressed on approximately 30-60% of adult peripheral blood effector/memory CD4+ T cells. CCR6 is involved in leukocyte homing to inflamed tissue, particularly the skin and lungs and is co-expressed on almost all T cells that have a skin homing phenotype, the CLA+ T cells. Thus CCR6 may be an important player in skin pathologies in which leukocytes participate.

CCR6 expression has been linked to psoriasis in the following manner. In humans, a large majority of skin-homing CD4 T cells in the peripheral blood express CCR6 with a greater degree of CCL20-mediated chemotaxis occurring in T cells isolated from psoriatic patients (Homey, et. al., *JI*, 2000). IL17 secreting cells are central agents in several inflammatory diseases. T cells, such as γδ T cells and TH17 T cells produce IL17 after activation. The pathogenic effects of IL17 have been associated with human diseases such as rheumatoid arthritis (Patel D D et. al., *Ann Rheum Dis* 2013), multiple sclerosis (Zepp J, Wu L, and X Li *Trends Immunol* 2011), and psoriasis (Martin D A et. al., *J Invest Dermatol* 2012). Evidence strongly linking IL17 with psoriasis include gene wide association studies that show strong association between psoriasis and genes upstream (IL-23) or downstream (NFκb) of IL17 signaling pathways as well as efficacy in targeting IL17 in a clinical setting (Martin D A et. al., *J Invest Dermat.* 2012; Papp et. al., *NEJM*, 2012; Papp et. al., *NEJM*, 2012). In addition to enhanced CCL20-mediated chemotaxis, CCR6+ T cells isolated from psoriatic patients may secrete IL-17A, IL22, and TNFα when compared to healthy controls (Kagami, et. al., *J. Invest. Dermatol.*, 2010). Lastly, ccl20 mRNA was up-regulated in lesional psoriatic skin samples (Homey, et. al., *JI*, 2000; Dieu-Nosjean, et. al., *JEM*, 2000). In mice, CCR6 knock-out mice were protected from IL-23 driven psoriasis. Thus, a multitude of evidence in both mice and men suggest a protective role for CCR6 blockade in psoriasis and psoriasis-like models.

Recent work on the search for CCR6 inhibitor compounds is described in Tawaraishi, et al., *Bioorg. Med. Chem. Lett.* 28:3067-3072 (2018).

In view of the clinical importance of CCR6, the identification of compounds that modulate CCR6 function represent an attractive avenue into the development of new therapeutic agents. Such compounds and methods for their use are provided herein.

BRIEF SUMMARY OF THE INVENTION

Described herein are compounds having formula (A):

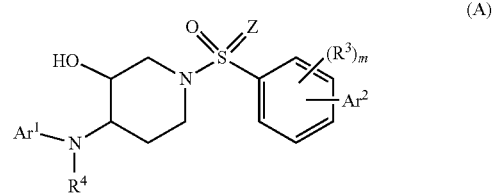

(A)

wherein Ar$^1$, Ar$^2$, R$^3$, R$^4$, Z, and m have the meanings provided in the Detailed Description, below. The compounds have utility in the treatment of diseases or conditions modulated at least in part by CCR6.

Described herein are compounds having formula (I):

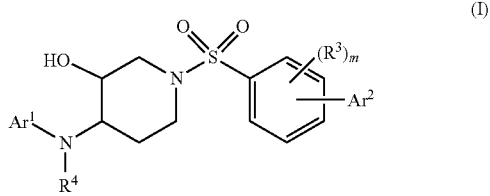

(I)

wherein Ar$^1$, Ar$^2$, R$^3$, R$^4$, and m have the meanings provided in the Detailed Description, below. The compounds have utility in the treatment of diseases or conditions modulated at least in part by CCR6.

Pharmaceutical compositions of the compounds of formula (I) are also provided.

Further provided in the present disclosure preparative methods for the synthesis of compounds of formula (I), as well as selected intermediates useful in the preparation.

BRIEF DESCRIPTION OF THE DRAWINGS

NOT APPLICABLE.

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system.

Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, ∼∼∼, that intersects a single, double or triple bond in any PGP-386 ART chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "hydroxyalkyl" refers to an alkyl group where one, two, or three of the hydrogen atoms is substituted with a hydroxy (—OH) group. In some embodiments, the hydroxyalkyl has one to two hydroxy groups. In some embodiments, the hydroxyalkyl has one hydroxy group. As for the alkyl portion, hydroxyalkyl groups can have any suitable number of carbon atoms, such as $C_{1-6}$, and can be straight or branched. Hydroxyalkyl groups include, for example, hydroxymethyl, 1-hydroxyethyl, 2-hydroxyethyl, 2-hydroxylpropan-2-yl, etc.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" or means, unless otherwise stated, a polyunsaturated, aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

The term "heterocyclic" or "heterocyclyl" refers to a non-aromatic ring having the indicated number of ring member vertices, at least one of which is a heteroatom selected from N, O and S. For example, the phrase "4- to 7-membered heterocyclic ring having 1 or 2 heteroatoms as ring vertices selected from N, O and S" refers to a single ring have 4 to 7 ring vertices, wherein 1 or 2 of the ring vertices are heteroatoms (N, O, or S). Examples of such rings include morpholine, pyrrolidine, tetrahydrofuran, thiomorpholine, piperidine, piperazine, and the like. The ring may have 0 or 1 double bond between ring vertices.

The phrase "bicyclic 9- or 10-membered fused aromatic or heteroaromatic ring having 0 to 4 heteroatoms as ring vertices selected from N, O and S" refers to a ring system in which two adjacent ring vertices of a first ring are also adjacent ring vertices of a second ring (i.e., a fused ring system), and wherein at least one of the two rings is aromatic. In some embodiments, both rings have aromatic character (e.g., naphthalene, quinolone, quinazoline, benzimidazole, benzothiophene, benzopyrazole). In some embodiments, only one ring is aromatic (e.g., indane, 1,2,3,4-tetrahydronaphthalene, 5,6,7,8-tetrahydroquinoline, 1,2,3,4-tetrahydroisoquinoline).

The phrase "monocyclic 5- or 6-membered aromatic or heteroaromatic ring having 0 to 3 heteroatoms as ring vertices selected from N, O and S" refers to a single ring which is aromatic (phenyl) or heteroaromatic (e.g., pyridine, thiophene, furan, pyrimidine, pyrazine).

A "3- to 6-membered spirocyclic ring" refers to a group having two points of attachment to a carbon atom that is a ring vertex or part of an alkylene group. For example, the group:

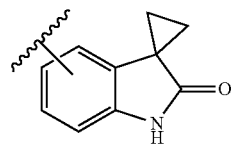

is a bicyclic 9- or 10-membered fused aromatic or heteroaromatic ring having 1 heteroatom as a ring vertex, an oxo substituent and two other substituents are joined to form a 3-membered spirocyclic ring and oxo.

The terms "spiroheterocyclic ring." "spiroheterocyclyl" or "spiroheterocycloalkyl" refer to a saturated or partially unsaturated bicyclic ring having 6 to 12 ring atoms, where the two rings are connected via a single carbon atom (also called the spiroatom). Spiroheterocyclyl groups have from one to five heteroatoms selected from N, O, and S as ring vertices, and the nitrogen atom(s) are optionally quaternized. Partially unsaturated spiroheterocycloalkyl groups have a double bond in one of the rings. Representative examples include, but are not limited to, 2,6-diazaspiro[3.3]heptane, 2,6-diazaspiro[3.4]octane, 2-azaspiro[3.4]octane, 2-azaspiro[3.5]-nonane, 2,7-diazaspiro[4.4]nonane, and the like.

The term "substituent" is an atom or group of atoms substituted in place of hydrogen atom(s) of the parent molecule. Non-limiting examples of substituents in this disclosure include $R^1$ and $R^2$, and these substituents can be monovalent or divalent substituents. Monovalent substituents are bonded to the parent moiety by replacing one hydrogen atom of the parent moiety through a single bond. The hydrogen atom that a monovalent substituent replaces may be an available hydrogen atom from a carbon or nitrogen atom of the parent moiety. Divalent substituents are bonded to the parent moiety by replacing two available hydrogen atoms of the parent moiety through a double bond. It is understood that substituents described in this disclosure cannot be attached to a parent moiety in a way that would result in an unstable molecule.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfinic acids, sulfonamides, acyl-sulfonamides, phosphonic acids, phosphinic acids, phosphoric acids, tetrazole, and oxo-oxadiazoles.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more σ bonds. Rotamers are conformers that differ by rotation about only a single a bond.

II. General

The present invention derives from the discovery that compounds of formula I act as potent antagonists of the CCR6 receptor. The compounds have in vivo anti-inflammatory activity and have superior pharmacokinetic properties. Accordingly, the compounds provided herein are useful in pharmaceutical compositions, methods for the treatment of CCR6-mediated diseases, and as controls in assays for the identification of competitive CCR6 antagonists.

III. Compounds

In one aspect, the present invention provides compounds of Formula A:

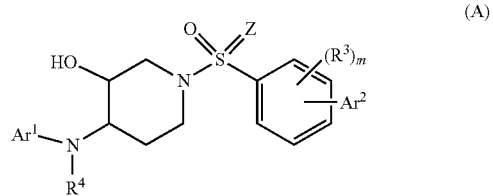

(A)

or a pharmaceutically acceptable salt, hydrate, solvate, N-oxide, optically enriched form, or rotamer thereof, wherein $Ar^1$ is a monocyclic 5- or 6-membered aromatic or heteroaromatic ring having 0 to 3 heteroatoms as ring vertices selected from N, O, and S that is substituted with from 0 to 5 $R^1$ substituents independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, and —$NR^aR^b$;

each $R^a$ and $R^b$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl;

$Ar^2$ is selected from the group consisting of:
  i) monocyclic 5- or 6-membered aromatic or heteroaromatic ring having 0 to 3 heteroatoms as ring vertices selected from N, O and S, and which is substituted with 0 to 5 $R^2$; and
  ii) bicyclic 9- or 10-membered fused aromatic or heteroaromatic ring having 0 to 4 heteroatoms as ring vertices selected from N, O and S, and which is substituted with 0 to 5 $R^2$;

each $R^2$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR, —SR, —$COR^c$, —$CO_2R^c$, —$NR^cR^d$, —$CONR^cR^d$, —$CO(NR^c)_2COR^d$, —$SO_2R^c$, —$SO_2NRWR^d$, —$X^2$—$CONR^cR^d$, —$X^2$—$NR^cSO_2R^d$, —$X^2$—$NR^cCO_2R^d$, —$X^2$—P(=O)(OR$^d$)$_2$, —$X^2$—O—P(=O)(OR$^d$)$_2$, —$NR^cR^d$, —$X^2$—$NR^cR^d$, oxo, 4- to 6-membered heterocyclyl, 7- to 10-membered spiroheterocyclyl and 5- or 6-membered heteroaryl; and wherein the heterocyclyl, spiroheterocyclyl and heteroaryl rings of $R^2$ have from 1 to 3 heteroatoms selected from N, O, and S, and are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxalkyl, and $C_{1-4}$ haloalkyl; and wherein two $R^2$ groups attached to the same carbon atom are optionally combined to form a 3- to 6-membered spirocyclic ring or a 3- to 6-membered spiroheterocyclic ring having from 1 to 3 heteroatoms selected from N, O, and S;

$R^c$ is independently selected from the group consisting of hydrogen, hydroxyl, $C_{1-4}$ alkyl, $C_{1-4}$ haloalkyl, and $C_{1-4}$ hydroxyalkyl;

$R^d$ is independently selected from the group consisting of hydrogen, hydroxyl, halogen, cyano, $C_{1-4}$ alkyl, $C_{1-4}$ haloalkyl, $C_{1-4}$ hydroxyalkyl, $C_{3-6}$ cycloalkyl, 4- to 6-membered heterocyclyl, and 5- or 6-membered heteroaryl; and wherein the $C_{3-6}$ cycloalkyl, 4- to 6-membered heterocyclyl, and 5- or 6-membered heteroaryl rings of $R^d$ have from 1 to 3 heteroatoms selected from N, O, and S, and are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl;

or $R^c$ and $R^d$, when attached to the same nitrogen atom are joined to form a 4- to 7-membered heterocyclic ring having from 0 to 2 additional heteroatoms as ring vertices selected from O, S, S(O), S(O)$_2$, NH and N($C_{1-4}$ alkyl);

$X^2$ is $C_{1-4}$ alkylene;

Z is a —O— or —N($R^e$)—, wherein $R^e$ is selected from the group consisting of hydrogen, $C_{1-4}$ alkyl, $C_{1-4}$ haloalkyl, $C_{1-4}$ hydroxyalkyl, and $C_{3-6}$ cycloalkyl;

the subscript m is 0, 1 or 2;

each $R^3$ is a member selected from the group consisting of halogen, CN, $C_{1-4}$ alkyl, $C_{1-4}$ alkoxy, $C_{3-8}$ cycloalkyl, $C_{1-4}$ haloalkyl, $C_{1-4}$ haloalkoxy, and $C_{2-4}$ hydroxyalkyl; and $R^4$ is a member selected from the group consisting of H, $C_{1-4}$ alkyl, $C_{3-8}$ cycloalkyl, and $C_{1-4}$ haloalkyl In one aspect, the present invention provides compounds of Formula A:

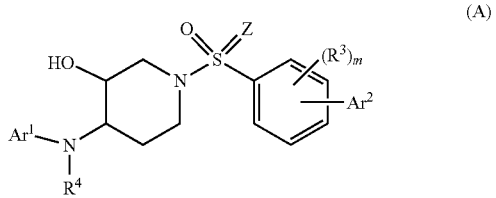

(A)

or a pharmaceutically acceptable salt, hydrate, solvate, N-oxide, optically enriched form, or rotamer thereof, wherein $Ar^1$ is a 5- or 6-membered aromatic or heteroaromatic ring that is substituted with from 0 to 5 $R^1$ substituents independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, and —$NR^aR^b$;

each $R^a$ and $R^b$ is independently selected from the group consisting of hydrogen, halogen, cyano, $C_{1-4}$ alkyl, $C_{1-4}$ haloalkyl, $C_{1-4}$ hydroxyalkyl, and $C_{3-6}$ cycloalkyl; $Ar^2$ is selected from the group consisting of:

i) monocyclic 5- or 6-membered aromatic or heteroaromatic ring having 0 to 3 heteroatoms as ring vertices selected from N, O and S, and which is substituted with 0 to 5 $R^2$; and ii) bicyclic 9- or 10-membered fused aromatic or heteroaromatic ring having 0 to 4 heteroatoms as ring vertices selected from N, O and S, and which is substituted with 0 to 5 $R^2$;

each $R^2$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR, —SR, —COR, —$CO_2R^c$, —$NR^cR^d$, —$CONR^cR^d$, —$CO(NR^c)_2COR^d$, —$SO_2R^c$, —$SO_2NRWR^d$, —$X^2$—$CONR^cR^d$, —$X^2$—$NR^cSO_2R^d$, —$X^2$—$NR^cCO_2R^d$, —$X^2$—P(=O)(O$R^d$)$_2$, —$X^2$—O—P(=O)(O$R^d$)$_2$, —$NR^cR^d$, —$X^2$—$NR^cR^d$, oxo, 4- to 6-membered heterocyclyl, 7- to 10-membered spiroheterocyclyl and 5- or 6-membered heteroaryl; and wherein the heterocyclyl, spiroheterocyclyl and heteroaryl rings of $R^2$ are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl; and wherein two $R^2$ groups attached to the same carbon atom are optionally combined to form a 3- to 6-membered spirocyclic ring;

$R^c$ is independently selected from the group consisting of hydrogen, hydroxyl, halogen, cyano, $C_{1-4}$ alkyl, $C_{1-4}$ haloalkyl, and $C_{1-4}$ hydroxyalkyl;

$R^d$ is independently selected from the group consisting of hydrogen, hydroxyl, halogen, cyano, $C_{1-4}$ alkyl, $C_{1-4}$ haloalkyl, $C_{1-4}$ hydroxyalkyl, $C_{3-6}$ cycloalkyl, 4- to 6-membered heterocyclyl, and 5- or 6-membered heteroaryl; and wherein the $C_{3-6}$ cycloalkyl, 4- to 6-membered heterocyclyl, and 5- or 6-membered heteroaryl rings of $R^d$ are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl;

or $R^c$ and $R^d$, when attached to the same nitrogen atom are joined to form a 4- to 7-membered heterocyclic ring having from 0 to 2 additional heteroatoms as ring vertices selected from O, S, S(O), S(O)$_2$, NH and N($C_{1-4}$ alkyl);

$X^2$ is $C_{1-4}$ alkylene;

Z is a —O— or —N($R^e$)—, wherein $R^e$ is selected from the group consisting of hydrogen, $C_{1-4}$ alkyl, $C_{1-4}$ haloalkyl, $C_{1-4}$ hydroxyalkyl, and $C_{3-6}$ cycloalkyl;

the subscript m is 0, 1 or 2;

each $R^3$ is a member selected from the group consisting of halogen, CN, $C_{1-4}$ alkyl, $C_{1-4}$ alkoxy, $C_{3-8}$ cycloalkyl, $C_{1-4}$ haloalkyl, $C_{1-4}$ haloalkoxy, and $C_{2-4}$ hydroxyalkyl; and $R^4$ is a member selected from the group consisting of H, $C_{1-4}$ alkyl, $C_{3-8}$ cycloalkyl, and $C_{1-4}$ haloalkyl.

In one aspect, the present invention provides compounds of Formula L:

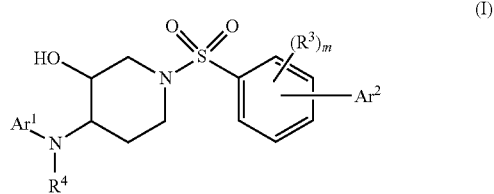

(I)

or a pharmaceutically acceptable salt, hydrate, solvate, N-oxide, optically enriched form, or rotamer thereof, wherein Ar$^1$ is a 5- or 6-membered aromatic or heteroaromatic ring that is substituted with from 0 to 5 R$^1$ substituents independently selected from the group consisting of halogen, CN, C$_{1-8}$ alkyl, C$_{3-8}$ cycloalkyl, C$_{2-8}$ alkenyl, C$_{2-8}$ alkynyl, C$_{1-8}$ haloalkyl, C$_{1-8}$ hydroxyalkyl, —OR$^a$, and —NR$^a$R$^b$;

each R$^a$ and R$^b$ is independently selected from the group consisting of hydrogen, halogen, cyano, C$_{1-4}$ alkyl, C$_{1-4}$ haloalkyl, C$_{1-4}$ hydroxyalkyl, and C$_{3-6}$ cycloalkyl;

Ar$^2$ is selected from the group consisting of:
i) monocyclic 5- or 6-membered aromatic or heteroaromatic ring having 0 to 3 heteroatoms as ring vertices selected from N, O and S, and which is substituted with 0 to 5 R$^2$; and
ii) bicyclic 9- or 10-membered fused aromatic or heteroaromatic ring having 0 to 4 heteroatoms as ring vertices selected from N, O and S, and which is substituted with 0 to 5 R$^2$;

each R$^2$ is independently selected from the group consisting of halogen, CN, C$_{1-8}$ alkyl, C$_{3-8}$ cycloalkyl, C$_{2-8}$ alkenyl, C$_{2-8}$ alkynyl, C$_{1-8}$ haloalkyl, C$_{1-8}$ hydroxyalkyl, —OR, —SR, —COR, —CO$_2$R$^c$, —NR$^c$R$^d$, —CONR$^c$R$^d$, —CO(NR$^c$)$_2$COR$^d$, —SO$_2$R$^c$, —SO$_2$NRWR$^d$, —X$^2$—CONR$^c$R$^d$, —X$^2$—NR$^c$SO$_2$R$^d$, —X$^2$—NR$^c$CO$_2$R$^d$, —NR$^c$R$^d$, —X$^2$—NR$^c$R$^d$, oxo, 4- to 6-membered heterocyclyl, 7- to 10-membered spiroheterocyclyl and 5- or 6-membered heteroaryl; and wherein the heterocyclyl, spiroheterocyclyl and heteroaryl rings of R$^2$ are each unsubstituted or substituted with one or two members independently selected from the group consisting of halogen, hydroxyl, oxo, C$_{1-4}$ alkyl, amino, C$_{1-4}$ alkylamino, di-C$_{1-4}$ alkylamino, C$_{1-4}$ alkoxy and C$_{1-4}$ haloalkyl; and wherein two R$^2$ groups attached to the same carbon atom are optionally combined to form a 3- to 6-membered spirocyclic ring;

each R$^c$ and R$^d$ is independently selected from the group consisting of hydrogen, hydroxyl, halogen, cyano, C$_{1-4}$ alkyl, C$_{1-4}$ haloalkyl, C$_{1-4}$ hydroxyalkyl, and C$_{3-6}$ cycloalkyl; or R$^c$ and R$^d$, when attached to the same nitrogen atom are joined to form a 4- to 7-membered heterocyclic ring having from 0 to 2 additional heteroatoms as ring vertices selected from O, S, S(O), S(O)$_2$, NH and N(C$_{1-4}$ alkyl);

X$^2$ is C$_{1-4}$ alkylene;
the subscript m is 0, 1 or 2;
each R$^3$ is a member selected from the group consisting of halogen, CN, C$_{1-4}$ alkyl, C$_{1-4}$ alkoxy, C$_{3-8}$ cycloalkyl, C$_{1-4}$ haloalkyl, C$_{1-4}$ haloalkoxy, and C$_{2-4}$ hydroxyalkyl; and R$^4$ is a member selected from the group consisting of H, C$_{1-4}$ alkyl, C$_{3-8}$ cycloalkyl, and C$_{1-4}$ haloalkyl.

In one group of selected embodiments for the compounds of formula (I), Ar$^2$ is a bicyclic 9- or 10-membered aromatic or heteroaromatic ring that is substituted with 0 to 5 R$^2$. In another group of selected embodiments for the compounds of formula (I), Ar$^2$ is a monocyclic 5- or 6-membered aromatic or heteroaromatic ring that is substituted with 0 to 5 R$^2$.

In other selected embodiments for the compounds of formula (I), and for each of noted embodiments above, Ar$^1$ is phenyl, substituted with from 1 to 3 R$^1$ substituents. In still other selected embodiments for the compounds of formula (I), and for each of noted embodiments above, Ar$^1$ is pyridyl, substituted with from 1 to 3 R$^1$ substituents.

In some embodiments Z is O. In some embodiments, Z is —N(R$^e$)—, wherein R$^e$ is selected from the group consisting of hydrogen, C$_{1-4}$ alkyl, C$_{1-4}$ haloalkyl, C$_{1-4}$ hydroxyalkyl, and C$_{3-6}$ cycloalkyl.

In still other selected embodiments, provided herein are compounds of formula (I), wherein Ar$^2$ is selected from the group consisting of

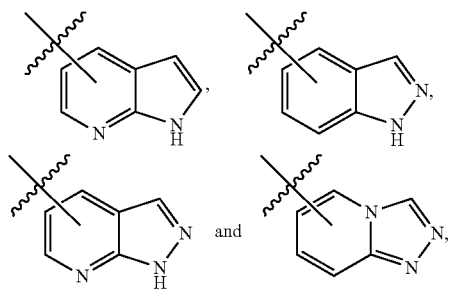

each of which is substituted with from 0-3 R$^2$.

In still other selected embodiments, provided herein are compounds of formula (I), wherein Ar$^2$ is selected from the group consisting of

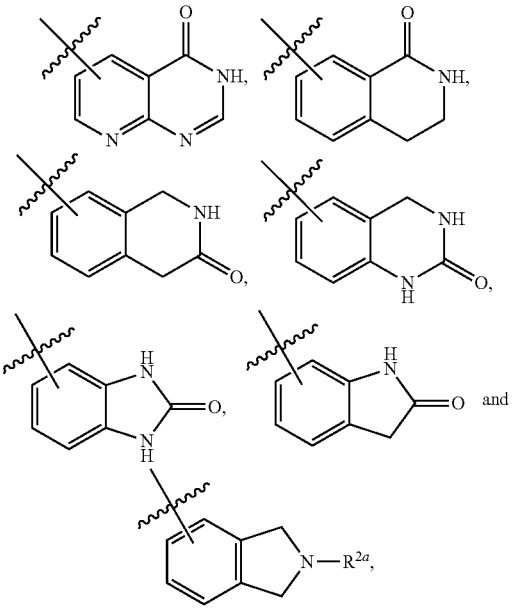

each of which is substituted with from 0-3 R$^2$. In some embodiments, R$^{2a}$ is selected from the group consisting of hydrogen, C$_{1-4}$ alkyl, C$_{1-4}$ haloalkyl, C$_{1-4}$ hydroxyalkyl, —C(O)NH$_2$, —C(O)N(H)C$_{1-4}$alkyl, —C(O)N(C$_{1-4}$alkyl)$_2$, —S(O)$_2$C$_{1-4}$alkyl, —S(O)$_2$N(H)C$_{1-4}$alkyl, —C(O)OC$_{1-4}$alkyl, and —C(O)C$_{1-4}$alkyl.

In some embodiments, provided herein are compounds of formula (I), wherein Ar$^2$ is selected from the group consisting of phenyl, pyridyl, thiazolyl, oxadiazolyl, imidazolyl, pyridazinyl, and oxazolyl, each of which is substituted with from 0-3 R$^2$. In still other selected embodiments, provided herein are compounds of formula (I), wherein Ar$^2$ is selected from the group consisting of phenyl, pyridyl, thiazolyl, and oxazolyl, each of which is substituted with from 0-3 R$^2$.

In still other selected embodiments, provided herein are compounds of formula (I), wherein $Ar^2$ is pyridyl, which is substituted with from 0-3 $R^2$. In some embodiments, provided herein are compounds of formula (I), wherein $Ar^2$ is thiazolyl, which is substituted with from 0-2 $R^2$. In some embodiments, provided herein are compounds of formula (I), wherein $Ar^2$ is 1,3,4-oxadiazolyl, which is substituted with from 0-2 $R^2$. In some embodiments, provided herein are compounds of formula (I), wherein $Ar^2$ is imidazolyl, which is substituted with from 0-2 $R^2$.

In other embodiments, compounds of formula (I) are provided having formula (Ia):

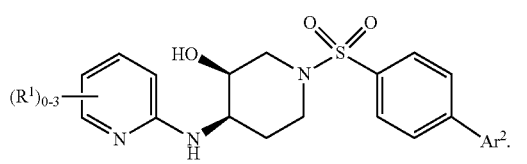

(Ia)

In some selected embodiments, the compounds of formula (Ia) are compounds wherein $R^1$ is independently selected from the group consisting of $CH_3$, $CF_3$, Cl and CN.

In some selected embodiments, the compounds of formula (Ia) are compounds wherein $Ar^2$ is a bicyclic 9- or 10-membered aromatic or heteroaromatic ring that is substituted with 0 to 5 $R^2$.

In some selected embodiments, the compounds of formula (Ia) are compounds wherein $Ar^2$ is a monocyclic 5- or 6-membered aromatic or heteroaromatic ring that is substituted with 0 to 5 $R^2$.

In other embodiments, compounds of formula (I) are provided having formula (Ia1):

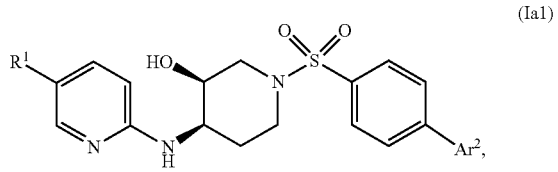

(Ia1)

wherein $R^1$ is —CN or —CF$_3$.

In related embodiments, compounds of formula (Ia1) are provided wherein $R^1$ is —CN or —CF$_3$; and $Ar^2$ is selected from the group consisting of

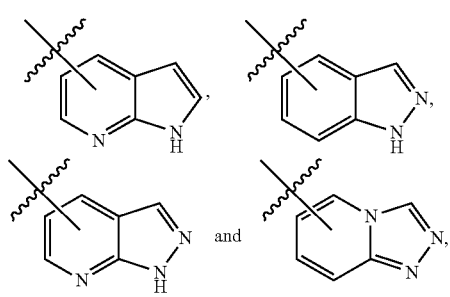

each of which is substituted with from 0-3 $R^2$.

In related embodiments, compounds of formula (Ia1) are provided wherein $R^1$ is —CN or —CF$_3$; and $Ar^2$ is selected from the group consisting of

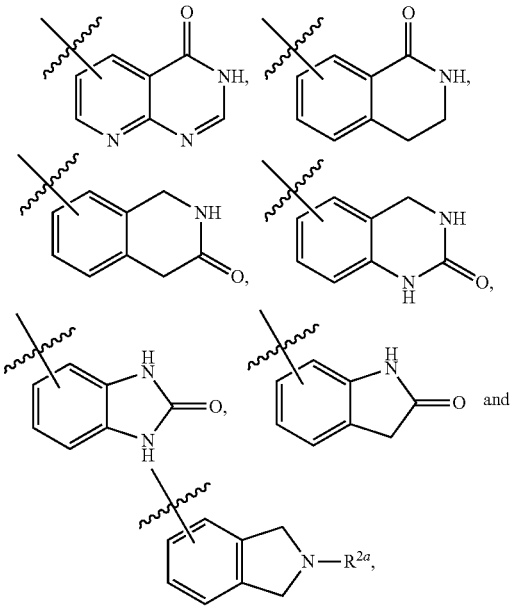

each of which is substituted with from 0-3 $R^2$. In some embodiments, $R^{2a}$ is selected from the group consisting of hydrogen, $C_{1-4}$ alkyl, $C_{1-4}$ haloalkyl, $C_{1-4}$ hydroxyalkyl, —C(O)NH$_2$, —C(O)N(H)C$_{1-4}$alkyl, —C(O)N(C$_{1-4}$alkyl)$_2$, —S(O)$_2$C$_{1-4}$alkyl, —S(O)$_2$N(H)C$_{1-4}$alkyl, —C(O)OC$_{1-4}$alkyl, and —C(O)C$_{1-4}$alkyl. In some embodiments, $R^{2a}$ is selected from the group consisting of hydrogen, $C_{1-4}$ alkyl, $C_{1-4}$ haloalkyl, $C_{1-4}$ hydroxyalkyl, —C(O)NH$_2$, —C(O)N(H)C$_{1-4}$alkyl, —C(O)N(C$_{1-4}$alkyl)$_2$, and —C(O)C$_{1-4}$alkyl.

In some embodiments, compounds of formula (Ia1) are provided wherein $R^1$ is —CN or —CF$_3$; and $Ar^2$ is selected from the group consisting of phenyl, pyridyl, thiazolyl, oxadiazolyl, imidazolyl, pyridazinyl, and oxazolyl, each of which is substituted with from 0-2 $R^2$. In related embodiments, compounds of formula (Ia1) are provided wherein $R^1$ is —CN or —CF$_3$; and $Ar^2$ is selected from the group consisting of phenyl, pyridyl, thiazolyl, and oxazolyl, each of which is substituted with from 0-3 $R^2$.

In some embodiments, compounds of formula (Ia1) are provided wherein $Ar^2$ is selected from the group consisting of

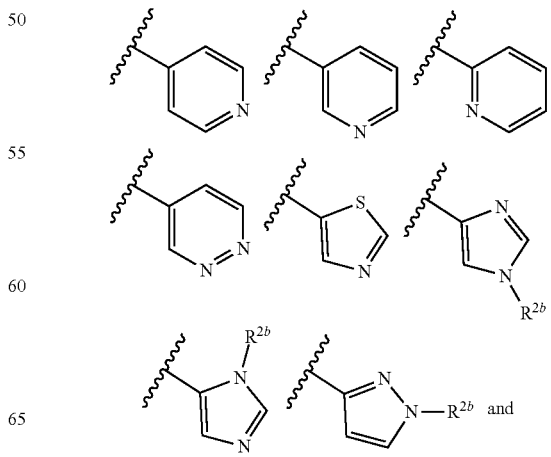

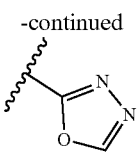

each of which is substituted with from 0-2 $R^2$; and wherein $R^{2b}$ is selected from the group consisting of hydrogen, $C_{1-4}$ alkyl, $C_{1-4}$ haloalkyl, and $C_{1-4}$ hydroxyalkyl.

In some embodiments, compounds of formula (Ia1) are provided wherein $Ar^2$ is selected from the group consisting of

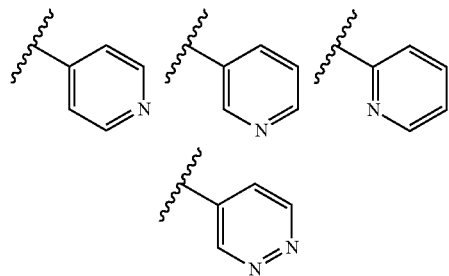

each of which is substituted with from 0-2 $R^2$; and wherein $R^a$ is selected from the group consisting of hydrogen, $C_{1-4}$ alkyl, $C_{1-4}$ haloalkyl, and $C_{1-4}$ hydroxyalkyl.

In some embodiments, compounds of formula (Ia1) are provided wherein $Ar^2$ is selected from the group consisting of

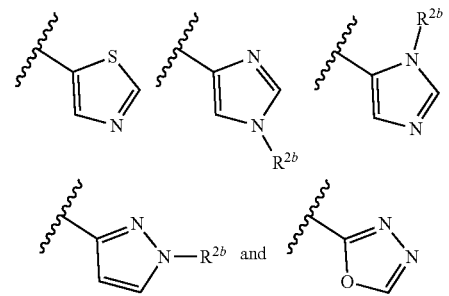

each of which is substituted with from 0-1 $R^2$; and wherein $R^{2b}$ is selected from the group consisting of hydrogen, $C_{1-4}$ alkyl, $C_{1-4}$ haloalkyl, and $C_{1-4}$ hydroxyalkyl.

In some embodiments, including the embodiments noted above, $R^1$ is $CF_3$; and $R^2$ is CN, —$CH_3$, —OH, —$NH_2$, —$N(CH_3)_2$, —C(O)$NH_2$, —C(O)N(H)($CH_3$), —C(O)N($CH_3$)$_2$, —C(O)$CH_3$, —C(O)O$CH_3$, —S(O)$_2NH_2$, Cl, F, —$N(CH_3)_2$, —O$CH_3$, —$CH_2OH$, —N(H)$R^d$, piperazinyl, piperidinyl, morpholinyl, triazolyl, 1,3,4-oxadiazolyl, pyrrolidiny, or azetidinyl, wherein the piperazinyl, piperidinyl, morpholinyl, triazolyl, 1,3,4-oxadiazolyl, pyrrolidiny and azetidinyl groups can be optionally substituted with 1 or 2 substituents selected from the group consisting of —$CH_3$, C($CH_3$)$_2$OH, OH, —O$CH_3$, —$NH_2$, and —N($CH_3$)$_2$.

In some embodiments, including the embodiments noted above, $R^2$ is CN, —$CH_3$, —OH, —$NH_2$, —$N(CH_3)_2$, —C(O)$NH_2$, —C(O)N(H)($CH_3$), —C(O)N($CH_3$)$_2$, —C(O)$CH_3$, —C(O)O$CH_3$, —S(O)$_2NH_2$, Cl, F, —$N(CH_3)_2$, —O$CH_3$, or —$CH_2OH$.

In some embodiments, including the embodiments noted above, $R^2$ is piperazinyl, piperidinyl, morpholinyl, triazolyl, 1,3,4-oxadiazolyl, pyrrolidiny, or azetidinyl, wherein the piperazinyl, piperidinyl, morpholinyl, triazolyl, 1,3,4-oxadiazolyl, pyrrolidiny and azetidinyl groups can be optionally substituted with 1 or 2 substituents selected from the group consisting of —$CH_3$, C($CH_3$)$_2$OH, OH, —O$CH_3$, —$NH_2$, and —N($CH_3$)$_2$.

In some embodiments, including the embodiments noted above, each $R^a$ and $R^b$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl. In some embodiments, including the embodiments noted above, each $R^a$ and $R^b$ is independently selected from the group consisting of hydrogen, $C_{1-4}$ alkyl, $C_{1-4}$ haloalkyl, and $C_{1-4}$ hydroxyalkyl. In some embodiments, including the embodiments noted above, each $R^a$ and $R^b$ is independently selected from the group consisting of hydrogen, $C_{1-4}$ alkyl, and $C_{1-4}$ haloalkyl.

In some embodiments, including the embodiments noted above, each $R^c$ and $R^d$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl. In some embodiments, including the embodiments noted above, each $R^c$ and $R^d$ is independently selected from the group consisting of hydrogen, $C_{1-4}$ alkyl, $C_{1-4}$ haloalkyl, and $C_{1-4}$ hydroxyalkyl. In some embodiments, including the embodiments noted above, each $R^c$ and $R^d$ is independently selected from the group consisting of hydrogen, $C_{1-4}$ alkyl, and $C_{1-4}$ haloalkyl.

In some embodiments, including the embodiments noted above, the subscript m is 0 ($R^3$ is absent). In other embodiments, including the embodiments noted above, the subscript m is 1. In still other embodiments, including the embodiments noted above, the subscript m is 2.

In some selected embodiments, provided herein are compounds of formula (I) wherein the compounds are selected from the Examples below and/or are provided in Tables 1-3.

A. Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

B. General Synthetic Methods

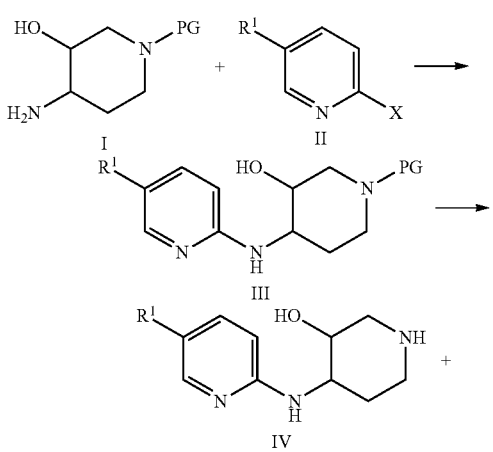

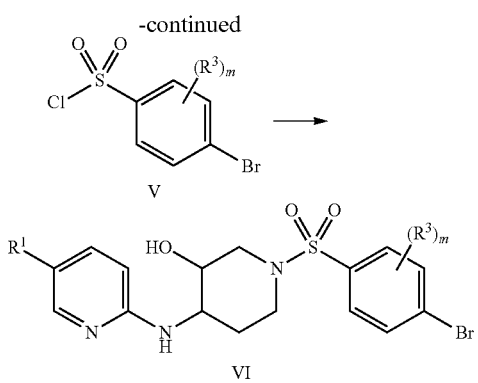

Suitably 1-N-protected 4-amino-3-hydroxy piperidines (I) can be reacted with 2-halo-5-substituted pyridines (II) (X=F, Br, or Cl) and base in an $S_NAr$ displacement reaction to form 4-aminopyridyl-3-hydroxy piperidines (III). The protecting group can be removed under appropriate conditions to give 1-NH piperidines (IV) as a free-base or protonated species with counterion. This amine can be further treated with base and 4-bromosulfonyl chlorides (V) bearing, substitutions if required, in a sulfonamidation reaction to give 4-aminopyridyl-3-hydroxy-1-N-sulfonamides (VI).

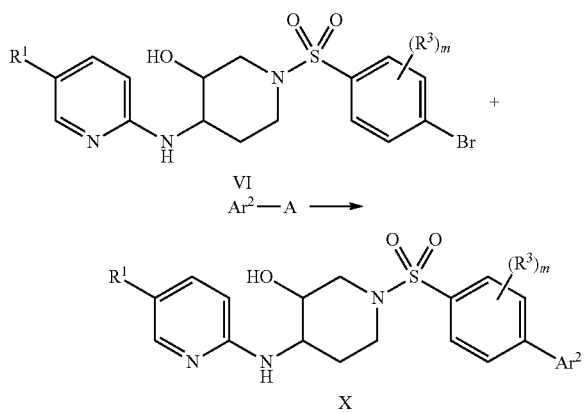

4-Aminopyridyl-3-hydroxy-1-N-piperidinyl-sulfonamides (VI) can be further elaborated in a direct Suzuki cross-coupling reaction (A=Boron species; Aryl/Heteroaryl boronic acids or esters) or a Miyura Bromide/Boronic ester exchange on bromide (VI), followed by Suzuki coupling with Aryl/Heteroaryl bromides (A=Br) to give final compounds (X).

IV. Pharmaceutical Compositions

In addition the compounds provided above, the compositions for modulating CCR6, activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In other embodiments of the invention, the inhibitory agent is formulated for release from the polymer coating into the environment in which the medical device is placed. The inhibitory agent may be released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CCR6

In one aspect, the present invention provides methods of treating or preventing a CCR6-mediated condition or disease by administering to a subject having such a condition or disease, a therapeutically effective amount of any compound of the invention. Exemplary compounds for use in the present methods are those compounds provided above, as well as compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In other embodiments, the subject is a human.

As used herein, the phrase "CCR6-mediated condition or disease" and related phrases and terms refer to a condition or disease characterized by inappropriate, e.g., less than or greater than normal, CCR6 functional activity. Inappropriate CCR6 functional activity might arise as the result of CCR6 expression in cells which normally do not express CCR6, increased CCR6 expression (leading to, e.g., inflammatory and immunoregulatory disorders and diseases) or decreased CCR6 expression. Inappropriate CCR6 functional activity might also arise as the result of CCL20 secretion by cells which normally do not secrete CCL20, increased CCL20 expression (leading to, e.g., inflammatory and immunoregulatory disorders and diseases) or decreased CCL20 expression. A CCR6-mediated condition or disease may be completely or partially mediated by inappropriate CCR6 functional activity. However, a CCR6-mediated condition or disease is one in which modulation of CCR6 results in some effect on the underlying condition or disease (e.g., a CCR6 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR6 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, Vitiligo (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic) as well as for instance Hashimoto's thyroiditis and Grave's disease, multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

In another embodiment, the present methods are directed to the treatment of diseases or conditions selected from allergic diseases, psoriasis, skin conditions such as atopic dermatitis and asthma and scleroderma.

In another group of embodiments, modulation of CCR6 dependent regulatory T cell trafficking may be modulated to treat diseases or conditions including cancers, infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CCR6 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

The compounds of the present invention are accordingly useful in the prevention and treatment of a wide variety of inflammatory and immunoregulatory disorders and diseases.

In the treatment or prevention of conditions which require chemokine receptor modulation an appropriate dosage level will generally be about 0.001 to 100 mg per kg patient body weight per day which can be administered in single or multiple doses. In another embodiment, the dosage level will be about 0.01 to about 25 mg/kg per day In another embodiment, the dosage level will be about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions can be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or in other embodiments, once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention may also be employed. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (1) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof, hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, and in other embodiments, from about 200:1 to about 1:200. Combinations of a compound of the present invention and other active ingredients will generally also be within the aforementioned range, but in each case, an effective dose of each active ingredient should be used.

VI. Examples

The following examples are offered to illustrate, but not to limit the claimed invention.

Reagents and solvents used below can be obtained from commercial sources such as Aldrich Chemical Co. (Milwaukee, Wisconsin, USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5 μcolumn for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium(0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example A: Preparation of Bromine Intermediate (3S,4R)-1-((4-bromophenyl)sulfonyl)-4-((5-(trifluoromethyl)pyridin-2-yl)amino)piperidin-3-ol

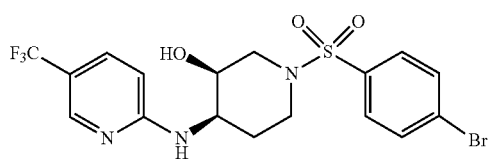 [SMILES: O=S(=O)(c1ccc(Br)cc1)N1CC[C@@H](Nc2ccc(C(F)(F)F)cn2)[C@@H](O)C1]

To a round-bottom flask were added tert-butyl (3S,4R)-4-amino-3-hydroxypiperidine-1-carboxylate (8.65 g, 40 mmol), 2-bromo-5-(trifluoromethyl)pyridine (18.08 g, 80 mmol), NMP (40 mL), and N,N-diisopropylethylamine (21 mL, 120 mmol). The reaction mixture was stirred at 100° C. for 24 hours. The reaction mixture was cooled to room temperature and diluted with 2 M HCl (100 mL, 200 mmol). The reaction mixture was stirred at 60° C. for 1 hour. The reaction mixture was cooled to room temperature and washed with 2-methyltetrahydrofuran (2×100 mL). The organic layer was discarded, and the aqueous layer was basified to pH 13-14 by the addition of 50% aq. sodium hydroxide and extracted with 2-methyltetrahydrofuran (5×100 mL). The combined organic layers were stirred, and a solution of sodium bicarbonate (5.04 g, 60 mmol) in water (100 mL) was added, followed by 4-bromobenzenesulfonyl chloride (10.22 g, 40 mmol). The reaction mixture was stirred at room temperature for 45 minutes. The layers were separated, and the organic layer was washed with water (100 mL) and concentrated. The solvent was swapped to toluene, and a white solid appeared. The solid was filtered, washed with toluene, and dried to give (3S,4R)-1-((4-bromophenyl)sulfonyl)-4-((5-(trifluoromethyl)pyridin-2-yl)amino)piperidin-3-ol. MS: (ES) m/z calculated for C$_{17}$H$_{18}$F$_3$N$_3$O$_3$S [M+H]$^+$ 480.0, found 480.1.

Example B: (3S,4R)-1-((4-bromophenyl)sulfonyl)-4-((3-methyl-5-(trifluoromethyl)pyridin-2-yl)amino)piperidin-3-ol

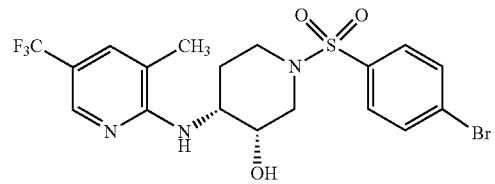

To tert-butyl N-[(3S,4R)-3-hydroxy-4-piperidyl]carbamate (10.0 g, 0.046 mol) in 100 mL of CH$_2$Cl$_2$ is added 100 mL of sat. NaHCO$_3$ and 4-bromobenzenesulfonyl chloride (12.32 g, 0.048 mol). The heterogeneous mixture is stirred with an overhead stirrer for 16 h. The solids are collected by filtration and the precipitate rinsed with CH$_2$Cl$_2$. The material was dried under vacuum to give tert-butyl N-[(3S,4R)-1-(4-bromophenyl)sulfonyl-3-hydroxy-4-piperidyl]carbamate.

To tert-butyl N-[(3S,4R)-1-(4-bromophenyl)sulfonyl-3-hydroxy-4-piperidyl]carbamate (17.28 g, 0.040 mol) in a 200 mL round-bottom flask is added 4 M HCl/Dioxane (84.4 mL, 0.336 mol). The heterogenous mixture is heated to 70° C. for 2 h. The mixture is poured into 500 mL of Et$_2$O. The solids are filtered off and air dried to give (3S,4R)-4-amino-1-(4-bromophenyl)sulfonyl-piperidin-3-ol hydrochloride.

To (3S,4R)-4-amino-1-(4-bromophenyl)sulfonyl-piperidin-3-ol hydrochloride (250 mg, 0.67 mmol) in 1 mL of NMP is added 2-chloro-3-methyl-5-(trifluoromethyl)pyridine (275 mg, 1.40 mmol) and N,N-diisopropylethylamine (337 uL, 1.93 mmol). The mixture is heated at 100° C. for 16 h, then at 120° C. for 24 h. The mixture is diluted with EtOAc (30 mL), washed with H$_2$O (4×15 mL) and brine (30 mL). The organic phase is partitioned, dried with MgSO$_4$, filtered and concentrated. The crude material is purified via SiO$_2$ chromatography (hexanes/ethyl acetate) to give (3S, 4R)-1-(4-bromophenyl)sulfonyl-4-[[3-methyl-5-(trifluoromethyl)-2-pyridyl]amino]piperidin-3-ol MS: (ES) m/z calculated for $C_{18}H_{19}BrF_3N_3O_3S$ [M+H]$^+$ 494.0/496.0, found 493.9/495.9.

Example C: 2-(((3S,4R)-1-((4-bromophenyl)sulfonyl)-3-hydroxypiperidin-4-yl)amino)-5-(trifluoromethyl)nicotinonitrile

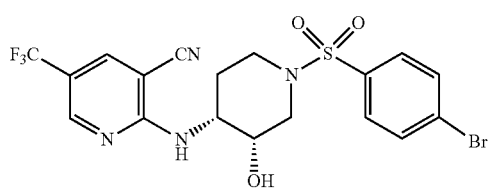 [SMILES: N#Cc1cc(C(F)(F)F)cnc1N[C@@H]1CCN(S(=O)(=O)c2ccc(Br)cc2)C[C@@H]1O]

A mixture of 2-chloro-5-(trifluoromethyl)nicotinonitrile (103 mg, 0.50 mmol), (3S,4R)-4-amino-1-((4-bromophenyl)sulfonyl)piperidin-3-ol hydrochloride (279 mg, 0.75 mmol), and N,N-diisopropylethylamine (0.26 mL, 1.5 mmol) in NMP (1 mL) was stirred at 100° C. for 16 hours. The reaction mixture was cooled to room temperature and diluted with water. The resulting solid was filtered, washed with water, and purified by SiO$_2$ gel chromatography (hexanes/ethyl acetate) to give 2-(((3S,4R)-1-((4-bromophenyl)sulfonyl)-3-hydroxypiperidin-4-yl)amino)-5-(trifluoromethyl)nicotinonitrile. MS: (ES) m/z calculated for $C_{18}H_{19}BrF_3N_3O_3S$ [M+H]$^+$ 505.0, found 504.9.

Example D: 6-(((3S,4R)-1-((4-bromophenyl)sulfonyl)-3-hydroxypiperidin-4-yl)amino)nicotinonitrile

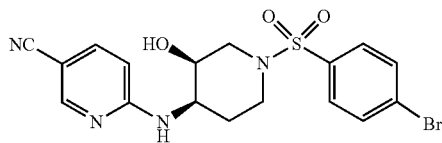 [SMILES: N#Cc1ccc(N[C@@H]2CCN(S(=O)(=O)c3ccc(Br)cc3)C[C@@H]2O)nc1]

6-(((3S,4R)-1-((4-bromophenyl)sulfonyl)-3-hydroxypiperidin-4-yl)amino)nicotinonitrile was synthesized via the procedure described in Example C, starting from (3S,4R)-4-amino-1-((4-bromophenyl)sulfonyl)piperidin-3-ol hydrochloride and 6-fluoronicotinonitrile.

Example 1: (3S,4R)-1-((4-(3-amino-1H-indazol-5-yl)phenyl)sulfonyl)-4-((5-(trifluoromethyl)pyridin-2-yl)amino)piperidin-3-ol

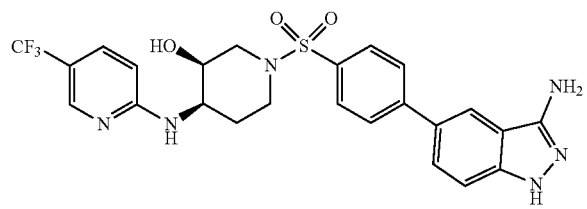 [SMILES: Nc1n[nH]c2ccc(-c3ccc(S(=O)(=O)N4CC[C@@H](Nc5ccc(C(F)(F)F)cn5)[C@@H](O)C4)cc3)cc12]

To (3S,4R)-1-((4-bromophenyl)sulfonyl)-4-((5-(trifluoromethyl)pyridin-2-yl)amino)piperidin-3-ol (70 mg, 0.14 mmol), were added 2 M $K_2CO_3$ (0.23 mL, 0.46 mmol), 5-(4,4,5,5-tetramethyl-1,3,2-dioxaborolan-2-yl)-1H-indazol-3-amine (42 mg, 0.16 mmol), Pd(dppf)Cl$_2$·DCM (12 mg, 0.014 mmol) in a septum-cap vial. To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give (3S,4R)-1-((4-(3-amino-1H-indazol-5-yl)phenyl)sulfonyl)-4-((5-(trifluoromethyl)pyridin-2-yl)amino)piperidin-3-ol. MS: (ES) m/z calculated for $C_{24}H_{23}F_3N_6O_3S$ [M+H]$^+$ 533.1, found 533.2. $^1$H NMR (400 MHz, Methanol-d$_4$) δ 8.26 (s, 1H), 8.18 (s, 1H), 7.97 (dd, J=8.6, 0.8 Hz, 1H), 7.96-7.88 (m, 4H), 7.71-7.65 (m, 1H), 7.57 (dd, J=8.6, 1.5 Hz, 1H), 6.80 (d, J=9.2 Hz, 1H), 4.02 (s, 1H), 3.94-3.86 (m, 1H), 3.75-3.65 (m, 2H), 2.80 (d, J=11.8 Hz, 1H), 2.69 (t, J=11.0 Hz, 1H), 2.10-2.01 (m, 1H), 1.88-1.80 (m, 1H).

Example 2: 6-(4-(((3S,4R)-3-hydroxy-4-((5-(trifluoromethyl)pyridin-2-yl)amino)piperidin-1-yl)sulfonyl)phenyl)-3,4-dihydroquinolin-2(1H)-one

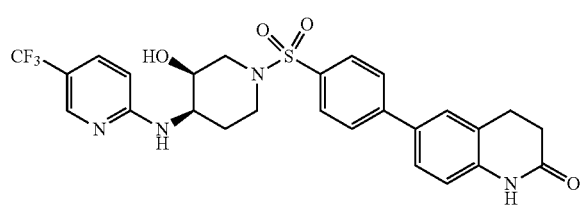 [SMILES: O=C1CCc2cc(-c3ccc(S(=O)(=O)N4CC[C@@H](Nc5ccc(C(F)(F)F)cn5)[C@@H](O)C4)cc3)ccc2N1]

To (3S,4R)-1-((4-bromophenyl)sulfonyl)-4-((5-(trifluoromethyl)pyridin-2-yl)amino)piperidin-3-ol (70 mg, 0.14 mmol) in a septum-cap vial were added 2 M $K_2CO_3$ (0.23 mL, 0.46 mmol), 6-(4,4,5,5-tetramethyl-1,3,2-dioxaborolan-2-yl)-3,4-dihydroquinolin-2(1H)-one (36 mg, 0.16 mmol), Pd(dppf)Cl$_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 6-(4-(((3S,4R)-3-hydroxy-4-((5-(trifluoromethyl)pyridin-2-yl)amino)piperidin-1-yl)sulfonyl)phenyl)-3,4-dihydroquinolin-2(1H)-one. MS: (ES) m/z calculated for $C_{26}H_{25}F_3N_4O_4S$ [M+H]$^+$ 547.2, found 547.2. $^1$H NMR (400 MHz, Methanol-d$_4$) δ 8.19 (s, 1H), 7.94-7.84 (m, 4H), 7.76 (d, J=9.3 Hz, 1H), 7.60-7.50 (m, 2H), 6.99 (d, J=8.2 Hz, 1H), 6.88 (d, J=9.4 Hz, 1H), 4.01 (s, 1H), 3.91-3.85 (m, 1H), 3.68-3.59 (m, 2H), 3.05 (t, J=7.6 Hz, 2H), 2.82 (d, J=11.9 Hz, 1H), 2.75-2.66 (m, 1H), 2.62 (t, J=7.6 Hz, 2H), 2.12-2.01 (m, 1H), 1.91-1.83 (m, 1H).

Example 3: 7-(4-(((3S,4R)-3-hydroxy-4-((5-(trifluoromethyl)pyridin-2-yl)amino)piperidin-1-yl)sulfonyl)phenyl)-3,4-dihydroisoquinolin-1(2H)-one

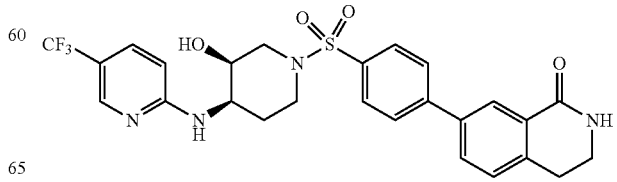

Step 1: Preparation of Boronic Ester Intermediate: (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol

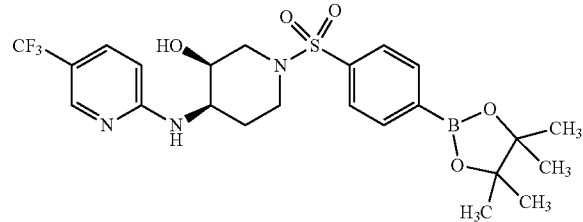 [SMILES: CC1(C)OB(c2ccc(S(=O)(=O)N3CC[C@@H](Nc4ccc(C(F)(F)F)cn4)[C@@H](O)C3)cc2)OC1(C)C]

To (3S,4R)-1-((4-bromophenyl)sulfonyl)-4-((5-(trifluoromethyl)pyridin-2-yl)amino)piperidin-3-ol (460 mg, 0.96 mmol), bis(pinacolato)diboron (300 mg, 1.2 mmol), KOAc (200 mg, 2.0 mmol) and Pd(dppf)Cl$_2$·DCM (14 mg, 0.017 mmol) in a septum-cap vial. To this was added to 5 mL of dioxane and the mixture was sparged with nitrogen for 20 minutes. The vial was sealed, the mixture stirred at 90° C. for 2.5 h. and cooled when the reaction had proceeded to completion. The mixture was diluted with ethyl acetate (10 mL) and filtered to remove inorganic solids. The filtrate was concentrated and the resulting residue was purified by silica gel flash chromatography (10-54% EtOAc, hexane) to provide the title pinacol boronic ester.

Step 2: To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M K$_2$CO$_3$ (0.23 mL, 0.46 mmol), 7-bromo-3,4-dihydroisoquinolin-1(2H)-one (36 mg, 0.16 mmol), Pd(dppf)Cl$_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 7-(4-(((3S,4R)-3-hydroxy-4-((5-(trifluoromethyl)pyridin-2-yl)amino)piperidin-1-yl)sulfonyl)phenyl)-3,4-dihydroisoquinolin-1(2H)-one. MS: (ES) m/z calculated for C$_{26}$H$_{25}$F$_3$N$_4$O$_4$S [M+H]$^+$ 547.2, found 547.2. $^1$H NMR (400 MHz, Methanol-d$_4$) δ 8.49-8.41 (m, 2H), 8.29-8.16 (m, 3H), 8.06 (d, J=8.1 Hz, 2H), 7.98 (d, J=8.3 Hz, 2H), 7.76 (d, J=9.2 Hz, 1H), 6.88 (d, J=9.3 Hz, 1H), 4.02 (s, 1H), 3.93-3.86 (m, 1H), 3.70-3.63 (m, 2H), 3.35-3.25 (m, 4H), 2.88-2.80 (m, 1H), 2.73 (t, J=11.0 Hz, 1H), 2.12-2.01 (m, 1H), 1.91-1.83 (m, 1H).

Example 4: 5-(4-(((3S,4R)-3-hydroxy-4-((5-(trifluoromethyl)pyridin-2-yl)amino)piperidin-1-yl)sulfonyl)phenyl)isoindoline-2-carboxamide

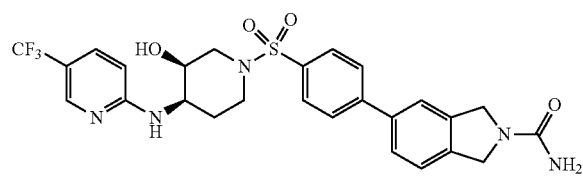 [SMILES: NC(=O)N1Cc2ccc(-c3ccc(S(=O)(=O)N4CC[C@@H](Nc5ccc(C(F)(F)F)cn5)[C@@H](O)C4)cc3)cc2C1]

Step 1: To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M K$_2$CO$_3$ (0.23 mL, 0.46 mmol), 5-bromoisoindoline (32 mg, 0.16 mmol), Pd(dppf)Cl$_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give intermediate (3S,4R)-1-((4-(isoindolin-5-yl)phenyl)sulfonyl)-4-((5-(trifluoromethyl)pyridin-2-yl)amino)piperidin-3-ol.

Step 2: To (3S,4R)-1-((4-(isoindolin-5-yl)phenyl)sulfonyl)-4-((5-(trifluoromethyl)pyridin-2-yl)amino)piperidin-3-ol (9 mg, 0.017 mmol) in a vial were added acetonitrile (1 mL), isocyanatotrimethylsilane (4 mg, 0.035 mmol) and DIPEA (8.8 mg, 0.068 mmol). The mixture was stirred at rt for 1 h and then purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)isoindoline-2-carboxamide. MS: (ES) m/z calculated for C$_{26}$H$_{26}$F$_3$N$_5$O$_4$S [M+H]$^+$ 562.2, found 562.2. $^1$H NMR (400 MHz, Methanol-d$_4$) δ 8.19 (s, 1H), 7.92-7.86 (m, 4H), 7.78 (d, J=9.2 Hz, 1H), 7.65 (d, J=8.4 Hz, 2H), 7.45 (d, J=7.9 Hz, 1H), 6.91 (d, J=9.2 Hz, 1H), 4.75 (d, J=9.0 Hz, 4H), 4.01 (s, 1H), 3.88 (d, J=10.1 Hz, 1H), 3.64 (d, J=11.9 Hz, 2H), 2.83 (d, J=12.4 Hz, 1H), 2.70 (d, J=11.7 Hz, 1H), 2.04 (t, J=11.3 Hz, 1H), 1.88 (d, J=5.2 Hz, 1H).

Example 5: 6-(4-(((3S,4R)-3-hydroxy-4-((5-(trifluoromethyl)pyridin-2-yl)amino)piperidin-1-yl)sulfonyl)phenyl)phthalazin-1(2H)-one

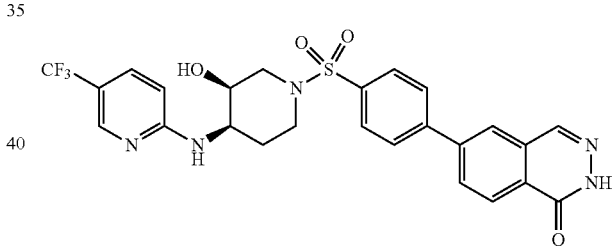

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M K$_2$CO$_3$ (0.23 mL, 0.46 mmol), 6-bromophthalazin-1(2H)-one (36 mg, 0.16 mmol), Pd(dppf)Cl$_2$·DCM (12 mg, 0.014 mmol). To this was added 1 mL dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 6-(4-(((3S,4R)-3-hydroxy-4-((5-(trifluoromethyl)pyridin-2-yl)amino)piperidin-1-yl)sulfonyl)phenyl)phthalazin-1(2H)-one. MS: (ES) m/z calculated for C$_{25}$H$_{22}$F$_3$N$_5$O$_4$S [M+H]$^+$ 546.1, found 546.2. $^1$H NMR (400 MHz, Methanol-d$_4$) δ 8.46 (d, J=8.5 Hz, 1H), 8.44 (s, 1H), 8.26 (d, J=1.6 Hz, 1H), 8.23-8.19 (m, 1H), 8.17 (d, J=2.2 Hz, 1H), 8.08-8.04 (m, 2H), 7.98 (d, J=8.2 Hz, 2H), 7.70-7.61 (m, 1H), 6.79-6.74 (m, 1H), 4.02 (s, 1H), 3.95-3.87 (m, 1H), 3.70 (dt, J=9.4, 4.6 Hz, 2H), 2.83 (d, J=12.3 Hz, 1H), 2.72 (t, J=11.1 Hz, 1H), 2.12-1.95 (m, 1H), 1.89-1.78 (m, 1H).

Example 6: 4-(4-(((3S,4R)-3-Hydroxy-4-((5-(trifluoromethyl)pyridin-2-yl)amino)piperidin-1-yl)sulfonyl)phenyl)-3-methylpicolinamide

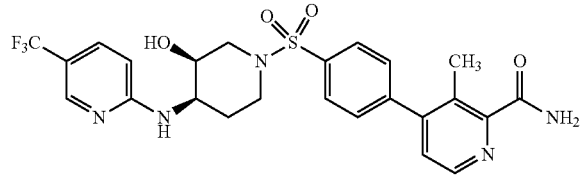 [SMILES: Cc1c(-c2ccc(S(=O)(=O)N3CC[C@@H](Nc4ccc(C(F)(F)F)cn4)[C@@H](O)C3)cc2)ccnc1C(N)=O]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (70 mg, 0.13 mmol) in a septum-cap vial were added $K_2CO_3$ (56 mg, 0.41 mmol), 4-bromo-3-methylpicolinamide (28 mg, 0.13 mmol), Pd(dppf)Cl$_2$·DCM (13 mg, 0.016 mmol). To this was added 3 mL dioxane and 0.7 mL of water. The mixture was sparged with nitrogen for 6 minutes. The vial was sealed, the mixture stirred at 100° C. for 4 hours and cooled when the reaction had proceeded to completion. The mixture was purified via preparative reverse-phase HPLC to give 4-(4-(((3S,4R)-3-hydroxy-4-((5-(trifluoromethyl)pyridin-2-yl)amino)piperidin-1-yl)sulfonyl)phenyl)-3-methylpicolinamide. MS: (ES) m/z calculated for $C_{24}H_{25}F_3N_5O_4S$ [M+H]$^+$ 536.2, found 536.1. $^1$H NMR (400 MHz, Methanol-d$_4$) δ 8.50 (d, 1H), 8.22 (s, 1H), 7.95 (d, J=8.0 Hz, 2H), 7.87 (d, J=9.4 Hz, 1H), 7.64 (d, J=8.1 Hz, 2H), 7.41 (d, J=4.8 Hz, 1H), 7.01 (d, J=9.4 Hz, 1H), 4.03 (s, 1H), 3.93-3.86 (m, 1H), 3.74-3.65 (m, 2H), 2.85 (d, J=12.3 Hz, 1H), 2.80-2.71 (m, 1H), 2.43 (s, 3H), 2.14-2.04 (m, 1H), 1.88 (d, J=13.0 Hz, 1H).

Example 7: 6-(4-(((3S,4R)-3-Hydroxy-4-((5-(trifluoromethyl)pyridin-2-yl)amino)piperidin-1-yl)sulfonyl)phenyl)picolinamide

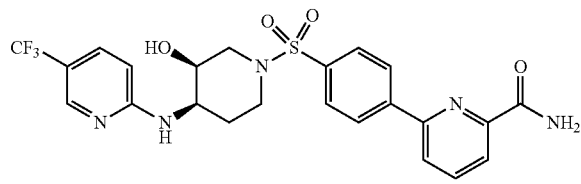 [SMILES: NC(=O)c1cccc(-c2ccc(S(=O)(=O)N3CC[C@@H](Nc4ccc(C(F)(F)F)cn4)[C@@H](O)C3)cc2)n1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (73 mg, 0.14 mmol) in a septum-cap vial were added $K_2CO_3$ (68 mg, 0.49 mmol), 6-bromopicolinamide (29 mg, 0.14 mmol), Pd(dppf)Cl$_2$·DCM (10 mg, 0.012 mmol). To this was added 3 mL dioxane and 0.7 mL of water. The mixture was sparged with nitrogen for 5 minutes. The vial was sealed, the mixture stirred at 100° C. for 2.4 hours and cooled when the reaction had proceeded to completion. The mixture was purified via silica gel chromatography to give 6-(4-(((3S,4R)-3-hydroxy-4-((5-(trifluoromethyl)pyridin-2-yl)amino)piperidin-1-yl)sulfonyl)phenyl)picolinamide. MS: (ES) m/z calculated for $C_{23}H_{23}F_3N_5O_4S$ [M+H]$^+$ 522.1, found 522.2. $^1$H NMR (400 MHz, Methanol-d$_4$) δ 8.45 (d, J=8.1 Hz, 2H), 8.24-8.05 (m, 4H), 7.94 (d, J=8.5 Hz, 2H), 7.55 (d, J=9.2 Hz, 1H), 6.64 (d, J=9.0 Hz, 1H), 4.01 (s, 1H), 3.95-3.86 (m, 1H), 3.76-3.65 (m, 2H), 2.78 (d, J=12.3 Hz, 1H), 2.67 (t, J=11.2 Hz, 1H), 2.08-1.95 (m, 1H), 1.82 (d, J=6.9 Hz, 1H).

Example 8: 7-(4-(((3S,4R)-3-hydroxy-4-((5-(trifluoromethyl)pyridin-2-yl)amino)piperidin-1-yl)sulfonyl)phenyl)-1,4-dihydroisoquinolin-3(2H)-one

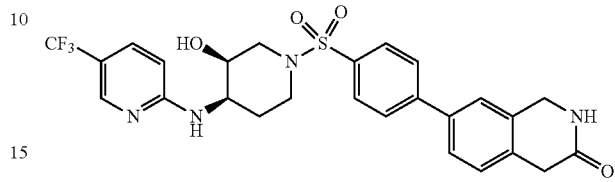

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 7-bromo-1,4-dihydroisoquinolin-3(2H)-one (36 mg, 0.16 mmol), Pd(dppf)Cl$_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 7-(4-(((3S,4R)-3-hydroxy-4-((5-(trifluoromethyl)pyridin-2-yl)amino)piperidin-1-yl)sulfonyl)phenyl)-1,4-dihydroisoquinolin-3(2H)-one. MS: (ES) m/z calculated for $C_{26}H_{25}F_3N_4O_4S$ [M+H]$^+$ 547.2, found 547.2. $^1$H NMR (400 MHz, Methanol-d$_4$) δ 8.20 (s, 1H), 7.94-7.84 (m, 4H), 7.82 (d, J=9.2 Hz, 1H), 7.65-7.60 (m, 2H), 7.36 (d, J=8.2 Hz, 1H), 6.95 (d, J=9.3 Hz, 1H), 4.56 (d, J=2.3 Hz, 2H), 4.01 (s, 1H), 3.91-3.84 (m, 1H), 3.67-3.58 (m, 4H), 2.84 (d, J=12.1 Hz, 1H), 2.78-2.68 (m, 1H), 2.12-2.01 (m, 1H), 1.91-1.83 (m, 1H).

Example 9: 6-(4-(((3S,4R)-3-hydroxy-4-((5-(trifluoromethyl)pyridin-2-yl)amino)piperidin-1-yl)sulfonyl)phenyl)indolin-2-one

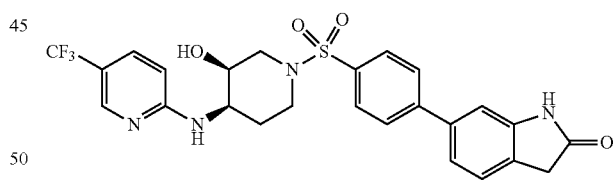

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 6-bromoindolin-2-one (34 mg, 0.16 mmol), Pd(dppf)Cl$_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 6-(4-(((3S,4R)-3-hydroxy-4-((5-(trifluoromethyl)pyridin-2-yl)amino)piperidin-1-yl)sulfonyl)phenyl)indolin-2-one. MS: (ES) m/z calculated for $C_{25}H_{23}F_3N_4O_4S$ [M+H]$^+$ 533.1, found 533.1. $^1$H NMR (400 MHz, Methanol-d$_4$) δ 8.20 (s, 1H), 7.94-7.84 (m, 4H), 7.82 (d, J=9.2 Hz, 1H), 7.65-7.60 (m, 2H), 7.36 (s, 1H), 6.95 (d, J=9.3 Hz, 1H), 4.01 (s, 1H), 3.91-3.84 (m, 1H), 3.72-3.65 (m, 2H), 3.61 (s, 2H), 2.92-2.74 (m, 2H), 2.12-2.01 (m, 1H), 1.91-1.83 (m, 1H).

Example 10: (3S,4R)-1-((4-(2-(hydroxymethyl)pyridin-4-yl)phenyl)sulfonyl)-4-((5-(trifluoromethyl)pyridin-2-yl)amino)piperidin-3-ol

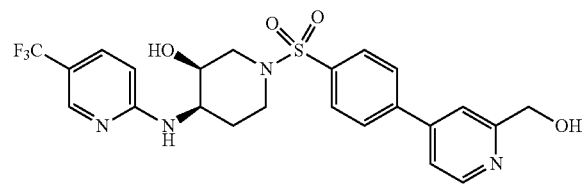 [SMILES: O=S(=O)(c1ccc(-c2ccnc(CO)c2)cc1)N1CC[C@@H](Nc2ccc(C(F)(F)F)cn2)[C@@H](O)C1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (71 mg, 0.13 mmol) in a septum-cap vial were added $K_2CO_3$ (66 mg, 0.48 mmol), (4-bromopyridin-2-yl)methanol (33 mg, 0.17 mmol), Pd(dppf)$Cl_2$·DCM (12 mg, 0.014 mmol). To this was added 3 mL dioxane and 0.7 mL of water. The mixture was sparged with nitrogen for 9 minutes. The vial was sealed, the mixture stirred at 100° C. for 1.4 hours and cooled when the reaction had proceeded to completion. The mixture was purified via silica gel chromatography to give (3S,4R)-1-((4-(2-(hydroxymethyl)pyridin-4-yl)phenyl)sulfonyl)-4-((5-(trifluoromethyl)pyridin-2-yl)amino)piperidin-3-ol. MS: (ES) m/z calculated for $C_{23}H_{24}F_3N_4O_4S$ [M+H]$^+$ 509.1, found 509.1. $^1$H NMR (400 MHz, Methanol-$d_4$) δ 8.64 (d, J=5.5 Hz, 1H), 8.17-8.13 (m, 1H), 8.10-7.94 (m, 5H), 7.85 (dd, J=5.7, 1.8 Hz, 1H), 7.56 (dd, J=9.6, 2.4 Hz, 1H), 6.64 (d, J=9.0 Hz, 1H), 4.87 (s, 2H), 4.00 (s, 1H), 3.91 (dt, J=10.9, 3.5 Hz, 1H), 3.77-3.66 (m, 2H), 2.79 (dd, J=12.4, 2.1 Hz, 1H), 2.73-2.62 (m, 1H), 2.08-1.93 (m, 1H), 1.80 (dd, J=13.2, 3.8 Hz, 1H).

Example 11: (3S,4R)-1-((4-(2-(5-methyl-1,3,4-oxadiazol-2-yl)pyridin-4-yl)phenyl)sulfonyl)-4-((5-(trifluoromethyl)pyridin-2-yl)amino)piperidin-3-ol

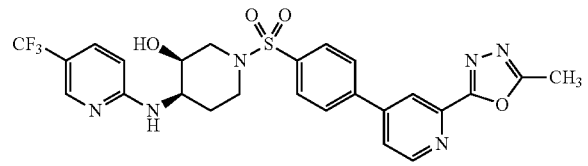 [SMILES: Cc1nnc(-c2cc(-c3ccc(S(=O)(=O)N4CC[C@@H](Nc5ccc(C(F)(F)F)cn5)[C@@H](O)C4)cc3)ccn2)o1]

A mixture of 4-bromopyridine-2-carboxylate (432 mg, 2.0 mmol) and hydrazine monohydrate (0.39 mL, 8.0 mmol) in ethanol (5 mL) was stirred at 70° C. for 1.5 hours. The reaction mixture was cooled to room temperature. The resulting solid was filtered, washed with ethanol, and dried to yield 4-bromopicolinohydrazide.

A mixture of 4-bromopicolinohydrazide (108 mg, 0.50 mmol), trimethyl orthoacetate (1.3 mL, 10.0 mmol) and 1 drop of conc. HCl was stirred at 110° C. for 1 hour. The reaction mixture was cooled to room temperature, 1,8-diazabicyclo[5.4.0]undec-7-ene (0.37 mL, 2.5 mmol) was added, and stirring continued at 110° C. for 16 hours. The reaction mixture was cooled to room temperature, diluted with water (10 mL), and extracted with ethyl acetate (3×10 mL). The combined organic layers were washed with brine (10 mL), dried over magnesium sulfate, filtered, and concentrated. Purification by $SiO_2$ gel chromatography (hexanes/ethyl acetate) gave 2-(4-bromopyridin-2-yl)-5-methyl-1,3,4-oxadiazole.

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (79 mg, 0.15 mmol) in a septum-cap vial were added $K_2CO_3$ (62 mg, 0.45 mmol), 2-(4-bromopyridin-2-yl)-5-methyl-1,3,4-oxadiazole (43 mg, 0.18 mmol), dioxane (1.5 mL) and water (0.5 mmol). The mixture was sparged with nitrogen for 20 minutes. Pd(dppf)$Cl_2$·DCM (12 mg, 0.015 mmol) was added, and the mixture was sparged with nitrogen for an additional 5 minutes. The vial was sealed, the mixture stirred at 100° C. for 16 hours and cooled when the reaction had proceeded to completion. The mixture was purified via $SiO_2$ gel chromatography (hexanes/ethyl acetate, then ethyl acetate/methanol) followed by preparative reverse-phase HPLC to give (3S,4R)-1-((4-(2-(5-methyl-1,3,4-oxadiazol-2-yl)pyridin-4-yl)phenyl)sulfonyl)-4-((5-(trifluoromethyl)pyridin-2-yl)amino)piperidin-3-ol. MS: (ES) m/z calculated for $C_{25}H_{24}F_3N_6O_4S$ [M+H]$^+$ 561.2, found 561.2. $^1$H NMR (400 MHz, DMSO-$d_6$) δ 8.89 (dd, J=5.2, 0.8 Hz, 1H), 8.46 (dt, J=1.7, 0.8 Hz, 1H), 8.19 (s, 1H), 8.17 (d, J=8.6 Hz, 2H), 8.04 (dd, J=5.2, 1.9 Hz, 1H), 7.92 (d, J=8.5 Hz, 2H), 7.58 (dd, J=9.0, 2.6 Hz, 1H), 7.12 (d, J=7.9 Hz, 1H), 6.69 (d, J=8.9 Hz, 1H), 5.26 (d, J=4.0 Hz, 1H), 3.97-3.85 (m, 2H), 3.60-3.45 (m, 2H), 2.74 (d, J=12.1 Hz, 1H), 2.68-2.58 (m, 4H), 1.97-1.82 (m, 1H), 1.70-1.61 (m, 1H).

Example 12: 5-(4-(((3S,4R)-3-hydroxy-4-((5-(trifluoromethyl)pyridin-2-yl)amino)piperidin-1-yl)sulfonyl)phenyl)isoindolin-1-one

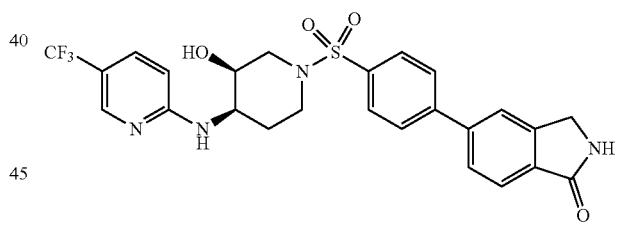

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 5-bromoisoindolin-1-one (34 mg, 0.16 mmol), Pd(dppf)$Cl_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)isoindolin-1-one. MS: (ES) m/z calculated for $C_{25}H_{23}F_3N_4O_4S$ [M+H]$^+$ 533.1, found 533.1. $^1$H NMR (400 MHz, Methanol-$d_4$) δ 8.20 (s, 1H), 7.94-7.84 (m, 4H), 7.82 (d, J=9.2 Hz, 1H), 7.65-7.60 (m, 2H), 7.36 (s, 1H), 6.95 (d, J=9.3 Hz, 1H), 4.56 (d, J=2.3 Hz, 2H), 4.01 (s, 1H), 3.91-3.84 (m, 1H), 3.72-3.65 (m, 2H), 2.92-2.74 (m, 2H), 2.12-2.01 (m, 1H), 1.91-1.83 (m, 1H).

Example 13: (3S,4R)-1-((4-(3-amino-[1,2,4]triazolo[4,3-a]pyridin-6-yl)phenyl)sulfonyl)-4-((5-(trifluoromethyl)pyridin-2-yl)amino)piperidin-3-ol

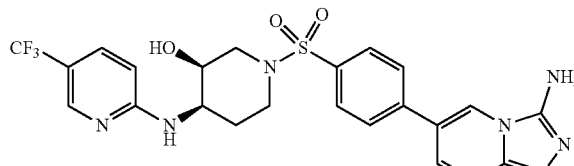

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 6-bromo-[1,2,4]triazolo[4,3-a]pyridin-3-amine (34 mg, 0.16 mmol), Pd(dppf)$Cl_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give (3S,4R)-1-((4-(3-amino-[1,2,4]triazolo[4,3-a]pyridin-6-yl)phenyl)sulfonyl)-4-((5-(trifluoromethyl)pyridin-2-yl)amino)piperidin-3-ol. MS: (ES) m/z calculated for $C_{23}H_{22}F_3N_7O_3S$ [M+H]$^+$ 534.1, found 534.1. $^1$H NMR (400 MHz, Methanol-$d_4$) δ 8.77 (s, 1H), 8.20-8.10 (m, 2H), 7.99 (s, 3H), 7.82 (d, J=9.2 Hz, 1H), 7.68-7.61 (m, 2H), 6.74 (d, J=9.3 Hz, 1H), 4.01 (s, 1H), 3.95-3.85 (m, 1H), 3.78-3.68 (m, 2H), 2.82-2.76 (m, 1H), 2.73-2.58 (m, 1H), 2.10-1.95 (m, 1H), 1.88-1.78 (m, 1H).

Example 14: 6-(4-(((3S,4R)-3-hydroxy-4-((5-(trifluoromethyl)pyridin-2-yl)amino)piperidin-1-yl)sulfonyl)phenyl)-3,4-dihydroquinazolin-2(1H)-one

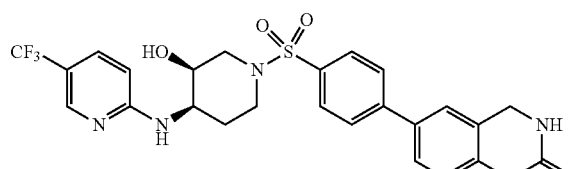

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 6-bromo-3,4-dihydroquinazolin-2(1H)-one (36 mg, 0.16 mmol), Pd(dppf)$Cl_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 6-(4-(((3S,4R)-3-hydroxy-4-((5-(trifluoromethyl)pyridin-2-yl)amino)piperidin-1-yl)sulfonyl)phenyl)-3,4-dihydroquinazolin-2(1H)-one. MS: (ES) m/z calculated for $C_{25}H_{24}F_3N_5O_4S$ [M+H]$^+$ 548.2, found 548.2. $^1$H NMR (400 MHz, Methanol-$d_4$) δ 8.18 (s, 1H), 7.90-7.82 (m, 4H), 7.72 (d, J=9.2 Hz, 1H), 7.56-7.46 (m, 2H), 6.92 (d, J=9.3 Hz, 1H), 6.84 (d, J=9.3 Hz, 1H), 4.55 (s, 2H), 4.01 (s, 1H), 3.93-3.85 (m, 1H), 3.70-3.60 (m, 2H), 2.85-2.76 (m, 1H), 2.74-2.65 (m, 1H), 2.10-2.00 (m, 1H), 1.90-1.80 (m, 1H).

Example 15: 5-(4-(((3S,4R)-3-hydroxy-4-((5-(trifluoromethyl)pyridin-2-yl)amino)piperidin-1-yl)sulfonyl)phenyl)-7-methoxyindolin-2-one

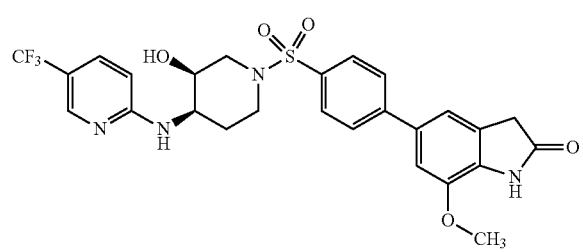 [SMILES: COc1cc(-c2ccc(S(=O)(=O)N3CC[C@@H](Nc4ccc(C(F)(F)F)cn4)[C@@H](O)C3)cc2)cc2c1NC(=O)C2]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added 2 M $K_2CO_3$ (0.23 mL, 0.46 mmol), 5-bromo-7-methoxyindolin-2-one (39 mg, 0.16 mmol), Pd(dppf)$Cl_2$·DCM (12 mg, 0.014 mmol). To this was added 1 mL Dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)-7-methoxyindolin-2-one. MS: (ES) m/z calculated for $C_{26}H_{25}F_3N_4O_5S$ [M+H]$^+$ 563.2, found 563.2. $^1$H NMR (400 MHz, Methanol-$d_4$) δ 8.19 (s, 1H), 7.90-7.84 (m, 4H), 7.76 (d, J=9.2 Hz, 1H), 7.26-7.20 (m, 2H), 6.90 (d, J=9.3 Hz, 1H), 4.03-3.99 (m, 1H), 3.97 (s, 3H), 3.91-3.84 (m, 1H), 3.70-3.58 (m, 4H), 2.81 (d, J=12.1 Hz, 1H), 2.75-2.66 (m, 1H), 2.11-2.00 (m, 1H), 1.90-1.83 (m, 1H).

Example 16: (3S,4R)-1-((4-(7-methyl-1H-indazol-5-yl)phenyl)sulfonyl)-4-((5-(trifluoromethyl)pyridin-2-yl)amino)piperidin-3-ol

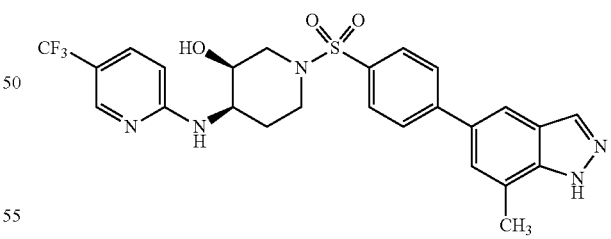

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added $K_2CO_3$ (0.65 mg, 0.47 mmol), 5-bromo-7-methyl-1H-indazole (33 mg, 0.16 mmol), Pd(dppf)$Cl_2$·DCM (0.12 mg, 0.015 mmol). To this was added 1 mL dioxane and 0.5 mL of water. The mixture was sparged with nitrogen for 10 minutes. The vial was sealed, the mixture stirred at 100° C. for 4 hours and cooled when the reaction had proceeded to completion. The mixture was purified via $SiO_2$ gel chromatography followed by preparative reverse-phase HPLC to give (3S,4R)-1-((4-(7-methyl-1H-indazol-5-yl)phenyl)sulfonyl)-4-((5-(trifluoromethyl)pyridin-2-yl)amino)piperidin-3-ol. MS: (ES) m/z calculated for $C_{25}H_{25}F_3N_5O_3S$ [M+H]$^+$ 532.2, found 532.2. $^1$H NMR (400 MHz, CD$_3$OD) δ 8.19 (bs, 1H), 8.13 (s, 1H), 7.95-7.91 (m, 3H), 7.90-7.86 (m, 2H), 7.79 (dd, J=9.6, 2 Hz, 1H), 7.54-7.53 (m, 1H), 6.93 (d, J=9.2 Hz, 1H), 4.03-4.00 (m, 1H), 3.88 (ddd, J=9.3, 4.0, 4.0 Hz, 1H), 3.71-3.56 (m, 2H), 2.85 (d, J=12.3 Hz, 1H), 2.74 (dd, J=11.3, 11.3 Hz, 1H), 2.65 (s, 3H), 2.19-1.97 (m, 1H), 1.91-1.83 (m, 1H).

Example 17: (3S,4R)-1-((4-(6-methyl-1H-pyrrolo[2,3-b]pyridin-5-yl)phenyl)sulfonyl)-4-((5-(trifluoromethyl)pyridin-2-yl)amino)piperidin-3-ol

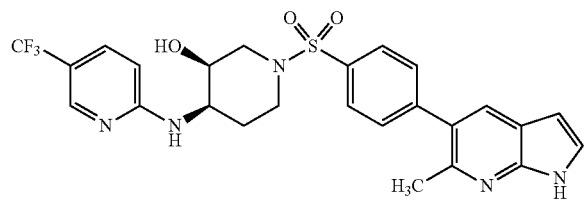 [SMILES: Cc1nc2[nH]ccc2cc1-c1ccc(S(=O)(=O)N2CC[C@@H](Nc3ccc(C(F)(F)F)cn3)[C@@H](O)C2)cc1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K$_2$CO$_3$ (65 mg, 0.47 mmol), 5-bromo-6-methyl-1H-pyrrolo[2,3-b]pyridine (33 mg, 0.16 mmol), Pd(dppf)Cl$_2$·DCM (12 mg, 0.014 mmol). To this was added 1 mL dioxane and 0.3 mL of water. The mixture was sparged with nitrogen for 10 minutes. The vial was sealed, the mixture stirred at 100° C. for 16 hours and cooled when the reaction had proceeded to completion. The mixture was purified via SiO$_2$ gel chromatography followed by preparative reverse-phase HPLC to give (3S,4R)-1-((4-(6-methyl-1H-pyrrolo[2,3-b]pyridin-5-yl)phenyl)sulfonyl)-4-((5-(trifluoromethyl)pyridin-2-yl)amino)piperidin-3-ol. MS: (ES) m/z calculated for $C_{25}H_{25}F_3N_5O_3S$ [M+H]$^+$ 532.2, found 532.0. $^1$H NMR (400 MHz, CD$_3$OD) δ 8.41 (s, 1H), 8.24-8.17 (m, 1H), 8.00-7.92 (m, 2H), 7.76-7.73 (m, 2H), 7.73-7.71 (m, 1H), 7.61 (d, J=3.5 Hz, 1H), 6.85 (d, J=9.1 Hz, 1H), 6.80 (d, J=3.5 Hz, 1H), 4.05-4.01 (m, 1H), 3.92 (ddd, J=10.4, 4.4, 4.4 Hz, 1H), 3.78-3.70 (m, 2H), 2.83 (d, J=13.0 Hz, 1H), 2.76-2.68 (m, 1H), 2.68 (s, 3H), 2.16-1.98 (m, 1H), 1.94-1.77 (m, 1H).

Example 18: 2-(4-(((3S,4R)-3-Hydroxy-4-((5-(trifluoromethyl)pyridin-2-yl)amino)piperidin-1-yl)sulfonyl)phenyl)isonicotinamide

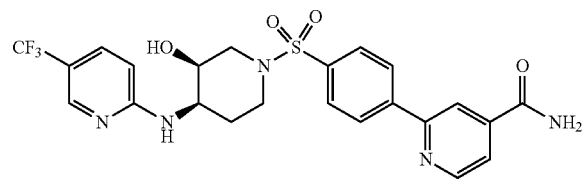 [SMILES: NC(=O)c1ccnc(-c2ccc(S(=O)(=O)N3CC[C@@H](Nc4ccc(C(F)(F)F)cn4)[C@@H](O)C3)cc2)c1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (70 mg, 0.13 mmol) in a septum-cap vial were added K$_2$CO$_3$ (59 mg, 0.43 mmol), 2-bromoisonicotinamide (28 mg, 0.14 mmol), Pd(dppf)Cl$_2$·DCM (12 mg, 0.015 mmol). To this was added 3 mL dioxane and 0.7 mL of water. The mixture was sparged with nitrogen for 14 minutes. The vial was sealed, the mixture stirred at 100° C. for 2.3 hours and cooled when the reaction had proceeded to completion. The mixture was purified via preparative reverse-phase HPLC to give 2-(4-(((3S,4R)-3-hydroxy-4-((5-(trifluoromethyl)pyridin-2-yl)amino)piperidin-1-yl)sulfonyl)phenyl)isonicotinamide. MS: (ES) m/z calculated for $C_{23}H_{23}F_3N_5O_4S$ [M+H]$^+$ 522.1, found 522.2. $^1$H NMR (400 MHz, Methanol-d$_4$) δ 8.84 (dd, J=5.1, 0.8 Hz, 1H), 8.38-8.36 (m, 1H), 8.35-8.31 (m, 2H), 8.20 (s, 1H), 8.00-7.92 (m, 2H), 7.87-7.79 (m, 2H), 6.97 (d, J=9.3 Hz, 1H), 4.05-3.99 (m, 1H), 3.91-3.84 (m, 1H), 3.65 (d, J=11.6 Hz, 2H), 2.87 (d, J=11.9 Hz, 1H), 2.76 (t, J=11.6 Hz, 1H), 2.05 (t, J=9.8 Hz, 1H), 1.92-1.83 (m, 1H).

Example 19: 3-Amino-5-(4-(((3S,4R)-3-hydroxy-4-((5-(trifluoromethyl)pyridin-2-yl)amino)piperidin-1-yl)sulfonyl)phenyl)picolinamide

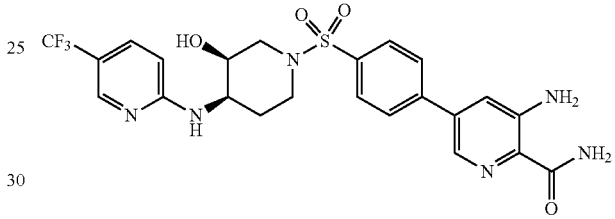

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (80 mg, 0.15 mmol) in a septum-cap vial were added K$_2$CO$_3$ (65 mg, 0.47 mmol), 3-amino-5-bromopicolinamide (37 mg, 0.17 mmol), Pd(dppf)Cl$_2$·DCM (12 mg, 0.015 mmol). To this was added 3 mL dioxane and 0.7 mL of water. The mixture was sparged with nitrogen for 5 minutes. The vial was sealed, the mixture stirred at 100° C. for 2.3 hours and cooled when the reaction had proceeded to completion. The mixture was purified via preparative reverse-phase HPLC to give 3-amino-5-(4-(((3S,4R)-3-hydroxy-4-((5-(trifluoromethyl)pyridin-2-yl)amino)piperidin-1-yl)sulfonyl)phenyl)picolinamide. MS: (ES) m/z calculated for $C_{23}H_{24}F_3N_6O_4S$ [M+H]$^+$ 537.2, found 537.2. $^1$H NMR (400 MHz, Methanol-d$_4$) δ 8.20 (d, J=2.3 Hz, 1H), 8.15 (d, J=2.0 Hz, 1H), 7.95-7.88 (m, 4H), 7.83 (dd, J=9.6, 2.4 Hz, 1H), 7.43 (d, J=2.0 Hz, 1H), 6.97 (d, J=9.3 Hz, 1H), 4.05-3.99 (m, 1H), 3.88 (dt, J=10.3, 3.9 Hz, 1H), 3.65 (d, J=12.3 Hz, 2H), 2.85 (d, J=12.3 Hz, 1H), 2.74 (t, J=10.8 Hz, 1H), 2.13-2.00 (m, 1H), 1.91-1.82 (m, 1H).

Example 20: 4-(4-(((3S,4R)-3-Hydroxy-4-((5-(trifluoromethyl)pyridin-2-yl)amino)piperidin-1-yl)sulfonyl)phenyl)-5-methylpicolinamide

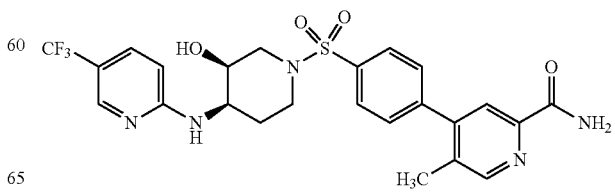

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (80 mg, 0.15 mmol) in a septum-cap vial were added K$_2$CO$_3$ (65 mg, 0.47 mmol), 4-bromo-5-methylpicolinamide (33 mg, 0.15 mmol), Pd(dppf)Cl$_2$·DCM (15 mg, 0.018 mmol). To this was added 3 mL dioxane and 0.7 mL of water. The mixture was sparged with nitrogen for 5 minutes. The vial was sealed, the mixture stirred at 100° C. for 4 hours and cooled when the reaction had proceeded to completion. The mixture was purified via preparative reverse-phase HPLC to give 4-(4-(((3S,4R)-3-hydroxy-4-((5-(trifluoromethyl)pyridin-2-yl)amino)piperidin-1-yl)sulfonyl)phenyl)-5-methylpicolinamide. MS: (ES) m/z calculated for C$_{24}$H$_{25}$F$_3$N$_5$O$_4$S [M+H]$^+$ 536.2, found 536.1. $^1$H NMR (400 MHz, Methanol-d$_4$) δ 8.51 (d, J=5.0 Hz, 1H), 8.25 (t, J=1.8 Hz, 1H), 7.99-7.87 (m, 3H), 7.68-7.60 (m, 2H), 7.41 (d, J=5.0 Hz, 1H), 7.07 (d, J=9.4 Hz, 1H), 4.03 (d, J=2.7 Hz, 1H), 3.90 (dt, J=10.4, 3.9 Hz, 1H), 3.71 (d, J=12.4 Hz, 2H), 2.90-2.79 (m, 1H), 2.80-2.69 (m, 1H), 2.43 (d, J=0.5 Hz, 3H), 2.17-2.00 (m, 1H), 1.93-1.84 (m, 1H).

Example 21: (3S,4R)-1-((4-(7-methoxy-1H-indazol-5-yl)phenyl)sulfonyl)-4-((5-(trifluoromethyl)pyridin-2-yl)amino)piperidin-3-ol

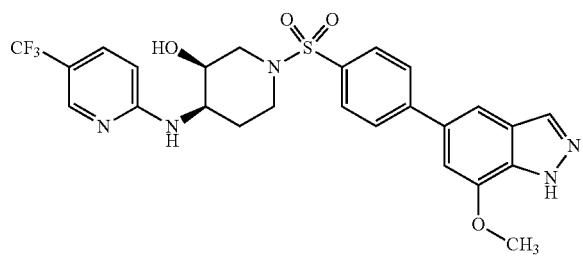 [SMILES: COc1cc(-c2ccc(S(=O)(=O)N3CC[C@@H](Nc4ccc(C(F)(F)F)cn4)[C@@H](O)C3)cc2)cc2cn[nH]c12]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K$_2$CO$_3$ (65 mg, 0.47 mmol), 5-bromo-6-methyl-1H-pyrrolo[2,3-b]pyridine (37 mg, 0.157 mmol), Pd(dppf)Cl$_2$·DCM (0.012 mg, 0.015 mmol). To this was added 1 mL dioxane and 0.35 mL of water. The mixture was sparged with nitrogen for 10 minutes. The vial was sealed, the mixture stirred at 100° C. for 2 hours and cooled when the reaction had proceeded to completion. The mixture was purified via SiO$_2$ gel chromatography followed by preparative reverse-phase HPLC to give (3S,4R)-1-((4-(7-methoxy-1H-indazol-5-yl)phenyl)sulfonyl)-4-((5-(trifluoromethyl)pyridin-2-yl)amino)piperidin-3-ol. MS: (ES) m/z calculated for C$_{25}$H$_{25}$F$_3$N$_5$O$_4$S [M+H]$^+$ 548.2, found 548.1. $^1$H NMR (400 MHz, CD$_3$OD) δ 8.18-8.15 (m, 1H), 8.06 (s, 1H), 7.96-7.90 (m, 2H), 7.87-7.83 (m, 2H), 7.78 (d, J=9.0 Hz, 1H), 7.64 (d, J=1.3 Hz, 1H), 7.10 (d, J=1.2 Hz, 1H), 6.92 (d, J=9.3 Hz, 1H), 4.07 (s, 3H), 4.01-3.98 (m, 1H), 3.85 (ddd, J=10.0, 3.2, 3.2 Hz, 1H), 3.68-3.53 (m, 2H), 2.82 (d, J=11.7 Hz, 1H), 2.72 (dd, J=10.0, 10.0 Hz, 1H), 2.10-1.98 (m, 1H), 1.88-1.80 (m, 1H).

Example 22: (3S,4R)-1-((4-(4-(trifluoromethyl)-1H-pyrrolo[2,3-b]pyridin-5-yl)phenyl)sulfonyl)-4-((5-(trifluoromethyl)pyridin-2-yl)amino)piperidin-3-ol

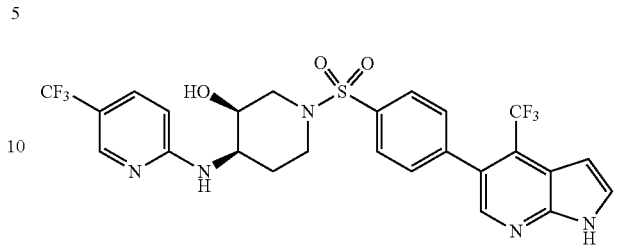

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K$_2$CO$_3$ (65 mg, 0.47 mmol), 5-bromo-4-(trifluoromethyl)-1H-pyrrolo[2,3-b]pyridine (41 mg, 0.16 mmol), Pd(dppf)Cl$_2$·DCM (12 mg, 0.015 mmol). To this was added 1 mL dioxane and 0.35 mL of water. The mixture was sparged with nitrogen for 10 minutes. The vial was sealed, the mixture stirred at 100° C. for 16 hours and cooled when the reaction had proceeded to completion. The mixture was purified via SiO$_2$ gel chromatography followed by preparative reverse-phase HPLC to give (3S,4R)-1-((4-(4-(trifluoromethyl)-1H-pyrrolo[2,3-b]pyridin-5-yl)phenyl)sulfonyl)-4-((5-(trifluoromethyl)pyridin-2-yl)amino)piperidin-3-ol. MS: (ES) m/z calculated for C$_{25}$H$_{22}$F$_6$N$_5$O$_3$S [M+H]$^+$ 586.1, found 586.0. $^1$H NMR (400 MHz, CD$_3$OD) δ 8.17 (bs, 1H), 8.15 (s, 1H), 7.86 (d, J=8.4 Hz, 2H), 7.80 (d, J=9.3 Hz, 1H), 7.64 (d, J=3.6 Hz, 1H), 7.60 (d, J=8.4 Hz, 2H), 6.95 (d, J=9.3 Hz, 1H), 6.70-6.66 (m, 1H), 4.00-3.96 (m, 1H), 3.84 (ddd, J=10.4, 4.0, 4.0 Hz, 1H), 3.67 (dd, J=12.8, 5.2 Hz, 2H), 2.78 (d, J=12.1 Hz, 1H), 2.67 (dd, J=10.8, 10.8 Hz, 1H), 2.15-1.99 (m, 1H), 1.89-1.74 (m, 1H).

Example 23: (3S,4R)-1-((4-(1H-indazol-5-yl)phenyl)sulfonyl)-4-((5-(trifluoromethyl)pyridin-2-yl)amino)piperidin-3-ol

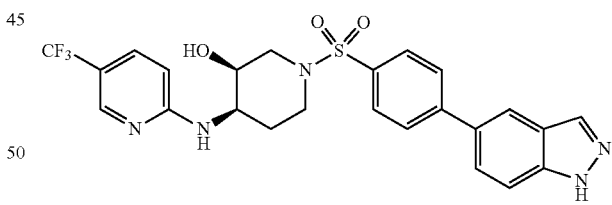

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K$_2$CO$_3$ (75 mg, 0.142 mmol), 5-bromo-1H-indazole (31 mg, 0.158 mmol), Pd(dppf)Cl$_2$·DCM (12 mg, 0.015 mmol). To this was added 1 mL dioxane and 0.35 mL of water. The mixture was sparged with nitrogen for 10 minutes. The vial was sealed, the mixture stirred at 110° C. for 16 hours and cooled when the reaction had proceeded to completion. The mixture was purified via SiO$_2$ gel chromatography followed by preparative reverse-phase HPLC to give (3S,4R)-1-((4-(1H-indazol-5-yl)phenyl)sulfonyl)-4-((5-(trifluoromethyl)pyridin-2-yl)amino)piperidin-3-ol. MS: (ES) m/z calculated for C$_{24}$H$_{23}$F$_3$N$_5$O$_3$S [M+H]$^+$ 518.1, found 517.9. ¹H NMR (400 MHz, CD₃OD) δ 8.15 (bs, 1H), 8.11 (d, J=1.0 Hz, 1H), 8.09 (dd, J=1.7, 0.9 Hz, 1H), 7.90 (d, J=8.8 Hz, 2H), 7.85 (d, J=8.8 Hz, 2H), 7.76-7.71 (m, 2H), 7.63 (ddd, J=8.8, 1.0, 1.0 Hz, 1H), 6.87 (d, J=9.2 Hz, 1H), 4.00-3.96 (m, 1H), 3.84 (d, J=10.2, 4.0, 4.0 Hz, 1H), 3.60 (dd, J=12.3, 3.6 Hz, 2H), 2.80 (d, J=12.1 Hz, 1H), 2.70 (dd, J=11.6, 11.6 Hz, 1H), 2.18-1.91 (m, 1H), 1.84 (s, 1H).

Example 24: (3S,4R)-1-((4-(1H-pyrrolo[2,3-b]pyridin-5-yl)phenyl)sulfonyl)-4-((5-(trifluoromethyl)pyridin-2-yl)amino)piperidin-3-ol

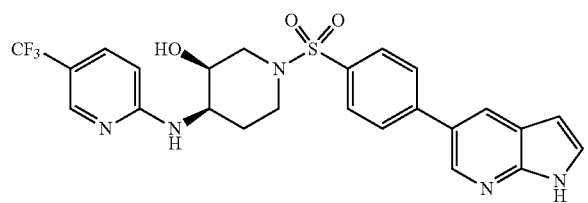 [SMILES: O=S(=O)(c1ccc(-c2cnc3[nH]ccc3c2)cc1)N1CC[C@@H](Nc2ccc(C(F)(F)F)cn2)[C@@H](O)C1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K₂CO₃ (65 mg, 0.47 mmol), 5-bromo-1H-pyrrolo[2,3-b]pyridine (31 mg, 0.16 mmol), Pd(dppf)Cl₂·DCM (12 mg, 0.015 mmol). To this was added 1 mL dioxane and 0.35 mL of water. The mixture was sparged with nitrogen for 10 minutes. The vial was sealed, the mixture stirred at 100° C. for 1 hour, and cooled when the reaction had proceeded to completion. The mixture was purified via SiO₂ gel chromatography followed by preparative reverse-phase HPLC to give (3S,4R)-1-((4-(1H-pyrrolo[2,3-b]pyridin-5-yl)phenyl)sulfonyl)-4-((5-(trifluoromethyl)pyridin-2-yl)amino)piperidin-3-ol. MS: (ES) m/z calculated for C₂₄H₂₃F₃N₅O₃S [M+H]⁺ 518.1, found 517.9. ¹H NMR (400 MHz, CD₃OD) δ 8.54 (dd, J=10.0, 2.0 Hz, 2H), 8.17-8.14 (m, 1H), 7.91 (d, J=8.8 Hz, 2H), 7.87 (d, J=8.8 Hz, 2H), 7.79 (dd, J=9.4, 2.4 Hz, 1H), 7.53 (d, J=3.5 Hz, 1H), 6.94 (d, J=9.3 Hz, 1H), 6.68 (d, J=3.5 Hz, 1H), 3.99-3.95 (m, 1H), 3.82 (ddd, J=10.3, 3.8, 3.8 Hz, 1H), 3.60 (d, J=12.2 Hz, 2H), 2.79 (dd, J=12.4, 2.0 Hz, 1H), 2.67 (ddd, J=8.0, 8.0, 3.2 Hz, 1H), 2.07-1.96 (m, 1H), 1.85-1.77 (m, 1H).

Example 25: (3S,4R)-1-((4-(6-methyl-1H-indazol-5-yl)phenyl)sulfonyl)-4-((5-(trifluoromethyl)pyridin-2-yl)amino)piperidin-3-ol

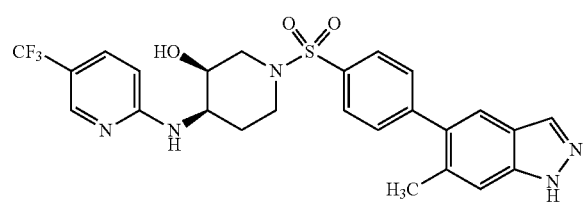 [SMILES: Cc1cc2[nH]ncc2cc1-c1ccc(S(=O)(=O)N2CC[C@@H](Nc3ccc(C(F)(F)F)cn3)[C@@H](O)C2)cc1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K₂CO₃ (65 mg, 0.47 mmol), 5-bromo-6-methyl-1H-indazole (33 mg, 0.16 mmol), Pd(dppf)Cl₂·DCM (12 mg, 0.015 mmol). To this was added 1 mL dioxane and 0.35 mL of water. The mixture was sparged with nitrogen for 10 minutes. The vial was sealed, the mixture stirred at 100° C. for 16 hours and cooled when the reaction had proceeded to completion. The mixture was purified via SiO₂ gel chromatography followed by preparative reverse-phase HPLC to give (3S,4R)-1-((4-(6-methyl-1H-indazol-5-yl)phenyl)sulfonyl)-4-((5-(trifluoromethyl)pyridin-2-yl)amino)piperidin-3-ol. MS: (ES) m/z calculated for C₂₅H₂₅F₃N₅O₃S [M+H]⁺ 531.2, found 531.9. ¹H NMR (400 MHz, CD₃OD) δ 8.19 (bs, 1H), 8.01 (d, J=1.0 Hz, 1H), 7.86 (d, J=8.8 Hz, 2H), 7.79 (d, J=9.1, 2.0 Hz, 1H), 7.62-7.59 (m, 3H), 7.46-7.45 (m, 1H), 6.92 (d, J=9.3 Hz, 1H), 4.02-3.99 (m, 1H), 3.88 (ddd, J=9.7, 3.6, 3.6 Hz, 1H), 3.67 (dd, J=12.3, 4.8 Hz, 2H), 2.82 (d, J=12.3 Hz, 1H), 2.70 (dd, J=11.5, 11.5 Hz, 1H), 2.35 (s, 3H), 2.12-2.00 (m, 1H), 1.90-1.81 (m, 1H).

Example 26: (3S,4R)-1-((4-(4-methyl-1H-indazol-5-yl)phenyl)sulfonyl)-4-((5-(trifluoromethyl)pyridin-2-yl)amino)piperidin-3-ol

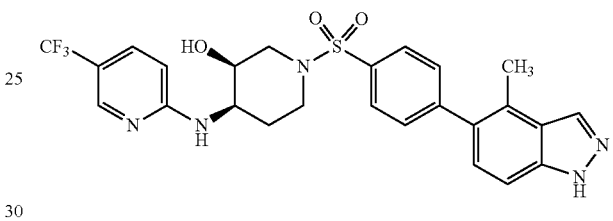

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (75 mg, 0.14 mmol) in a septum-cap vial were added K₂CO₃ (65 mg, 0.47 mmol), 5-bromo-4-methyl-1H-indazole (33 mg, 0.16 mmol), Pd(dppf)Cl₂·DCM (12 mg, 0.015 mmol). To this was added 1 mL dioxane and 0.35 mL of water. The mixture was sparged with nitrogen for 10 minutes. The vial was sealed, the mixture stirred at 100° C. for 16 hours and cooled when the reaction had proceeded to completion. The mixture was purified via SiO₂ gel chromatography followed by preparative reverse-phase HPLC to give (3S,4R)-1-((4-(4-methyl-1H-indazol-5-yl)phenyl)sulfonyl)-4-((5-(trifluoromethyl)pyridin-2-yl)amino)piperidin-3-ol. MS: (ES) m/z calculated for C₂₅H₂₅F₃N₅O₃S [M+H]⁺ 531.2, found 531.9. ¹H NMR (400 MHz, CD₃OD) δ 8.16 (bs, 1H), 8.15 (d, J=1.0 Hz, 1H), 7.85 (d, J=8.4 Hz, 2H), 7.76 (d, J=9.1, 2.0 Hz, 1H), 7.60 (d, J=8.8 Hz, 2H), 7.43 (d, J=8.6 Hz, 1H), 7.28 (d, J=8.6 Hz, 1H), 6.89 (d, J=9.3 Hz, 1H), 4.01-3.98 (m, 1H), 3.86 (ddd, J=10.5, 3.2, 3.2 Hz, 1H), 3.65 (d, J=11.8, 3.2 Hz, 2H), 2.81 (d, J=12.3 Hz, 1H), 2.68 (dd, J=11.5, 11.5 Hz, 1H), 2.52 (s, 3H), 2.10-1.96 (m, 1H), 1.88-1.80 (m, 1H).

Example 27: 5-(4-(((3S,4R)-3-Hydroxy-4-((5-(trifluoromethyl)pyridin-2-yl)amino)piperidin-1-yl)sulfonyl)phenyl)nicotinamide

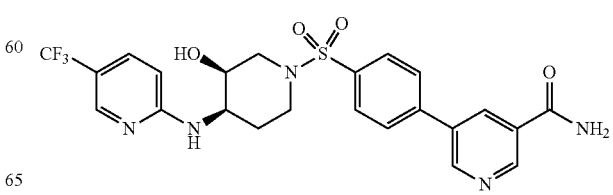

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (60 mg, 0.11 mmol) in a septum-cap vial were added $K_2CO_3$ (49 mg, 0.36 mmol), 5-bromonicotinamide (23 mg, 0.11 mmol), Pd(dppf)$Cl_2$·DCM (9.4 mg, 0.012 mmol). To this was added 3 mL dioxane and 0.7 mL of water. The mixture was sparged with nitrogen for 5 minutes. The vial was sealed, the mixture stirred at 100° C. for 2 hours and cooled when the reaction had proceeded to completion. The mixture was purified via silica gel chromatography to give 5-(4-(((3S,4R)-3-hydroxy-4-((5-(trifluoromethyl)pyridin-2-yl)amino)piperidin-1-yl)sulfonyl)phenyl)nicotinamide. MS: (ES) m/z calculated for $C_{23}H_{23}F_3N_5O_4S$ [M+H]$^+$ 522.1, found 521.9. $^1$H NMR (400 MHz, Methanol-$d_4$) δ 9.05 (dd, J=8.6, 2.1 Hz, 2H), 8.60 (t, J=2.1 Hz, 1H), 8.15 (t, J=1.7 Hz, 1H), 8.02 (d, J=8.6 Hz, 2H), 7.97 (d, J=8.6 Hz, 2H), 7.68 (d, J=7.3 Hz, 1H), 6.79 (d, J=9.2 Hz, 1H), 3.99 (d, J=3.7 Hz, 1H), 3.91-3.83 (m, 1H), 3.70-3.61 (m, 2H), 2.81 (d, J=11.7 Hz, 1H), 2.69 (t, J=11.1 Hz, 1H), 2.07-1.96 (m, 1H), 1.86-1.76 (m, 1H).

Example 28: 5-(4-(((3S,4R)-3-Hydroxy-4-((5-(trifluoromethyl)pyridin-2-yl)amino)piperidin-1-yl)sulfonyl)phenyl)picolinamide

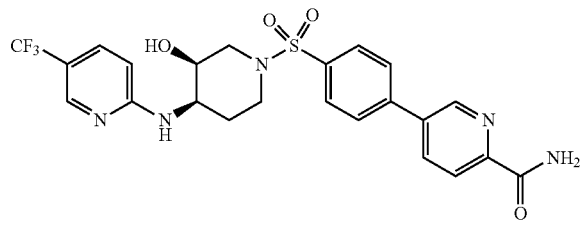 [SMILES: NC(=O)c1ccc(-c2ccc(S(=O)(=O)N3CC[C@@H](Nc4ccc(C(F)(F)F)cn4)[C@@H](O)C3)cc2)cn1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (60 mg, 0.11 mmol) in a septum-cap vial were added $K_2CO_3$ (45 mg, 0.33 mmol), 2-bromo-4-pyridinecarboxamide (25 mg, 0.12 mmol), Pd(dppf)$Cl_2$·DCM (9.4 mg, 0.012 mmol). To this was added 3 mL dioxane and 0.7 mL of water. The mixture was sparged with nitrogen for 15 minutes. The vial was sealed, the mixture stirred at 100° C. for 1.3 hours and cooled when the reaction had proceeded to completion. The mixture was purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)picolinamide. MS: (ES) m/z calculated for $C_{23}H_{23}F_3N_5O_4S$ [M+H]$^+$ 522.1, found 521.9. $^1$H NMR (400 MHz, DMSO-$d_6$) δ 9.03 (dd, J=2.3, 0.9 Hz, 1H), 8.37 (dd, J=8.2, 2.3 Hz, 1H), 8.25-8.20 (m, 2H), 8.16 (d, J=8.0 Hz, 1H), 8.11-8.06 (m, 2H), 7.93-7.86 (m, 2H), 7.75 (s, 1H), 7.63 (dd, J=9.0, 2.5 Hz, 1H), 7.30 (s, 1H), 6.75 (d, J=9.0 Hz, 1H), 3.90 (d, J=12.4 Hz, 2H), 3.59-3.46 (m, 2H), 2.71 (d, J=11.8 Hz, 1H), 2.63-2.55 (m, 1H), 1.95-1.82 (m, 1H), 1.73-1.62 (m, 1H).

Example 29: tert-Butyl (2-(3-cyano-5-(4-(((3S,4R)-3-hydroxy-4-((5-(trifluoromethyl)pyridin-2-yl)amino)piperidin-1-yl)sulfonyl)phenyl)-1H-pyrrolo[2,3-b]pyridin-1-yl)ethyl)carbamate

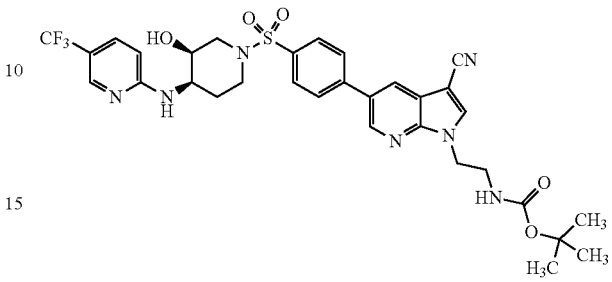

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (144 mg, 0.27 mmol) in a septum-cap vial were added $K_2CO_3$ (104 mg, 0.75 mmol), tert-butyl (2-(5-bromo-3-cyano-1H-pyrrolo[2,3-b]pyridin-1-yl)ethyl)carbamate (100 mg, 0.27 mmol), Pd(dppf)$Cl_2$·DCM (23 mg, 0.028 mmol). To this was added 6 mL dioxane and 1.5 mL of water. The mixture was sparged with nitrogen for 5 minutes. The vial was sealed, the mixture stirred at 100° C. for 16 hours and cooled when the reaction had proceeded to completion. The mixture was purified via silica gel chromatography to give tert-butyl (2-(3-cyano-5-(4-(((3S,4R)-3-hydroxy-4-((5-(trifluoromethyl)pyridin-2-yl)amino)piperidin-1-yl)sulfonyl)phenyl)-1H-pyrrolo[2,3-b]pyridin-1-yl)ethyl)carbamate. MS: (ES) m/z calculated for $C_{32}H_{35}F_3N_7O_5S$ [M+H]$^+$ 686.2, found 685.9. $^1$H NMR (400 MHz, DMSO-$d_6$) δ 8.82 (d, J=2.0 Hz, 1H), 8.48 (d, J=2.9 Hz, 2H), 8.18 (s, 1H), 8.08 (d, J=8.1 Hz, 2H), 7.84 (d, J=8.1 Hz, 2H), 7.56 (dd, J=9.4, 2.5 Hz, 1H), 7.10 (s, 1H), 6.96 (d, J=6.0 Hz, 1H), 6.68 (d, J=8.9 Hz, 1H), 5.23 (s, 1H), 4.38 (t, J=5.8 Hz, 2H), 3.88 (s, 2H), 3.58-3.44 (m, 2H), 3.43-3.35 (m, 2H), 2.71 (d, J=11.5 Hz, 1H), 2.66-2.53 (m, 1H), 1.93-1.81 (m, 1H), 1.70-1.62 (m, 1H), 1.27 (s, 9H).

Example 30: 2-amino-6-(4-(((3S,4R)-3-hydroxy-4-((5-(trifluoromethyl)pyridin-2-yl)amino)piperidin-1-yl)sulfonyl)phenyl)quinazolin-4(3H)-one

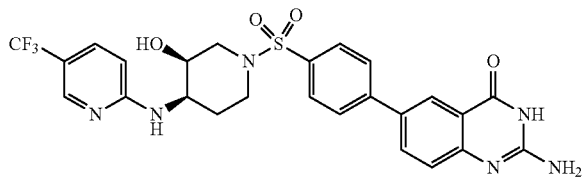 [SMILES: Nc1nc2ccc(-c3ccc(S(=O)(=O)N4CC[C@@H](Nc5ccc(C(F)(F)F)cn5)[C@@H](O)C4)cc3)cc2c(=O)[nH]1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (70 mg, 0.13 mmol) in a septum-cap vial were added $K_2CO_3$ (53 mg, 0.38 mmol), 2-amino-6-bromoquinazolin-4-ol (32 mg, 0.13 mmol) Pd(dppf)$Cl_2$·DCM (13 mg, 0.016 mmol). To this was added 3 mL Dioxane and 1 mL of water. The mixture was sparged with nitrogen for 5 minutes. The vial was sealed, the mixture stirred at 100° C. for 2 hours and cooled when the reaction had proceeded to completion. The mixture was purified via preparative reverse-phase HPLC to give 2-amino-6-(4-(((3S,4R)-3-hydroxy-4-((5-(trifluoromethyl)pyridin-2-yl)amino)piperidin-1-yl)sulfonyl)phenyl)quinazolin-4(3H)-one. MS: (ES) m/z calculated for $C_{25}H_{24}F_3N_6O_4S$ $[M+H]^+$ 561.2, found 561.3. $^1$H NMR (400 MHz, Methanol-$d_4$) δ 8.44 (d, J=2.2 Hz, 1H), 8.21-8.12 (m, 2H), 8.00-7.89 (m, 4H), 7.62-7.51 (m, 2H), 6.66 (d, J=9.0 Hz, 1H), 4.01 (q, J=4.1, 3.2 Hz, 1H), 3.91 (dt, J=10.8, 3.7 Hz, 1H), 3.76-3.64 (m, 2H), 2.82-2.74 (m, 1H), 2.67 (td, J=11.5, 3.0 Hz, 1H), 2.03-1.95 (m, 1H), 1.82 (dt, J=13.6, 3.9 Hz, 1H).

Example 31: 4-(4-(((3S,4R)-3-hydroxy-4-((5-(trifluoromethyl)pyridin-2-yl)amino)piperidin-1-yl)sulfonyl)phenyl)picolinamide

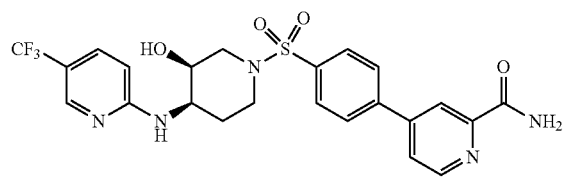 [SMILES: NC(=O)c1cc(-c2ccc(S(=O)(=O)N3CC[C@@H](Nc4ccc(C(F)(F)F)cn4)[C@@H](O)C3)cc2)ccn1]

To (3S,4R)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (50 mg, 0.095 mmol) in a septum-cap vial were added $K_2CO_3$ (41 mg, 0.30 mmol), 4-bromopicolinamide (19 mg, 0.095 mmol), Pd(dppf)Cl$_2$·DCM (7.3 mg, 0.089 mmol). To this was added 3.0 mL dioxane and 0.7 mL of water. The mixture was sparged with nitrogen for 5 minutes. The vial was sealed, the mixture stirred at 100° C. for 1.9 hours and cooled when the reaction had proceeded to completion. The reaction mixture was diluted with 0.1% aqueous trifluoroacetic acid (1 mL), acetic acid (0.5 mL), and 1-methyl-2-pyrrolidone (1 mL). This solution was injected through a syringe filter onto preparative HPLC (27-50% ACN, 0.1% TFA), with the product eluting at 33% ACN. Clean fractions were lyophilized to provide the title compound. MS: (ES) m/z calculated for $C_{23}H_{23}F_3N_5O_4S$ $[M+H]^+$ 522.1, found 522.3. $^1$H NMR (400 MHz, DMSO-d6) δ 8.75 (dd, J=5.1, 0.8 Hz, 1H), 8.35 (dd, J=2.0, 0.8 Hz, 1H), 8.26-8.18 (m, 2H), 8.15-8.07 (m, 2H), 8.00 (dd, J=5.1, 1.9 Hz, 1H), 7.93-7.85 (m, 2H), 7.77 (d, J=3.1 Hz, 1H), 7.65-7.58 (m, 1H), 7.29 (s, 1H), 6.73 (d, J=9.0 Hz, 1H), 3.94-3.83 (m, 2H), 3.56-3.45 (m, 2H), 2.71 (d, 11.7 Hz, 1H), 2.64-2.53 (m, 1H), 1.91-1.80 (m, 1H), 1.68-1.61 (m, 1H).

Example 32: 5-(4-(((3R,4S)-3-hydroxy-4-((5-(trifluoromethyl)pyridin-2-yl)amino)piperidin-1-yl)sulfonyl)phenyl)-1H-pyrrolo[2,3-b]pyridine-3-carbonitrile

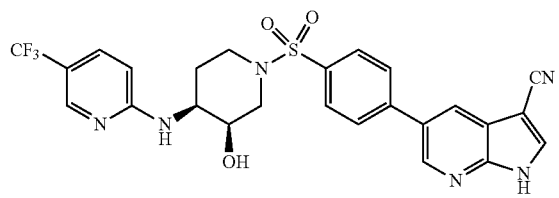 [SMILES: N#Cc1c[nH]c2ncc(-c3ccc(S(=O)(=O)N4CC[C@H](Nc5ccc(C(F)(F)F)cn5)[C@H](O)C4)cc3)cc12]

To (3R,4S)-1-((4-(4,4,5,5-tetramethyl-1,3,2-dioxaborolan-2-yl)phenyl)sulfonyl)-4-((5-(trifluoromethyl)pyridin-2-yl)amino)piperidin-3-ol (58 mg, 0.11 mmol) in a septum-cap vial were added $K_2CO_3$ (42 mg, 0.30 mmol), 5-bromo-3-cyano-1H-pyrrolo[2,3-b]pyridine (32 mg, 0.14 mmol), Pd(dppf)Cl$_2$·DCM (15 mg, 0.018 mmol). To this was added 4 mL Dioxane and 1 mL of water. The mixture was sparged with nitrogen for 12 minutes. The vial was sealed, the mixture stirred at 100° C. for 3.8 hours and cooled when the reaction had proceeded to completion. The mixture was purified via preparative reverse-phase HPLC to give 5-(4-(((3R,4S)-3-hydroxy-4-((5-(trifluoromethyl)pyridin-2-yl)amino)piperidin-1-yl)sulfonyl)phenyl)-1H-pyrrolo[2,3-b]pyridine-3-carbonitrile. MS: (ES) m/z calculated for $C_{25}H_{22}F_3N_6O_3S$ $[M+H]^+$ 543.1, found 543.3. $^1$H NMR (400 MHz, DMSO-$d_6$) δ 13.02 (d, J=3.1 Hz, 1H), 8.82 (d, J=2.1 Hz, 1H), 8.52 (dd, J=21.2, 2.6 Hz, 2H), 8.20 (d, J=2.4 Hz, 1H), 8.14-8.06 (m, 2H), 7.89-7.81 (m, 2H), 7.58 (dd, J=9.0, 2.6 Hz, 1H), 7.12 (s, 1H), 6.70 (d, J=9.0 Hz, 1H), 5.25 (s, 1H), 3.89 (s, 2H), 3.52 (t, J=13.5 Hz, 2H), 2.72 (d, J=11.8 Hz, 1H), 2.66-2.52 (m, 1H), 1.88 (dd, J=12.1, 8.5 Hz, 1H), 1.67 (d, J=12.8 Hz, 1H).

Example 33: 6-[[(3S,4R)-3-hydroxy-1-[4-(4-methyl-1H-pyrrolo[2,3-b]pyridin-5-yl)phenyl]sulfonyl-4-piperidyl]amino]pyridine-3-carbonitrile

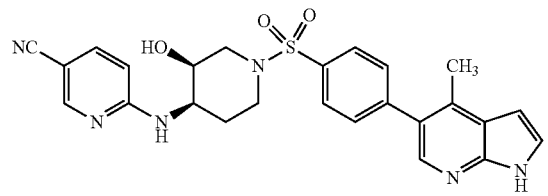 [SMILES: Cc1c(-c2ccc(S(=O)(=O)N3CC[C@@H](Nc4ccc(C#N)cn4)[C@@H](O)C3)cc2)cnc2[nH]ccc12]

6-(((3S,4R)-1-((4-bromophenyl)sulfonyl)-3-hydroxypiperidin-4-yl)amino)nicotinonitrile (80.0 mg, 0.18 mmol), bis(pinacolato)diboron (69.7 mg, 0.27 mmol), KOAc (53.9 mg, 0.55 mmol) and Pd(dppf)Cl$_2$·DCM (1.34 mg, 0.002 mmol) were placed in a septum-cap vial. To this was added 2 mL of dioxane and the mixture was sparged with nitrogen for 10 minutes. The vial was sealed, the mixture stirred at 100° C. for 2 h and cooled when the reaction was complete. To the mixture were added 5-bromo-4-methyl-1H-pyrrolo[2,3-b]pyridine (52.3 mg, 0.25 mmol), Pd(dppf)Cl$_2$·DCM (12.1 mg, 0.02 mmol) and 0.5 mL of water. The mixture was sparged with nitrogen for 10 minutes. The vial was sealed, the mixture stirred at 100° C. for 16 h, and cooled when the reaction had proceeded to completion. The mixture was purified preparative reverse-phase HPLC to give 6-[[(3S,4R)-3-hydroxy-1-[4-(4-methyl-1H-pyrrolo[2,3-b]pyridin-5-yl)phenyl]sulfonyl-4-piperidyl]amino]pyridine-3-carbonitrile. MS: (ES) m/z calculated for $C_{25}H_{24}N_6O_3S$ $[M+H]^+$ 489.1, found 489.2. $^1$H NMR (400 MHz, DMSO-$d_6$) δ 11.83 (s, 1H), 8.33 (d, J=2.2 Hz, 1H), 8.15 (s, 1H), 7.84 (d, J=8.0 Hz, 2H), 7.70 (d, J=8.0 Hz, 2H), 7.65 (d, J=8.9 Hz, 1H), 7.54 (m, 1H), 7.46 (bs, 1H), 6.70 (d, J=8.9 Hz, 1H), 3.91 (m, 3H), 3.65 (d, J=7.4 Hz, 1H), 3.54 (m, 1H), 2.77-2.69 (m, 1H), 2.61 (t, J=11.2 Hz, 1H), 1.96-1.88 (m, 1H), 1.73-1.63 (m, 1H). (Me occluded by solvent).

Example 34: 5-[4-[[(3S,4R)-4-[(5-cyano-2-pyridyl)amino]-3-hydroxy-1-piperidyl]sulfonyl]phenyl]-1H-pyrrolo[2,3-b]pyridine-3-carbonitrile

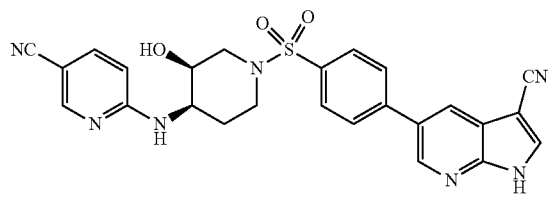 [SMILES: N#Cc1ccc(N[C@@H]2CCN(S(=O)(=O)c3ccc(-c4cnc5[nH]cc(C#N)c5c4)cc3)C[C@@H]2O)nc1]

6-(((3S,4R)-1-((4-bromophenyl)sulfonyl)-3-hydroxypiperidin-4-yl)amino)nicotinonitrile (80.0 mg, 0.18 mmol), bis(pinacolato)diboron (69.7 mg, 0.27 mmol), KOAc (53.9 mg, 0.55 mmol) and Pd(dppf)Cl$_2$·DCM (1.34 mg, 0.002 mmol) were placed in a septum-cap vial. To this was added 2 mL of dioxane and the mixture was sparged with nitrogen for 10 minutes. The vial was sealed, the mixture stirred at 100° C. for 2 h and cooled when the reaction was complete. To the mixture were added 5-bromo-1H-pyrrolo[2,3-b]pyridine-3-carbonitrile (55.0 mg, 0.25 mmol), Pd(dppf)Cl$_2$·DCM (12.1 mg, 0.02 mmol) and 0.5 mL of water. The mixture was sparged with nitrogen for 10 minutes. The vial was sealed, the mixture stirred at 100° C. for 16 h, and cooled when the reaction had proceeded to completion. The mixture was purified preparative reverse-phase HPLC to give 5-[4-[[(3S,4R)-4-[(5-cyano-2-pyridyl)amino]-3-hydroxy-1-piperidyl]sulfonyl]phenyl]-1H-pyrrolo[2,3-b]pyridine-3-carbonitrile. MS: (ES) m/z calculated for $C_{25}H_{21}N_7O_3S$ [M+H]$^+$ 500.1, found 500.1. $^1$H NMR (400 MHz, DMSO-d$_6$) δ 13.03 (d, J=3.0 Hz, 1H), 8.82 (s, 1H), 8.55 (d, J=2.0 Hz, 1H), 8.50 (s, 1H), 8.32 (s, 1H), 8.11 (d, J=8.1 Hz, 2H), 7.85 (d, J=8.0 Hz, 2H), 7.63 (dd, J=8.7, 2.3 Hz, 1H), 7.43 (bs, 1H), 6.68 (d, J=8.9 Hz, 1H), 3.91 (m, 3H), 3.67 (d, J=7.4 Hz, 1H), 3.53 (t, J=8.8 Hz, 1H), 2.72 (d, J=11.8 Hz, 1H), 2.61 (t, J=11.3 Hz, 1H), 1.88 (dd, J=13.4, 9.6 Hz, 1H), 1.71-1.62 (m, 1H).

Example 35: 5-(4-(((3S,4R)-3-hydroxy-4-((5-(trifluoromethyl)pyridin-2-yl)amino)piperidin-1-yl)sulfonyl)phenyl)-4-methyl-1H-indazole-3-carbonitrile

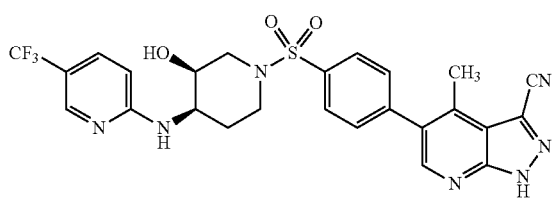 [SMILES: Cc1c(-c2ccc(S(=O)(=O)N3CC[C@@H](Nc4ccc(C(F)(F)F)cn4)[C@@H](O)C3)cc2)cnc2[nH]nc(C#N)c12]

(3S,4R)-1-((4-bromophenyl)sulfonyl)-4-((5-(trifluoromethyl)pyridin-2-yl)amino)piperidin-3-ol (50 mg, 0.10 mmol), bis(pinacolato)diboron (32 mg, 0.13 mmol), KOAc (30 mg, 0.31 mmol) and Pd(dppf)Cl$_2$·DCM (1 mg, 0.001 mmol) were placed in a septum-cap vial. To this was added 1 mL of dioxane and the mixture was sparged with nitrogen for 10 minutes. The vial was sealed, the mixture stirred at 110° C. for 30 min and cooled when the reaction had proceeded to completion. To the mixture were added K$_2$CO$_3$ (81 mg, 0.59 mmol), 5-bromo-4-methyl-1H-indazole-3-carbonitrile (16 mg, 0.07 mmol), Pd(dppf)Cl$_2$·DCM (10 mg, 0.021 mmol) and 0.25 mL of water. The mixture was sparged with nitrogen for 10 minutes. The vial was sealed, the mixture stirred at 110° C. for 16 hours and cooled when the reaction had proceeded to completion. The mixture was purified via SiO$_2$ gel chromatography followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-4-methyl-1H-indazole-3-carbonitrile. MS: (ES) m/z calculated for $C_{26}H_{24}F_3N_6O_3S$ [M+H]$^+$ 557.2, found 557.1. $^1$H NMR (400 MHz, CD$_3$OD) δ 8.22 (s, 1H), 7.92 (d, J=8.4 Hz, 2H), 7.83 (d, J=9.1 Hz, 1H), 7.64 (d, J=8.4 Hz, 2H), 7.60 (d, J=8.7 Hz, 1H), 7.41 (d, J=8.7 Hz, 1H), 6.97 (d, J=9.2 Hz, 1H), 4.04 (s, 1H), 3.91 (ddd, J=10.5, 3.9, 3.9 Hz, 1H), 3.71 (dd, J=11.3, 4.5 Hz, 2H), 2.94-2.81 (m, 1H), 2.79-2.70 (m, 1H), 2.70 (s, 3H), 2.26-1.96 (m, 1H), 1.96-1.71 (m, 1H).

Example 36: 5-(4-(((3S,4R)-3-hydroxy-4-((5-(trifluoromethyl)pyridin-2-yl)amino)piperidin-1-yl)sulfonyl)phenyl)-6-methyl-1H-indazole-3-carbonitrile

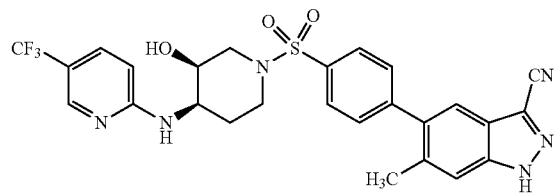 [SMILES: Cc1cc2[nH]nc(C#N)c2cc1-c1ccc(S(=O)(=O)N2CC[C@@H](Nc3ccc(C(F)(F)F)cn3)[C@@H](O)C2)cc1]

(3S,4R)-1-((4-bromophenyl)sulfonyl)-4-((5-(trifluoromethyl)pyridin-2-yl)amino)piperidin-3-ol (50 mg, 0.10 mmol), bis(pinacolato)diboron (32 mg, 0.13 mmol), KOAc (30 mg, 0.31 mmol) and Pd(dppf)Cl$_2$·DCM (1 mg, 0.001 mmol) were placed in a septum-cap vial. To this was added 1 mL of dioxane and the mixture was sparged with nitrogen for 10 minutes. The vial was sealed, the mixture stirred at 110° C. for 30 min and cooled when the reaction had proceeded to completion. To the mixture were added K$_2$CO$_3$ (81 mg, 0.59 mmol), 5-bromo-4-methyl-1H-indazole-3-carbonitrile (23 mg, 0.1 mmol), Pd(dppf)Cl$_2$·DCM (10 mg, 0.021 mmol) and 0.25 mL of water. The mixture was sparged with nitrogen for 10 minutes. The vial was sealed, the mixture stirred at 110° C. for 16 hours and cooled when the reaction had proceeded to completion. The mixture was purified via SiO$_2$ gel chromatography followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-7-methyl-1H-indazole-3-carbonitrile. MS: (ES) m/z calculated for $C_{26}H_{24}F_3N_6O_3S$ [M+H]$^+$ 557.2, found 557.1. $^1$H NMR (400 MHz, CD$_3$OD) δ 8.20 (s, 1H), 8.03-7.87 (m, 5H), 7.81 (dd, J=9.3, 2.4 Hz, 1H), 7.67 (dd, J=2.0, 1.0 Hz, 1H), 6.94 (d, J=9.3 Hz, 1H), 4.04-4.01 (m, 1H), 3.89 (ddd, J=10.3, 3.8, 3.8 Hz, 1H), 3.68-3.63 (m, 2H), 2.86 (d, J=11.9 Hz, 1H), 2.79-2.71 (m, 1H), 2.70 (s, 3H), 2.16-1.95 (m, 1H), 1.95-1.75 (m, 1H).

Example 37: 4-(4-(((3S,4R)-4-((5-cyanopyridin-2-yl)amino)-3-hydroxypiperidin-1-yl)sulfonyl)phenyl)picolinamide

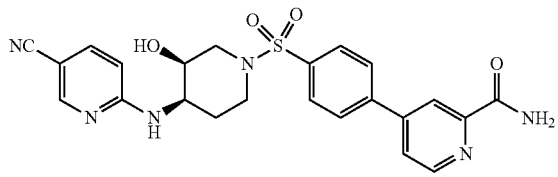 [SMILES: N#Cc1ccc(N[C@@H]2CCN(S(=O)(=O)c3ccc(-c4ccnc(C(N)=O)c4)cc3)C[C@@H]2O)nc1]

6-(((3S,4R)-1-((4-bromophenyl)sulfonyl)-3-hydroxypiperidin-4-yl)amino)nicotinonitrile (80.0 mg, 0.18 mmol), bis(pinacolato)diboron (69.7 mg, 0.27 mmol), KOAc (53.9 mg, 0.55 mmol) and Pd(dppf)Cl$_2$·DCM (1.34 mg, 0.002 mmol) were placed in a septum-cap vial. To this was added 2 mL of dioxane and the mixture was sparged with nitrogen for 10 minutes. The vial was sealed, the mixture stirred at 100° C. for 2 h. and cooled when the reaction had proceeded to completion. To the mixture were added K$_2$CO$_3$ (45.6 mg, 0.33 mmol), 4-bromopyridine-2-carboxamide (49.8 mg, 0.25 mmol), Pd(dppf)Cl$_2$·DCM (12.1 mg, 0.02 mmol) and 0.5 mL of water. The mixture was sparged with nitrogen for 10 minutes. The vial was sealed, the mixture stirred at 100° C. for 16 h, and cooled when the reaction had proceeded to completion. The mixture was purified via SiO$_2$ gel chromatography, followed by trituration from CH$_2$Cl$_2$ to give 4-(4-(((3S,4R)-4-((5-cyanopyridin-2-yl)amino)-3-hydroxypiperidin-1-yl)sulfonyl)phenyl)picolinamide. MS: (ES) m/z calculated for C$_{23}$H$_{22}$N$_6$O$_4$S [M+H]$^+$ 479.1, found 479.0. $^1$H NMR (400 MHz, DMSO-d$_6$) δ 8.78 (d, J=5.1 Hz, 1H), 8.37 (s, 1H), 8.32 (s, 1H), 8.24 (s, 1H), 8.12 (d, J 8.0 Hz, 2H), 8.01 (dd, J=5.1, 2.0 Hz, 1H), 7.91 (d, J=8.1 Hz, 2H), 7.78 (d, J=2.9 Hz, 1H), 7.63 (dd, J=8.7, 2.3 Hz, 1H), 7.41 (bs, 1H), 6.67 (d, J=8.9 Hz, 1H), 5.28 (d, J=4.6 Hz, 1H), 3.99-3.85 (m, 2H), 3.59-3.47 (m, 2H), 2.74 (d, J=11.9 Hz, 1H), 2.68-2.58 (m, 1H), 1.95-1.81 (m, 1H), 1.70-1.60 (m, 1H).

Example 38: (3S,4R)-1-((4-(3-amino-1H-pyrazolo[3,4-b]pyridin-5-yl)phenyl)sulfonyl)-4-((5-(trifluoromethyl)pyridin-2-yl)amino)piperidin-3-ol

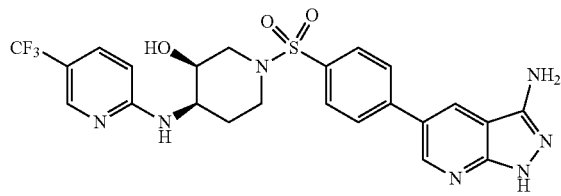 [SMILES: Nc1n[nH]c2ncc(-c3ccc(S(=O)(=O)N4CC[C@@H](Nc5ccc(C(F)(F)F)cn5)[C@@H](O)C4)cc3)cc12]

To (3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) in a septum-cap vial. To this was added to 1 mL of dioxane and the mixture was purged with nitrogen for 5 minutes. The vial was sealed, the mixture stirred at 100° C. for 3 h. and cooled when the reaction had proceeded to completion. To the mixture were added 2 M K$_2$CO$_3$ (0.53 mL, 1.06 mmol), 5-bromo-1H-pyrazolo[3,4-b]pyridin-3-amine (45 mg, 0.21 mmol), Pd(dppf)Cl$_2$·DCM (17 mg, 0.21 mmol). The mixture was sparged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give (3S,4R)-1-((4-(3-amino-1H-pyrazolo[3,4-b]pyridin-5-yl)phenyl)sulfonyl)-4-((5-(trifluoromethyl)pyridin-2-yl)amino)piperidin-3-ol. MS: (ES) m/z calculated for C$_{23}$H$_{22}$F$_3$N$_7$O$_3$S [M+H]$^+$ 534.1, found 534.2. $^1$H NMR (400 MHz, Methanol-d$_4$) δ 8.84 (d, J=2.2 Hz, 1H), 8.62 (d, J=2.2 Hz, 1H), 8.19 (s, 1H), 7.95 (d, J=0.7 Hz, 4H), 7.77 (dd, J=9.2, 2.4 Hz, 1H), 6.90 (d, J=9.2 Hz, 1H), 4.02 (s, 1H), 3.93-3.86 (m, 1H), 3.70-3.63 (m, 2H), 2.88-2.80 (m, 1H), 2.73 (t, J=11.0 Hz, 1H), 2.12-2.01 (m, 1H), 1.91-1.83 (m, 1H).

Example 39: Methyl 4-(4-(((3S,4R)-3-hydroxy-4-((5-(trifluoromethyl)pyridin-2-yl)amino)piperidin-1-yl)sulfonyl)phenyl)picolinate

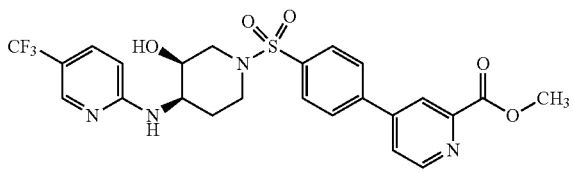 [SMILES: COC(=O)c1cc(-c2ccc(S(=O)(=O)N3CC[C@@H](Nc4ccc(C(F)(F)F)cn4)[C@@H](O)C3)cc2)ccn1]

To (3S,4R)-1-((4-bromophenyl)sulfonyl)-4-((5-(trifluoromethyl)pyridin-2-yl)amino)piperidin-3-ol (80 mg, 0.17 mmol) was added bis(pinacolato)diboron (52 mg, 0.20 mmol), KOAc (54 mg, 0.55 mmol) and Pd(dppf)Cl$_2$·DCM (1.3 mg, 0.0016 mmol) in a 4 mL vial. To this was added 2 mL of dioxane and the mixture was sparged with nitrogen for 7 minutes. The vial was sealed with a Teflon-lined cap, the mixture stirred at 100° C. for 1.5 h. and cooled when the reaction had proceeded to completion. To the mixture were added K$_2$CO$_3$ (120 mg, 0.87 mmol), 4-bromopyridine-2-carboxylic acid methyl ester (36 mg, 0.17 mmol), Pd(dppf)Cl$_2$·DCM (13 mg, 0.016 mmol) and 0.5 mL of water. The mixture was sparged with nitrogen for 5 minutes. The vial was sealed, the mixture stirred at 100° C. for 1 hour, and cooled when the reaction had proceeded to completion. The mixture was purified via silica gel chromatography to give methyl 4-(4-(((3S,4R)-3-hydroxy-4-((5-(trifluoromethyl)pyridin-2-yl)amino)piperidin-1-yl)sulfonyl)phenyl)picolinate. MS: (ES) m/z calculated for C$_{24}$H$_{24}$F$_3$N$_4$O$_5$S [M+H]$^+$ 537.1, found 537.2. $^1$H NMR (400 MHz, Methanol-d$_4$) δ 8.79 (d, J=5.0 Hz, 1H), 8.49 (s, 1H), 8.15 (s, 1H), 8.10-7.92 (m, 5H), 7.54 (d, J=9.1 Hz, 1H), 6.62 (d, J=9.0 Hz, 1H), 4.05-3.97 (m, 4H), 3.94-3.88 (m, 1H), 3.77-3.66 (m, 2H), 2.79 (d, J=12.4 Hz, 1H), 2.71-2.62 (m, 1H), 2.06-1.95 (m, 1H), 1.80 (d, J=12.9 Hz, 1H).

Example 40: 4-(4-(((3S,4R)-3-Hydroxy-4-((5-(trifluoromethyl)pyridin-2-yl)amino)piperidin-1-yl)sulfonyl)phenyl)-N,N-dimethylpicolinamide

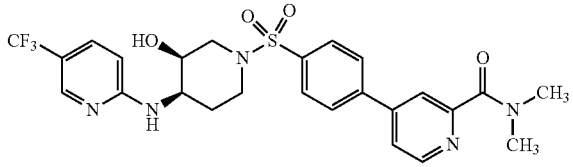 [SMILES: CN(C)C(=O)c1cc(-c2ccc(S(=O)(=O)N3CC[C@@H](Nc4ccc(C(F)(F)F)cn4)[C@@H](O)C3)cc2)ccn1]

In a 40 mL vial, methyl 4-(4-(((3S,4R)-3-hydroxy-4-((5-(trifluoromethyl)pyridin-2-yl)amino)piperidin-1-yl)sulfonyl)phenyl)picolinate (50 mg, 0.093 mmol) was dissolved in acetonitrile (1 mL). To this solution was added 40% dimethylamine in water (1 mL, 12 mmol). The vial was sealed and heated at 60° C. for 2 hours, after which the reaction was concentrated in vacuo and the residue was purified by preparative reverse-phase chromatography to give 4-(4-(((3S,4R)-3-hydroxy-4-((5-(trifluoromethyl)pyridin-2-yl)amino)piperidin-1-yl)sulfonyl)phenyl)-N,N-dimethylpicolinamide. MS: (ES) m/z calculated for $C_{25}H_{27}F_3N_5O_4S$ [M+H]$^+$ 550.2, found 550.1. $^1$H NMR (400 MHz, DMSO-$d_6$) δ 8.72 (s, 1H), 8.22 (s, 1H), 8.12 (d, J=8.1 Hz, 2H), 8.04-7.83 (m, 4H), 7.74-7.56 (m, 1H), 7.27 (s, 1H), 6.74 (d, J=9.0 Hz, 1H), 3.88 (s, 2H), 3.60-3.45 (m, 2H), 3.05 (s, 3H), 2.97 (s, 3H), 2.72 (d, J=12.0 Hz, 1H), 2.66-2.56 (m, 1H), 1.94-1.82 (m, 1H), 1.70-1.62 (m, 1H).

Example 41: 4-(4-(((3S,4R)-3-Hydroxy-4-((5-(trifluoromethyl)pyridin-2-yl)amino)piperidin-1-1 sulfonyl)phenyl)-N-(2-hydroxyethyl)picolinamide

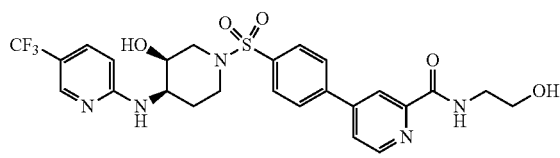 [SMILES: O=C(NCCO)c1cc(-c2ccc(S(=O)(=O)N3CC[C@@H](Nc4ccc(C(F)(F)F)cn4)[C@@H](O)C3)cc2)ccn1]

In a 40 mL vial, methyl 4-(4-(((3S,4R)-3-hydroxy-4-((5-(trifluoromethyl)pyridin-2-yl)amino)piperidin-1-yl)sulfonyl)phenyl)picolinate (52 mg, 0.097 mmol) was dissolved in acetonitrile (1 mL). To this was added ethanolamine (90 mg, 1.5 mmol) and the solution was heated for 3.7 h, after which the reaction was concentrated and purified by preparative reverse-phase chromatography to give 4-(4-(((3S,4R)-3-hydroxy-4-((5-(trifluoromethyl)pyridin-2-yl)amino)piperidin-1-yl)sulfonyl)phenyl)-N-(2-hydroxyethyl)picolinamide. MS: (ES) m/z calculated for $C_{25}H_{27}F_3N_5O_5S$ [M+H]$^+$ 566.2, found 566.2. $^1$H NMR (400 MHz, Methanol-$d_4$) δ 8.75 (dd, J=5.1, 0.8 Hz, 1H), 8.42 (dd, J=1.9, 0.8 Hz, 1H), 8.19 (d, J=2.3 Hz, 1H), 8.13-8.03 (m, 2H), 8.02-7.95 (m, 2H), 7.91 (dd, J=5.1, 1.9 Hz, 1H), 7.76 (dd, J=9.2, 2.4 Hz, 1H), 6.88 (d, J=9.2 Hz, 1H), 4.01 (s, 1H), 3.93-3.84 (m, 1H), 3.75 (t, J=5.6 Hz, 2H), 3.72-3.63 (m, 2H), 3.59 (t, J=5.6 Hz, 2H), 2.85 (d, J=12.1 Hz, 1H), 2.74 (t, J=10.2 Hz, 1H), 2.10-1.99 (m, 1H), 1.89-1.81 (m, 1H).

Example 42: 5-(4-(((3S,4R)-3-Hydroxy-4-((5-(trifluoromethyl)pyridin-2-yl)amino)piperidin-1-yl)sulfonyl)phenyl)thiazole-2-carboxamide

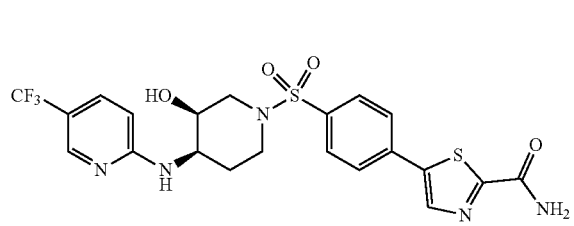 [SMILES: NC(=O)c1ncc(-c2ccc(S(=O)(=O)N3CC[C@@H](Nc4ccc(C(F)(F)F)cn4)[C@@H](O)C3)cc2)s1]

To (3S,4R)-1-((4-bromophenyl)sulfonyl)-4-((5-(trifluoromethyl)pyridin-2-yl)amino)piperidin-3-ol (80 mg, 0.17 mmol), bis(pinacolato)diboron (52 mg, 0.20 mmol), KOAc (53 mg, 0.54 mmol) and Pd(dppf)Cl$_2$·DCM (2.6 mg, 0.0032 mmol) in a septum-cap vial. To this was added 1 mL of dioxane and the mixture was sparged with nitrogen for 10 minutes. The vial was sealed, the mixture stirred at 100° C. for 3.5 h. and cooled when the reaction had proceeded to completion. To the mixture were added K$_2$CO$_3$ (122 mg, 0.88 mmol), 5-bromothiazole-2-carboxamide (38 mg, 0.18 mmol), Pd(dppf)Cl$_2$·DCM (13 mg, 0.015 mmol) and 0.5 mL of water. The mixture was sparged with nitrogen for 5 minutes. The vial was sealed, the mixture stirred at 100° C. for 3 hours and cooled when the reaction had proceeded to completion. The mixture was purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)thiazole-2-carboxamide. MS: (ES) m/z calculated for $C_{21}H_{21}F_3N_5O_4S_2$ [M+H]$^+$ 528.1, found 528.1. $^1$H NMR (400 MHz, DMSO-$d_6$) δ 8.56 (s, 1H), 8.28 (s, 1H), 8.23-8.17 (m, 1H), 8.06-7.98 (m, 2H), 7.98-7.92 (m, 1H), 7.85-7.77 (m, 2H), 7.60 (dd, J=9.1, 2.5 Hz, 1H), 7.25 (s, 1H), 6.71 (d, J=9.0 Hz, 1H), 3.94-3.83 (m, 2H), 3.53-3.42 (m, 2H), 2.70 (d, J=12.0 Hz, 1H), 2.65-2.54 (m, 1H), 1.83 (dd, J=12.1, 8.8 Hz, 1H), 1.68-1.59 (m, 1H).

Example 43: 5-(4-(((3S,4R)-3-hydroxy-4-((5-(trifluoromethyl)pyridin-2-yl)amino)piperidin-1-yl)sulfonyl)phenyl)-7-methyl-1H-indazole-3-carbonitrile

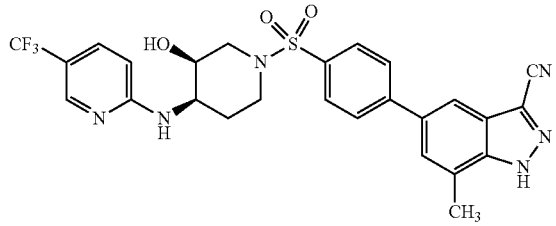 [SMILES: Cc1cc(-c2ccc(S(=O)(=O)N3CC[C@@H](Nc4ccc(C(F)(F)F)cn4)[C@@H](O)C3)cc2)cc2c(C#N)n[nH]c12]

(3S,4R)-1-((4-bromophenyl)sulfonyl)-4-((5-(trifluoromethyl)pyridin-2-yl)amino)piperidin-3-ol (50 mg, 0.10 mmol), bis(pinacolato)diboron (32 mg, 0.13 mmol), KOAc (30 mg, 0.31 mmol) and Pd(dppf)Cl$_2$·DCM (1 mg, 0.001 mmol) were placed in a septum-cap vial. To this was added 1 mL of dioxane and the mixture was sparged with nitrogen for 10 minutes. The vial was sealed, the mixture stirred at 110° C. for 30 min and cooled when the reaction had proceeded to completion. To the mixture were added K$_2$CO$_3$ (81 mg, 0.59 mmol), 5-bromo-7-methyl-1H-indazole-3-carbonitrile (23 mg, 0.1 mmol), Pd(dppf)Cl$_2$·DCM (10 mg, 0.021 mmol) and 0.25 mL of water. The mixture was sparged with nitrogen for 10 minutes. The vial was sealed, the mixture stirred at 110° C. for 16 hours and cooled when the reaction had proceeded to completion. The mixture was purified via SiO$_2$ gel chromatography followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-7-methyl-1H-indazole-3-carbonitrile. MS: (ES) m/z calculated for C$_{26}$H$_{24}$F$_3$N$_6$O$_3$S [M+H]$^+$ 557.2, found 557.1. $^1$H NMR (400 MHz, CD$_3$OD) δ 8.20 (s, 1H), 8.03-7.87 (m, 5H), 7.81 (dd, J=9.3, 2.4 Hz, 1H), 7.67 (dd, J=2.0, 1.0 Hz, 1H), 6.94 (d, J=9.3 Hz, 1H), 4.04-4.01 (m, 1H), 3.89 (ddd, J=10.3, 3.8, 3.8 Hz, 1H), 3.68-3.63 (m, 2H), 2.86 (d, J=11.9 Hz, 1H), 2.79-2.71 (m, 1H), 2.70 (s, 3H), 2.16-1.95 (m, 1H), 1.95-1.75 (m, 1H).

Example 44: 4-(4-(((3S,4R)-3-Hydroxy-4-((5-(trifluoromethyl)pyridin-2-yl)amino)piperidin-1-yl)sulfonyl)phenyl)-6-methoxypicolinamide

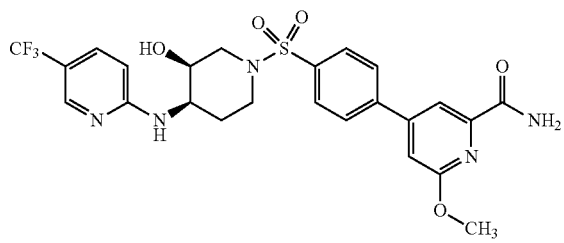 [SMILES: COc1cc(-c2ccc(S(=O)(=O)N3CC[C@@H](Nc4ccc(C(F)(F)F)cn4)[C@@H](O)C3)cc2)cc(C(N)=O)n1]

(3S,4R)-1-((4-bromophenyl)sulfonyl)-4-((5-(trifluoromethyl)pyridin-2-yl)amino)piperidin-3-ol (80 mg, 0.17 mmol), bis(pinacolato)diboron (52 mg, 0.20 mmol), KOAc (49 mg, 0.50 mmol) and Pd(dppf)Cl$_2$·DCM (1.6 mg, 0.0020 mmol) were placed in a septum-cap vial. To this was added 1 mL of dioxane and the mixture was sparged with nitrogen for 10 minutes. The vial was sealed, the mixture stirred at 100° C. for 2.5 h. and cooled when the reaction had proceeded to completion. To the mixture were added K$_2$CO$_3$ (125 mg, 0.91 mmol), 4-bromo-6-methoxypicolinamide (41 mg, 0.18 mmol), Pd(dppf)Cl$_2$·DCM (14 mg, 0.017 mmol) and 0.5 mL of water. The mixture was sparged with nitrogen for 5 minutes. The vial was sealed, the mixture stirred at 100° C. for 1.2 hours and cooled when the reaction had proceeded to completion. The mixture was purified via preparative reverse-phase HPLC to give 4-(4-(((3S,4R)-3-hydroxy-4-((5-(trifluoromethyl)pyridin-2-yl)amino)piperidin-1-yl)sulfonyl)phenyl)-6-methoxypicolinamide. MS: (ES) m/z calculated for C$_{24}$H$_{25}$F$_3$N$_5$O$_5$S [M+H]$^+$ 552.2, found 552.2. $^1$H NMR (400 MHz, DMSO-d$_6$) δ 8.23 (s, 1H), 8.15-8.05 (m, 3H), 7.96 (d, J=1.4 Hz, 1H), 7.87 (d, J=8.1 Hz, 2H), 7.77 (s, 1H), 7.69-7.61 (m, 1H), 7.44-7.34 (m, 2H), 6.77 (d, J=9.0 Hz, 1H), 4.03 (s, 3H), 3.96-3.85 (m, 2H), 3.57-3.46 (m, 2H), 2.71 (d, J=11.9 Hz, 1H), 2.67-2.54 (m, 1H), 1.95-1.80 (m, 1H), 1.66 (d, J=12.4 Hz, 1H).

Example 45: (3S,4R)-1-((4-(4,6-dimethyl-1H-pyrrolo[2,3-b]pyridin-5-yl)phenyl)sulfonyl)-4-((5-(trifluoromethyl)pyridin-2-yl)amino)piperidin-3-ol

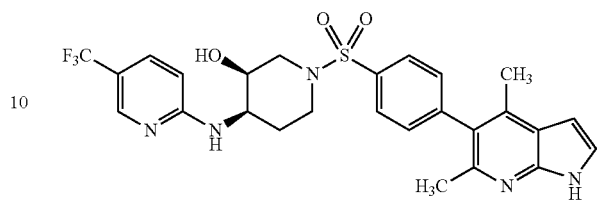

(3S,4R)-1-((4-bromophenyl)sulfonyl)-4-((5-(trifluoromethyl)pyridin-2-yl)amino)piperidin-3-ol (98 mg, 0.204 mmol), bis(pinacolato)diboron (62 mg, 0.245 mmol, 1.2 equiv.), potassium acetate (60 mg, 0.612 mmol, 3 equiv.) and [1,1'-bis(diphenylphosphino)ferrocene]dichloropalladium (II), complex with dichloromethane (3 mg, 0.004 mmol, 0.02 equiv.) were added to 1 mL of dioxane in a 20 mL septum-cap vial and the mixture was sparged with nitrogen for 5 minutes. The vial was sealed and the mixture was stirred at 125° C. for 15 minutes, then cooled down under the nitrogen atmosphere to reveal complete conversion to the boronate ester intermediate. To that mixture were added: potassium carbonate (141 mg, 1.02 mmol, 5 equiv.), 5-bromo-4,6-dimethyl-1H-pyrrolo[2,3-b]pyridine (46 mg, 0.204 mmol, 1 equiv.), [1,1'-bis(diphenylphosphino)ferrocene]dichloropalladium(II), complex with dichloromethane (20 mg, 0.025 mmol, 0.12 equiv.) and 0.5 mL of water. The mixture was sparged with nitrogen for 5 minutes. The vial was sealed and the mixture was stirred at 105° C. for 16 hours, then cooled down under the nitrogen atmosphere to reveal complete conversion of the boronate ester intermediate. The mixture was diluted with 3 mL of EtOAc and 2 mL of water. The aqueous layer was discarded; the organic layer was concentrated under a stream of nitrogen and dissolved in 4 mL of DMSO. The solution was injected through a syringe filter onto preparative HPLC (20-50% ACN, 0.1% TFA) to afford the title compound. MS: (ES) m/z calculated for C$_{26}$H$_{26}$F$_3$N$_5$O$_3$S [M+H]$^+$ 546.2, found 546.2. $^1$H NMR (400 MHz, DMSO-d6) δ 11.48 (s, 1H), 8.21 (s, 1H), 7.81 (d, J=7.9 Hz, 2H), 7.58 (dd, J=8.8, 2.5 Hz, 1H), 7.49 (d, J=7.9 Hz, 2H), 7.39-7.32 (m, 1H), 7.20-7.05 (m, 1H), 6.70 (d, J=8.9 Hz, 1H), 6.49-6.43 (m, 1H), 5.26 (d, J=4.2 Hz, 1H), 3.95-3.85 (m, 2H), 3.60-3.46 (m, 2H), 2.68 (d, J=11.8 Hz, 1H), 2.56 (t, J=12 Hz, 1H), 2.20 (s, 3H), 2.16 (s, 3H), 1.90 (q, J=11.6 Hz, 1H), 1.73-1.63 (m, 1H).

Example 46: 5-(4-(((3S,4R)-3-hydroxy-4-((5-(trifluoromethyl)pyridin-2-yl)amino)piperidin-1-yl)sulfonyl)phenyl)-6-methyl-1H-pyrrolo[2,3-b]pyridine-3-carbonitrile

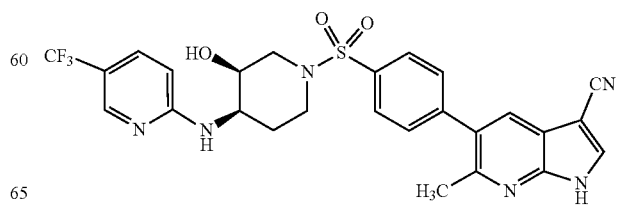

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (61 mg, 0.62 mmol) and Pd(dppf)Cl$_2$·DCM (2 mg, 0.002 mmol) were placed in a septum-cap vial. To this was added 1 mL of dioxane and the mixture was sparged with nitrogen for 10 minutes. The vial was sealed, the mixture stirred at 100° C. for 1 h. and cooled when the reaction had proceeded to completion. To the mixture were added K$_2$CO$_3$ (163 mg, 0.62 mmol), 5-bromo-6-methyl-1H-pyrrolo[2,3-b]pyridine-3-carbonitrile (54 mg, 0.23 mmol), Pd(dppf)Cl$_2$·DCM (20 mg, 0.021 mmol) and 0.25 mL of water. The mixture was sparged with nitrogen for 10 minutes. The vial was sealed, the mixture stirred at 100° C. for 16 hours and cooled when the reaction had proceeded to completion. The mixture was purified via SiO$_2$ gel chromatography followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-6-methyl-1H-pyrrolo[2,3-b]pyridine-3-carbonitrile. MS: (ES) m/z calculated for C$_{26}$H$_{24}$F$_3$N$_6$O$_3$S [M+H]$^+$ 557.2, found 557.2. $^1$H NMR (400 MHz, DMSO-d$_6$) δ 12.80 (d, J=3.1 Hz, 1H), 8.42 (d, J=3.0 Hz, 1H), 8.20 (ddd, J=2.3, 1.0, 1.0 Hz, 1H), 7.94 (s, 1H), 7.82 (d, J=8.4 Hz, 2H), 7.72 (d, J=8.4 Hz, 2H), 7.59 (dd, J=9.1, 2.6 Hz, 1H), 7.18 (s, 1H), 6.71 (d, J=9.0 Hz, 1H), 3.95-3.85 (m, 1H), 3.57-3.46 (m, 2H), 2.69 (d, J=12 Hz, 2H), 2.62-2.52 (m, 1H), 2.51 (s, 3H), 1.95-1.84 (m, 1H), 1.70-1.63 (m, 1H).

Example 47: 5-(4-(((3S,4R)-3-hydroxy-4-((5-(trifluoromethyl)pyridin-2-yl)amino)piperidin-1-yl)sulfonyl)phenyl)-1,3-dihydro-2H-benzo[d]imidazol-2-one

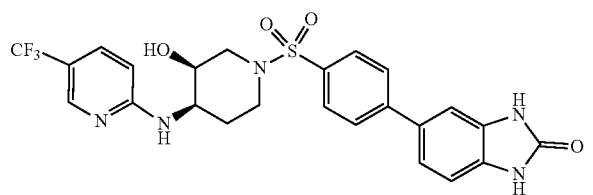 [SMILES: O=c1[nH]c2ccc(-c3ccc(S(=O)(=O)N4CC[C@@H](Nc5ccc(C(F)(F)F)cn5)[C@@H](O)C4)cc3)cc2[nH]1]

To (3S,4R)-1-((4-bromophenyl)sulfonyl)-4-((5-(trifluoromethyl)pyridin-2-yl)amino)piperidin-3-ol were added 2 M K$_2$CO$_3$ (0.26 mL, 0.53 mmol), 5-(4,4,5,5-tetramethyl-1,3,2-dioxaborolan-2-yl)-1,3-dihydro-2H-benzo[d]imidazol-2-one (41 mg, 0.16 mmol), Pd(dppf)Cl$_2$·DCM (13 mg, 0.016 mmol) in a septum-cap vial. To this was added 1 mL dioxane. The mixture was purged with nitrogen for 5 minutes. The vial was sealed, the mixture stirred at 100° C. for 16 hours and cooled when the reaction had proceeded to completion. The mixture was purified via preparative reverse-phase HPLC to give 5-(4-(((3S,4R)-3-hydroxy-4-((5-(trifluoromethyl)pyridin-2-yl)amino)piperidin-1-yl)sulfonyl)phenyl)-1,3-dihydro-2H-benzo[d]imidazol-2-one. MS: (ES) m/z calculated for C$_{24}$H$_{22}$F$_3$N$_5$O$_4$S [M+H]$^+$ 534.1, found 534.2. $^1$H NMR (400 MHz, Methanol-d$_4$) δ 8.19 (s, 1H), 7.85 (s, 4H), 7.80-7.75 (m, 1H), 7.44-7.33 (m, 2H), 7.16 (d, J=8.1 Hz, 1H), 6.90 (d, J=9.3 Hz, 1H), 4.05-3.98 (m, 1H), 3.92-3.84 (m, 1H), 3.68-3.60 (m, 2H), 2.88-2.78 (m, 1H), 2.76-2.67 (m, 1H), 2.11-2.01 (q, J=10.1 Hz, 1H), 1.91-1.82 (m, 1H).

Example 48: 3-(4-(((3S,4R)-3-hydroxy-4-((5-(trifluoromethyl)pyridin-2-yl)amino)piperidin-1-yl)sulfonyl)phenyl)-6,7-dihydro-5H-pyrrolo[3,4-b]pyridin-5-one

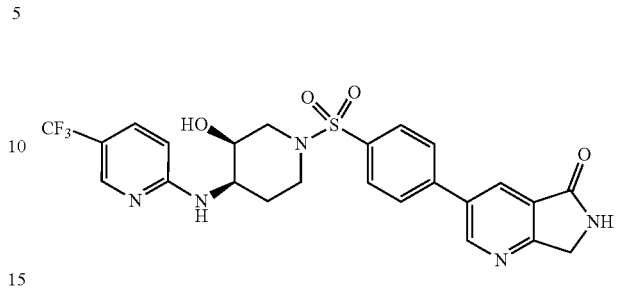

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) were placed in a septum-cap vial. To this was added 1 mL of dioxane and the mixture was purged with nitrogen for 5 minutes. The vial was sealed, the mixture stirred at 100° C. for 3 h and cooled when the reaction had proceeded to completion. To the mixture were added 2 M K$_2$CO$_3$ (0.53 mL, 1.06 mmol), 3-bromo-6,7-dihydro-5H-pyrrolo[3,4-b]pyridin-5-one (45 mg, 0.21 mmol), Pd(dppf)Cl$_2$·DCM (17 mg, 0.021 mmol). The mixture was sparged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give 3-(4-(((3S,4R)-3-hydroxy-4-((5-(trifluoromethyl)pyridin-2-yl)amino)piperidin-1-yl)sulfonyl)phenyl)-6,7-dihydro-5H-pyrrolo[3,4-b]pyridin-5-one. MS: (ES) m/z calculated for C$_{24}$H$_{22}$F$_3$N$_5$O$_4$S [M+H]$^+$ 534.1, found 534.2. $^1$H NMR (400 MHz, Methanol-d$_4$) δ 9.10 (s, 1H), 8.46 (s, 1H), 8.21 (s, 1H), 8.05-7.94 (m, 4H), 7.87 (d, J=9.3 Hz, 1H), 7.01 (d, J=9.4 Hz, 1H), 4.59 (s, 2H), 4.02 (s, 1H), 3.94-3.78 (m, 1H), 3.70-3.60 (m, 2H), 2.92-2.74 (m, 2H), 2.13-1.85 (m, 2H).

Example 49: (3S,4R)-1-((4-(3-amino-1-methyl-1H-indazol-5-yl)phenyl)sulfonyl)-4-((5-(trifluoromethyl)pyridin-2-yl)amino)piperidin-3-ol

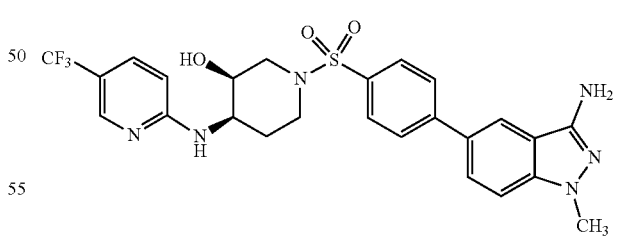

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) were placed in a septum-cap vial. To this was added 1 mL of dioxane and the mixture was purged with nitrogen for 5 minutes. The vial was sealed, the mixture stirred at 100° C. for 3 h. and cooled when the reaction had proceeded to completion. To the mixture were added 2 M K$_2$CO$_3$ (0.53 mL, 1.06 mmol), 5-bromo-1-methyl-1H-indazol-3-amine (47 mg, 0.21 mmol), Pd(dppf)Cl$_2$·DCM (17 mg, 0.21 mmol). The mixture was sparged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give (3S,4R)-1-((4-(3-amino-1-methyl-1H-indazol-5-yl)phenyl)sulfonyl)-4-((5-(trifluoromethyl)pyridin-2-yl)amino)piperidin-3-ol. MS: (ES) m/z calculated for C$_{25}$H$_{25}$F$_3$N$_6$O$_3$S [M+H]$^+$ 547.2, found 547.2. $^1$H NMR (400 MHz, Methanol-d$_4$) δ 8.19 (s, 1H), 8.12 (s, 1H), 7.95-7.83 (m, 5H), 7.77 (dd, J=9.2, 2.4 Hz, 1H), 7.55 (s, 1H), 6.90 (d, J=9.1 Hz, 1H), 4.02 (s, 1H), 3.95-4.80 (m, 4H), 3.71-3.62 (m, 2H), 2.82 (d, J=12.2 Hz, 1H), 2.71 (t, J=11.2 Hz, 1H), 2.11-2.03 (m, 1H), 1.90-1.82 (m, 1H).

Example 50: 4-(4-(((3S,4R)-3-hydroxy-4-((5-(trifluoromethyl)pyridin-2-yl)amino)piperidin-1-yl)sulfonyl)phenyl)-N-methylpicolinamide

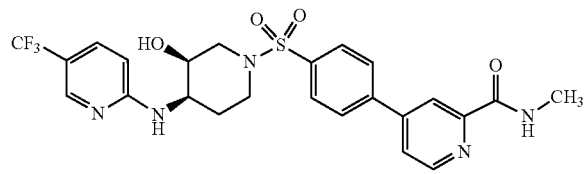 [SMILES: CNC(=O)c1cc(-c2ccc(S(=O)(=O)N3CC[C@@H](Nc4ccc(C(F)(F)F)cn4)[C@@H](O)C3)cc2)ccn1]

In a 40 mL vial, methyl 4-(4-(((3S,4R)-3-hydroxy-4-((5-(trifluoromethyl)pyridin-2-yl)amino)piperidin-1-yl)sulfonyl)phenyl)picolinate (34 mg, 0.063 mmol) was dissolved in 33% methylamine in ethanol (4 mL, 34 mmol). The vial was sealed and heated at 50° C. for 2 hours, after which the reaction was concentrated in vacuo and the residue was purified by preparative reverse-phase chromatography to give 4-(4-(((3S,4R)-3-hydroxy-4-((5-(trifluoromethyl)pyridin-2-yl)amino)piperidin-1-yl)sulfonyl)phenyl)-N-methylpicolinamide. MS: (ES) m/z calculated for C$_{24}$H$_{25}$F$_3$N$_5$O$_4$S [M+H]$^+$ 536.2, found 536.1. $^1$H NMR (400 MHz, Methanol-d$_4$) δ 8.74 (dd, J=5.0, 0.8 Hz, 1H), 8.41 (dd, J=1.9, 0.8 Hz, 1H), 8.17-8.13 (m, 1H), 8.10-8.02 (m, 2H), 8.02-7.93 (m, 2H), 7.90 (dd, J=5.1, 1.9 Hz, 1H), 7.55 (dd, J=9.0, 2.5 Hz, 1H), 6.63 (d, J=8.9 Hz, 1H), 4.01 (s, 1H), 3.92 (d, J=10.9 Hz, 1H), 3.76-3.65 (m, 2H), 3.01 (s, 3H), 2.79 (d, J=12.3 Hz, 1H), 2.68 (t, J=10.8 Hz, 1H), 2.09-1.92 (m, 1H), 1.85-1.77 (m, 1H).

Example 51: 2-Hydroxy-5-(4-(((3S,4R)-3-hydroxy-4-((5-(trifluoromethyl)pyridin-2-yl)amino)piperidin-1-yl)sulfonyl)phenyl)nicotinamide

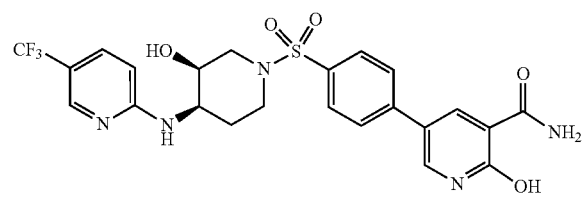 [SMILES: NC(=O)c1cc(-c2ccc(S(=O)(=O)N3CC[C@@H](Nc4ccc(C(F)(F)F)cn4)[C@@H](O)C3)cc2)cnc1O]

To (3S,4R)-1-((4-bromophenyl)sulfonyl)-4-((5-(trifluoromethyl)pyridin-2-yl)amino)piperidin-3-ol (80 mg, 0.17 mmol) was added bis(pinacolato)diboron (52 mg, 0.20 mmol), KOAc (51 mg, 0.52 mmol) and Pd(dppf)Cl$_2$·DCM (1.4 mg, 0.0017 mmol) in a 4 mL vial. To this was added 1 mL of dioxane and the mixture was sparged with nitrogen for 10 minutes. The vial was sealed with a Teflon-lined cap, the mixture stirred at 100° C. for 2.7 h. and cooled when the reaction had proceeded to completion. To the mixture were added K$_2$CO$_3$ (121 mg, 0.88 mmol), 5-bromo-2-hydroxynicotinamide (37 mg, 0.17 mmol), Pd(dppf)Cl$_2$·DCM (13 mg, 0.016 mmol) and 0.5 mL of water. The mixture was sparged with nitrogen for 8 minutes, the vial was sealed, the mixture stirred at 100° C. for 1.3 hour and cooled when the reaction had proceeded to completion. The mixture was purified via preparative reverse-phase HPLC to give 2-hydroxy-5-(4-(((3S,4R)-3-hydroxy-4-((5-(trifluoromethyl)pyridin-2-yl)amino)piperidin-1-yl)sulfonyl)phenyl)nicotinamide. MS: (ES) m/z calculated for C$_{23}$H$_{23}$F$_3$N$_5$O$_5$S [M+H]$^+$ 538.1, found 538.0. $^1$H NMR (400 MHz, Methanol-d$_4$) δ 8.85 (d, J=2.9 Hz, 1H), 8.19 (s, 1H), 8.12 (d, J=2.9 Hz, 1H), 7.93-7.82 (m, 4H), 7.79 (d, J=8.0 Hz, 1H), 6.92 (d, J=9.3 Hz, 1H), 4.01 (s, 1H), 3.91-3.84 (m, 1H), 3.68-3.59 (m, 2H), 2.82 (d, J=12.4 Hz, 1H), 2.72 (t, J=11.3 Hz, 1H), 2.10-2.00 (m, 1H), 1.85 (d, J=12.6 Hz, 1H).

Example 52: (3S,4R)-1-((4-(2-(1H-imidazol-2-yl)pyridin-4-yl)phenyl)sulfonyl)-4-((5-(trifluoromethyl)pyridin-2-yl)amino)piperidin-3-ol

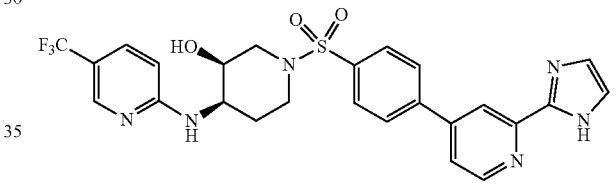

Step a: To (3S,4R)-1-((4-bromophenyl)sulfonyl)-4-((5-(trifluoromethyl)pyridin-2-yl)amino)piperidin-3-ol (190 mg, 0.40 mmol) were added bis(pinacolato)diboron (122 mg, 0.48 mmol), KOAc (118 mg, 1.2 mmol), dioxane (2 mL) and Pd(dppf)Cl$_2$·DCM (3 mg, 0.0040 mmol) in a septum-cap vial. The mixture was sparged with nitrogen for 5 minutes. The vial was sealed, the mixture stirred at 100° C. for 1.5 h and cooled when the reaction had proceeded to completion. To the mixture were added K$_2$CO$_3$ (276 mg, 2.0 mmol), 4-bromopicolinaldehyde (89 mg, 0.48 mmol), water (1 mL), and Pd(dppf)Cl$_2$·DCM (33 mg, 0.040 mmol). The mixture was sparged with nitrogen for 5 minutes. The vial was sealed, the mixture stirred at 100° C. for 1.5 hours and cooled when the reaction had proceeded to completion. The mixture was purified via SiO$_2$ gel chromatography to give 4-(4-(((3S,4R)-3-hydroxy-4-((5-(trifluoromethyl)pyridin-2-yl)amino)piperidin-1-yl)sulfonyl)phenyl)picolinaldehyde.

Step b: A mixture of (3S,4R)-1-((4-(2-(1H-imidazol-2-yl)pyridin-4-yl)phenyl)sulfonyl)-4-((5-(trifluoromethyl)pyridin-2-yl)amino)piperidin-3-ol (130 mg, 0.26 mmol), glyoxal (40 wt % in water, 60 μL, 0.52 mmol), and ammonium acetate (100 mg, 1.3 mmol) in methanol (2 mL) was stirred at rt for 16 h. The reaction mixture was diluted with water (20 mL). The resulting solid was filtered and purified by preparative reverse-phase HPLC, followed by SiO$_2$ gel chromatography, to give (3S,4R)-1-((4-(2-(1H-imidazol-2-yl)pyridin-4-yl)phenyl)sulfonyl)-4-((5-(trifluoromethyl)pyridin-2-yl)amino)piperidin-3-ol. MS: (ES) m/z calculated for C$_{25}$H$_{24}$F$_3$N$_6$O$_3$S [M+H]$^+$ 545.2, found 545.1. $^1$H NMR (400

MHz, DMSO-d$_6$) δ 12.99 (s, 1H), 8.73 (d, J=5.2 Hz, 1H), 8.37 (s, 1H), 8.19 (s, 1H), 8.12 (d, J=8.0 Hz, 2H), 7.91 (d, J=7.9 Hz, 2H), 7.81-7.73 (m, 1H), 7.62-7.54 (m, 1H), 7.22 (s, 2H), 7.12 (s, 1H), 6.69 (d, J=9.0 Hz, 1H), 5.25 (d, J=4.4 Hz, 1H), 3.98-3.84 (m, 2H), 3.58-3.44 (m, 2H), 2.78-2.70 (m, 1H), 2.68-2.58 (m, 1H), 1.95-1.79 (m, 1H), 1.70-1.61 (m, 1H).

Example 53: 2-Amino-5-(4-(((3S,4R)-3-hydroxy-4-((5-(trifluoromethyl)pyridin-2-yl)amino)piperidin-1-yl)sulfonyl)phenyl)nicotinamide

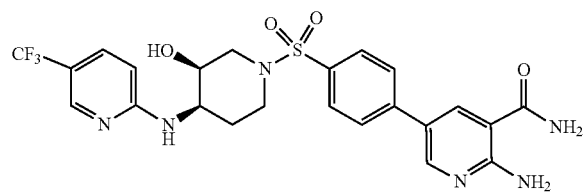 [SMILES: NC(=O)c1cc(-c2ccc(S(=O)(=O)N3CC[C@@H](Nc4ccc(C(F)(F)F)cn4)[C@@H](O)C3)cc2)cnc1N]

To (3S,4R)-1-((4-bromophenyl)sulfonyl)-4-((5-(trifluoromethyl)pyridin-2-yl)amino)piperidin-3-ol (82 mg, 0.17 mmol) was added bis(pinacolato)diboron (54 mg, 0.21 mmol), KOAc (51 mg, 0.52 mmol) and Pd(dppf)Cl$_2$·DCM (2.4 mg, 0.0029 mmol) in a 4 mL vial. To this was added 1 mL of dioxane and the mixture was sparged with nitrogen for 8 minutes. The vial was sealed with a Teflon-lined cap, the mixture stirred at 100° C. for 3.6 h and cooled when the reaction had proceeded to completion. To the mixture were added K$_2$CO$_3$ (117 mg, 0.85 mmol), 2-amino-5-bromonicotinamide (37 mg, 0.17 mmol), Pd(dppf)Cl$_2$·DCM (13 mg, 0.016 mmol) and 0.5 mL of water. The mixture was sparged with nitrogen for 10 minutes. The vial was sealed, the mixture stirred at 100° C. for 1.3 hour and cooled when the reaction had proceeded to completion. The mixture was purified via preparative reverse-phase HPLC to give 2-amino-5-(4-(((3S,4R)-3-hydroxy-4-((5-(trifluoromethyl)pyridin-2-yl)amino)piperidin-1-yl)sulfonyl)phenyl)nicotinamide. MS: (ES) m/z calculated for C$_{23}$H$_{24}$F$_3$N$_6$O$_4$S [M+H]$^+$ 537.2, found 537.2. $^1$H NMR (400 MHz, Methanol-d$_4$) δ 8.78 (d, J=2.0 Hz, 1H), 8.49-8.43 (m, 1H), 8.17 (s, 1H), 7.94 (d, J=2.1 Hz, 4H), 7.65 (d, J=8.9 Hz, 1H), 6.75 (d, J=9.1 Hz, 1H), 4.01 (s, 1H), 3.89 (d, J=10.4 Hz, 1H), 3.77-3.64 (m, 2H), 2.76 (d, J=12.2 Hz, 1H), 2.64 (t, J=11.5 Hz, 1H), 2.02 (dd, J=13.3, 9.5 Hz, 1H), 1.82 (d, J=15.1 Hz, 1H).

Example 54: 6-(4-(((3S,4R)-3-hydroxy-4-((5-(trifluoromethyl)pyridin-2-yl)amino)piperidin-1-yl)sulfonyl)phenyl)-1,3-dihydro-2H-imidazo[4,5-b]pyridin-2-one

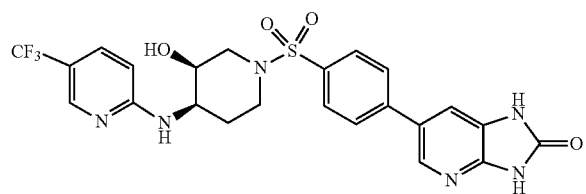 [SMILES: O=c1[nH]c2cc(-c3ccc(S(=O)(=O)N4CC[C@@H](Nc5ccc(C(F)(F)F)cn5)[C@@H](O)C4)cc3)cnc2[nH]1]

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) were placed in a septum-cap vial. To this was added 1 mL of dioxane and the mixture was sparged with nitrogen for 5 minutes. The vial was sealed, the mixture stirred at 100° C. for 3 h and cooled when the reaction had proceeded to completion. To the mixture were added 2 M K$_2$CO$_3$ (0.53 mL, 1.06 mmol), 6-bromo-1,3-dihydro-2H-imidazo[4,5-b]pyridin-2-one (37 mg, 0.21 mmol), Pd(dppf)Cl$_2$·DCM (17 mg, 0.21 mmol). The mixture was purged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give 6-(4-(((3S,4R)-3-hydroxy-4-((5-(trifluoromethyl)pyridin-2-yl)amino)piperidin-1-yl)sulfonyl)phenyl)-1,3-dihydro-2H-imidazo[4,5-b]pyridin-2-one. MS: (ES) m/z calculated for C$_{23}$H$_{21}$F$_3$N$_6$O$_4$S [M+H]$^+$ 535.1, found 535.2. $^1$H NMR (400 MHz, Methanol-d$_4$) δ 8.27 (s, 1H), 8.19 (s, 1H), 7.92-7.87 (m, 4H), 7.78-7.74 (m, 1H), 7.683 (s, 1H), 6.90 (d, J=9.3 Hz, 1H), 4.05-3.98 (m, 1H), 3.92-3.84 (m, 1H), 3.68-3.60 (m, 2H), 2.88-2.78 (m, 1H), 2.76-2.67 (m, 1H), 2.11-2.01 (q, J=10.1 Hz, 1H), 1.91-1.82 (m, 1H).

Example 55: (3S,4R)-1-((4-(3-amino-1H-indazol-6-yl)phenyl)sulfonyl)-4-((5-(trifluoromethyl)pyridin-2-yl)amino)piperidin-3-ol

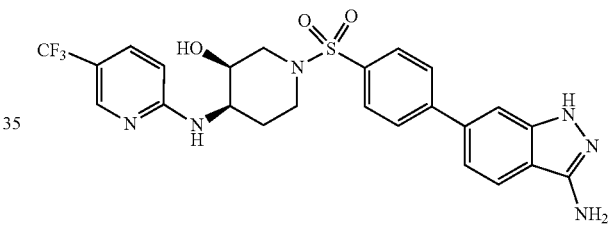

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) were placed in a septum-cap vial. To this was added 1 mL of dioxane and the mixture was sparged with nitrogen for 5 minutes. The vial was sealed, the mixture stirred at 100° C. for 3 h and cooled when the reaction had proceeded to completion. To the mixture were added 2 M K$_2$CO$_3$ (0.53 mL, 1.06 mmol), 6-bromo-1H-indazol-3-amine (45 mg, 0.21 mmol), Pd(dppf)Cl$_2$·DCM (17 mg, 0.21 mmol). The mixture was purged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give (3S,4R)-1-((4-(3-amino-1H-indazol-6-yl)phenyl)sulfonyl)-4-((5-(trifluoromethyl)pyridin-2-yl)amino)piperidin-3-ol. MS: (ES) m/z calculated for C$_{24}$H$_{23}$F$_3$N$_6$O$_3$S [M+H]$^+$ 533.1, found 533.1. $^1$H NMR (400 MHz, Methanol-d$_4$) δ 8.18 (s, 1H), 8.04 (dd, J=8.6, 0.8 Hz, 1H), 7.98-7.90 (m, 4H), 7.74-7.65 (m, 2H), 7.57 (dd, J=8.6, 1.5 Hz, 1H), 6.80 (d, J=9.2 Hz, 1H), 4.02 (s, 1H), 3.94-3.86 (m, 1H), 3.75-3.65 (m, 2H), 2.80 (d, J=11.8 Hz, 1H), 2.69 (t, J=11.0 Hz, 1H), 2.10-2.01 (m, 1H), 1.88-1.80 (m, 1H). MS: (ES) m/z calculated for C$_{24}$H$_{23}$F$_3$N$_6$O$_3$S [M+H]$^+$ 533.1, found 533.1.

Example 56: 5-(4-(((3S,4R)-3-hydroxy-4-((5-(trifluoromethyl)pyridin-2-yl)amino)piperidin-1-yl)sulfonyl)phenyl)-4-methyl-1H-pyrrolo[2,3-b]pyridine-3-carbonitrile

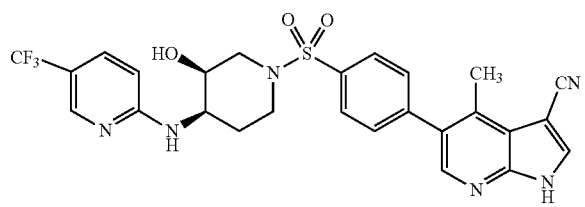 [SMILES: Cc1c(-c2ccc(S(=O)(=O)N3CC[C@@H](Nc4ccc(C(F)(F)F)cn4)[C@@H](O)C3)cc2)cnc2[nH]cc(C#N)c12]

A mixture of 5-bromo-4-methyl-1H-pyrrolo[2,3-b]pyridine (422 mg, 2.0 mmol), paraformaldehyde (66 mg, 2.2 mmol), and dimethylamine hydrochloride (179 mg, 2.2 mmol) in 1-butanol (10 mL) was stirred at 100° C. for 5 hours. The reaction mixture was cooled to room temperature and concentrated. The residue was suspended in 1M HCl (20 mL) and washed with diethyl ether (3×10 mL). The ether extracts were discarded, and the aqueous layer was basified to pH~12 by the addition of solid potassium carbonate and extracted with ethyl acetate (3×20 mL). The combined ethyl acetate extracts were dried over sodium sulfate, filtered, and concentrated to give 1-(5-bromo-4-methyl-1H-pyrrolo[2,3-b]pyridin-3-yl)-N,N-dimethylmethanamine, which was used directly without purification.

A mixture of 1-(5-bromo-4-methyl-1H-pyrrolo[2,3-b]pyridin-3-yl)-N,N-dimethylmethanamine (300 mg, 1.1 mmol) and hexamethylenetetramine (154 mg, 1.1 mmol) in propionic acid (1 mL) and water (0.5 mL) was stirred at 120° C. for 3.5 hours. The reaction mixture was cooled to room temperature and diluted with water (10 mL). The resulting solid was filtered, washed with water and acetonitrile, and dried to give 5-bromo-4-methyl-1H-pyrrolo[2,3-b]pyridine-3-carbaldehyde, which was used directly without purification.

A mixture of 5-bromo-4-methyl-1H-pyrrolo[2,3-b]pyridine-3-carbaldehyde (120 mg, 0.50 mmol) and hydroxylamine hydrochloride (42 mg, 0.60 mmol) in pyridine (1 mL) was stirred at room temperature for 1 hour. Acetic anhydride (2.5 mL) was added, and stirring continued at 100° C. for 1.5 hours. The reaction mixture was cooled to room temperature and diluted with water (10 mL). The resulting solid was filtered, washed with water, and purified by $SiO_2$ gel chromatography (hexanes/ethyl acetate) to give 1-acetyl-5-bromo-4-methyl-1H-pyrrolo[2,3-b]pyridine-3-carbonitrile.

1-acetyl-5-bromo-4-methyl-1H-pyrrolo[2,3-b]pyridine-3-carbonitrile (100 mg, 0.36 mmol) was dissolved in methanol (2 mL), and 1 M NaOH (2 mL) was added. The reaction mixture was stirred at room temperature for 1 hour. The reaction mixture was diluted with water (20 mL) and extracted with ethyl acetate (3×10 mL). The combined organic layers were dried over magnesium sulfate, filtered, and concentrated to give 5-bromo-4-methyl-1H-pyrrolo[2,3-b]pyridine-3-carbonitrile, which was used directly without purification.

To (3S,4R)-1-((4-bromophenyl)sulfonyl)-4-((5-(trifluoromethyl)pyridin-2-yl)amino)piperidin-3-ol (96 mg, 0.20 mmol) were added bis(pinacolato)diboron (61 mg, 0.24 mmol), KOAc (59 mg, 0.60 mmol), dioxane (1 mL) and Pd(dppf)Cl$_2$·DCM (2 mg, 0.0020 mmol) in a septum-cap vial. The mixture was sparged with nitrogen for 5 minutes. The vial was sealed, the mixture stirred at 100° C. for 1 h and cooled when the reaction had proceeded to completion. To the mixture were added $K_2CO_3$ (83 mg, 0.60 mmol), 5-bromo-4-methyl-1H-pyrrolo[2,3-b]pyridine-3-carbonitrile (57 mg, 0.24 mmol), dioxane (2 mL), water (1 mL), and Pd(dppf)Cl$_2$·DCM (16 mg, 0.020 mmol). The mixture was sparged with nitrogen for 5 minutes. The vial was sealed, the mixture stirred at 100° C. for 16 hours and cooled when the reaction had proceeded to completion. The mixture was purified via $SiO_2$ gel chromatography, followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-4-methyl-1H-pyrrolo[2,3-b]pyridine-3-carbonitrile. MS: (ES) m/z calculated for $C_{26}H_{24}F_3N_6O_3S$ [M+H]$^+$ 557.2, found 557.1. $^1$H NMR (400 MHz, DMSO-$d_6$) δ 12.93 (s, 1H), 8.51 (d, J=1.6 Hz, 1H), 8.28 (s, 1H), 8.22 (d, J=2.5 Hz, 1H), 7.86 (d, J=7.7 Hz, 2H), 7.72 (d, J=7.7 Hz, 2H), 7.60 (d, J=8.7 Hz, 1H), 7.15 (s, 1H), 6.72 (d, J=8.9 Hz, 1H), 5.27 (d, J=4.4 Hz, 1H), 3.99-3.86 (m, 2H), 3.61-3.48 (m, 2H), 2.74 (d, J=11.8 Hz, 1H), 2.68-2.58 (m, 4H), 1.97-1.84 (m, 1H), 1.73-1.64 (m, 1H).

Example 57: 4-(4-(((3S,4R)-3-hydroxy-4-((5-(trifluoromethyl)pyridin-2-yl)amino)piperidin-1-yl)sulfonyl)phenyl)picolinonitrile

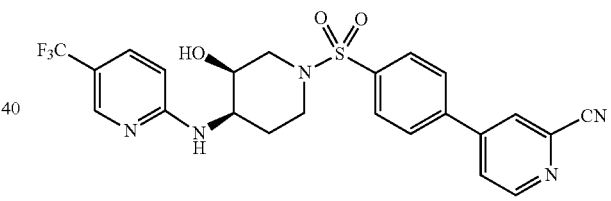

To (3S,4R)-1-((4-bromophenyl)sulfonyl)-4-((5-(trifluoromethyl)pyridin-2-yl)amino)piperidin-3-ol (190 mg, 0.40 mmol) were added $K_2CO_3$ (166 mg, 1.2 mmol), 4-(4,4,5,5-tetramethyl-1,3,2-dioxaborolan-2-yl)picolinonitrile (110 mg, 0.48 mmol), dioxane (2 mL), water (1 mL), and Pd(dppf)Cl$_2$·DCM (33 mg, 0.040 mmol) in a septum-cap vial. The mixture was sparged with nitrogen for 10 minutes. The vial was sealed, the mixture stirred at 100° C. for 17 hours and cooled when the reaction had proceeded to completion. The mixture was purified via $SiO_2$ gel chromatography (0-100% EtOAc/hexanes) to give 4-(4-(((3S,4R)-3-hydroxy-4-((5-(trifluoromethyl)pyridin-2-yl)amino)piperidin-1-yl)sulfonyl)phenyl)picolinonitrile. MS: (ES) m/z calculated for $C_{23}H_{21}F_3N_5O_3S$ [M+H]$^+$ 504.1, found 504.0. $^1$H NMR (400 MHz, DMSO-$d_6$) δ 8.88 (d, J=5.2 Hz, 1H), 8.54 (d, J=1.8 Hz, 1H), 8.21-8.14 (m, 4H), 7.92 (d, J=8.2 Hz, 2H), 7.58 (d, J=9.1 Hz, 1H), 7.12 (s, 1H), 6.69 (d, J=8.9 Hz, 1H), 5.25 (d, J=4.3 Hz, 1H), 3.96-3.84 (m, 2H), 3.60-3.46 (m, 2H), 2.73 (d, J=11.8 Hz, 1H), 2.68-2.57 (m, 1H), 1.93-1.80 (m, 1H), 1.70-1.60 (m, 1H).

Example 58: (3S,4R)-1-((4-(4-methoxy-1H-pyrrolo[2,3-b]pyridin-5-yl)phenyl)sulfonyl)-4-((5-(trifluoromethyl)pyridin-2-yl)amino)piperidin-3-ol

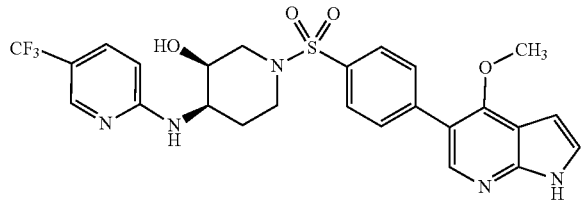 [SMILES: COc1c(-c2ccc(S(=O)(=O)N3CC[C@@H](Nc4ccc(C(F)(F)F)cn4)[C@@H](O)C3)cc2)cnc2[nH]ccc12]

(3S,4R)-1-((4-bromophenyl)sulfonyl)-4-((5-(trifluoromethyl)pyridin-2-yl)amino)piperidin-3-ol (65 mg, 0.135 mmol), bis(pinacolato)diboron (48 mg, 0.162 mmol), KOAc (46 mg, 0.46 mmol) and Pd(dppf)Cl$_2$·DCM (1 mg, 0.01 mmol) were placed in a septum-cap vial. To this was added 1 mL of dioxane and the mixture was sparged with nitrogen for 10 minutes. The vial was sealed, the mixture stirred at 100° C. for 1 h. and cooled when the reaction had proceeded to completion. To the mixture were added K$_2$CO$_3$ (112 mg, 0.81 mmol), 5-bromo-4-methoxy-1H-pyrrolo[2,3-b]pyridine (34 mg, 0.15 mmol), Pd(dppf)Cl$_2$·DCM (10 mg, 0.010 mmol) and 0.5 mL of water. The mixture was sparged with nitrogen for 10 minutes. The vial was sealed, the mixture stirred at 100° C. for 16 hours and cooled when the reaction had proceeded to completion. The mixture was purified via SiO$_2$ gel chromatography followed by preparative reverse-phase HPLC to give (3S,4R)-1-((4-(4-methoxy-1H-pyrrolo[2,3-b]pyridin-5-yl)phenyl)sulfonyl)-4-((5-(trifluoromethyl)pyridin-2-yl)amino)piperidin-3-ol. MS: (ES) m/z calculated for C$_{25}$H$_{25}$F$_3$N$_5$O$_4$S [M+H]$^+$ 548.2, found 548.1. $^1$H NMR (400 MHz, CD$_3$OD) δ 8.27 (s, 1H), 8.20 (s, 1H), 7.91 (d, J=7.6 Hz, 2H), 7.80 (d, J=8.1 Hz, 2H), 7.72 (d, J=9.1 Hz, 1H), 7.57 (d, J=3.2 Hz, 1H), 7.25 (d, J=3.6 Hz, 1H), 6.84 (d, J=8.9 Hz, 1H), 4.54 (s, 3H), 4.03 (s, 1H), 3.91 (d, J=10.3 Hz, 1H), 3.75-3.66 (m, 2H), 2.81 (d, J=12.2 Hz, 1H), 2.70 (dd, J=11.3, 11.3 Hz, 1H), 2.19-1.98 (m, 1H), 1.89-1.81 (m, 1H).

Example 59: 3-(4-(((3S,4R)-3-hydroxy-4-((5-(trifluoromethyl)pyridin-2-yl)amino)piperidin-1-yl)sulfonyl)phenyl)pyrido[2,3-d]pyridazin-5(6H)-one

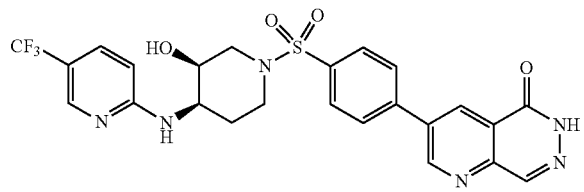 [SMILES: O=c1[nH]ncc2ncc(-c3ccc(S(=O)(=O)N4CC[C@@H](Nc5ccc(C(F)(F)F)cn5)[C@@H](O)C4)cc3)cc12]

(3S,4R)-1-((4-bromophenyl)sulfonyl)-4-((5-(trifluoromethyl)pyridin-2-yl)amino)piperidin-3-ol (100 mg, 0.21 mmol), bis(pinacolato)diboron (64 mg, 0.25 mmol), KOAc (62 mg, 0.63 mmol) and Pd(dppf)Cl$_2$·DCM (2 mg, 0.0021 mmol) were placed in a septum-cap vial. To this was added 1 mL of dioxane and the mixture was purged with nitrogen for 5 minutes. The vial was sealed, the mixture stirred at 100° C. for 3 h. and cooled when the reaction had proceeded to completion. To the mixture were added 2 M K$_2$CO$_3$ (0.53 mL, 1.06 mmol), 3-bromopyrido[2,3-d]pyridazin-5(6H)-one (48 mg, 0.21 mmol), Pd(dppf)Cl$_2$·DCM (17 mg, 0.21 mmol). The mixture was sparged with nitrogen for 5 minutes. The vial was sealed, the mixture stirred at 100° C. for 16 hours and cooled when the reaction had proceeded to completion. The mixture was purified via SiO$_2$ gel chromatography and then preparative reverse-phase HPLC to give 3-(4-(((3S,4R)-3-hydroxy-4-((5-(trifluoromethyl)pyridin-2-yl)amino)piperidin-1-yl)sulfonyl)phenyl)pyrido[2,3-d]pyridazin-5(6H)-one. MS: (ES) m/z calculated for C$_{24}$H$_{21}$F$_3$N$_6$O$_4$S [M+H]$^+$ 547.1, found 547.2. $^1$H NMR (400 MHz, DMSO-d$_6$) δ 9.32 (d, J=2.8 Hz, 1H), 8.75-8.69 (m, 1H), 8.32 (s, 1H), 8.16-8.05 (m, 3H), 7.82 (d, J=8.1 Hz, 2H), 7.51 (dd, J=8.9, 2.5 Hz, 1H), 7.05 (d, J=7.3 Hz, 1H), 6.63 (d, J=8.9 Hz, 1H), 5.18 (d, J=4.4 Hz, 1H), 3.90-3.80 (m, 2H), 3.52-3.40 (m, 2H), 2.67 (d, J=11.7 Hz, 1H), 2.62-2.50 (m, 1H), 1.88-1.75 (m, 1H), 1.64-1.55 (m, 1H).

Example 60: (3S,4R)-1-((4-(4-methyl-1H-pyrrolo[2,3-b]pyridin-5-yl)phenyl)sulfonyl)-4-((5-(trifluoromethyl)pyridin-2-yl)amino)piperidin-3-ol

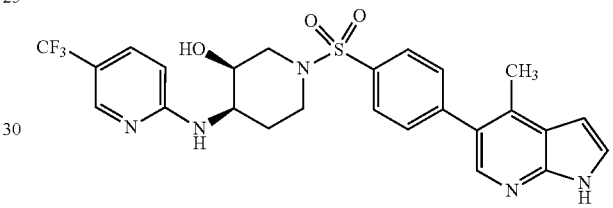

To (3S,4R)-1-((4-bromophenyl)sulfonyl)-4-((5-(trifluoromethyl)pyridin-2-yl)amino)piperidin-3-ol (800 mg, 1.7 mmol), were added bis(pinacolato)diboron (510 mg, 2.0 mmol), KOAc (530 mg, 5.4 mmol) and Pd(dppf)Cl$_2$·DCM (14 mg, 0.017 mmol) in a septum-cap vial. To this was added to 13 mL of dioxane and the mixture was sparged with nitrogen for 10 minutes. The vial was sealed, the mixture stirred at 100° C. for 1.3 h. and cooled when the reaction had proceeded to completion. To the mixture were added K$_2$CO$_3$ (1.2 g, 8.3 mmol), 5-bromo-4-methyl-1H-pyrrolo[2,3-b]pyridine (390 mg, 1.8 mmol), Pd(dppf)Cl$_2$·DCM (140 mg, 0.17 mmol) and 7 mL of water. The mixture was sparged with nitrogen for 10 minutes. The vial was sealed, the mixture stirred at 100° C. for 2.5 hours and cooled when the reaction had proceeded to completion. The mixture was allowed to cool to room temperature and sat overnight, after which a significant amount of precipitate was noted. 5 mL of water was added to the mixture, and a dark brown precipitate was collected by filtration, washed with water (10 mL) and dried in vacuo, leaving 820 mg of a brown powder. The residue was purified by SiO$_2$ gel chromatography (20-100% EtOAc, dichloromethane). Clean fractions were concentrated to dryness and triturated with dichloromethane to provide the title compound as an off-white powder. MS: (ES) m/z calculated for C$_{25}$H$_{25}$F$_3$N$_5$O$_3$S [M+H]$^+$ 532.2, found 532.3. $^1$H NMR (400 MHz, Methanol-d$_4$) δ 8.19-8.14 (m, 1H), 8.08 (s, 1H), 7.95-7.87 (m, 2H), 7.67 (d, J=8.0 Hz, 2H), 7.60-7.52 (m, 1H), 7.43 (d, J=3.1 Hz, 1H), 6.68-6.60 (m, 2H), 4.05-3.90 (m, 2H), 3.79-3.67 (m, 2H), 2.79 (d, J=11.8 Hz, 1H), 2.68 (td, J=11.5, 3.0 Hz, 1H), 2.54 (d, J=1.0 Hz, 3H), 2.07-1.96 (m, 1H), 1.89-1.79 (m, 1H).

Example 61: 5-(4-(((3S,4R)-3-hydroxy-4-((5-(trifluoromethyl)pyridin-2-yl)amino)piperidin-1-yl)sulfonyl)phenyl)-1H-pyrrolo[2,3-b]pyridine-3-carbonitrile

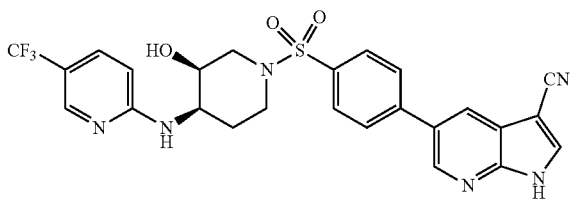 [SMILES: N#Cc1c[nH]c2ncc(-c3ccc(S(=O)(=O)N4CC[C@@H](Nc5ccc(C(F)(F)F)cn5)[C@@H](O)C4)cc3)cc12]

(3S,4R)-1-((4-bromophenyl)sulfonyl)-4-((5-(trifluoromethyl)pyridin-2-yl)amino)piperidin-3-ol (800 mg, 1.7 mmol), bis(pinacolato)diboron (510 mg, 2.0 mmol), KOAc (490 mg, 5.0 mmol) and Pd(dppf)Cl$_2$·DCM (14 mg, 0.017 mmol) were placed in a septum-cap vial. To this was added 3 mL of dioxane and the mixture was sparged with nitrogen for 20 minutes. The vial was sealed, the mixture stirred at 100° C. for 45 minutes and cooled when the reaction had proceeded to completion. To the mixture were added K$_2$CO$_3$ (1.2 g, 8.7 mmol), 5-bromo-3-cyano-1H-pyrrolo[2,3-b]pyridine (370 mg, 1.7 mmol), Pd(dppf)Cl$_2$·DCM (136 mg, 0.17 mmol) and 2 mL of water. The mixture was sparged with nitrogen for 20 minutes. The vial was sealed, the mixture stirred at 100° C. for 16 hours and cooled when the reaction had proceeded to completion. The mixture was purified via silica gel chromatography (50-100% EtOAc/DCM) to give 5-(4-(((3S,4R)-3-hydroxy-4-((5-(trifluoromethyl)pyridin-2-yl)amino)piperidin-1-yl)sulfonyl)phenyl)-1H-pyrrolo[2,3-b]pyridine-3-carbonitrile. MS: (ES) m/z calculated for C$_{25}$H$_{22}$F$_3$N$_6$O$_3$S [M+H]$^+$ 543.1, found 543.3. $^1$H NMR (400 MHz, DMSO-d$_6$) δ 13.02 (d, J=3.1 Hz, 1H), 8.85-8.80 (m, 1H), 8.58-8.47 (m, 2H), 8.24-8.18 (m, 1H), 8.11 (d, J=8.1 Hz, 2H), 7.86 (d, J=8.1 Hz, 2H), 7.59 (dd, J=9.0, 2.5 Hz, 1H), 7.16-7.09 (m, 1H), 6.71 (d, J=9.0 Hz, 1H), 5.29-5.23 (m, 1H), 3.96-3.88 (m, 2H), 3.60-3.47 (m, 2H), 2.73 (d, J=11.8 Hz, 1H), 2.62 (t, J=11.0 Hz, 1H), 2.02-1.83 (m, 1H), 1.72-1.63 (m, 1H).

Example 62: 5-(4-(((3S,4R)-3-hydroxy-4-((5-(trifluoromethyl)pyridin-2-yl)amino)piperidin-1-yl)sulfonyl)phenyl)-4,6-dimethyl-1H-pyrrolo[2,3-b]pyridine 7-oxide

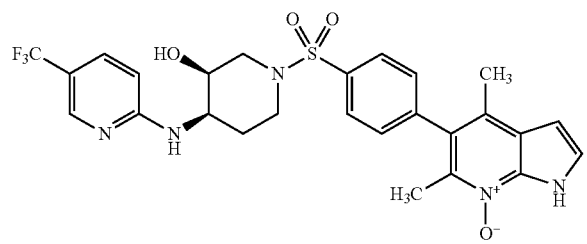 [SMILES: Cc1c(-c2ccc(S(=O)(=O)N3CC[C@@H](Nc4ccc(C(F)(F)F)cn4)[C@@H](O)C3)cc2)c(C)[n+]([O-])c2[nH]ccc12]

((3S,4R)-1-((4-(4,6-dimethyl-1H-pyrrolo[2,3-b]pyridin-5-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 5-bromo-4,6-dimethyl-1H-pyrrolo[2,3-b]pyridine via the one-pot Miyaura/Suzuki procedure described in Example 33.

((3S,4R)-1-((4-(4,6-dimethyl-1H-pyrrolo[2,3-b]pyridin-5-yl)phenyl)sulfonyl)-4-((5-(trifluoromethyl)pyridin-2-yl)amino)piperidin-3-ol (94 mg, 0.17 mmol) was dissolved in acetic acid (4 mL) in a septum-capped vial. Peracetic acid (32%, 54 μL, 1.5 equiv.) was added and the solution was stirred for 24 hours at room temperature. An additional portion of peracetic acid (32%, 18 μL, 0.5 equiv.) was added and the solution was stirred overnight at 30° C., then a third portion of peracetic acid (32%, 18 μL, 0.5 equiv.) was added and the solution was stirred for 6 hours at 35° C. The mixture was injected directly onto a preparative reverse-phase HPLC to give 5-(4-(((3S,4R)-3-hydroxy-4-((5-(trifluoromethyl)pyridin-2-yl)amino)piperidin-1-yl)sulfonyl)phenyl)-4,6-dimethyl-1H-pyrrolo[2,3-b]pyridine 7-oxide. MS: (ES) m/z calculated for C$_{26}$H$_{26}$F$_3$N$_5$O$_4$S [M+H]$^+$ 562.2, found 562.2. 1H NMR (400 MHz, DMSO-d6) δ 12.35 (s, 1H), 8.30-8.17 (m, 1H), 7.95-7.79 (m, 2H), 7.61 (dd, J=9.0, 2.5 Hz, 1H), 7.58-7.52 (m, 2H), 7.40 (dd, J=3.4, 1.9 Hz, 1H), 7.13 (d, J=7.5 Hz, 1H), 6.73 (d, J=8.9 Hz, 1H), 6.66 (dd, J=3.4, 1.7 Hz, 1H), 5.26 (d, J=4.5 Hz, 1H), 4.00-3.89 (m, 2H), 3.63-3.49 (m, 2H), 2.82-2.70 (m, 1H), 2.70-2.56 (m, 1H), 2.25 (s, 3H), 2.18 (s, 3H), 1.98-1.84 (m, 1H), 1.77-1.61 (m, 1H).

Example 63: 5-(4-(((3S,4R)-3-hydroxy-4-((5-(trifluoromethyl)pyridin-2-yl)amino)piperidin-1-yl)sulfonyl)phenyl)-4,6-dimethyl-1H-pyrrolo[2,3-b]pyridine-3-carbonitrile

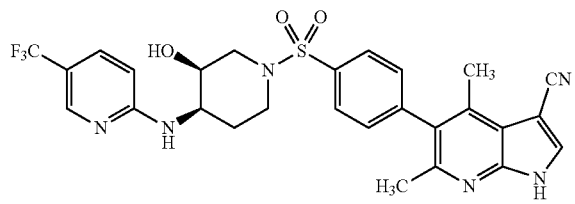 [SMILES: Cc1nc2[nH]cc(C#N)c2c(C)c1-c1ccc(S(=O)(=O)N2CC[C@@H](Nc3ccc(C(F)(F)F)cn3)[C@@H](O)C2)cc1]

To 5-bromo-4,6-dimethyl-1H-pyrrolo[2,3-b]pyridine (337 mg, 1.50 mmol) dissolved in NMP (5 mL) were added 60% NaH (72 mg, 1.80 mmol, 1.2 equiv.) and iodine (404 mg, 1.59 mmol, 1.06 equiv.) in a septum-capped vial. Stirring at room temperature for 1 h was followed by addition of 30 mL of water and 0.1 mL of acetic acid. The solids were filtered off and washed with 30 mL of water on the funnel, dried, and then washed with 5 mL of cyclohexane and dried again to give 5-bromo-3-iodo-4,6-dimethyl-1H-pyrrolo[2,3-b]pyridine. This material was used in the next step without additional purification. To a 172 mg sample of thus obtained solid (0.49 mmol) placed in a septum-capped vial, was added 1 mL of THF, and the slurry was cooled down to 0° C. under nitrogen. To the slurry was added 0.16 mL of 3M methylmagnesium bromide solution in diethyl ether (0.48 mmol, 0.98 equiv.), followed by 0.25 mL of 2M isopropylmagnesium chloride in THF (1.02 equiv.). The temperature was raised to 20° C. and 0.4 mL of 1.3M isopropylmagnesium chloride lithium chloride complex in THF (turbo-Grignard, 1.06 equiv.) was added, followed by temperature increase to 30° C. An additional 0.2 mL of the turbo-Grignard solution (0.53 equiv.) was added and the solution was stirred at 30° C. for an additional 2 hours. The solution was cooled down to 20° C. and dimethylmalononitrile (141 mg, 1.50 mmol, 3.06 equiv.) dissolved in THF (1 mL) was added. After 15 minutes the mixture was quenched by the addition of 10% aqueous acetic acid and extracted with DCM. The evaporated extract was purified on silica gel using 10-50% gradient of ethyl acetate in hexanes as eluent.

Concentrated product-containing fractions provided residue that was triturated with 1 mL of diethyl ether to provide pure 5-bromo-4,6-dimethyl-1H-pyrrolo[2,3-b]pyridine-3-carbonitrile as white powder. MS: (ES) m/z calculated for $C_{10}H_8BrN_3$ [M+H]$^+$ 250.0, found 250.2.

5-(4-(((3S,4R)-3-hydroxy-4-((5-(trifluoromethyl)pyridin-2-yl)amino)piperidin-1-yl)sulfonyl)phenyl)-4,6-dimethyl-1H-pyrrolo[2,3-b]pyridine-3-carbonitrile was synthesized from (3S,4R)-1-((4-bromophenyl)sulfonyl)-4-((5-(trifluoromethyl)pyridin-2-yl)amino)piperidin-3-ol and 5-bromo-4,6-dimethyl-1H-pyrrolo[2,3-b]pyridine-3-carbonitrile via the one-pot Miyaura/Suzuki procedure described in Example 33. MS: (ES) m/z calculated for $C_{27}H_{26}F_3N_6O_3S$ [M+H]$^+$ 571.2, found 571.2. $^1$H NMR (400 MHz, DMSO-d$_6$) δ 12.70 (d, J=3.1 Hz, 1H), 8.38 (d, J=3.0 Hz, 1H), 8.24-8.21 (m, 1H), 7.86 (d, J=8.2 Hz, 2H), 7.60 (dd, J=9.0, 2.5 Hz, 1H), 7.54 (d, J=8.2 Hz, 2H), 7.12 (d, J=7.4 Hz, 1H), 6.72 (d, J=8.9 Hz, 1H), 5.25 (d, J=4.5 Hz, 1H), 3.98-3.88 (m, 2H), 3.63-3.48 (m, 2H), 2.76-2.70 (m, 1H), 2.61 (t, J=10.6 Hz, 1H), 2.36 (s, 3H), 2.24 (s, 3H), 1.98-1.86 (m, 1H), 1.73-1.64 (m, 1H).

Example 64: (3S,4R)-1-((4-(2-(5-methyl-4H-1,2,4-triazol-3-yl)pyridin-4-yl)phenyl)sulfonyl)-4-((5-(trifluoromethyl)pyridin-2-yl)amino)piperidin-3-ol

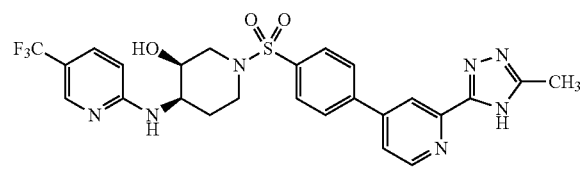 [SMILES: Cc1nnc(-c2cc(-c3ccc(S(=O)(=O)N4CC[C@@H](Nc5ccc(C(F)(F)F)cn5)[C@@H](O)C4)cc3)ccn2)[nH]1]

A mixture of methyl 4-(4-(((3S,4R)-3-hydroxy-4-((5-(trifluoromethyl)pyridin-2-yl)amino)piperidin-1-yl)sulfonyl)phenyl)picolinate (134 mg, 0.25 mmol) and hydrazine monohydrate (48 μL, 1.0 mmol) in ethanol (1 mL) was stirred at 70° C. for 1.5 hours. The reaction mixture was cooled to room temperature, diluted with water (10 mL), and extracted with dichloromethane (3×10 mL). The combined organic layers were dried over magnesium sulfate, filtered, and concentrated to give 4-(4-(((3S,4R)-3-hydroxy-4-((5-(trifluoromethyl)pyridin-2-yl)amino)piperidin-1-yl)sulfonyl)phenyl)picolinohydrazide, which was used directly without purification.

A mixture of 4-(4-(((3S,4R)-3-hydroxy-4-((5-(trifluoromethyl)pyridin-2-yl)amino)piperidin-1-yl)sulfonyl)phenyl)picolinohydrazide (47 mg, 0.088 mmol), acetamidine hydrochloride (17 mg, 0.18 mmol), and potassium carbonate (36 mg, 0.26 mmol) in 1-butanol (1 mL) was stirred at 100° C. for 17 hours. The reaction mixture was cooled to room temperature and purified by preparative reverse-phase HPLC to give (3S,4R)-1-((4-(2-(5-methyl-4H-1,2,4-triazol-3-yl)pyridin-4-yl)phenyl)sulfonyl)-4-((5-(trifluoromethyl)pyridin-2-yl)amino)piperidin-3-ol. MS: (ES) m/z calculated for $C_{25}H_{25}F_3N_7O_3S$ [M+H]$^+$ 560.2, found 560.1. $^1$H NMR (400 MHz, DMSO-d$_6$) δ 8.79 (s, 1H), 8.35 (d, J=1.8 Hz, 1H), 8.20 (d, J=2.4 Hz, 1H), 8.13 (d, J=7.4 Hz, 2H), 7.91 (d, J=8.3 Hz, 2H), 7.87 (br s, 1H), 7.58 (dd, J=9.0, 2.5 Hz, 1H), 7.11 (d, J=7.6 Hz, 1H), 6.69 (d, J=8.9 Hz, 1H), 5.25 (d, J=4.5 Hz, 1H), 3.99-3.83 (m, 2H), 3.52 (t, J=13.0 Hz, 2H), 2.77-2.71 (m, 1H), 2.68-2.58 (m, 1H), 2.40 (s, 3H), 1.97-1.80 (m, 1H), 1.70-1.62 (m, 1H).

Example 65: (3S,4R)-1-((4-(2-(1-methyl-1H-imidazol-2-yl)pyridin-4-yl)phenyl)sulfonyl)-4-((5-(trifluoromethyl)pyridin-2-yl)amino)piperidin-3-ol

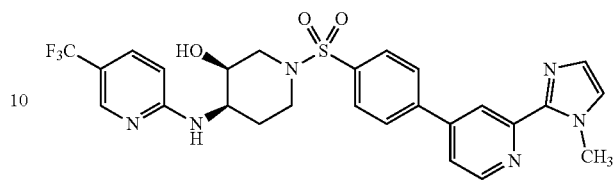

A mixture of 4-bromopyridine-2-carboxaldehyde (186 mg, 1.0 mmol), glyoxal (40 wt % in water, 0.23 mL, 2.0 mmol), and ammonium acetate (385 mg, 5.0 mmol) in methanol (2 mL) was stirred at room temperature overnight. The reaction mixture was diluted with water (20 mL) and extracted with dichloromethane (3×10 mL). The combined organic layers were dried over magnesium sulfate, filtered, and concentrated. Purification by SiO$_2$ gel chromatography (hexanes/ethyl acetate) gave 4-bromo-2-(1H-imidazol-2-yl)pyridine.

A mixture of 4-bromo-2-(1H-imidazol-2-yl)pyridine (90 mg, 0.40 mmol) and cesium carbonate (169 mg, 0.52 mmol) in tetrahydrofuran (2 mL) was stirred at 0° C. Iodomethane (62 μL, 1.0 mmol) was added, and the reaction mixture was stirred overnight while allowing to warm to room temperature gradually. The reaction mixture was diluted with ethyl acetate (10 mL), filtered, and concentrated. Purification by SiO$_2$ gel chromatography (hexanes/ethyl acetate) gave 4-bromo-2-(1-methyl-1H-imidazol-2-yl)pyridine. MS: (ES) m/z calculated for $C_9H_9BrN_3$ [M+H]$^+$ 238.0, found 238.0.

(3S,4R)-1-((4-(2-(1-methyl-1H-imidazol-2-yl)pyridin-4-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 4-bromo-2-(1-methyl-1H-imidazol-2-yl)pyridine via the one-pot Miyaura/Suzuki procedure described in Example 33. MS: (ES) m/z calculated for $C_{26}H_{26}F_3N_6O_3S$ [M+H]$^+$ 559.2, found 559.2. $^1$H NMR (400 MHz, DMSO-d$_6$) δ 8.75 (d, J=5.2 Hz, 1H), 8.43-8.39 (m, 1H), 8.22-8.18 (m, 1H), 8.10 (d, J=8.1 Hz, 2H), 7.91 (d, J=8.1 Hz, 2H), 7.79-7.74 (m, 1H), 7.61-7.54 (m, 1H), 7.37 (s, 1H), 7.13-7.09 (m, 1H), 7.07 (s, 1H), 6.69 (d, J=8.9 Hz, 1H), 5.25 (d, J=4.4 Hz, 1H), 4.10 (s, 3H), 3.98-3.84 (m, 2H), 3.58-3.46 (m, 2H), 2.79-2.72 (m, 1H), 2.69-2.59 (m, 1H), 1.94-1.80 (m, 1H), 1.71-1.61 (m, 1H).

Example 66: (3S,4R)-1-((4-(2-(3-methyl-1,2,4-oxadiazol-5-yl)pyridin-4-yl)phenyl)sulfonyl)-4-((5-(trifluoromethyl)pyridin-2-yl)amino)piperidin-3-ol

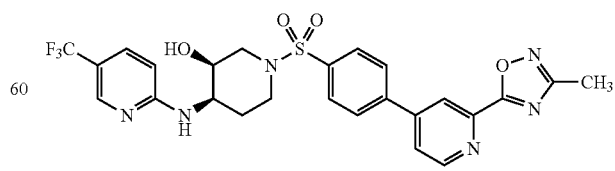

A mixture of 4-bromopicolinic acid (202 mg, 1.0 mmol) and 1,1'-carbonyldiimidazole (178 mg, 1.1 mmol) in N,N-dimethylformamide (1 mL) was stirred at room temperature for 3 hours. N-hydroxyacetamidine (148 mg, 2.0 mmol) was added, and stirring continued at 100° C. overnight. The reaction mixture was cooled to room temperature and diluted with water (10 mL). The resulting solid was filtered, washed with water, and purified by SiO$_2$ gel chromatography (hexanes/ethyl acetate) to give 5-(4-bromopyridin-2-yl)-3-methyl-1,2,4-oxadiazole.

To (3S,4R)-1-((4-bromophenyl)sulfonyl)-4-((5-(trifluoromethyl)pyridin-2-yl)amino)piperidin-3-ol (82 mg, 0.17 mmol) were added bis(pinacolato)diboron (52 mg, 0.20 mmol), KOAc (49 mg, 0.50 mmol), dioxane (1 mL) and Pd(dppf)Cl$_2$·DCM (1 mg, 0.0017 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (70 mg, 0.51 mmol), 5-(4-bromopyridin-2-yl)-3-methyl-1,2,4-oxadiazole (48 mg, 0.20 mmol), water (0.5 mL), and Pd(dppf)Cl$_2$·DCM (14 mg, 0.017 mmol).

The mixture was sparged with nitrogen for 5 minutes. The vial was sealed, the mixture stirred at 100° C. for 3 hours, and cooled when the reaction had proceeded to completion. The reaction mixture was diluted with ethyl acetate (10 mL), filtered through celite, and concentrated. The mixture was purified via SiO$_2$ gel chromatography (dichloromethane/ethyl acetate), followed by preparative reverse-phase HPLC to give (3S,4R)-1-((4-(2-(3-methyl-1,2,4-oxadiazol-5-yl)pyridin-4-yl)phenyl)sulfonyl)-4-((5-(trifluoromethyl)pyridin-2-yl)amino)piperidin-3-ol. MS: (ES) m/z calculated for C$_{25}$H$_{24}$F$_3$N$_6$O$_4$S [M+H]$^+$ 561.2, found 561.2. $^1$H NMR (400 MHz, DMSO-d$_6$) δ 8.95 (d, J=5.1 Hz, 1H), 8.54 (s, 1H), 8.21-8.16 (m, 3H), 8.13 (dt, J=5.2, 1.4 Hz, 1H), 7.92 (d, J=7.6 Hz, 2H), 7.61-7.53 (m, 1H), 7.11 (d, J=7.5 Hz, 1H), 6.69 (d, J=9.0 Hz, 1H), 5.25 (d, J=4.4 Hz, 1H), 3.97-3.85 (m, 2H), 3.59-3.46 (m, 2H), 2.74 (d, J=11.5 Hz, 1H), 2.63 (dd, J=12.7, 9.6 Hz, 1H), 2.49 (s, 3H), 1.94-1.77 (m, 1H), 1.70-1.62 (m, 1H).

Example 67: (3S,4R)-1-((4-(2-(5-methyl-1,2,4-oxadiazol-3-yl)pyridin-4-yl)phenyl)sulfonyl)-4-((5-(trifluoromethyl)pyridin-2-yl)amino)piperidin-3-ol

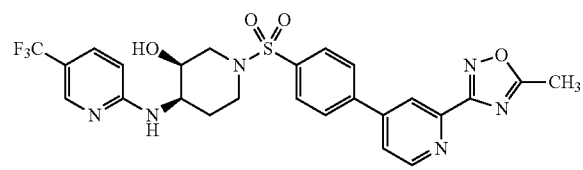 [SMILES: Cc1nc(-c2cc(-c3ccc(S(=O)(=O)N4CC[C@@H](Nc5ccc(C(F)(F)F)cn5)[C@@H](O)C4)cc3)ccn2)no1]

A mixture of 4-bromopicolinonitrile (549 mg, 3.0 mmol), hydroxylamine hydrochloride (313 mg, 4.5 mmol), and N,N-diisopropylethylamine (0.84 mL, 4.8 mmol) in ethanol (3 mL) was stirred at 70° C. for 16 hours. The reaction mixture was cooled to room temperature, diluted with water (20 mL), and extracted with ethyl acetate (3×10 mL). The combined organic layers were washed with brine (10 mL), dried over magnesium sulfate, filtered, and concentrated to give 4-bromo-N-hydroxypicolinamidine, which was used without purification.

A mixture of 4-bromo-N-hydroxypicolinamidine (216 mg, 1.0 mmol) and acetic anhydride (2 mL) was stirred at 110° C. for 20 hours. The reaction mixture was cooled to room temperature, diluted with saturated sodium bicarbonate (50 mL), and extracted with ethyl acetate (3×10 mL). The combined organic layers were dried over magnesium sulfate, filtered, and concentrated. Purification by SiO$_2$ gel chromatography (hexanes/ethyl acetate) gave 3-(4-bromopyridin-2-yl)-5-methyl-1,2,4-oxadiazole.

To (3S,4R)-1-((4-bromophenyl)sulfonyl)-4-((5-(trifluoromethyl)pyridin-2-yl)amino)piperidin-3-ol (82 mg, 0.17 mmol) were added bis(pinacolato)diboron (52 mg, 0.20 mmol), KOAc (49 mg, 0.50 mmol), dioxane (1 mL) and Pd(dppf)Cl$_2$·DCM (1 mg, 0.0017 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (117 mg, 0.85 mmol), 3-(4-bromopyridin-2-yl)-5-methyl-1,2,4-oxadiazole (50 mg, 0.20 mmol), water (0.5 mL), and Pd(dppf)Cl$_2$·DCM (14 mg, 0.017 mmol). The mixture was sparged with nitrogen for 5 minutes. The vial was sealed, the mixture stirred at 100° C. for 1.5 hours, and cooled when the reaction had proceeded to completion. The reaction mixture was diluted with ethyl acetate (10 mL), filtered through celite, and concentrated. The mixture was purified via SiO$_2$ gel chromatography (hexanes/ethyl acetate), followed by preparative reverse-phase HPLC to give (3S,4R)-1-((4-(2-(5-methyl-1,2,4-oxadiazol-3-yl)pyridin-4-yl)phenyl)sulfonyl)-4-((5-(trifluoromethyl)pyridin-2-yl)amino)piperidin-3-ol. MS: (ES) m/z calculated for C$_{25}$H$_{24}$F$_3$N$_6$O$_4$S [M+H]$^+$ 561.2, found 561.2. $^1$H NMR (400 MHz, DMSO-d$_6$) δ 8.89 (dd, J=5.1, 0.8 Hz, 1H), 8.39-8.32 (m, 1H), 8.21-8.19 (m, 1H), 8.14 (d, J=8.5 Hz, 2H), 8.02 (dd, J=5.1, 1.9 Hz, 1H), 7.92 (d, J=8.4 Hz, 2H), 7.59 (dd, J=9.0, 2.5 Hz, 1H), 7.13 (s, 1H), 6.70 (d, J=9.0 Hz, 1H), 5.23 (s, 1H), 3.99-3.82 (m, 2H), 3.57-3.47 (m, 2H), 2.78-2.70 (m, 4H), 2.69-2.58 (m, 1H), 1.95-1.81 (m, 1H), 1.72-1.61 (m, 1H).

Example 68: (3S,4R)-1-((4-(2-(1,3,4-oxadiazol-2-yl)pyridin-4-yl)phenyl)sulfonyl)-4-((5-(trifluoromethyl)pyridin-2-yl)amino)piperidin-3-ol

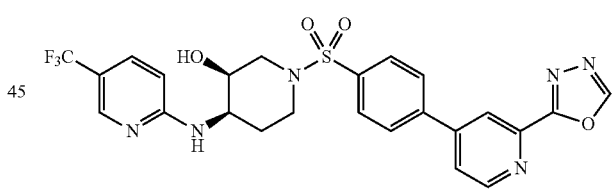

A mixture of formic hydrazide (180 mg, 3.0 mmol) and 4-bromopicolinic acid (404 mg, 2.0 mmol) in DMF (4 mL) was stirred, and N-(3-dimethylaminopropyl)-N'-ethylcarbodiimide hydrochloride (460 mg, 2.4 mmol) was added, followed by 1-hydroxybenzotriazole monohydrate (337 mg, 2.2 mmol). The reaction mixture was stirred at room temperature for 2.5 hours. The reaction mixture was diluted with water (25 mL) and extracted with ethyl acetate (3×10 mL). The combined organic layers were washed with brine (2×10 mL), dried over magnesium sulfate, filtered, and concentrated. The crude residue was dissolved in tetrahydrofuran (20 mL), and trimethylamine (1.1 mL, 8.0 mmol) was added, followed by benzenesulfonyl chloride (0.51 mL, 4.0 mmol). The reaction mixture was stirred at 60° C. for 17 hours. The reaction mixture was cooled to room temperature. The solid was filtered and washed with tetrahydrofuran. The filtrate was concentrated and purified by SiO$_2$ gel chromatography (hexanes/ethyl acetate) to give 2-(4-bromopyridin-2-yl)-1,3,4-oxadiazole. MS: (ES) m/z calculated for $C_7H_5BrN_3O$ [M+H]$^+$ 226.0, found 226.0.

(3S,4R)-1-((4-(2-(1,3,4-oxadiazol-2-yl)pyridin-4-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 2-(4-bromopyridin-2-yl)-1,3,4-oxadiazole via the one-pot Miyaura/Suzuki procedure described in Example 33. MS: (ES) m/z calculated for $C_{24}H_{22}F_3N_6O_4S$ [M+H]$^+$ 547.2, found 547.2. $^1$H NMR (400 MHz, DMSO-d$_6$) δ 9.49 (s, 1H), 8.92 (dd, J=5.1, 0.8 Hz, 1H), 8.52 (dd, J=1.7, 0.8 Hz, 1H), 8.22-8.15 (m, 3H), 8.07 (dd, J=5.2, 1.8 Hz, 1H), 7.93 (d, J=8.5 Hz, 2H), 7.58 (dd, J=8.9, 2.6 Hz, 1H), 7.09 (d, J=7.5 Hz, 1H), 6.69 (d, J=8.9 Hz, 1H), 5.24 (d, J=4.4 Hz, 1H), 3.97-3.86 (m, 2H), 3.54 (dt, J=16.3, 8.3 Hz, 2H), 2.75 (d, J=12.2 Hz, 1H), 2.69-2.59 (m, 1H), 1.94-1.82 (m, 1H), 1.72-1.61 (m, 1H).

Example 69: (3S,4R)-1-((4-(2-(5-amino-1,3,4-oxadiazol-2-yl)pyridin-4-yl)phenyl)sulfonyl)-4-((5-(trifluoromethyl)pyridin-2-yl)amino)piperidin-3-ol

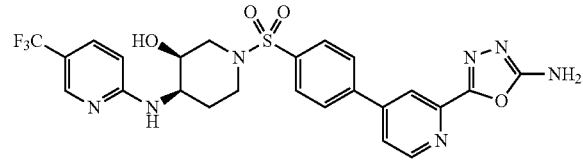 [SMILES: Nc1nnc(-c2cc(-c3ccc(S(=O)(=O)N4CC[C@@H](Nc5ccc(C(F)(F)F)cn5)[C@@H](O)C4)cc3)ccn2)o1]

A mixture of semicarbazide hydrochloride (167 mg, 1.5 mmol) and sodium acetate (164 mg, 2.0 mmol) in ethanol (8 mL) and water (2 mL) was stirred, and 4-bromopyridine-2-carboxaldehyde (186 mg, 1.0 mmol) was added. The reaction mixture was stirred at room temperature for 1.5 hours. The resulting solid was filtered, washed with ethanol, and dried to give 2-((4-bromopyridin-2-yl)methylene)hydrazine-1-carboxamide.

A mixture of 2-((4-bromopyridin-2-yl)methylene)hydrazine-1-carboxamide (180 mg, 0.74 mmol) and potassium carbonate (152 mg, 1.1 mmol) in dioxane (8 mL) was stirred, and iodine (226 mg, 0.89 mmol) was added. The reaction mixture was stirred at room temperature for 16 hours. An additional portion of potassium carbonate (152 mg, 1.1 mmol) and iodine (226 mg, 0.89 mmol) was added, and the reaction mixture was stirred at 60° C. for 2 hours. The reaction mixture was cooled to room temperature, quenched with saturated sodium sulfite (10 mL), and extracted with 2:1 chloroform:isopropanol (3×10 mL). The combined organic layers were washed with brine (10 mL), dried over magnesium sulfate, filtered, and concentrated to give 5-(4-bromopyridin-2-yl)-1,3,4-oxadiazol-2-amine. MS: (ES) m/z calculated for $C_7H_6BrN_4O$ [M+H]$^+$ 241.0, found 241.0.

(3S,4R)-1-((4-(2-(5-amino-1,3,4-oxadiazol-2-yl)pyridin-4-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 5-(4-bromopyridin-2-yl)-1,3,4-oxadiazol-2-amine via the one-pot Miyaura/Suzuki procedure described in Example 33. MS: (ES) m/z calculated for $C_{24}H_{23}F_3N_7O_4S$ [M+H]$^+$ 562.1, found 562.0. $^1$H NMR (400 MHz, DMSO-d$_6$) δ 8.79 (d, J=5.2 Hz, 1H), 8.28 (d, J=1.7 Hz, 1H), 8.22-8.18 (m, 1H), 8.12 (d, J=8.2 Hz, 2H), 7.94-7.88 (m, 3H), 7.58 (dd, J=9.0, 2.5 Hz, 1H), 7.46 (s, 2H), 7.09 (d, J=7.5 Hz, 1H), 6.69 (d, J=8.9 Hz, 1H), 5.23 (s, 1H), 3.97-3.85 (m, 2H), 3.53 (dt, J=16.0, 8.2 Hz, 2H), 2.80-2.72 (m, 1H), 2.64 (dd, J=11.8, 9.1 Hz, 1H), 1.95-1.82 (m, 1H), 1.66 (dq, J=12.3, 3.7 Hz, 1H).

Example 70: (3S,4R)-1-((4-(2-(5-methyloxazol-2-yl)pyridin-4-yl)phenyl)sulfonyl)-4-((5-(trifluoromethyl)pyridin-2-yl)amino)piperidin-3-ol

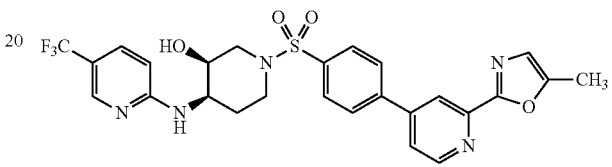

A mixture of 4-bromopicolinic acid (404 mg, 2.0 mmol), propargylamine (0.26 mL, 4.0 mmol), and N,N-diisopropylethylamine (1.1 mL, 3.0 mmol) in DMF (4 mL) was stirred, and HATU (1.14 g, 3.0 mmol) was added. The reaction mixture was stirred at room temperature for 2 hours. The reaction mixture was diluted with water (30 mL). The resulting solid was filtered, washed with water, and dried to give 4-bromo-N-(prop-2-yn-1-yl)picolinamide.

4-bromo-N-(prop-2-yn-1-yl)picolinamide (120 mg, 0.50 mmol) was dissolved in 1,2-dichloroethane (2 mL), and trifluoromethanesulfonic acid (0.44 mL, 5.0 mmol) was added dropwise. The reaction mixture was stirred at 80° C. for 17 hours. The reaction mixture was cooled to room temperature, poured into saturated sodium bicarbonate (50 mL), and extracted with 2:1 chloroform:isopropanol (3×10 mL). The combined organic layers were dried over magnesium sulfate, filtered, and concentrated to give 2-(4-bromopyridin-2-yl)-5-methyloxazole. MS: (ES) m/z calculated for $C_9H_8BrN_2O$ [M+H]$^+$ 239.0, found 239.0.

(3S,4R)-1-((4-(2-(5-methyloxazol-2-yl)pyridin-4-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 2-(4-bromopyridin-2-yl)-5-methyloxazole via the one-pot Miyaura/Suzuki procedure described in Example 33. MS: (ES) m/z calculated for $C_{26}H_{25}F_3N_5O_4S$ [M+H]$^+$ 560.2, found 560.1. $^1$H NMR (400 MHz, DMSO-d$_6$) δ 8.80 (dd, J=5.2, 0.8 Hz, 1H), 8.35 (dd, J=1.8, 0.8 Hz, 1H), 8.20 (dt, J=2.3, 1.1 Hz, 1H), 8.13 (d, J=8.4 Hz, 2H), 7.94-7.88 (m, 3H), 7.58 (dd, J=9.0, 2.6 Hz, 1H), 7.13 (d, J=1.3 Hz, 1H), 7.09 (d, J=7.6 Hz, 1H), 6.69 (d, J=8.9 Hz, 1H), 5.23 (d, J=4.5 Hz, 1H), 4.00-3.84 (m, 2H), 3.53 (dt, J=16.2, 8.2 Hz, 2H), 2.75 (d, J=12.0 Hz, 1H), 2.69-2.59 (m, 1H), 2.44 (d, J=1.2 Hz, 3H), 1.94-1.81 (m, 1H), 1.71-1.61 (m, 1H).

Example 71: 5-(4-(((3S,4R)-3-hydroxy-4-((5-(trifluoromethyl)pyridin-2-yl)amino)piperidin-1-yl)sulfonyl)phenyl)-1-methyl-1H-imidazole-2-carboxamide

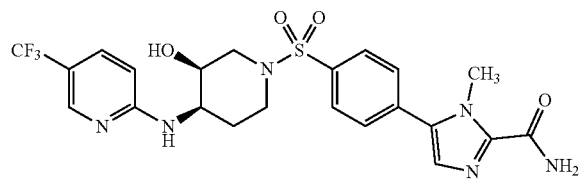 [SMILES: Cn1c(-c2ccc(S(=O)(=O)N3CC[C@@H](Nc4ccc(C(F)(F)F)cn4)[C@@H](O)C3)cc2)cnc1C(N)=O]

To a solution of 5-bromo-1-methyl-1H-imidazole-2-carboxaldehyde (200 mg, 1.06 mmol) in pyridine (1 mL) was added hydroxylamine hydrochloride (93 mg, 1.3 mmol). The mixture was stirred at room temperature for 2 h. To the mixture was then added acetic anhydride (2.0 mL, 21 mmol) and the mixture was stirred at 100° C. for 44 hours. After cooling, the reaction mixture was added to a mixture of ethyl acetate and water and the aqueous layer was discarded. The organic phase was concentrated, and the residue was purified via $SiO_2$ gel chromatography (hexanes/ethyl acetate) to obtain 5-bromo-1-methyl-1H-imidazole-2-carbonitrile.

To (3S,4R)-1-((4-bromophenyl)sulfonyl)-4-((5-(trifluoromethyl)pyridin-2-yl)amino)piperidin-3-ol (96 mg, 0.20 mmol) were added bis(pinacolato)diboron (77 mg, 0.16 mmol), KOAc (49 mg, 0.50 mmol), dioxane (1.5 mL) and Pd(dppf)Cl$_2$·DCM (1.7 mg, 0.0021 mmol) in a septum-cap vial. The mixture was sparged with nitrogen for 10 minutes. The vial was sealed, the mixture stirred at 100° C. for 1 h and cooled when the reaction had proceeded to completion. To the mixture were added $K_2CO_3$ (114 mg, 0.83 mmol), 5-bromo-1-methyl-1H-imidazole-2-carbonitrile (33 mg, 0.18 mmol), water (0.7 mL), and Pd(dppf)Cl$_2$·DCM (11 mg, 0.013 mmol). The mixture was sparged with nitrogen for 10 minutes. The vial was sealed, the mixture stirred at 100° C. for 1 hour, and cooled when the reaction had proceeded to completion. The mixture was purified via $SiO_2$ gel chromatography (hexanes/ethyl acetate, followed by dichloromethane/ethyl acetate) to obtain 5-(4-(((3 S,4R)-3-hydroxy-4-((5-(trifluoromethyl)pyridin-2-yl)amino)piperidin-1-yl)sulfonyl)phenyl)-1-methyl-1H-imidazole-2-carbonitrile.

To a solution of 5-(4-(((3S,4R)-3-hydroxy-4-((5-(trifluoromethyl)pyridin-2-yl)amino)piperidin-1-yl)sulfonyl)phenyl)-1-methyl-1H-imidazole-2-carbonitrile (60 mg, 0.12 mmol) in DMSO (1 mL) was added 30% hydrogen peroxide (33 mg, 0.29 mmol) followed immediately by 1 M sodium hydroxide (0.32 mL, 0.32 mmol). LCMS indicated immediate formation of the desired product. The mixture was treated with acetic acid to obtain slightly acidic pH and purified by reverse-phase HPLC to give 5-(4-(((3S,4R)-3-hydroxy-4-((5-(trifluoromethyl)pyridin-2-yl)amino)piperidin-1-yl)sulfonyl)phenyl)-1-methyl-1H-imidazole-2-carboxamide. MS: (ES) m/z calculated for $C_{22}H_{24}F_3N_6O_4S$ [M+H]$^+$ 525.2, found 525.2. $^1$H NMR (400 MHz, DMSO-$d_6$) δ 8.24-8.17 (m, 1H), 7.89-7.82 (m, 3H), 7.79 (d, J=8.4 Hz, 2H), 7.59 (dd, J=8.9, 2.6 Hz, 1H), 7.54 (d, J=2.3 Hz, 1H), 7.29 (s, 1H), 7.10 (d, J=7.5 Hz, 1H), 6.70 (d, J=8.9 Hz, 1H), 5.23 (d, J=4.5 Hz, 1H), 3.99 (s, 3H), 3.96-3.85 (m, 2H), 3.58-3.45 (m, 2H), 2.76-2.69 (m, 1H), 2.61 (td, J=10.7, 10.2, 2.5 Hz, 1H), 1.88 (qd, J=10.8, 4.0 Hz, 1H), 1.72-1.60 (m, 1H).

Example 72: 4-(4-(((3S,4R)-3-hydroxy-4-((5-(trifluoromethyl)pyridin-2-yl)amino)piperidin-1-yl)sulfonyl)phenyl)-1-methyl-1H-imidazole-2-carboxamide

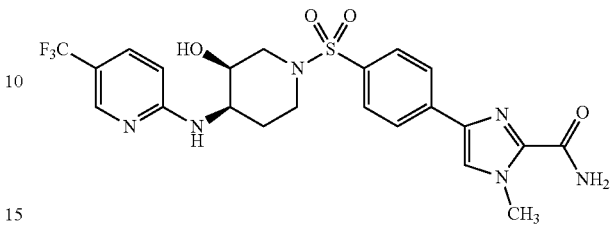

To a solution of 4-bromo-1-methyl-1H-imidazole (500 mg, 3.1 mmol) dissolved in tetrahydrofuran (2 mL) and cooled in an acetone/$CO_2$ bath was slowly added via syringe a 0.8 M THF/diethyl ether solution of lithium diisopropylamide (4.0 mL, 3.2 mmol). After 20 minutes the mixture was transferred to an ice bath and stirred for 30 minutes, after which N,N-dimethylformamide (0.50 mL, 6.5 mmol) was added. The mixture was stirred for one hour at 0° C., quenched with 1 M HCl, and the pH was adjusted to 7. The organic phase was separated and the aqueous phase was extracted twice with 3 mL ethyl acetate. The combined organic phases were concentrated and purified by flash chromatography (ethyl acetate/hexane) to provide 4-bromo-1H-imidazole-2-carbaldehyde.

To a solution of 4-bromo-1H-imidazole-2-carbaldehyde (260 mg, 1.4 mmol) in pyridine (1 mL) was added hydroxylamine hydrochloride (140 mg, 2.0 mmol) and the mixture was stirred for 1 hour. Acetic anhydride (2.0 mL, 21 mmol) was added and the resulting mixture was stirred at 100° C. for 17 hours. The mixture was concentrated under high vacuum to remove most volatiles, and the resulting residue was taken up in ethyl acetate and water. The aqueous phase was separated and discarded and the organic phase was concentrated and purified by $SiO_2$ chromatography (ethyl acetate/dichloromethane) to provide 4-bromo-1H-imidazole-2-carbonitrile.

4-(4-(((3S,4R)-3-hydroxy-4-((5-(trifluoromethyl)pyridin-2-yl)amino)piperidin-1-yl)sulfonyl)phenyl)-1-methyl-1H-imidazole-2-carbonitrile was synthesized from (3S,4R)-1-((4-bromophenyl)sulfonyl)-4-((5-(trifluoromethyl)pyridin-2-yl)amino)piperidin-3-ol and 4-bromo-1H-imidazole-2-carbonitrile via the one-pot Miyaura/Suzuki procedure described in Example 33. Nitrile hydrolysis with hydrogen peroxide via the procedure described in Example 71 gave 4-(4-(((3S,4R)-3-hydroxy-4-((5-(trifluoromethyl)pyridin-2-yl)amino)piperidin-1-yl)sulfonyl)phenyl)-1-methyl-1H-imidazole-2-carboxamide. MS: (ES) m/z calculated for $C_{22}H_{24}F_3N_6O_4S$ [M+H]$^+$ 525.2, found 525.2. $^1$H NMR (400 MHz, Methanol-$d_4$) δ 8.15 (d, J=2.3 Hz, 1H), 8.05 (d, J=8.4 Hz, 2H), 7.82-7.78 (m, 3H), 7.54 (dd, J=8.9, 2.5 Hz, 1H), 6.62 (d, J=9.0 Hz, 1H), 4.07 (s, 3H), 4.02-3.97 (m, 1H), 3.91 (dt, J=10.7, 3.8 Hz, 1H), 3.72-3.61 (m, 2H), 2.75 (dd, J=12.2, 2.1 Hz, 1H), 2.64 (dt, J=11.6, 6.1 Hz, 1H), 2.00 (qd, J=11.0, 4.1 Hz, 1H), 1.81 (dt, J=13.5, 3.7 Hz, 1H).

Example 73: 3-(4-(((3S,4R)-3-hydroxy-4-((5-(trifluoromethyl)pyridin-2-yl)amino)piperidin-1-yl)sulfonyl)phenyl)-1H-pyrazole-5-carboxamide

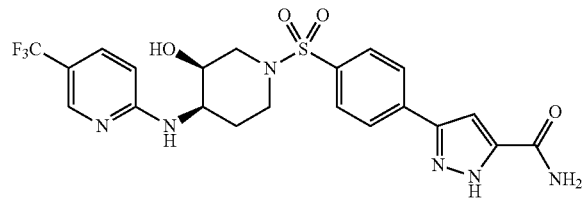 [SMILES: NC(=O)c1cc(-c2ccc(S(=O)(=O)N3CC[C@@H](Nc4ccc(C(F)(F)F)cn4)[C@@H](O)C3)cc2)n[nH]1]

Methyl 3-(4-(((3S,4R)-3-hydroxy-4-((5-(trifluoromethyl)pyridin-2-yl)amino)piperidin-1-yl)sulfonyl)phenyl)-1H-pyrazole-5-carboxylate was synthesized from (3S,4R)-1-((4-bromophenyl)sulfonyl)-4-((5-(trifluoromethyl)pyridin-2-yl)amino)piperidin-3-ol and methyl 3-bromo-1H-pyrazole-5-carboxylate via the one-pot Miyaura/Suzuki procedure described in Example 33.

To a solution of methyl 3-(4-(((3S,4R)-3-hydroxy-4-((5-(trifluoromethyl)pyridin-2-yl)amino)piperidin-1-yl)sulfonyl)phenyl)-1H-pyrazole-5-carboxylate (48 mg, 0.091 mmol) in methanol (0.50 mL) was added 28% ammonium hydroxide (0.45 g, 7.4 mmol). The mixture was stirred at 40° C. for 16 hours and purified by reverse-phase HPLC to give 3-(4-(((3S,4R)-3-hydroxy-4-((5-(trifluoromethyl)pyridin-2-yl)amino)piperidin-1-yl)sulfonyl)phenyl)-1H-pyrazole-5-carboxamide. MS: (ES) m/z calculated for $C_{21}H_{22}F_3N_6O_4S$ [M+H]$^+$ 511.1, found 511.0. $^1$H NMR (400 MHz, Methanol-d$_4$) δ 8.15 (d, J=2.4 Hz, 1H), 8.07-7.93 (m, 2H), 7.88 (d, J=8.1 Hz, 2H), 7.54 (dd, J=9.0, 2.5 Hz, 1H), 7.23 (s, 1H), 6.62 (d, J=9.0 Hz, 1H), 4.02-3.98 (m, 1H), 3.92 (dt, J=10.9, 3.7 Hz, 1H), 3.73-3.63 (m, 2H), 2.83-2.74 (m, 1H), 2.70-2.61 (m, 1H), 2.07-1.93 (m, 1H), 1.84-1.76 (m, 1H).

Example 74: N-hydroxy-4-(4-(((3S,4R)-3-hydroxy-4-((5-(trifluoromethyl)pyridin-2-yl)amino)piperidin-1-yl)sulfonyl)phenyl)picolinamide

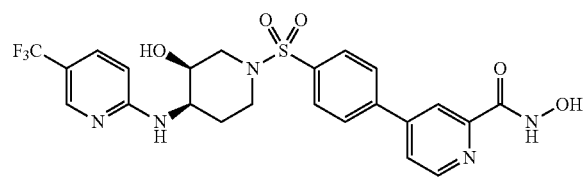 [SMILES: O=C(NO)c1cc(-c2ccc(S(=O)(=O)N3CC[C@@H](Nc4ccc(C(F)(F)F)cn4)[C@@H](O)C3)cc2)ccn1]

To a stirred solution of methyl 4-(4-(((3S,4R)-3-hydroxy-4-((5-(trifluoromethyl)pyridin-2-yl)amino)piperidin-1-yl)sulfonyl)phenyl)picolinate (53 mg, 0.099 mmol) dissolved in methanol (0.50 mL) and THF (0.50 mL) was added 50 wt. % hydroxylamine in water (190 mg, 3.3 mmol). The mixture was stirred for two days at room temperature, after which time it was diluted with NMP, methanol and 0.1% trifluoroacetic acid and purified by reverse-phase HPLC to give N-hydroxy-4-(4-(((3S,4R)-3-hydroxy-4-((5-(trifluoromethyl)pyridin-2-yl)amino)piperidin-1-yl)sulfonyl)phenyl)picolinamide. MS: (ES) m/z calculated for $C_{23}H_{23}F_3N_5O_5S$ [M+H]$^+$ 538.1, found 538.2. $^1$H NMR (400 MHz, Methanol-d$_4$) δ 8.72 (d, J=5.1 Hz, 1H), 8.38 (d, J=2.1 Hz, 1H), 8.18 (d, J=2.2 Hz, 1H), 8.05 (d, J=8.3 Hz, 2H), 7.98 (d, J=8.5 Hz, 2H), 7.89 (dd, J=5.1, 1.9 Hz, 1H), 7.69 (dd, J=9.2, 2.4 Hz, 1H), 6.82-6.78 (m, 1H), 4.03-3.99 (m, 1H), 3.91 (dt, J=10.4, 3.7 Hz, 1H), 3.73-3.64 (m, 2H), 2.88-2.81 (m, 1H), 2.78-2.69 (m, 1H), 2.03 (ddt, J=14.3, 10.4, 5.3 Hz, 1H), 1.88-1.79 (m, 1H).

Example 75: 4-(4-(((3S,4R)-3-hydroxy-4-((5-(trifluoromethyl)pyridin-2-yl)amino)piperidin-1-yl)sulfonyl)phenyl)-3,5-dimethylpicolinonitrile

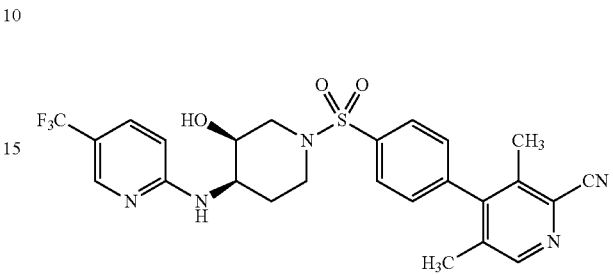

To a solution of (4-bromo-3,5-dimethylpyridin-2-yl)methanol (300 mg, 1.4 mmol) dissolved in dichloromethane (6 mL) was added manganese dioxide (300 mg, 3.5 mmol) and the mixture was stirred for 30 hours. TLC indicated some remaining starting material was present. Additional manganese dioxide (300 mg, 3.5 mmol) was added and the mixture was stirred an additional 21 hours, at which point TLC indicated complete conversion. Dichloromethane was removed in vacuo, and the residue was purified by SiO$_2$ gel chromatography (ethyl acetate/hexane) to provide 4-bromo-3,5-dimethylpicolinaldehyde.

To a solution of 4-bromo-3.5-picolinaldehyde (217 mg, 1.0 mmol) in pyridine (1 mL) was added hydroxylamine hydrochloride (104 mg, 1.5 mmol). The mixture was stirred at room temperature for 50 minutes. To the mixture was then added acetic anhydride (2.0 mL, 21 mmol) and the mixture was stirred at 100° C. for 17 hours. After cooling, the reaction mixture was concentrated under reduced pressure, diluted with ethyl acetate (10 mL) and stirred with water (5 mL). The aqueous phase was discarded and the organic layer was concentrated and purified via SiO$_2$ gel chromatography to obtain 4-bromo-3.5-dimethylpicolinonitrile.

4-(4-(((3S,4R)-3-hydroxy-4-((5-(trifluoromethyl)pyridin-2-yl)amino)piperidin-1-yl)sulfonyl)phenyl)-3,5-dimethylpicolinonitrile was synthesized from (3S,4R)-1-((4-bromophenyl)sulfonyl)-4-((5-(trifluoromethyl)pyridin-2-yl)amino)piperidin-3-ol and 4-bromo-3,5-dimethylpicolinonitrile via the one-pot Miyaura/Suzuki procedure described in Example 33. MS: (ES) m/z calculated for $C_{26}H_{25}F_3N_5O_4S$ [M+H]$^+$ 532.2, found 532.2. $^1$H NMR (400 MHz, DMSO-d$_6$) δ 8.60 (s, 1H), 8.24-8.19 (m, 1H), 7.90 (d, J=8.3 Hz, 2H), 7.59 (dd, J=8.9, 2.6 Hz, 1H), 7.54 (d, J=8.5 Hz, 2H), 7.11 (d, J=7.3 Hz, 1H), 6.71 (d, J=8.9 Hz, 1H), 5.25 (d, J=4.4 Hz, 1H), 3.98-3.86 (m, 2H), 3.62-3.47 (m, 2H), 2.77-2.69 (m, 1H), 2.60 (dd, J=11.8, 9.0 Hz, 1H), 2.20 (s, 3H), 2.09 (s, 3H), 1.97-1.84 (m, 1H), 1.73-1.63 (m, 1H).

Example 76: (3S,4R)-1-((4-(5-(piperazin-1-yl)pyridin-3-yl)phenyl)sulfonyl)-4-((5-(trifluoromethyl)pyridin-2-yl)amino)piperidin-3-ol

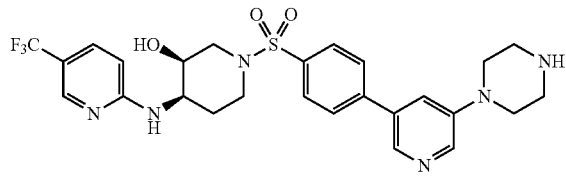 [SMILES: O=S(=O)(c1ccc(-c2cncc(N3CCNCC3)c2)cc1)N1CC[C@@H](Nc2ccc(C(F)(F)F)cn2)[C@@H](O)C1]

To a vial containing 3,5-dibromopyridine (1 g, 4.2 mmol) was added piperazine (730 mg, 8.5 mmol). The contents were heated at 130° C. for 16 h then purified by silica gel column chromatography to provide 1-(5-bromopyridin-3-yl)piperazine.

(3S,4R)-1-((4-(5-(piperazin-1-yl)pyridin-3-yl)phenyl)sulfonyl)-4-((5-(trifluoromethyl)pyridin-2-yl)amino)piperidin-3-ol was synthesized from (3S,4R)-1-((4-bromophenyl)sulfonyl)-4-((5-(trifluoromethyl)pyridin-2-yl)amino)piperidin-3-ol and 1-(5-bromopyridin-3-yl)piperazine via the one-pot Miyaura/Suzuki procedure described in Example 33. MS: (ES) m/z calculated for $C_{26}H_{30}F_3N_6O_3S$ [M+H]+ 563.2, found 563.1. $^1$H NMR (400 MHz, Methanol-$d_4$) δ 8.43 (d, J=1.8 Hz, 1H), 8.38 (d, J=2.7 Hz, 1H), 8.15 (s, 1H), 7.93 (s, 4H), 7.76 (t, J=2.3 Hz, 1H), 7.55 (dd, J=9.1, 2.5 Hz, 1H), 6.63 (d, J=8.9 Hz, 1H), 4.02-3.99 (m, 1H), 3.94-3.88 (m, 1H), 3.76-3.66 (m, 2H), 3.64-3.57 (m, 4H), 3.46-3.41 (m, 4H), 2.79-2.73 (m, 1H), 2.68-2.60 (m, 1H), 2.08-1.95 (m, 1H), 1.84-1.76 (m, 1H).

Example 77: 7-fluoro-5-(4-(((3S,4R)-3-hydroxy-4-((5-(trifluoromethyl)pyridin-2-yl)amino)piperidin-1-yl)sulfonyl)phenyl)-1H-indazole-3-carbonitrile

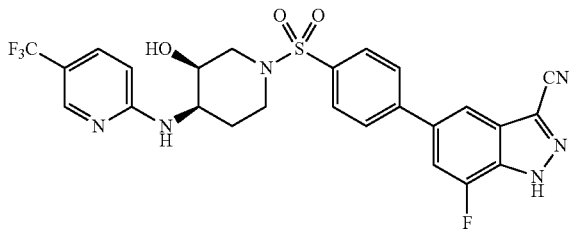 [SMILES: N#Cc1n[nH]c2c(F)cc(-c3ccc(S(=O)(=O)N4CC[C@@H](Nc5ccc(C(F)(F)F)cn5)[C@@H](O)C4)cc3)cc12]

To a vial containing 5-bromo-7-fluoro-1H-indazole (500 mg, 2.3 mmol) in DMF (6 mL) was added KOH (260 mg, 4.6 mmol) and $I_2$ (1.2 g, 4.7 mmol). The reaction mixture was stirred at room temperature for 16 h and then purified by silica gel column chromatography to give 5-bromo-7-fluoro-3-iodo-1H-indazole.

To a vial containing 5-bromo-7-fluoro-3-iodo-1H-indazole (350 mg, 1.0 mmol) in DMA (3 mL) was added Zn (40 mg, 0.62 mmol), Zn(CN)$_2$ (200 mg, 1.7 mmol), CuI (200 mg, 1.05 mmol), and Pd(dppf)Cl$_2$-dichloromethane complex (117 mg, 0.14 mmol). The reaction mixture was heated at 140° C. for 16 h. The contents were filtered through Celite, concentrated and then purified by silica gel column chromatography to yield 5-bromo-7-fluoro-1H-indazole-3-carbonitrile. MS: (ES) m/z calculated for $C_8H_4BrFN_3$ [M+H]+ 240.0, found 239.9.

7-fluoro-5-(4-(((3S,4R)-3-hydroxy-4-((5-(trifluoromethyl)pyridin-2-yl)amino)piperidin-1-yl)sulfonyl)phenyl)-1H-indazole-3-carbonitrile was synthesized from (3S,4R)-1-((4-bromophenyl)sulfonyl)-4-((5-(trifluoromethyl)pyridin-2-yl)amino)piperidin-3-ol and 5-bromo-7-fluoro-3-iodo-1H-indazole via the one-pot Miyaura/Suzuki procedure described in Example 33. MS: (ES) m/z calculated for $C_{25}H_{31}F_4N_6O_3S$ [M+H]+ 561.1, found 561.2. $^1$H NMR (400 MHz, Methanol-$d_4$) δ 8.19 (s, 1H), 8.02-7.97 (m, 3H), 7.95-7.91 (m, 2H), 7.78-7.73 (m, 1H), 7.70 (dd, J=12.0, 1.3 Hz, 1H), 6.88 (d, J=9.2 Hz, 1H), 4.04-4.00 (m, 1H), 3.90 (dt, J=10.3, 3.7 Hz, 1H), 3.71-3.62 (m, 2H), 2.90-2.82 (m, 1H), 2.80-2.71 (m, 1H), 2.12-1.98 (m, 1H), 1.90-1.82 (m, 1H).

Example 78: 5-(4-(((3S,4R)-3-hydroxy-4-((5-(trifluoromethyl)pyridin-2-yl)amino)piperidin-1-yl)sulfonyl)phenyl)-7-methylisoindolin-1-one

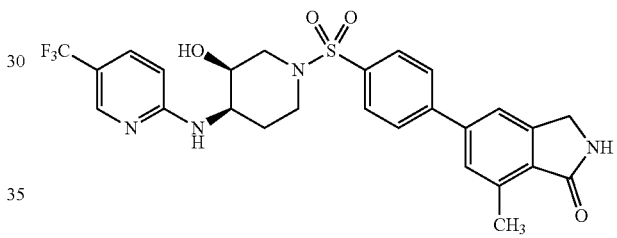

To (3S,4R)-1-((4-bromophenyl)sulfonyl)-4-((5-(trifluoromethyl)pyridin-2-yl)amino)piperidin-3-ol (100 mg, 0.21 mmol) were added bis(pinacolato)diboron (64 mg, 0.25 mmol), KOAc (62 mg, 0.63 mmol), dioxane (1 mL) and Pd(dppf)Cl$_2$·DCM (2 mg, 0.0021 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (83 mg, 0.60 mmol), 5-bromo-7-methylisoindolin-1-one (47 mg, 0.21 mmol), dioxane (2 mL), water (1 mL), and Pd(dppf)Cl$_2$·DCM (17 mg, 0.021 mmol). The mixture was sparged with nitrogen for 5 minutes. The vial was sealed, the mixture stirred at 100° C. for 16 hours, and cooled when the reaction had proceeded to completion. The mixture was purified via SiO$_2$ gel chromatography, followed by preparative reverse-phase HPLC to give 5-(4-(((3S,4R)-3-hydroxy-4-((5-(trifluoromethyl)pyridin-2-yl)amino)piperidin-1-yl)sulfonyl)phenyl)-7-methylisoindolin-1-one. MS: (ES) m/z calculated for $C_{26}H_{26}F_3N_4O_4S$ [M+H]+ 547.2, found 547.2. $^1$H NMR (400 MHz, Methanol-$d_4$) δ 8.19 (s, 1H), 7.99-7.88 (m, 4H), 7.77 (d, J=9.2 Hz, 1H), 7.69 (s, 1H), 7.57 (s, 1H), 6.90 (d, J=9.2 Hz, 1H), 4.47 (s, 2H), 4.02 (s, 1H), 3.93-3.86 (m, 1H), 3.71-3.61 (m, 2H), 2.89-2.81 (m, 1H), 2.75 (s, 3H), 2.79-2.69 (m, 1H), 2.13-1.98 (m, 1H), 1.91-1.82 (m, 1H).

Example 79: 6-(4-(((3S,4R)-3-hydroxy-4-((5-(trifluoromethyl)pyridin-2-yl)amino)piperidin-1-yl)sulfonyl)phenyl)-8-methoxyphthalazin-1(2H)-one

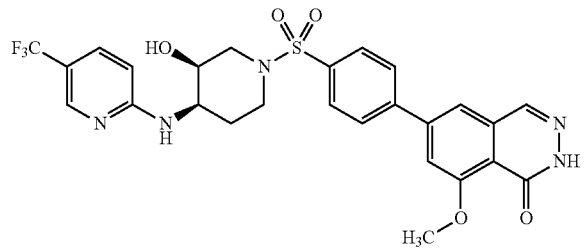 [SMILES: COc1cc(-c2ccc(S(=O)(=O)N3CC[C@@H](Nc4ccc(C(F)(F)F)cn4)[C@@H](O)C3)cc2)cc2cn[nH]c(=O)c12]

In a vial with methyl 4-bromo-2-formyl-6-methoxybenzoate (270 mg, 0.99 mmol) was added hydrazine (1 mL). The mixture was stirred at rt and white solid formed instantly. The solid was filtered, rinsed with TBME (1 mL) and air dried to give 6-bromo-8-methoxyphthalazin-1(2H)-one.

To (3S,4R)-1-((4-bromophenyl)sulfonyl)-4-((5-(trifluoromethyl)pyridin-2-yl)amino)piperidin-3-ol (100 mg, 0.21 mmol) were added bis(pinacolato)diboron (64 mg, 0.25 mmol), KOAc (62 mg, 0.63 mmol), dioxane (1 mL) and Pd(dppf)Cl$_2$·DCM (2 mg, 0.0021 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (83 mg, 0.60 mmol), 6-bromo-8-methoxyphthalazin-1(2H)-one (54 mg, 0.21 mmol), dioxane (2 mL), water (1 mL), and Pd(dppf)Cl$_2$·DCM (17 mg, 0.021 mmol). The mixture was sparged with nitrogen for 5 minutes. The vial was sealed, the mixture stirred at 100° C. for 16 hours, and cooled when the reaction had proceeded to completion. The mixture was purified via SiO$_2$ gel chromatography, followed by preparative reverse-phase HPLC to give 6-(4-(((3S,4R)-3-hydroxy-4-((5-(trifluoromethyl)pyridin-2-yl)amino)piperidin-1-yl)sulfonyl)phenyl)-8-methoxyphthalazin-1(2H)-one. MS: (ES) m/z calculated for C$_{26}$H$_{25}$F$_3$N$_5$O$_5$S [M+H]$^+$ 576.2, found 576.2. $^1$H NMR (400 MHz, Methanol-d$_4$) δ 8.70 (s, 1H), 8.56 (s, 1H), 8.22 (s, 1H), 8.02-7.94 (m, 2H), 7.87-7.81 (m, 1H), 7.71-7.64 (m, 2H), 6.98 (d, J=9.2 Hz, 1H), 4.03 (s, 2.4 Hz, 1H), 3.95-3.88 (m, 1H), 3.77-3.68 (m, 2H), 2.90-2.82 (m, 1H), 2.80-2.70 (m, 1H), 2.45 (s, 3H). 2.15-2.01 (m, 1H), 1.92-1.82 (m, 1H).

Example 80: 6-(4-(((3S,4R)-3-hydroxy-4-((5-(trifluoromethyl)pyridin-2-yl)amino)piperidin-1-yl)sulfonyl)phenyl)-N,N,4-trimethylisoindoline-2-carboxamide

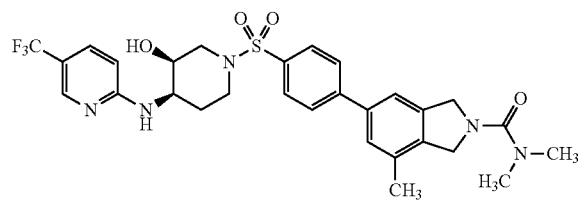 [SMILES: Cc1cc(-c2ccc(S(=O)(=O)N3CC[C@@H](Nc4ccc(C(F)(F)F)cn4)[C@@H](O)C3)cc2)cc2c1CN(C(=O)N(C)C)C2]

To the solution of 6-bromo-4-methylisoindoline (70 mg, 0.33 mmol) and N,N-diisopropylethylamine (0.1 mL) in DCM (1 mL) was added dimethylcarbamic chloride (39 mg, 0.36 mmol). The mixture was stirred at rt for 1 h and concentrated to dryness. Purification by SiO$_2$ gel chromatography (hexanes/ethyl acetate) gave 6-bromo-N,N,4-trimethylisoindoline-2-carboxamide.

To (3S,4R)-1-((4-bromophenyl)sulfonyl)-4-((5-(trifluoromethyl)pyridin-2-yl)amino)piperidin-3-ol (100 mg, 0.21 mmol) were added bis(pinacolato)diboron (64 mg, 0.25 mmol), KOAc (62 mg, 0.63 mmol), dioxane (1 mL) and Pd(dppf)Cl$_2$·DCM (2 mg, 0.0021 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (83 mg, 0.60 mmol), 6-bromo-N,N,4-trimethylisoindoline-2-carboxamide (60 mg, 0.21 mmol), dioxane (2 mL), water (1 mL), and Pd(dppf)Cl$_2$·DCM (17 mg, 0.021 mmol). The mixture was sparged with nitrogen for 5 minutes. The vial was sealed, the mixture stirred at 100° C. for 16 hours, and cooled when the reaction had proceeded to completion. The mixture was purified via SiO$_2$ gel chromatography, followed by preparative reverse-phase HPLC to give 6-(4-(((3S,4R)-3-hydroxy-4-((5-(trifluoromethyl)pyridin-2-yl)amino)piperidin-1-yl)sulfonyl)phenyl)-N,N,4-trimethylisoindoline-2-carboxamide. MS: (ES) m/z calculated for C$_{29}$H$_{33}$F$_3$N$_5$O$_4$S [M+H]$^+$ 604.2, found 604.2. $^1$H NMR (400 MHz, Methanol-d$_4$) δ 8.19 (s, 1H), 7.89-7.85 (m, 4H), 7.77 (dd, J=9.3, 2.4 Hz, 1H), 7.44 (d, J=9.0 Hz, 2H), 6.89 (d, J=9.2 Hz, 1H), 4.87 (s, 2H), 4.80 (s, 2H), 4.04-3.99 (m, 1H), 3.93-3.85 (m, 1H), 3.68-3.59 (m, 2H), 2.98 (s, 6H), 2.88-2.80 (m, 1H), 2.77-2.68 (m, 1H), 2.37 (s, 3H), 2.10-2.01 (m, 1H), 1.86 (m, 1H).

Example 81: 4-(4-(((3S,4R)-3-hydroxy-4-((4-(trifluoromethyl)phenyl)amino)piperidin-1-yl)sulfonyl)phenyl)picolinamide

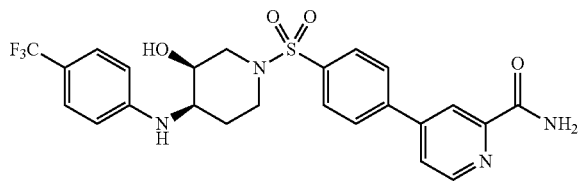 [SMILES: NC(=O)c1cc(-c2ccc(S(=O)(=O)N3CC[C@@H](Nc4ccc(C(F)(F)F)cc4)[C@@H](O)C3)cc2)ccn1]

A mixture of tert-butyl (3S,4R)-4-amino-3-hydroxypiperidine-1-carboxylate (216 mg, 1.0 mmol) and cesium carbonate (652 mg 2.0 mmol) in DMSO (2 mL) and water (1 mL) was stirred, and copper(I) iodide (19 mg, 0.10 mmol) was added, followed by 4-iodobenzotrifluoride (0.15 mL, 1.0 mmol). The reaction mixture was stirred at 90° C. for 20 hours. The reaction mixture was cooled to room temperature, diluted with 28% aq. NH$_3$ (10 mL) and water (10 mL), and extracted with ethyl acetate (3×10 mL). The combined organic layers were washed with brine (2×10 mL), dried over magnesium sulfate, filtered, and concentrated. Purification by SiO$_2$ gel chromatography (hexanes/ethyl acetate) gave tert-butyl (3S,4R)-3-hydroxy-4-((4-(trifluoromethyl)phenyl)amino)piperidine-1-carboxylate.

Tert-butyl (3S,4R)-3-hydroxy-4-((4-(trifluoromethyl)phenyl)amino)piperidine-1-carboxylate (85 mg, 0.24 mmol) was stirred in dioxane (2 mL), and HCl (4M in dioxane, 2 mL) was added. The reaction mixture was stirred at room temperature for 16 hours. The reaction mixture was concentrated, and the crude residue was suspended in 2-methyltetrahydrofuran (5 mL). A solution of potassium carbonate (133 mg, 0.96 mmol) in water (1 mL) was added, followed by 4-bromobenzenesulfonyl chloride (92 mg, 0.36 mmol). The reaction mixture was stirred at room temperature for 2 hours. The aqueous layer was removed, and the organic layer was concentrated. Purification by $SiO_2$ gel chromatography (hexanes/ethyl acetate) gave (3S,4R)-1-((4-bromophenyl)sulfonyl)-4-((4-(trifluoromethyl)phenyl)amino)piperidin-3-ol.

4-(4-(((3S,4R)-3-hydroxy-4-((4-(trifluoromethyl)phenyl)amino)piperidin-1-yl)sulfonyl)phenyl)picolinamide was synthesized from (3S,4R)-1-((4-bromophenyl)sulfonyl)-4-((4-(trifluoromethyl)phenyl)amino)piperidin-3-ol and 4-bromopicolinamide via the one-pot Miyaura/Suzuki procedure described in Example 33. MS: (ES) m/z calculated for $C_{24}H_{24}F_3N_4O_4S$ [M+H]$^+$ 521.1, found 521.1. $^1$H NMR (400 MHz, DMSO-d$_6$) δ 8.77 (d, J=5.1 Hz, 1H), 8.36 (d, J=1.9 Hz, 1H), 8.22 (d, J=2.6 Hz, 1H), 8.14 (d, J=8.3 Hz, 2H), 8.01 (dd, J=5.2, 1.9 Hz, 1H), 7.90 (d, J=8.3 Hz, 2H), 7.76 (d, J=2.7 Hz, 1H), 7.29 (d, J=8.5 Hz, 2H), 6.72 (d, J=8.6 Hz, 2H), 5.99 (d, J=8.2 Hz, 1H), 5.17 (s, 1H), 3.88-3.83 (m, 1H), 3.59-3.50 (m, 2H), 3.50-3.41 (m, 1H), 2.75-2.69 (m, 1H), 2.65-2.57 (m, 1H), 1.82 (qd, J=11.7, 10.8, 3.7 Hz, 1H), 1.66 (dd, J=13.5, 4.1 Hz, 1H).

Example 82: 4-[4-[[(3S,4R)-3-hydroxy-4-[[3-methyl-5-(trifluoromethyl)-2-pyridyl]amino]-1-piperidyl]sulfonyl]phenyl]pyridine-2-carboxamide

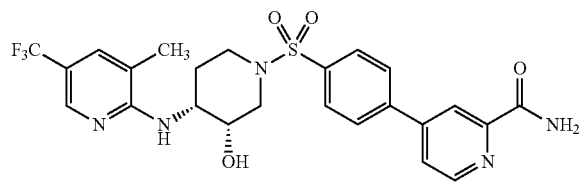

A solution of (3S,4R)-1-(4-bromophenyl)sulfonyl-4-[[3-methyl-5-(trifluoromethyl)-2-pyridyl]amino]piperidin-3-ol (200 mg; 0.40 mmol), Bis-pinacoldiboron (150 mg, 0.28 mml), KOAc (90 mg; 0.92 mmol) and Pd(dppf)Cl$_2$ (6 mg, 0.007 mmol) in 6 mL of dioxane is degassed with N$_2$ bubbling for 30 min. The mixture is heated for 1 h at 100° C. The mixture is diluted with 1.4 mL of H$_2$O and degassed for 10 min. To this is added K$_2$CO$_3$ (130 mg, 0.87 mmol), 4-bromopyridine-2-carboxamide (175 mg, 0.87 mmol) and Pd(dppf)Cl$_2$·DCM (35 mg, 0.043 mmol). The mixture is heated at 100° C. for 16 h. The reaction is cooled to room temperature, concentrated and the residue purified by column chromatography on silica gel (hexanes/ethyl acetate) to give 4-[4-[[(3S,4R)-3-hydroxy-4-[[3-methyl-5-(trifluoromethyl)-2-pyridyl]amino]-1-piperidyl]sulfonyl]phenyl]pyridine-2-carboxamide. MS: (ES) m/z calculated for $C_{24}H_{24}F_3N_5O_4S$ [M+H]$^+$ 536.2, found 536.1. $^1$H NMR (400 MHz, DMSO-d$_6$) δ 8.78 (dd, J=5.2, 0.8 Hz, 1H), 8.37 (dd, J=2.1, 0.9 Hz, 1H), 8.27-8.18 (m, 1H), 8.16-8.09 (m, 3H), 8.01 (dd, J=5.1, 1.9 Hz, 1H), 7.96-7.88 (m, 2H), 7.77 (d, J=2.7 Hz, 1H), 7.57-7.52 (m, 1H), 5.83-5.74 (m, 1H), 5.28 (d, J=4.5 Hz, 1H), 4.01 (ddt, J=11.5, 7.4, 3.7 Hz, 1H), 3.93 (s, 1H), 3.68 (dd, J=15.5, 12.0 Hz, 2H), 2.69-2.61 (m, 1H), 2.55 (m, 1H), 2.11 (s, 3H), 1.97 (qd, J=12.5, 4.5 Hz, 1H), 1.71 (dd, J=12.9, 3.8 Hz, 1H).

Example 83: 5-[4-[[(3S,4R)-3-hydroxy-4-[[3-methyl-5-(trifluoromethyl)-2-pyridyl]amino]-1-piperidyl]sulfonyl]phenyl]-1-methyl-imidazole-2-carboxamide

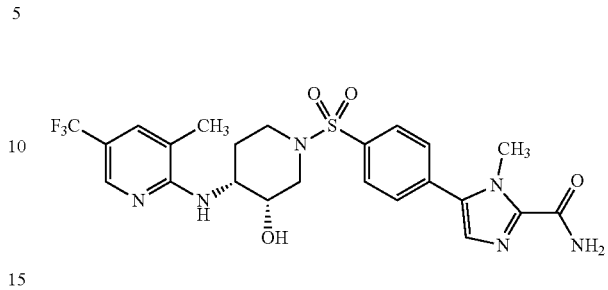

A solution of (3S,4R)-1-(4-bromophenyl)sulfonyl-4-[[3-methyl-5-(trifluoromethyl)-2-pyridyl]amino]piperidin-3-ol (200 mg; 0.40 mmol), Bis-pinacoldiboron (150 mg, 0.28 mml), KOAc (90 mg; 0.92 mmol) and Pd(dppf)Cl$_2$ (6 mg, 0.007 mmol) in 6 mL of dioxane is degassed with N$_2$ bubbling for 30 min. The mixture is heated for 1 h at 100° C. The mixture is diluted with 1.4 mL of H$_2$O and degassed for 10 min. To this is added K$_2$CO$_3$ (130 mg, 0.87 mmol), 5-bromo-1-methyl-imidazole-2-carbonitrile (125 mg, 0.67 mmol) and Pd(dppf)Cl$_2$·DCM (35 mg, 0.043 mmol). The mixture is heated at 100° C. for 16 h. The reaction is cooled to room temperature, concentrated and the residue purified by column chromatography on silica gel (0-100% EtOAc/CH$_2$Cl$_2$) to give 5-[4-[[(3S,4R)-3-hydroxy-4-[[3-methyl-5-(trifluoromethyl)-2-pyridyl]amino]-1-piperidyl]sulfonyl]phenyl]-1-methyl-imidazole-2-carbonitrile.

To a solution of 5-[4-[[(3S,4R)-3-hydroxy-4-[[3-methyl-5-(trifluoromethyl)-2-pyridyl]amino]-1-piperidyl]sulfonyl]phenyl]-1-methyl-imidazole-2-carbonitrile (165.4 mg; 0.32 mmol) in DMSO (1 mL) is added 1 M NaOH (1 mL) and 30% H$_2$O$_2$ (70 μL). The mixture stirs for 30 min. The reaction is diluted with 30 mL of EtOAc. To this is added Sat. NH$_4$Cl and the phases are separated. The organic phase is separated, dried with MgSO$_4$, filtered and concentrated and the residue purified by prep HPLC to give 5-[4-[[(3S,4R)-3-hydroxy-4-[[3-methyl-5-(trifluoromethyl)-2-pyridyl]amino]-1-piperidyl]sulfonyl]phenyl]-1-methyl-imidazole-2-carboxamide. MS: (ES) m/z calculated for $C_{23}H_{26}F_3N_6O_4S$ [M+H]$^+$ 539.2, found 539.1. $^1$H NMR (400 MHz, DMSO-d$_6$) δ 8.14 (d, J=2.5 Hz, 1H), 7.98-7.71 (m, 5H), 7.55 (s, 2H), 7.30 (s, 1H), 5.79 (d, J=7.6 Hz, 1H), 5.29 (d, J=4.4 Hz, 1H), 4.08-3.97 (m, 4H), 3.93 (s, 1H), 3.66 (t, J=15.2 Hz, 2H), 2.64 (d, J=11.9 Hz, 1H), 2.55 (m, 1H), 2.12 (s, 3H), 1.97 (qd, J=12.6, 4.4 Hz, 1H), 1.79-1.65 (m, 1H).

Example 84: (3S,4R)-1-[4-[2-(5-methyl-1,3,4-oxadiazol-2-yl)-4-pyridyl]phenyl]sulfonyl-4-[[3-methyl-5-(trifluoromethyl)-2-pyridyl]amino]piperidin-3-ol

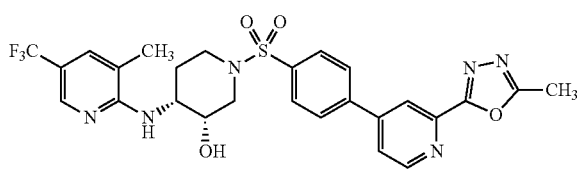 [SMILES: Cc1nnc(-c2cc(-c3ccc(S(=O)(=O)N4CC[C@@H](Nc5ncc(C(F)(F)F)cc5C)[C@@H](O)C4)cc3)ccn2)o1]

A solution of (3S,4R)-1-(4-bromophenyl)sulfonyl-4-[[3-methyl-5-(trifluoromethyl)-2-pyridyl]amino]piperidin-3-ol (200 mg; 0.40 mmol), Bis-pinacoldiboron (150 mg, 0.28 mml), KOAc (90 mg; 0.92 mmol) and Pd(dppf)Cl$_2$·DCM (6 mg, 0.007 mmol) in 6 mL of dioxane is degassed with N$_2$ bubbling for 30 min. The mixture is heated for 1 h at 100° C. LC-MS indicates the desired borylation product. The mixture is diluted with 1.4 mL of H$_2$O and degassed for 10 min. To this is added K$_2$CO$_3$ (130 mg, 0.87 mmol), 2-(4-bromo-2-pyridyl)-5-methyl-1,3,4-oxadiazole (175 mg, 0.87 mmol) and Pd(dppf)Cl$_2$ (35 mg, 0.043 mmol). The mixture is heated at 100° C. for 16 h. The reaction is cooled to room temperature, concentrated and the residue purified by column chromatography on silica gel (0-100% EtOAc/hexanes) to give (3S,4R)-1-[4-[2-(5-methyl-1,3,4-oxadiazol-2-yl)-4-pyridyl]phenyl]sulfonyl-4-[[3-methyl-5-(trifluoromethyl)-2-pyridyl]amino]piperidin-3-ol. MS: (ES) m/z calculated for C$_{26}$H$_{26}$F$_3$N$_6$O$_4$S [M+H]$^+$ 575.2, found 575.1. $^1$H NMR (400 MHz, DMSO-d$_6$) δ 8.90 (d, J=5.1 Hz, 1H), 8.47 (s, 1H), 8.21-8.11 (m, 3H), 8.05 (d, J=5.2 Hz, 1H), 7.93 (d, J=8.1 Hz, 2H), 7.55 (d, J=2.5 Hz, 1H), 5.80 (d, J=7.6 Hz, 1H), 4.01 (ddt, J=11.9, 7.7, 3.7 Hz, 1H), 3.93 (s, 1H), 3.75-3.62 (m, 2H), 2.66 (d, J=4.9 Hz, 5H), 2.11 (s, 3H), 1.97 (dt, J=14.7, 10.9 Hz, 1H), 1.72 (dd, J=13.1, 4.3 Hz, 1H).

Example 85: 4-(4-(((3S,4R)-4-((3-cyano-5-(trifluoromethyl)pyridin-2-yl)amino)-3-hydroxypiperidin-1-yl)sulfonyl)phenyl)picolinamide

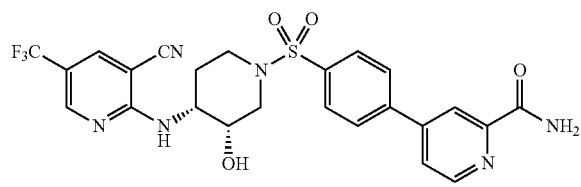 [SMILES: N#Cc1cc(C(F)(F)F)cnc1N[C@@H]1CCN(S(=O)(=O)c2ccc(-c3ccnc(C(N)=O)c3)cc2)C[C@@H]1O]

To 2-(((3S,4R)-1-((4-bromophenyl)sulfonyl)-3-hydroxypiperidin-4-yl)amino)-5-(trifluoromethyl)nicotinonitrile (190 mg, 0.38 mmol) were added bis(pinacolato)diboron (117 mg, 0.46 mmol), KOAc (118 mg, 1.2 mmol), dioxane (2 mL) and Pd(dppf)Cl$_2$·DCM (3 mg, 0.0038 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (263 mg, 0.85 mmol), 4-bromopicolinamide (92 mg, 0.46 mmol), water (1 mL), and Pd(dppf)Cl$_2$·DCM (31 mg, 0.038 mmol). The mixture was sparged with nitrogen for 5 minutes. The vial was sealed, the mixture stirred at 100° C. for 18 hours, and cooled when the reaction had proceeded to completion. The reaction mixture was diluted with ethyl acetate (10 mL), filtered through celite, and concentrated. The mixture was purified via SiO$_2$ gel chromatography (hexanes/ethyl acetate), followed by preparative reverse-phase HPLC to give 4-(4-(((3S,4R)-4-((3-cyano-5-(trifluoromethyl)pyridin-2-yl)amino)-3-hydroxypiperidin-1-yl)sulfonyl)phenyl)picolinamide. MS: (ES) m/z calculated for C$_{24}$H$_{22}$F$_3$N$_6$O$_4$S [M+H]$^+$ 547.1, found 547.0. $^1$H NMR (400 MHz, DMSO-d$_6$) δ 8.77 (d, J=5.1 Hz, 1H), 8.57-8.54 (m, 1H), 8.43 (d, J=2.4 Hz, 1H), 8.36 (d, J=1.8 Hz, 1H), 8.22 (d, J=2.8 Hz, 1H), 8.12 (d, J=8.1 Hz, 2H), 8.03-7.99 (m, 1H), 7.91 (d, J=8.1 Hz, 2H), 7.80-7.74 (m, 1H), 6.74 (d, J=7.5 Hz, 1H), 4.05 (ddt, J=11.4, 7.3, 3.6 Hz, 1H), 3.92 (d, J=3.0 Hz, 1H), 3.74-3.61 (m, 2H), 2.65 (d, J=12.2 Hz, 1H), 2.55-2.46 (m, 1H), 1.96 (qd, J=12.4, 4.1 Hz, 1H), 1.80-1.68 (m, 1H).

Example 86: 4-(4-(((3S,4R)-3-hydroxy-4-((5-(trifluoromethyl)pyrimidin-2-yl)amino)piperidin-1-yl)sulfonyl)phenyl)picolinamide

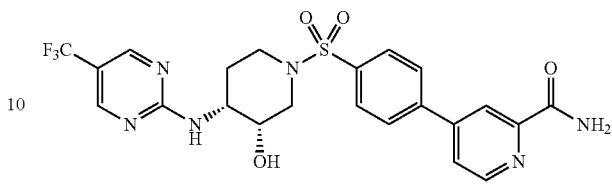

A mixture of 2-chloro-5-(trifluoromethyl)pyrimidine (110 mg, 0.60 mmol), (3S,4R)-4-amino-1-((4-bromophenyl)sulfonyl)piperidin-3-ol hydrochloride (446 mg, 1.2 mmol), and N,N-diisopropylethylamine (0.42 mL, 2.4 mmol) in NMP (1 mL) was stirred at 100° C. for 16 hours. The reaction mixture was cooled to room temperature and diluted with water. The resulting solid was filtered, washed with water, and purified by SiO$_2$ gel chromatography (hexanes/ethyl acetate) to give (3S,4R)-1-((4-bromophenyl)sulfonyl)-4-((5-(trifluoromethyl)pyrimidin-2-yl)amino)piperidin-3-ol. MS: (ES) m/z calculated for C$_{16}$H$_{17}$F$_3$N$_4$O$_3$S [M+H]$^+$ 481.0, found 480.9.

4-(4-(((3S,4R)-3-hydroxy-4-((5-(trifluoromethyl)pyrimidin-2-yl)amino)piperidin-1-yl)sulfonyl)phenyl)picolinamide was synthesized from (3S,4R)-1-((4-bromophenyl)sulfonyl)-4-((5-(trifluoromethyl)pyrimidin-2-yl)amino)piperidin-3-ol and 4-bromopicolinamide via the one-pot Miyaura/Suzuki procedure described in Example 33. MS: (ES) m/z calculated for C$_{22}$H$_{22}$F$_3$N$_6$O$_4$S [M+H]$^+$ 523.1, found 523.0. $^1$H NMR (400 MHz, DMSO-d$_6$) δ 8.77 (d, J=5.1 Hz, 1H), 8.59 (s, 2H), 8.36 (d, J=1.9 Hz, 1H), 8.21 (d, J=2.6 Hz, 1H), 8.12 (d, J=8.2 Hz, 2H), 8.00 (dd, J=5.0, 1.9 Hz, 1H), 7.90 (d, J=8.2 Hz, 2H), 7.76 (d, J=2.7 Hz, 1H), 7.65 (d, J=7.4 Hz, 1H), 5.22-5.14 (m, 1H), 3.95-3.87 (m, 2H), 3.59-3.43 (m, 2H), 2.82-2.74 (m, 1H), 2.72-2.62 (m, 1H), 1.93 (dtd, J=13.7, 10.2, 3.9 Hz, 1H), 1.68 (dt, J=13.4, 4.2 Hz, 1H).

Example 87: [(3S,4R)-1-[4-(4,4,5,5-tetramethyl-1,3,2-dioxaborolan-2-yl)phenyl]sulfonyl-4-[[5-(trifluoromethyl)-2-pyridyl]amino]-3-piperidyl]methanol

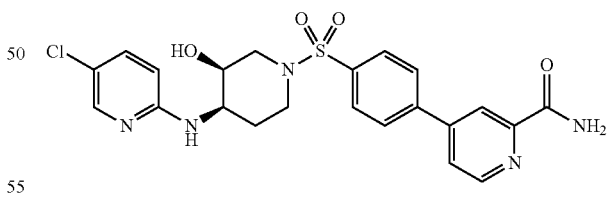

To (3S,4R)-4-amino-1-(4-bromophenyl)sulfonyl-piperidin-3-ol; hydrochloride (250 mg, 0.67 mmol) in 1 mL of NMP is added 5-chloro-2-fluropyridine (200 mg, 1.52 mmol) and DIPEA (270 uL, 1.54 mmol) The mixture is heated at 100° C. for 16 h, then at 120° C. for 24 h. The mixture is diluted with EtOAc (30 mL), washed with H$_2$O (4×15 mL) and brine (30 mL). The organic phase is partitioned, dried with MgSO$_4$, filtered and concentrated. The crude material is purified via SiO$_2$ chromatography (0-100% EtOAc/hexanes) to give (3S,4R)-1-(4-bromophenyl)sulfonyl-4-[(5-chloro-2-pyridyl)amino]piperidin-3-ol.

A solution of [(3S,4R)-1-(4-bromophenyl)sulfonyl-4-[[5-(trifluoromethyl)-2-pyridyl]amino]-3-piperidyl]methanol, Bis-pinacolatodiboron (90 mg; 0.35 mmol), KOAc (35 mg; 0.36 mmol) and Pd(dppf)Cl$_2$ (3 mg, 0.004 mmol) in 2 mL of dioxane is degassed with N$_2$ bubbling for 30 min. The mixture is heated for 1 h at 100° C. The mixture is diluted with 0.5 mL of H$_2$O and degassed for 10 min. To this is added K$_2$CO$_3$ (55 mg, 0.37 mmol), 4-bromopyridine-2-carboxamide (38 mg, 0.18 mmol) and Pd(dppf)Cl$_2$·DCM (12 mg, 0.02 mmol). The mixture is heated at 110° C. for 16 h. The reaction is cooled to room temperature, concentrated and the residue purified by column chromatography on silica gel (0-100% EtOAc/hexanes) to give impure material. This residue is purified by preparative thin-layer chromatography on silica (1 mm, 5% MeOH/CH$_2$Cl$_2$) to give [(3S,4R)-1-[4-(4,4,5,5-tetramethyl-1,3,2-dioxaborolan-2-yl)phenyl]sulfonyl-4-[[5-(trifluoromethyl)-2-pyridyl]amino]-3-piperidyl]methanol. MS: (ES) m/z calculated for C$_{22}$H$_{22}$C$_1$N$_5$O$_4$S [M+H]$^+$ 490.1, found 490.0. $^1$H NMR (400 MHz, DMSO-d$_6$) δ 8.77 (d, J=5.2 Hz, 1H), 8.37 (d, J=1.9 Hz, 1H), 8.22 (d, J=2.6 Hz, 1H), 8.12 (d, J=8.1 Hz, 2H), 8.01 (dd, J=5.2, 1.9 Hz, 1H), 7.94-7.85 (m, 3H), 7.77 (d, J=2.6 Hz, 1H), 7.38 (dd, J=9.0, 2.7 Hz, 1H), 6.61 (d, J=9.0 Hz, 1H), 6.49 (dd, J=8.9, 2.9 Hz, 1H), 5.18 (d, J=5.4 Hz, 1H), 3.90-3.74 (m, 2H), 3.56-3.45 (m, 2H), 2.78-2.68 (m, 1H), 2.68-2.57 (m, 1H), 1.94-1.77 (m, 1H), 1.69-1.60 (m, 1H).

Example 88: 1-(4-(4-(((3S,4R)-3-hydroxy-4-((5-(trifluoromethyl)pyridin-2-yl)amino)piperidin-1-yl)sulfonyl)phenyl)pyridin-2-yl)piperazin-2-one

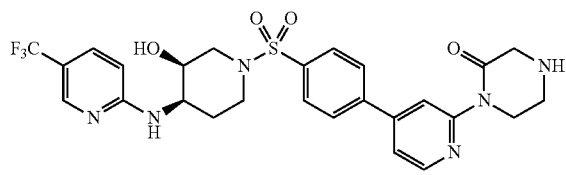 [SMILES: O=C1CNCCN1c1cc(-c2ccc(S(=O)(=O)N3CC[C@@H](Nc4ccc(C(F)(F)F)cn4)[C@@H](O)C3)cc2)ccn1]

To (3S,4R)-1-((4-bromophenyl)sulfonyl)-4-((5-(trifluoromethyl)pyridin-2-yl)amino)piperidin-3-ol (50 mg, 0.11 mmol) were added bis(pinacolato)diboron (32 mg, 0.12 mmol), KOAc (33 mg, 0.33 mmol), dioxane (1 mL) and Pd(dppf)Cl$_2$·DCM (2 mg, 0.0021 mmol) in a septum-cap vial. The mixture was sparged with nitrogen for 5 minutes. The vial was sealed, the mixture stirred at 100° C. for 1 h and cooled when the reaction had proceeded to completion. To the mixture were added K$_2$CO$_3$ (40 mg, 0.30 mmol), tert-butyl 4-(4-bromopyridin-2-yl)-3-oxopiperazine-1-carboxylate (39 mg, 0.11 mmol), dioxane (2 mL), water (1 mL), and Pd(dppf)Cl$_2$·DCM (9.0 mg, 0.011 mmol). The mixture was sparged with nitrogen for 5 minutes. The vial was sealed, the mixture stirred at 100° C. for 16 hours, and cooled when the reaction had proceeded to completion. The mixture was purified via SiO$_2$ gel chromatography to give tert-butyl 4-(4-(4-(((3S,4R)-3-hydroxy-4-((5-(trifluoromethyl)pyridin-2-yl)amino)piperidin-1-yl)sulfonyl)phenyl)pyridin-2-yl)-3-oxopiperazine-1-carboxylate (34 mg, yield: 29.6%). MS: (ES) m/z calculated for C$_{26}$H$_{28}$F$_3$N$_6$O$_4$S [M−Boc]$^+$ 577.2, found 577.2.

To a vial containing tert-butyl 4-(4-(4-(((3S,4R)-3-hydroxy-4-((5-(trifluoromethyl)pyridin-2-yl)amino)piperidin-1-yl)sulfonyl)phenyl)pyridin-2-yl)-3-oxopiperazine-1-carboxylate (34 mg, 0.05 mmol) in CH$_2$Cl$_2$ (0.5 mL) was added trifluoroacetic acid (0.5 mL). The mixture was stirred at rt for 1 h till the reaction had proceeded to completion. The reaction mixture was concentrated to dryness and purified by preparative reverse-phase HPLC to give 1-(4-(4-(((3S,4R)-3-hydroxy-4-((5-(trifluoromethyl)pyridin-2-yl)amino)piperidin-1-yl)sulfonyl)phenyl)pyridin-2-yl)piperazin-2-one. MS: (ES) m/z calculated for C$_{26}$H$_{28}$F$_3$N$_6$O$_4$S [M+H]$^+$ 577.2, found 577.2. $^1$H NMR (400 MHz, Methanol-d$_4$) δ 8.60 (d, J=4.0 Hz, 1H), 8.25 (s, 1H), 8.18 (s, 1H), 8.02-7.94 (m, 4H), 7.70-7.62 (m, 2H), 6.78 (d, J=9.2 Hz, 1H), 4.33 (dd, J=6.5, 4.8 Hz, 2H), 4.10 (s, 2H), 3.95-3.87 (m, 2H), 3.77-3.68 (m, 4H), 2.85-2.65 (m, 2H), 2.10-1.95 (m, 1H), 1.88-1.78 (m, 1H).

Example 89: (3S,4R)-1-((4-(6-morpholinopyridin-3-yl)phenyl)sulfonyl)-4-((5-(trifluoromethyl)pyridin-2-yl)amino)piperidin-3-ol

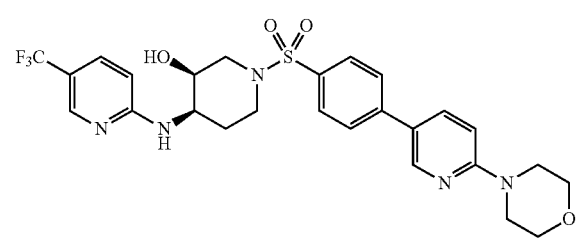 [SMILES: O=S(=O)(c1ccc(-c2ccc(N3CCOCC3)nc2)cc1)N1CC[C@@H](Nc2ccc(C(F)(F)F)cn2)[C@@H](O)C1]

To a vial containing (3S,4R)-1-((4-bromophenyl)sulfonyl)-4-((5-(trifluoromethyl)pyridin-2-yl)amino)piperidin-3-ol (1 g, 2.09 mmol) and (6-fluoropyridin-3-yl)boronic acid (360 mg, 2.56 mmol) in H$_2$O (3 mL) and dioxane (6 mL) was added potassium carbonate (860 mg, 6.23 mmol). The mixture was degassed with N$_2$ for 10 min and Pd(dppf)Cl$_2$-dichloromethane complex (160 mg, 0.20 mmol) was added. The contents were heated at 105° C. for 2 h, then extracted with EtOAc. The combined organic layers were dried with sodium sulfate, filtered and concentrated. The crude material was purified by silica gel column chromatography to give (3S,4R)-1-((4-(6-fluoropyridin-3-yl)phenyl)sulfonyl)-4-((5-(trifluoromethyl)pyridin-2-yl)amino)piperidin-3-ol.

To a vial containing (3S,4R)-1-((4-(6-fluoropyridin-3-yl)phenyl)sulfonyl)-4-((5-(trifluoromethyl)pyridin-2-yl)amino)piperidin-3-ol (75 mg, 0.15 mmol) in NMP (0.5 mL) was added morpholine (66 mg, 0.75 mmol). The contents were heated to 130° C. for 2 h and then purified by silica gel column chromatography followed by preparative HPLC to yield (3S,4R)-1-((4-(6-morpholinopyridin-3-yl)phenyl)sulfonyl)-4-((5-(trifluoromethyl)pyridin-2-yl)amino)piperidin-3-ol. MS: (ES) m/z calculated for C$_{26}$H$_{29}$F$_3$N$_5$O$_4$S [M+H]$^+$ 564.2, found 564.2. $^1$H NMR (400 MHz, CD$_3$OD) δ 8.49 (d, J=2.5 Hz, 1H), 8.15 (d, J=2.4 Hz, 1H), 8.00-7.92 (m, 1H), 7.88-7.81 (m, 4H), 7.54 (dd, J=9.0, 2.5 Hz, 1H), 6.94 (d, J=8.9 Hz, 1H), 6.62 (d, J=8.9 Hz, 1H), 3.99 (bs, 1H), 3.92 (dd, J=10.5, 3.9 Hz, 1H), 3.81 (dd, J=4.8, 4.8 Hz, 4H), 3.67 (t, J=12.9 Hz, 2H), 3.57 (dd, J=4.8, 4.8 Hz, 4H), 2.76 (dd, J=12.4, 2.1 Hz, 1H), 2.64 (ddd, J=12.0, 12.0, 3.2 Hz, 1H), 2.00 (dddd, J=10.8, 10.8, 10.8, 4.0 Hz, 1H), 1.80 (dd, J=13.3, 4.1 Hz, 1H).

Example 90: (3S,4R)-1-((4-(2-(pyrrolidin-1-yl)pyridin-4-yl)phenyl)sulfonyl)-4-((5-(trifluoromethyl)pyridin-2-yl)amino)piperidin-3-ol

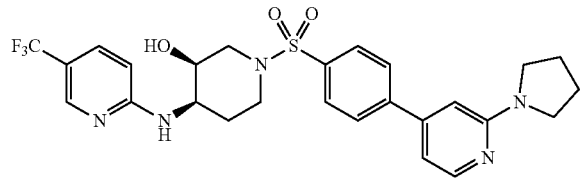 [SMILES: O=S(=O)(c1ccc(-c2ccnc(N3CCCC3)c2)cc1)N1CC[C@@H](Nc2ccc(C(F)(F)F)cn2)[C@@H](O)C1]

To a septum-cap vial equipped with stir bar were added (3S,4R)-1-((4-bromophenyl)sulfonyl)-4-((5-(trifluoromethyl)pyridin-2-yl)amino)piperidin-3-ol (0.50 g, 1.0 mmol), (2-fluoropyridin-4-yl)boronic acid (0.15 g, 1.0 mmol), $K_2CO_3$ (0.43 g, 3.1 mmol), and Pd(dppf)Cl$_2$·DCM (0.085 g, 0.10 mmol) followed by 3.0 mL of 4:1 dioxane:H$_2$O. The reaction mixture was sparged with N$_2$ for 20 min and then heated to 100° C. for 1 h. Once complete, the reaction was cooled and the contents were adhered to Celite and the product was isolated using SiO$_2$ chromatography (hexanes/ethyl acetate) to yield (3S,4R)-1-((4-(2-fluoropyridin-4-yl)phenyl)sulfonyl)-4-((5-(trifluoromethyl)pyridin-2-yl)amino)piperidin-3-ol. MS: (ES) m/z calculated for $C_{22}H_{21}F_4N_4O_3S$ [M+H]$^+$ 497.1, found 497.0.

To a septum-cap vial equipped with stir bar were added (3S,4R)-1-((4-(2-fluoropyridin-4-yl)phenyl)sulfonyl)-4-((5-(trifluoromethyl)pyridin-2-yl)amino)piperidin-3-ol (0.050 g, 0.10 mmol) followed by 1.5 mL NMP and pyrrolidine (0.072 g, 1.0 mmol). The reaction mixture was heated to 150° C. and stirred for 16 h. Once complete, reaction was cooled to RT, quenched with water, extracted with EtOAc, and purified via reverse phase HPLC to yield (3S,4R)-1-((4-(2-(pyrrolidin-1-yl)pyridin-4-yl)phenyl)sulfonyl)-4-((5-(trifluoromethyl)pyridin-2-yl)amino)piperidin-3-ol. MS: (ES) m/z calculated for $C_{26}H_{29}F_3N_5O_3S$ [M+H]$^+$ 548.2, found 548.0; $^1$H NMR (400 MHz, DMSO-d$_6$) δ 8.20 (s, 1H), 8.16 (d, J=5.5 Hz, 1H), 8.02 (d, J=8.1 Hz, 2H), 7.86 (d, J=8.2 Hz, 2H), 7.58 (dd, J=9.0, 2.2 Hz, 1H), 7.10 (d, J=7.1 Hz, 1H), 6.95 (d, J=3.3 Hz, 1H), 6.82 (bs, 1H), 6.69 (d, J=9.0 Hz, 1H), 5.22 (bs, 1H), 3.95-3.83 (m, 2H), 3.58-3.45 (m, 6H), 2.72 (d, J=11.5 Hz, 1H), 2.60 (t, J=11.5 Hz, 1H), 2.03-1.94 (m, 4H), 1.87 (m, 1H), 1.66 (m, 1H).

Biological Example 1: Migration Assay

A chemotaxis assay can be used to determine the efficacy of potential receptor antagonists at blocking the migration mediated through chemokine receptors, such as CCR6. This assay is routinely performed using the ChemoTX® microchamber system with a 5-μm pore-sized polycarbonate membrane. Chemokine receptor-expressing cells are required for such an assay. In this case, Ba/F3 cells (Palacios et al., Nature, 309:126, 1984) transfected with the gene for human CCR6 under control of the CMV promotor were used. To begin such an assay, hCCR6-transfected Ba/F$_3$ cells are first grown for 24 hr in medium supplemented with sodium butyrate, which increases CCR6 transcription via the CMV promotor. The prepared Ba/F$_3$ cells, are collected by centrifugation at 400×g at room temperature, then suspended at 4 million/ml in human serum. The compound being tested is serially diluted from a maximum final concentration of 1 μM (or an equivalent volume of its solvent (DMSO)) and is then added to the cell/serum mixture. Separately, recombinant human CCL20 (MIP-3α/LARC) at its EC$_{50}$ concentration (10 nM) is placed in the lower wells of the ChemoTX® plate. The 5-μm (pore size) polycarbonate membrane is placed onto the plate, and 20 μL of the cell/compound mixture is transferred onto each well of the membrane. The plates are incubated at 37° C. for 45 minutes, after which the polycarbonate membranes are removed and 5 μl of the DNA-intercalating dye CyQUANT (Invitrogen, Carlsbad, CA) is added to the lower wells. The amount of fluorescence, corresponding to the number of migrated cells, is measured using a Spectrafluor Plus plate reader (TECAN, San Jose, CA).

Compounds in Tables 1-3 having an IC$_{50}$ value in the migration assay of less than 1 nM are labeled (+++); from 1-10 nM are labeled (++); and less than or equal to 1000 nM but above 10 nM are labeled (+).

TABLE 1

| Compound | Structure | m/z | Potency |
|---|---|---|---|
| 1 | ![structure] | 533.2 | +++ |
| 2 | ![structure] | 547.2 | +++ |

TABLE 1-continued
| Compound | Structure | m/z | Potency |
|---|---|---|---|
| 3 | 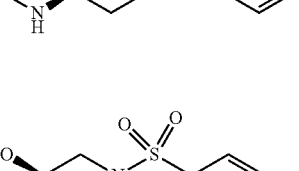 | 547.2 | +++ |
| 4 | 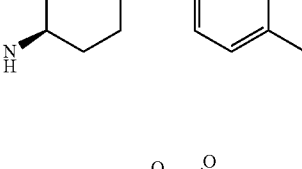 | 562.2 | +++ |
| 5 | 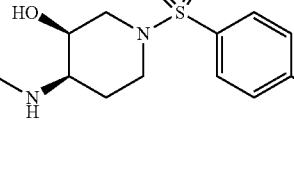 | 546.2 | +++ |
| 6 | 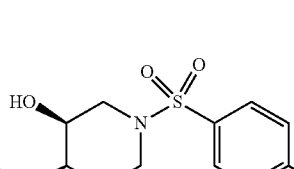 | 536.1 | +++ |
| 7 | 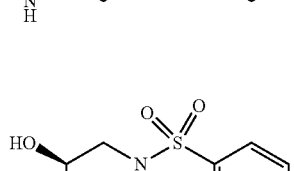 | 522.2 | +++ |
| 8 | 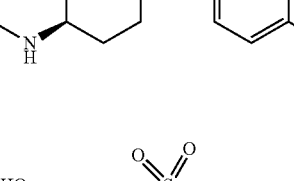 | 547.2 | +++ |
| 9 | 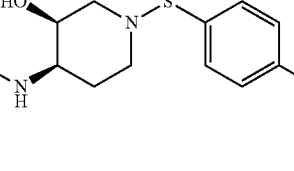 | 533.1 | +++ |

TABLE 1-continued
| Compound | Structure | m/z | Potency |
|---|---|---|---|
| 10 | 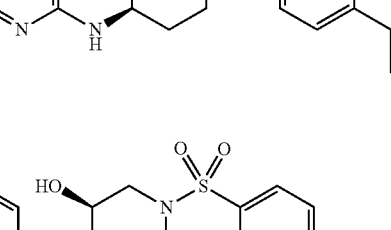 | 509.1 | ++ |
| 11 | 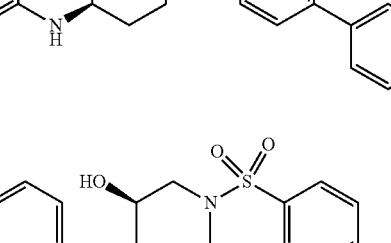 | 561.2 | +++ |
| 12 | 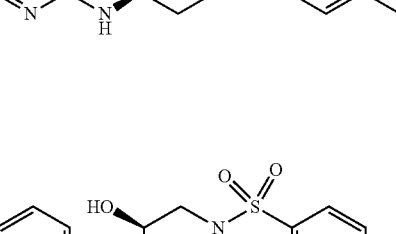 | 533.1 | +++ |
| 13 | 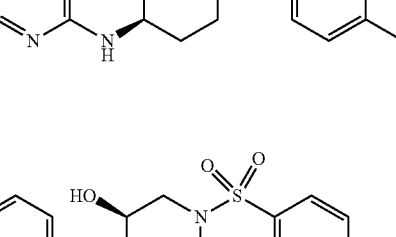 | 534.1 | +++ |
| 14 | 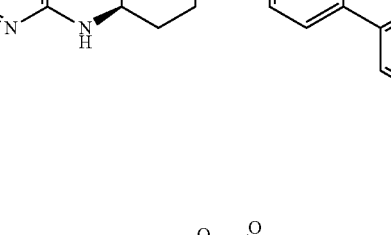 | 548.2 | +++ |
| 15 | 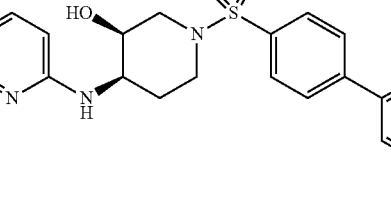 | 563.2 | +++ |

TABLE 1-continued

| Compound | Structure | m/z | Potency |
|---|---|---|---|
| 16 | 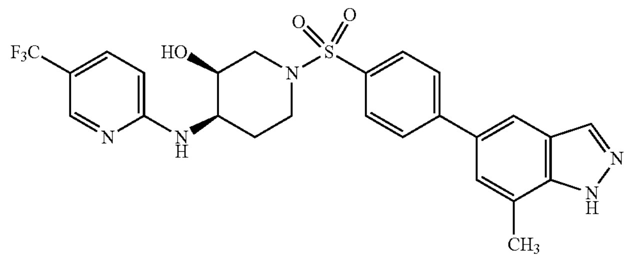 [SMILES: Cc1cc(-c2ccc(S(=O)(=O)N3CC[C@@H](Nc4ccc(C(F)(F)F)cn4)[C@@H](O)C3)cc2)cc2cn[nH]c12] | 532.2 | +++ |
| 17 | 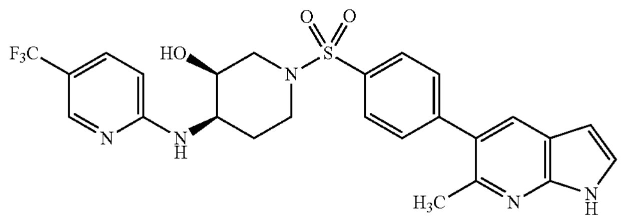 [SMILES: Cc1nc2[nH]ccc2cc1-c1ccc(S(=O)(=O)N2CC[C@@H](Nc3ccc(C(F)(F)F)cn3)[C@@H](O)C2)cc1] | 532.0 | ++ |
| 18 | 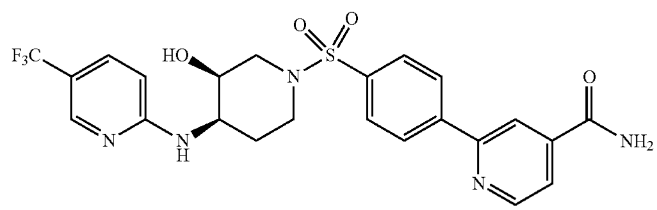 [SMILES: NC(=O)c1ccnc(-c2ccc(S(=O)(=O)N3CC[C@@H](Nc4ccc(C(F)(F)F)cn4)[C@@H](O)C3)cc2)c1] | 522.2 | ++ |
| 19 | 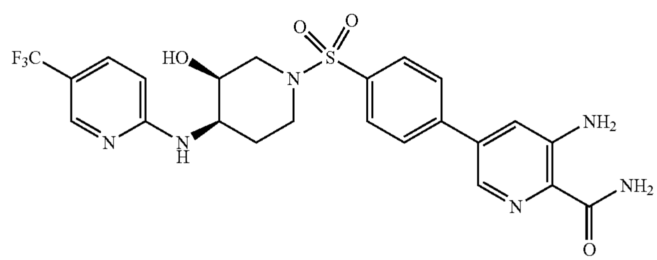 [SMILES: NC(=O)c1ncc(-c2ccc(S(=O)(=O)N3CC[C@@H](Nc4ccc(C(F)(F)F)cn4)[C@@H](O)C3)cc2)cc1N] | 537.2 | ++ |
| 20 | 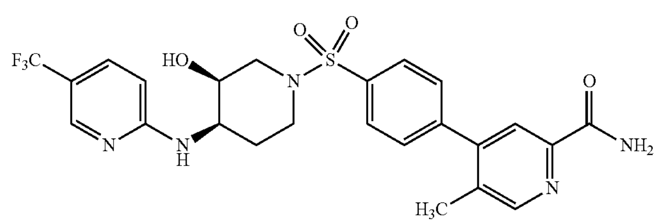 | 536.1 | +++ |
| 21 | 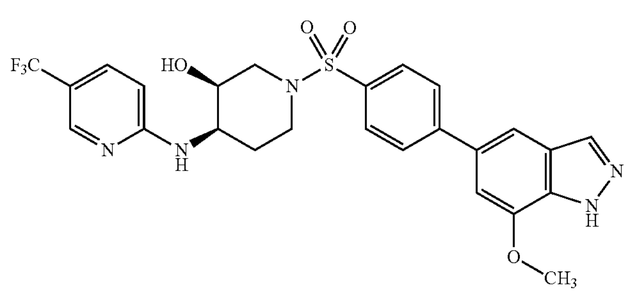 [SMILES: COc1cc(-c2ccc(S(=O)(=O)N3CC[C@@H](Nc4ccc(C(F)(F)F)cn4)[C@@H](O)C3)cc2)cc2cn[nH]c12] | 548.1 | +++ |

TABLE 1-continued

| Compound | Structure | m/z | Potency |
|---|---|---|---|
| 22 | 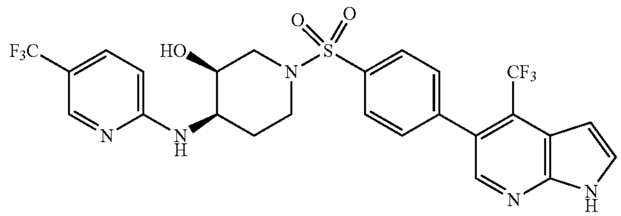 [SMILES: O=S(=O)(c1ccc(-c2cnc3[nH]ccc3c2C(F)(F)F)cc1)N1CC[C@@H](Nc2ccc(C(F)(F)F)cn2)[C@@H](O)C1] | 586.0 | +++ |
| 23 | 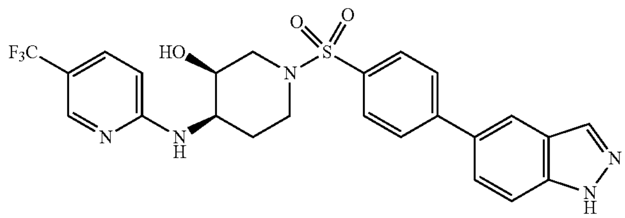 [SMILES: O=S(=O)(c1ccc(-c2ccc3[nH]ncc3c2)cc1)N1CC[C@@H](Nc2ccc(C(F)(F)F)cn2)[C@@H](O)C1] | 517.9 | +++ |
| 24 | 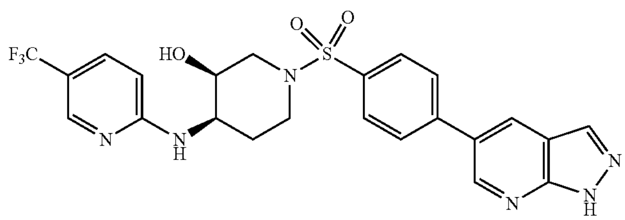 [SMILES: O=S(=O)(c1ccc(-c2cnc3[nH]ncc3c2)cc1)N1CC[C@@H](Nc2ccc(C(F)(F)F)cn2)[C@@H](O)C1] | 517.9 | +++ |
| 25 | 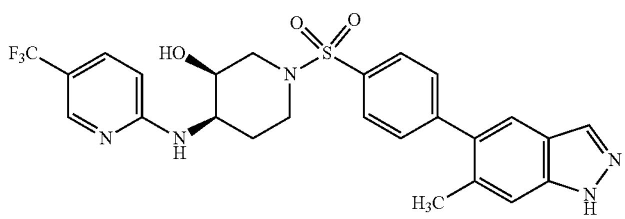 [SMILES: Cc1cc2[nH]ncc2cc1-c1ccc(S(=O)(=O)N2CC[C@@H](Nc3ccc(C(F)(F)F)cn3)[C@@H](O)C2)cc1] | 531.9 | ++ |
| 26 | 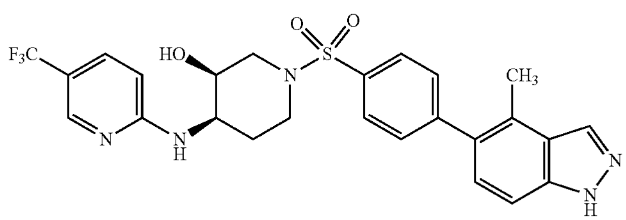 [SMILES: Cc1c(-c2ccc(S(=O)(=O)N3CC[C@@H](Nc4ccc(C(F)(F)F)cn4)[C@@H](O)C3)cc2)ccc2[nH]ncc12] | 531.9 | +++ |
| 27 | 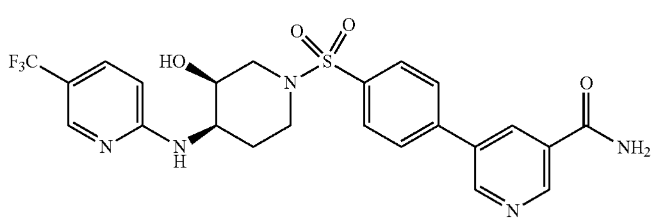 [SMILES: NC(=O)c1cncc(-c2ccc(S(=O)(=O)N3CC[C@@H](Nc4ccc(C(F)(F)F)cn4)[C@@H](O)C3)cc2)c1] | 521.9 | ++ |
| 28 | 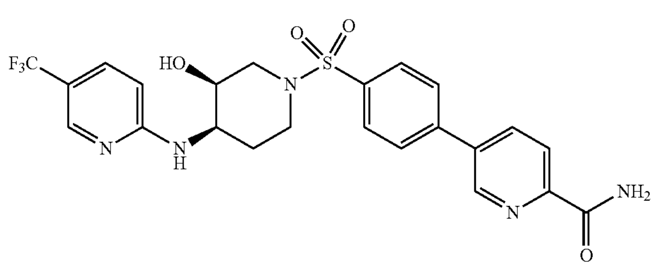 [SMILES: NC(=O)c1ccc(-c2ccc(S(=O)(=O)N3CC[C@@H](Nc4ccc(C(F)(F)F)cn4)[C@@H](O)C3)cc2)cn1] | 521.9 | +++ |

TABLE 1-continued

| Compound | Structure | m/z | Potency |
|---|---|---|---|
| 29 | 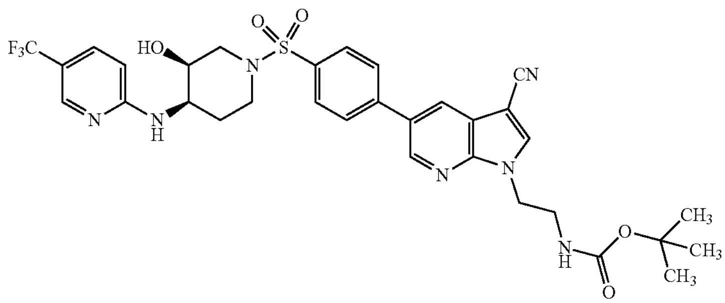 [SMILES: CC(C)(C)OC(=O)NCCn1cc(C#N)c2cc(-c3ccc(S(=O)(=O)N4CC[C@@H](Nc5ccc(C(F)(F)F)cn5)[C@@H](O)C4)cc3)cnc21] | 685.9 | +++ |
| 30 | 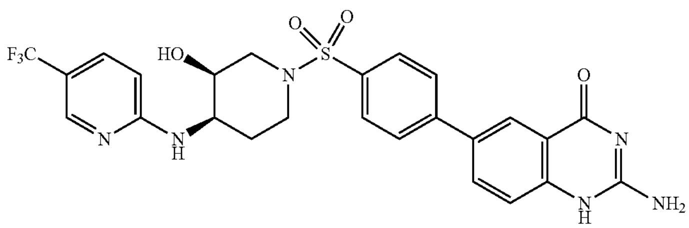 [SMILES: Nc1nc(=O)c2cc(-c3ccc(S(=O)(=O)N4CC[C@@H](Nc5ccc(C(F)(F)F)cn5)[C@@H](O)C4)cc3)ccc2[nH]1] | 561.3 | +++ |
| 31 | 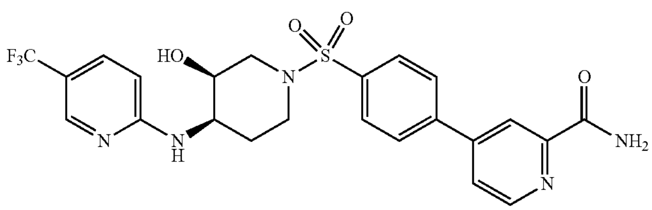 | 522.3 | +++ |
| 32 | 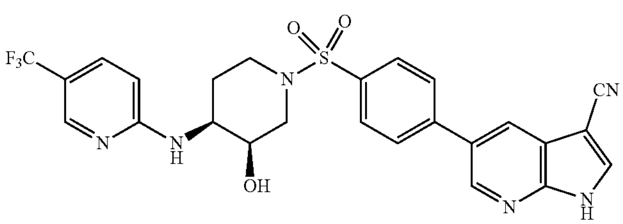 [SMILES: N#Cc1c[nH]c2ncc(-c3ccc(S(=O)(=O)N4CC[C@H](Nc5ccc(C(F)(F)F)cn5)[C@H](O)C4)cc3)cc12] | 543.3 | ++ |
| 33 | 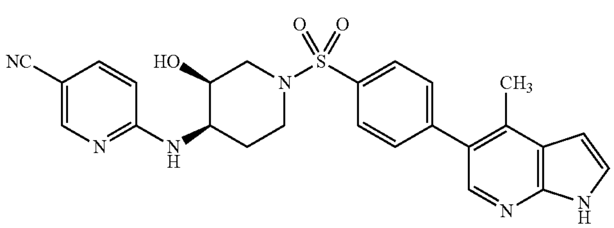 [SMILES: Cc1c(-c2ccc(S(=O)(=O)N3CC[C@@H](Nc4ccc(C#N)cn4)[C@@H](O)C3)cc2)cnc2[nH]ccc12] | 489.2 | +++ |
| 34 | 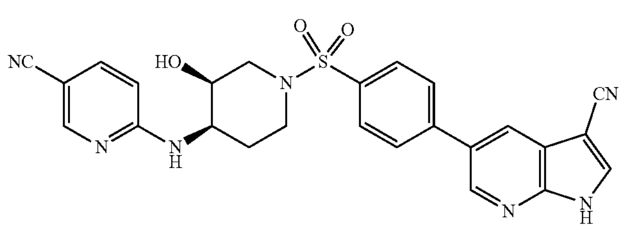 [SMILES: N#Cc1ccc(N[C@@H]2CCN(S(=O)(=O)c3ccc(-c4cnc5[nH]cc(C#N)c5c4)cc3)C[C@@H]2O)nc1] | 500.1 | +++ |

TABLE 1-continued

| Compound | Structure | m/z | Potency |
|---|---|---|---|
| 35 | 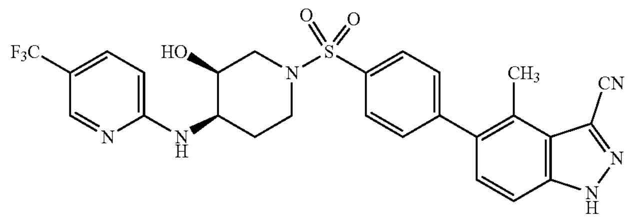 [SMILES: Cc1c(-c2ccc(S(=O)(=O)N3CC[C@@H](Nc4ccc(C(F)(F)F)cn4)[C@@H](O)C3)cc2)ccc2[nH]nc(C#N)c12] | 557.1 | +++ |
| 36 | 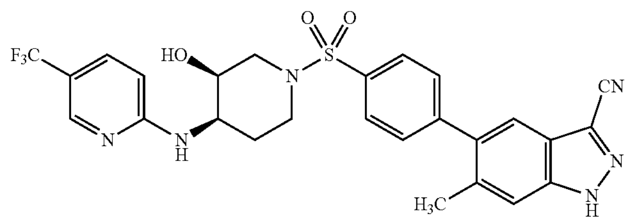 [SMILES: Cc1cc2[nH]nc(C#N)c2cc1-c1ccc(S(=O)(=O)N2CC[C@@H](Nc3ccc(C(F)(F)F)cn3)[C@@H](O)C2)cc1] | 557.1 | +++ |
| 37 | 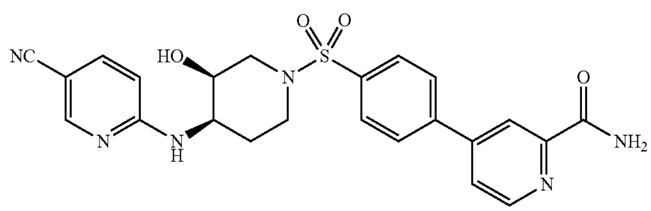 [SMILES: N#Cc1ccc(N[C@@H]2CCN(S(=O)(=O)c3ccc(-c4ccnc(C(N)=O)c4)cc3)C[C@@H]2O)nc1] | 479.0 | +++ |
| 38 | 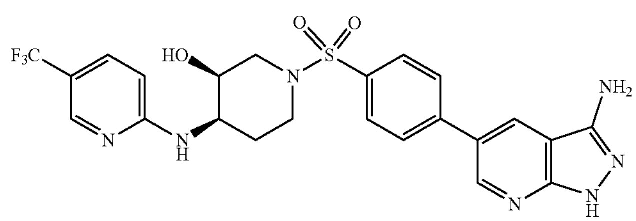 [SMILES: Nc1n[nH]c2ncc(-c3ccc(S(=O)(=O)N4CC[C@@H](Nc5ccc(C(F)(F)F)cn5)[C@@H](O)C4)cc3)cc12] | 534.2 | +++ |
| 39 | 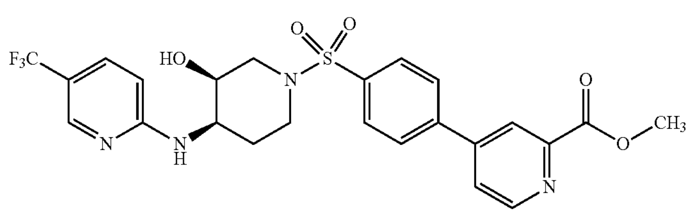 [SMILES: COC(=O)c1cc(-c2ccc(S(=O)(=O)N3CC[C@@H](Nc4ccc(C(F)(F)F)cn4)[C@@H](O)C3)cc2)ccn1] | 537.2 | +++ |
| 40 | 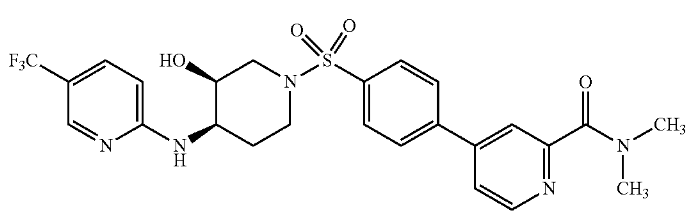 [SMILES: CN(C)C(=O)c1cc(-c2ccc(S(=O)(=O)N3CC[C@@H](Nc4ccc(C(F)(F)F)cn4)[C@@H](O)C3)cc2)ccn1] | 550.1 | ++ |
| 41 | 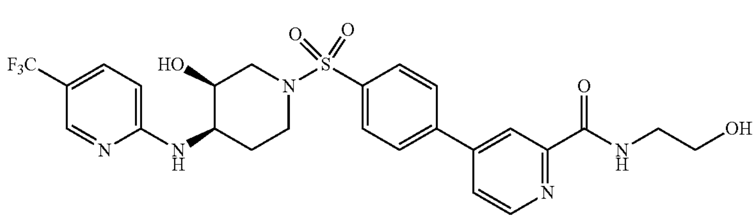 [SMILES: O=C(NCCO)c1cc(-c2ccc(S(=O)(=O)N3CC[C@@H](Nc4ccc(C(F)(F)F)cn4)[C@@H](O)C3)cc2)ccn1] | 566.2 | +++ |

TABLE 1-continued

| Compound | Structure | m/z | Potency |
|---|---|---|---|
| 42 | 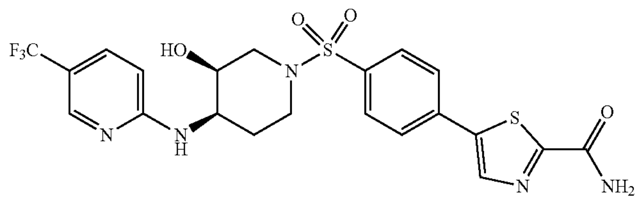 [SMILES: NC(=O)c1ncc(-c2ccc(S(=O)(=O)N3CC[C@@H](Nc4ccc(C(F)(F)F)cn4)[C@@H](O)C3)cc2)s1] | 528.1 | +++ |
| 43 | 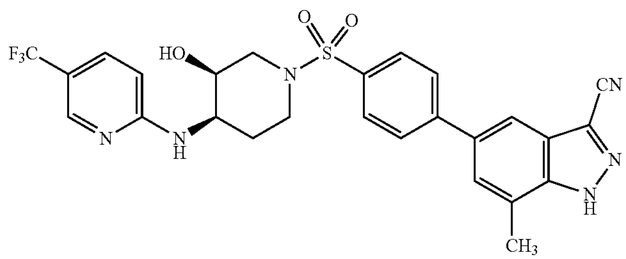 [SMILES: Cc1cc(-c2ccc(S(=O)(=O)N3CC[C@@H](Nc4ccc(C(F)(F)F)cn4)[C@@H](O)C3)cc2)cc2c(C#N)n[nH]c12] | 557.1 | +++ |
| 44 | 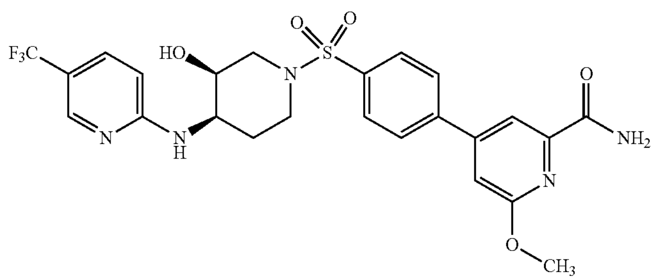 [SMILES: COc1cc(-c2ccc(S(=O)(=O)N3CC[C@@H](Nc4ccc(C(F)(F)F)cn4)[C@@H](O)C3)cc2)cc(C(N)=O)n1] | 552.2 | +++ |
| 45 | 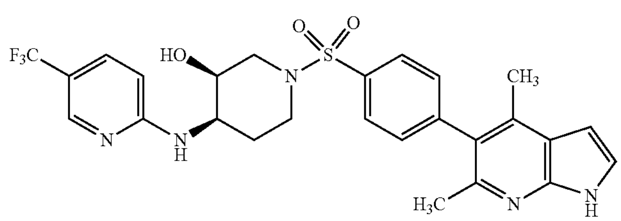 [SMILES: Cc1nc2[nH]ccc2c(C)c1-c1ccc(S(=O)(=O)N2CC[C@@H](Nc3ccc(C(F)(F)F)cn3)[C@@H](O)C2)cc1] | 546.2 | +++ |
| 46 | 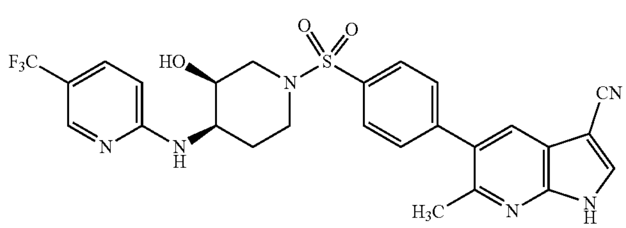 [SMILES: Cc1nc2[nH]cc(C#N)c2cc1-c1ccc(S(=O)(=O)N2CC[C@@H](Nc3ccc(C(F)(F)F)cn3)[C@@H](O)C2)cc1] | 557.2 | +++ |
| 47 | 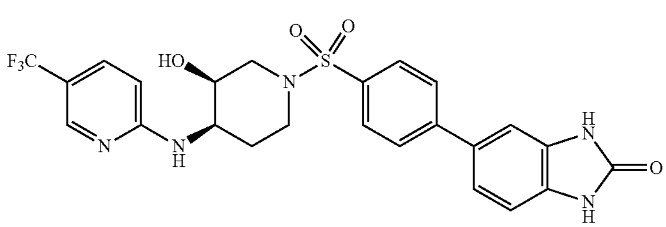 [SMILES: O=c1[nH]c2ccc(-c3ccc(S(=O)(=O)N4CC[C@@H](Nc5ccc(C(F)(F)F)cn5)[C@@H](O)C4)cc3)cc2[nH]1] | 534.2 | +++ |

TABLE 1-continued

| Compound | Structure | m/z | Potency |
|---|---|---|---|
| 48 | 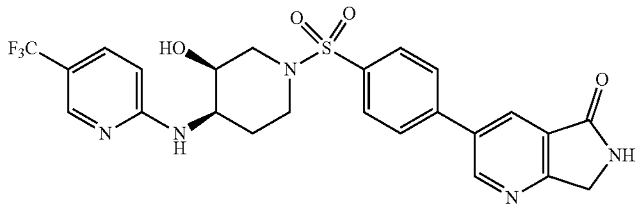 [SMILES: O=C1NCc2ncc(-c3ccc(S(=O)(=O)N4CC[C@@H](Nc5ccc(C(F)(F)F)cn5)[C@@H](O)C4)cc3)cc21] | 534.2 | +++ |
| 49 | 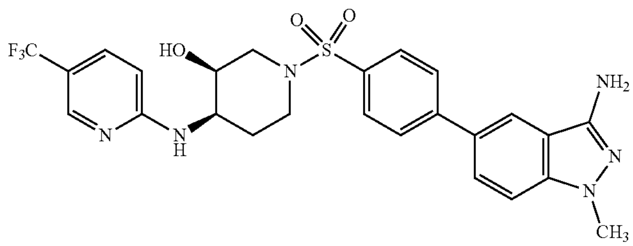 [SMILES: Cn1nc(N)c2cc(-c3ccc(S(=O)(=O)N4CC[C@@H](Nc5ccc(C(F)(F)F)cn5)[C@@H](O)C4)cc3)ccc21] | 547.2 | +++ |
| 50 | 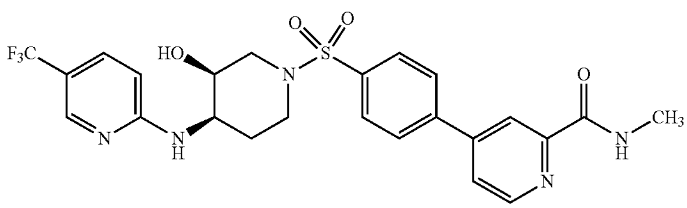 [SMILES: CNC(=O)c1cc(-c2ccc(S(=O)(=O)N3CC[C@@H](Nc4ccc(C(F)(F)F)cn4)[C@@H](O)C3)cc2)ccn1] | 536.1 | +++ |
| 51 | 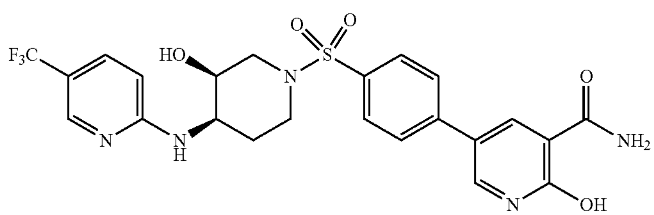 [SMILES: NC(=O)c1cc(-c2ccc(S(=O)(=O)N3CC[C@@H](Nc4ccc(C(F)(F)F)cn4)[C@@H](O)C3)cc2)cnc1O] | 538.0 | +++ |
| 52 | 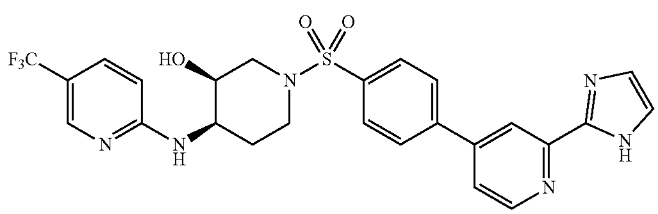 [SMILES: O=S(=O)(c1ccc(-c2ccnc(-c3ncc[nH]3)c2)cc1)N1CC[C@@H](Nc2ccc(C(F)(F)F)cn2)[C@@H](O)C1] | 545.1 | +++ |
| 53 | 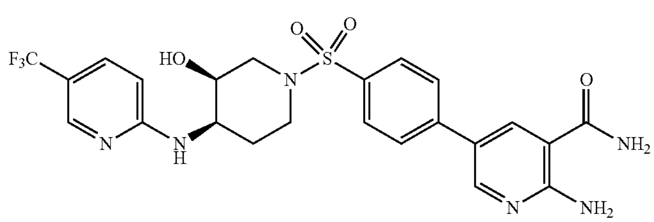 [SMILES: NC(=O)c1cc(-c2ccc(S(=O)(=O)N3CC[C@@H](Nc4ccc(C(F)(F)F)cn4)[C@@H](O)C3)cc2)cnc1N] | 537.2 | +++ |
| 54 | 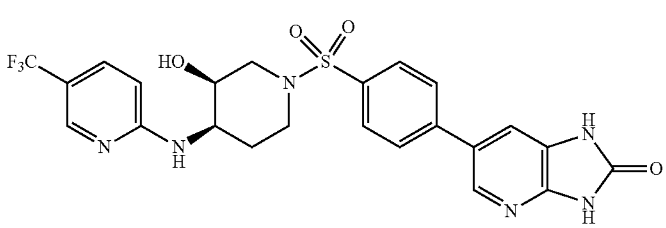 | 535.2 | +++ |

TABLE 1-continued

| Compound | Structure | m/z | Potency |
|---|---|---|---|
| 55 | 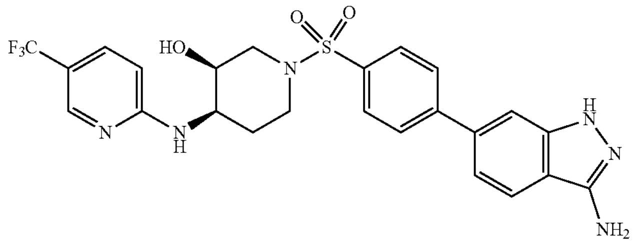 [SMILES: Nc1n[nH]c2cc(-c3ccc(S(=O)(=O)N4CC[C@@H](Nc5ccc(C(F)(F)F)cn5)[C@@H](O)C4)cc3)ccc12] | 533.1 | +++ |
| 56 | 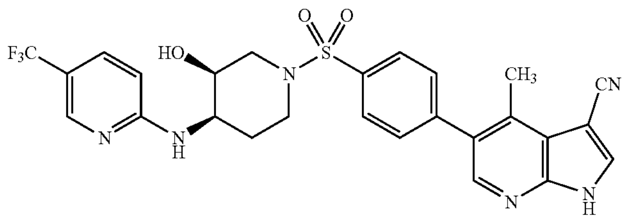 [SMILES: Cc1c(-c2ccc(S(=O)(=O)N3CC[C@@H](Nc4ccc(C(F)(F)F)cn4)[C@@H](O)C3)cc2)cnc2[nH]cc(C#N)c12] | 557.1 | +++ |
| 57 | 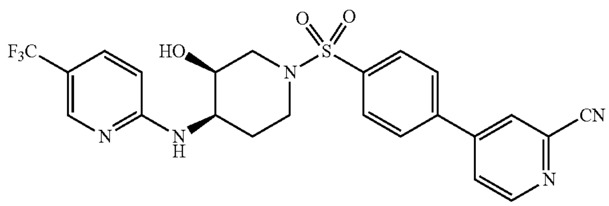 [SMILES: N#Cc1cc(-c2ccc(S(=O)(=O)N3CC[C@@H](Nc4ccc(C(F)(F)F)cn4)[C@@H](O)C3)cc2)ccn1] | 504.0 | +++ |
| 58 | 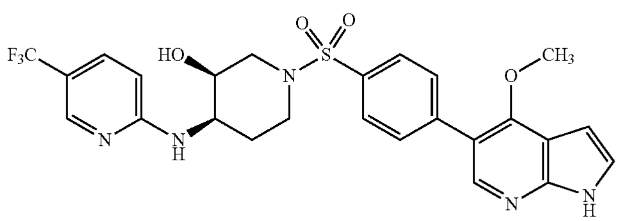 [SMILES: COc1c(-c2ccc(S(=O)(=O)N3CC[C@@H](Nc4ccc(C(F)(F)F)cn4)[C@@H](O)C3)cc2)cnc2[nH]ccc12] | 548.1 | +++ |
| 59 | 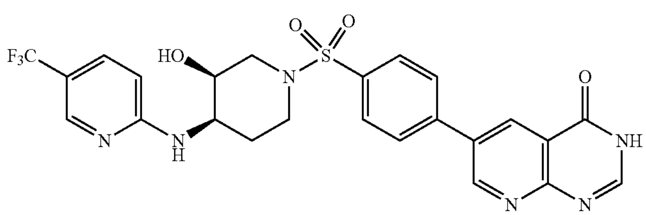 [SMILES: O=c1[nH]cnc2ncc(-c3ccc(S(=O)(=O)N4CC[C@@H](Nc5ccc(C(F)(F)F)cn5)[C@@H](O)C4)cc3)cc12] | 547.2 | +++ |
| 60 | 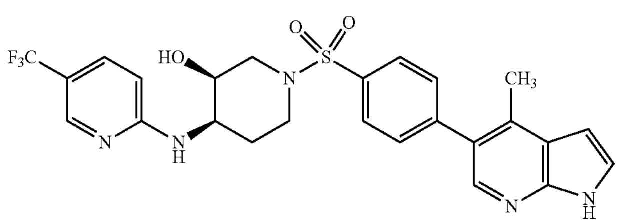 [SMILES: Cc1c(-c2ccc(S(=O)(=O)N3CC[C@@H](Nc4ccc(C(F)(F)F)cn4)[C@@H](O)C3)cc2)cnc2[nH]ccc12] | 532.3 | +++ |
| 61 | 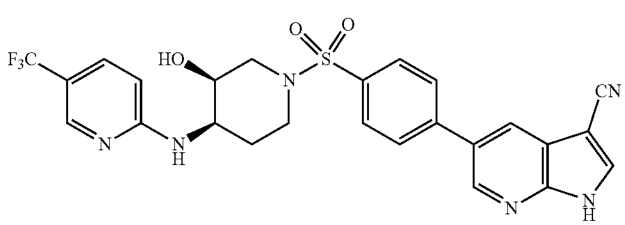 [SMILES: N#Cc1c[nH]c2ncc(-c3ccc(S(=O)(=O)N4CC[C@@H](Nc5ccc(C(F)(F)F)cn5)[C@@H](O)C4)cc3)cc12] | 543.3 | +++ |

TABLE 1-continued

| Compound | Structure | m/z | Potency |
|---|---|---|---|
| 62 | 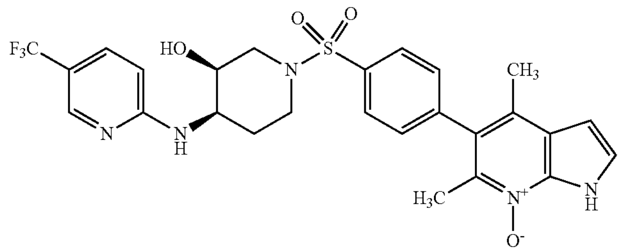 [SMILES: Cc1c(-c2ccc(S(=O)(=O)N3CC[C@@H](Nc4ccc(C(F)(F)F)cn4)[C@@H](O)C3)cc2)c(C)[n+]([O-])c2[nH]ccc12] | 562.2 | +++ |
| 63 | 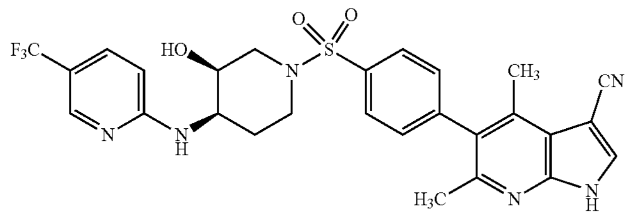 [SMILES: Cc1nc2[nH]cc(C#N)c2c(C)c1-c1ccc(S(=O)(=O)N2CC[C@@H](Nc3ccc(C(F)(F)F)cn3)[C@@H](O)C2)cc1] | 571.2 | +++ |
| 64 | 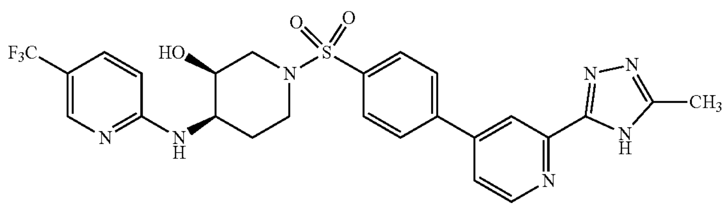 [SMILES: Cc1nnc(-c2cc(-c3ccc(S(=O)(=O)N4CC[C@@H](Nc5ccc(C(F)(F)F)cn5)[C@@H](O)C4)cc3)ccn2)[nH]1] | 560.1 | ++ |
| 65 | 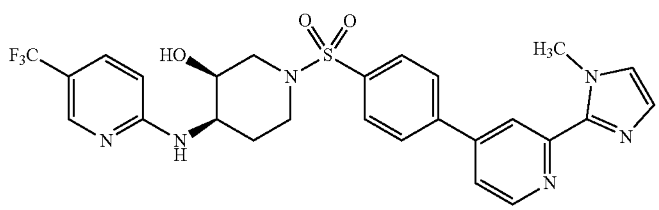 [SMILES: Cn1ccnc1-c1cc(-c2ccc(S(=O)(=O)N3CC[C@@H](Nc4ccc(C(F)(F)F)cn4)[C@@H](O)C3)cc2)ccn1] | 559.2 | + |
| 66 | 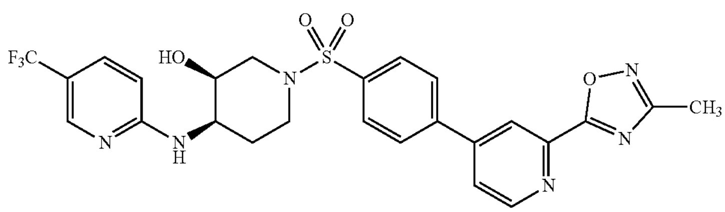 [SMILES: Cc1noc(-c2cc(-c3ccc(S(=O)(=O)N4CC[C@@H](Nc5ccc(C(F)(F)F)cn5)[C@@H](O)C4)cc3)ccn2)n1] | 561.2 | ++ |
| 67 | 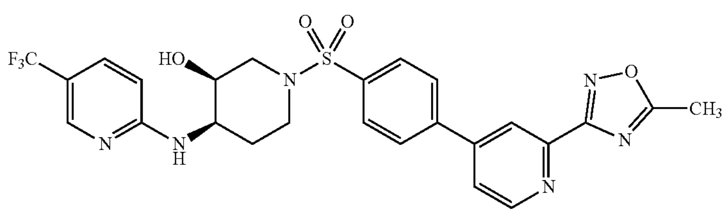 | 561.2 | +++ |
| 68 | 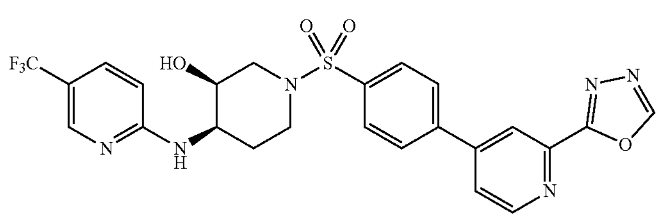 [SMILES: O=S(=O)(c1ccc(-c2ccnc(-c3nnco3)c2)cc1)N1CC[C@@H](Nc2ccc(C(F)(F)F)cn2)[C@@H](O)C1] | 547.2 | +++ |

TABLE 1-continued

| Compound | Structure | m/z | Potency |
|---|---|---|---|
| 69 | 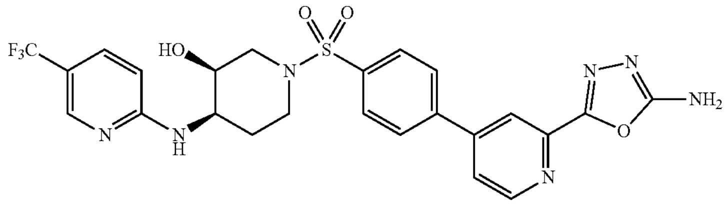 [SMILES: Nc1nnc(-c2cc(-c3ccc(S(=O)(=O)N4CC[C@@H](Nc5ccc(C(F)(F)F)cn5)[C@@H](O)C4)cc3)ccn2)o1] | 562.0 | +++ |
| 70 | 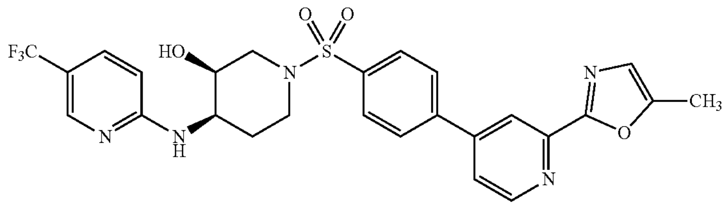 | 560.1 | +++ |
| 71 | 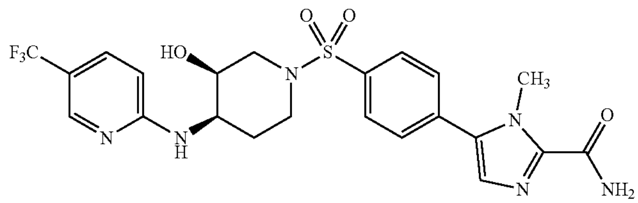 [SMILES: Cn1c(-c2ccc(S(=O)(=O)N3CC[C@@H](Nc4ccc(C(F)(F)F)cn4)[C@@H](O)C3)cc2)cnc1C(N)=O] | 525.2 | +++ |
| 72 | 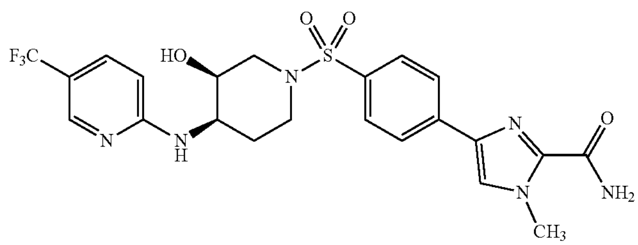 [SMILES: Cn1cc(-c2ccc(S(=O)(=O)N3CC[C@@H](Nc4ccc(C(F)(F)F)cn4)[C@@H](O)C3)cc2)nc1C(N)=O] | 525.2 | ++ |
| 73 | 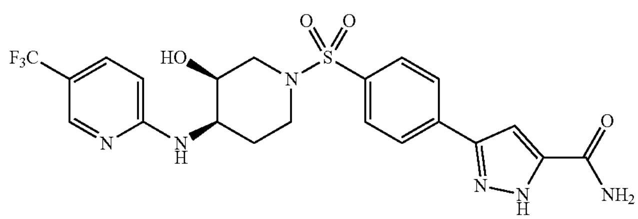 [SMILES: NC(=O)c1cc(-c2ccc(S(=O)(=O)N3CC[C@@H](Nc4ccc(C(F)(F)F)cn4)[C@@H](O)C3)cc2)n[nH]1] | 511.0 | ++ |
| 74 | 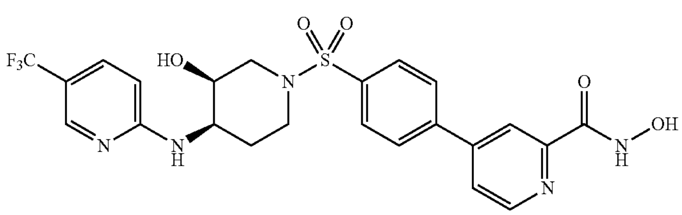 [SMILES: O=C(NO)c1cc(-c2ccc(S(=O)(=O)N3CC[C@@H](Nc4ccc(C(F)(F)F)cn4)[C@@H](O)C3)cc2)ccn1] | 538.2 | ++ |
| 75 | 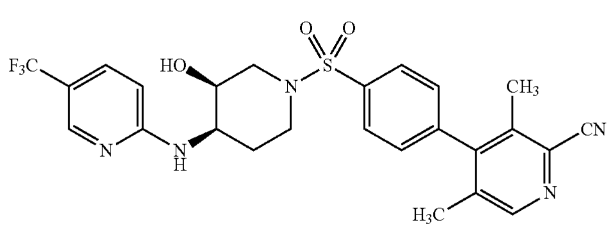 [SMILES: Cc1cnc(C#N)c(C)c1-c1ccc(S(=O)(=O)N2CC[C@@H](Nc3ccc(C(F)(F)F)cn3)[C@@H](O)C2)cc1] | 532.2 | +++ |

TABLE 1-continued

| Compound | Structure | m/z | Potency |
|---|---|---|---|
| 76 | 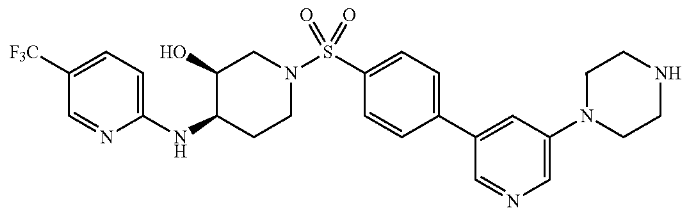 [SMILES: O=S(=O)(c1ccc(-c2cncc(N3CCNCC3)c2)cc1)N1CC[C@@H](Nc2ccc(C(F)(F)F)cn2)[C@@H](O)C1] | 563.1 | ++ |
| 77 | 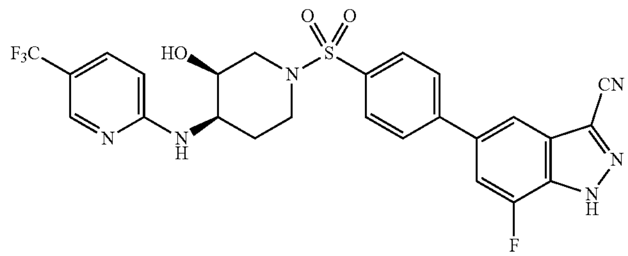 [SMILES: N#Cc1n[nH]c2c(F)cc(-c3ccc(S(=O)(=O)N4CC[C@@H](Nc5ccc(C(F)(F)F)cn5)[C@@H](O)C4)cc3)cc12] | 561.2 | +++ |
| 78 | 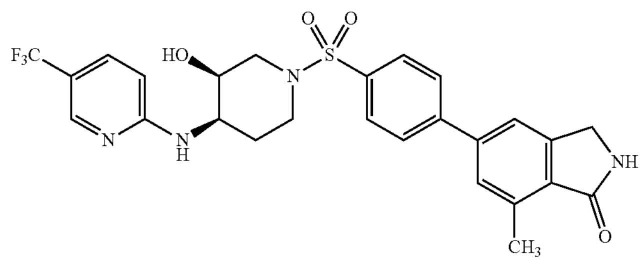 [SMILES: Cc1cc(-c2ccc(S(=O)(=O)N3CC[C@@H](Nc4ccc(C(F)(F)F)cn4)[C@@H](O)C3)cc2)cc2c1C(=O)NC2] | 547.2 | +++ |
| 79 | 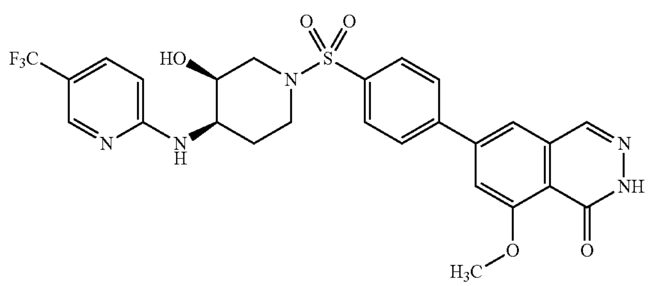 [SMILES: COc1cc(-c2ccc(S(=O)(=O)N3CC[C@@H](Nc4ccc(C(F)(F)F)cn4)[C@@H](O)C3)cc2)cc2cn[nH]c(=O)c12] | 576.2 | +++ |
| 80 | 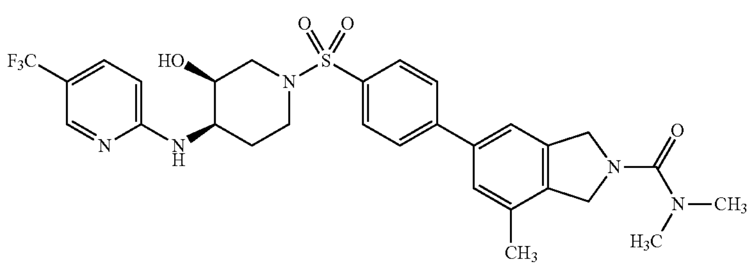 [SMILES: Cc1cc(-c2ccc(S(=O)(=O)N3CC[C@@H](Nc4ccc(C(F)(F)F)cn4)[C@@H](O)C3)cc2)cc2c1CN(C(=O)N(C)C)C2] | 604.2 | +++ |
| 81 | 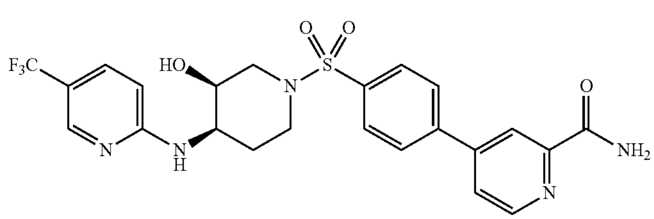 [SMILES: NC(=O)c1cc(-c2ccc(S(=O)(=O)N3CC[C@@H](Nc4ccc(C(F)(F)F)cn4)[C@@H](O)C3)cc2)ccn1] | 521.1 | +++ |

TABLE 1-continued

| Compound | Structure | m/z | Potency |
|---|---|---|---|
| 82 | 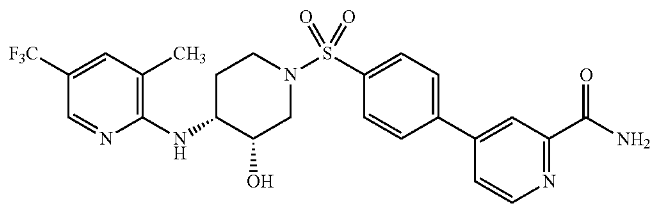 [SMILES: Cc1cc(C(F)(F)F)cnc1N[C@@H]1CCN(S(=O)(=O)c2ccc(-c3ccnc(C(N)=O)c3)cc2)C[C@@H]1O] | 536.1 | +++ |
| 83 | 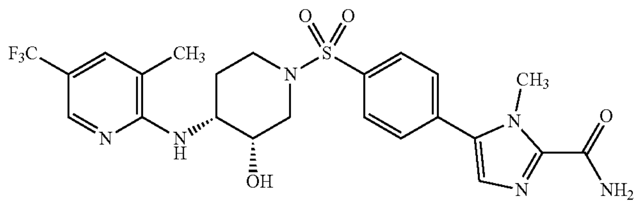 [SMILES: Cc1cc(C(F)(F)F)cnc1N[C@@H]1CCN(S(=O)(=O)c2ccc(-c3cnc(C(N)=O)n3C)cc2)C[C@@H]1O] | 539.1 | +++ |
| 84 | 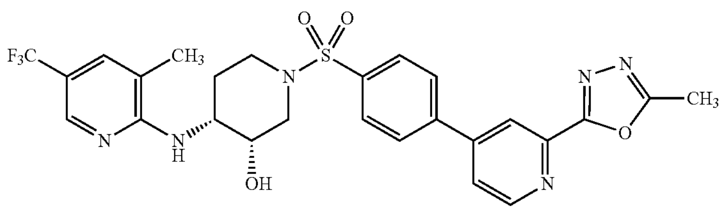 [SMILES: Cc1nnc(-c2cc(-c3ccc(S(=O)(=O)N4CC[C@@H](Nc5ncc(C(F)(F)F)cc5C)[C@@H](O)C4)cc3)ccn2)o1] | 575.1 | +++ |
| 85 | 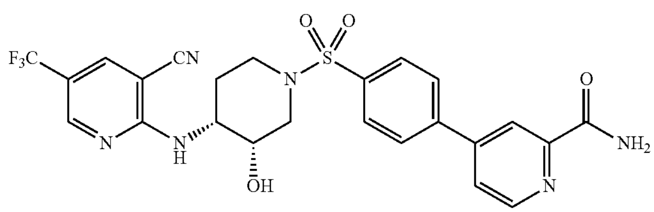 [SMILES: N#Cc1cc(C(F)(F)F)cnc1N[C@@H]1CCN(S(=O)(=O)c2ccc(-c3ccnc(C(N)=O)c3)cc2)C[C@@H]1O] | 547.0 | + |
| 86 | 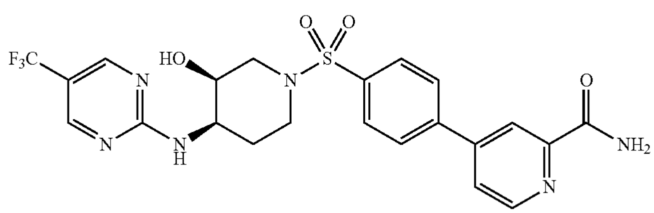 [SMILES: NC(=O)c1cc(-c2ccc(S(=O)(=O)N3CC[C@@H](Nc4ncc(C(F)(F)F)cn4)[C@@H](O)C3)cc2)ccn1] | 523.0 | + |
| 87 | 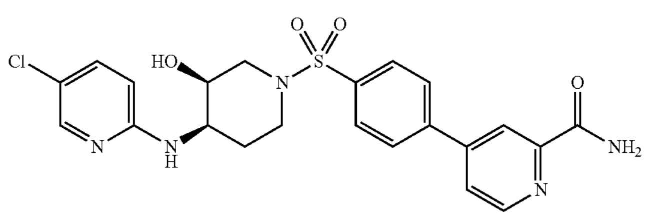 [SMILES: NC(=O)c1cc(-c2ccc(S(=O)(=O)N3CC[C@@H](Nc4ccc(Cl)cn4)[C@@H](O)C3)cc2)ccn1] | 490.0 | +++ |
| 88 | 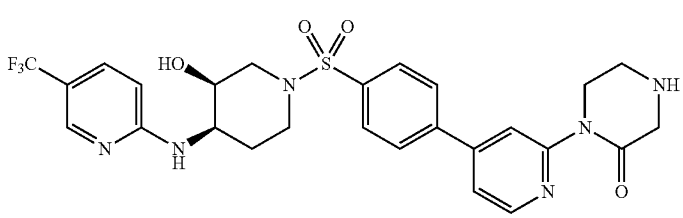 [SMILES: O=C1CNCCN1c1cc(-c2ccc(S(=O)(=O)N3CC[C@@H](Nc4ccc(C(F)(F)F)cn4)[C@@H](O)C3)cc2)ccn1] | 577.2 | ++ |

TABLE 1-continued

| Compound | Structure | m/z | Potency |
|---|---|---|---|
| 89 | 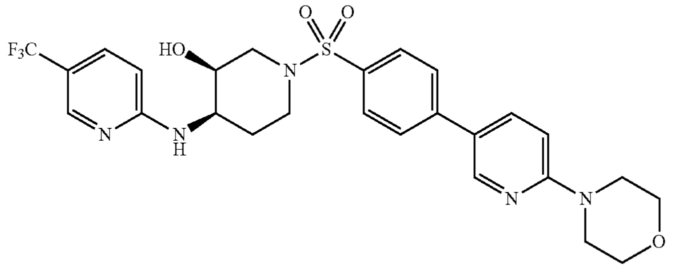 [SMILES: O=S(=O)(c1ccc(-c2ccc(N3CCOCC3)nc2)cc1)N1CC[C@@H](Nc2ccc(C(F)(F)F)cn2)[C@@H](O)C1] | 564.2 | +++ |
| 90 | 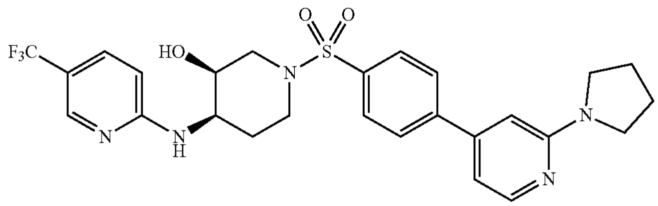 [SMILES: O=S(=O)(c1ccc(-c2ccnc(N3CCCC3)c2)cc1)N1CC[C@@H](Nc2ccc(C(F)(F)F)cn2)[C@@H](O)C1] | 548.0 | +++ |
| 91 | 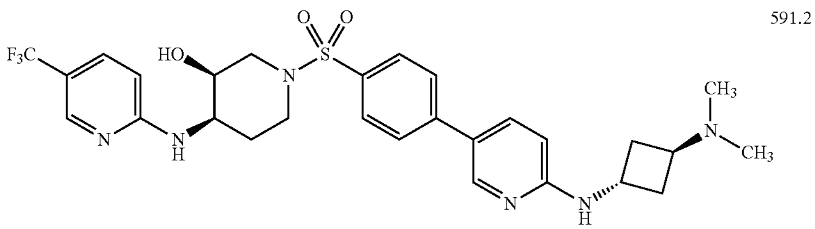 | 591.2 | ++ |
| 92 | 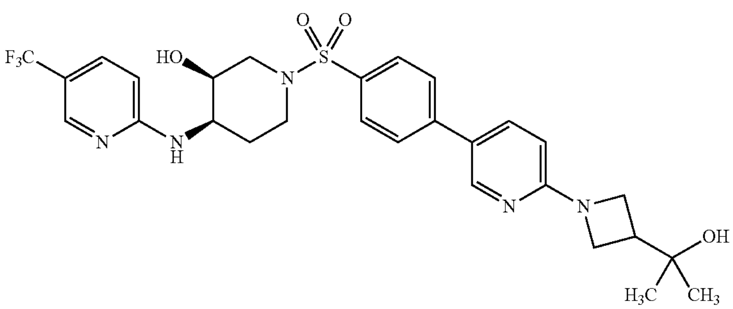 [SMILES: CC(C)(O)C1CN(c2ccc(-c3ccc(S(=O)(=O)N4CC[C@@H](Nc5ccc(C(F)(F)F)cn5)[C@@H](O)C4)cc3)cn2)C1] | 592.2 | +++ |
| 93 | 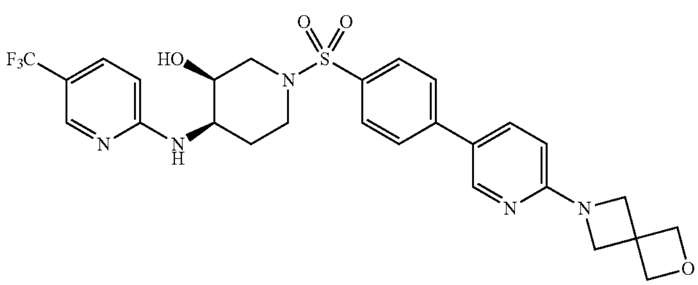 [SMILES: O=S(=O)(c1ccc(-c2ccc(N3CC4(COC4)C3)nc2)cc1)N1CC[C@@H](Nc2ccc(C(F)(F)F)cn2)[C@@H](O)C1] | 576.2 | +++ |
| 94 | 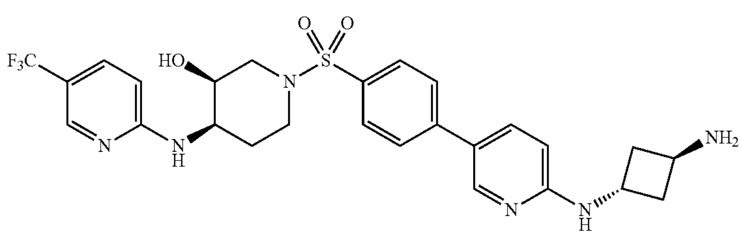 [SMILES: N[C@H]1C[C@H](Nc2ccc(-c3ccc(S(=O)(=O)N4CC[C@@H](Nc5ccc(C(F)(F)F)cn5)[C@@H](O)C4)cc3)cn2)C1] | 563.2 | +++ |

TABLE 1-continued

| Compound | Structure | m/z | Potency |
|---|---|---|---|
| 95 | 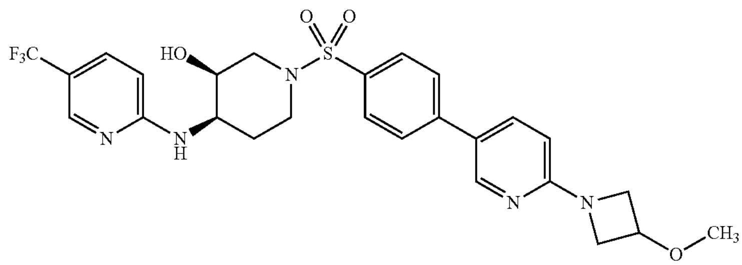 [SMILES: COC1CN(c2ccc(-c3ccc(S(=O)(=O)N4CC[C@@H](Nc5ccc(C(F)(F)F)cn5)[C@@H](O)C4)cc3)cn2)C1] | 564.1 | ++ |
| 96 | 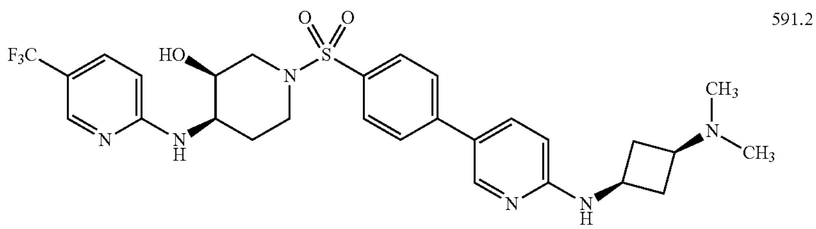 | 591.2 | +++ |
| 97 | 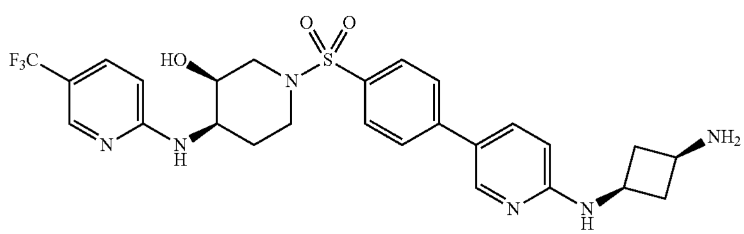 [SMILES: N[C@H]1C[C@@H](Nc2ccc(-c3ccc(S(=O)(=O)N4CC[C@@H](Nc5ccc(C(F)(F)F)cn5)[C@@H](O)C4)cc3)cn2)C1] | 563.1 | +++ |
| 98 | 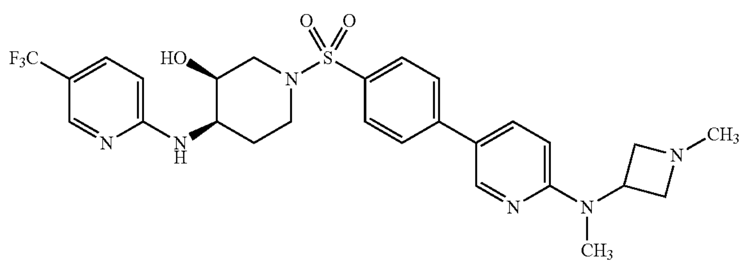 [SMILES: CN1CC(N(C)c2ccc(-c3ccc(S(=O)(=O)N4CC[C@@H](Nc5ccc(C(F)(F)F)cn5)[C@@H](O)C4)cc3)cn2)C1] | 577.2 | ++ |
| 99 | 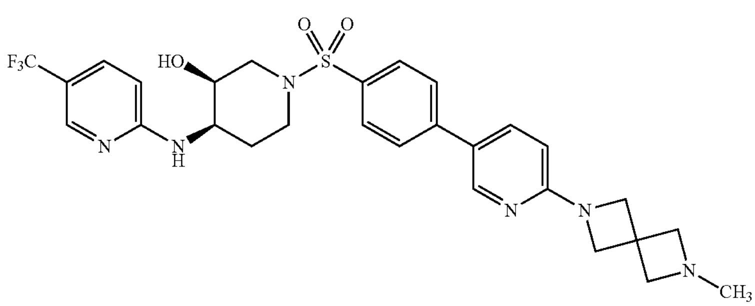 [SMILES: CN1CC2(C1)CN(c1ccc(-c3ccc(S(=O)(=O)N4CC[C@@H](Nc5ccc(C(F)(F)F)cn5)[C@@H](O)C4)cc3)cn1)C2] | 589.2 | +++ |
| 100 | 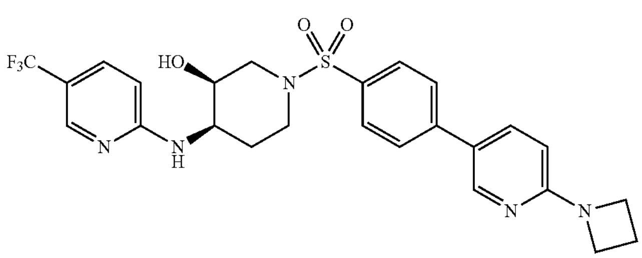 [SMILES: O=S(=O)(c1ccc(-c2ccc(N3CCC3)nc2)cc1)N1CC[C@@H](Nc2ccc(C(F)(F)F)cn2)[C@@H](O)C1] | 534.2 | +++ |

TABLE 1-continued

| Compound | Structure | m/z | Potency |
|---|---|---|---|
| 101 | 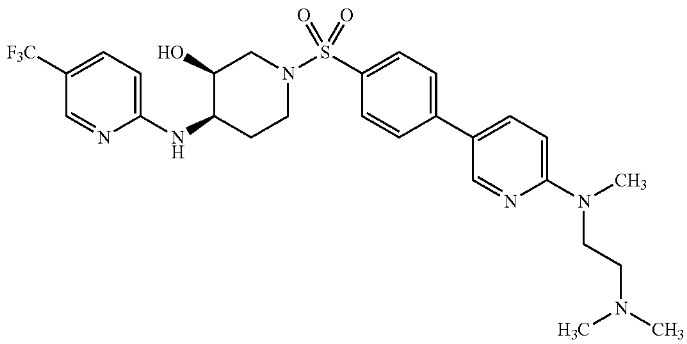 [SMILES: CN(C)CCN(C)c1ccc(-c2ccc(S(=O)(=O)N3CC[C@@H](Nc4ccc(C(F)(F)F)cn4)[C@@H](O)C3)cc2)cn1] | 579.2 | + |
| 102 | 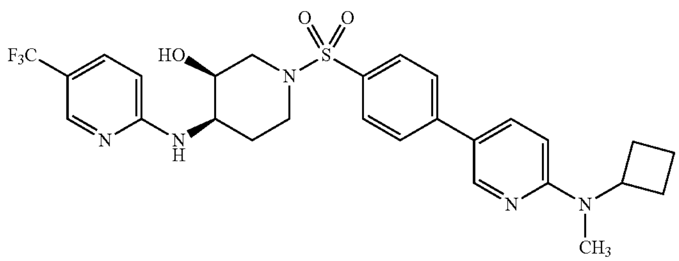 [SMILES: CN(c1ccc(-c2ccc(S(=O)(=O)N3CC[C@@H](Nc4ccc(C(F)(F)F)cn4)[C@@H](O)C3)cc2)cn1)C1CCC1] | 562.2 | ++ |
| 103 | 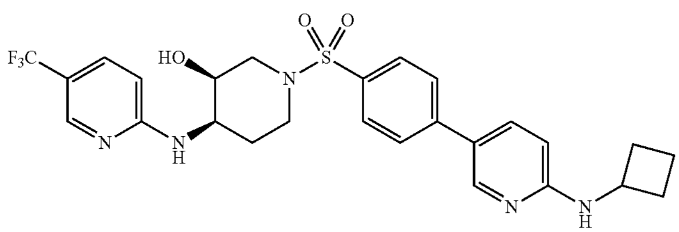 [SMILES: O=S(=O)(c1ccc(-c2ccc(NC3CCC3)nc2)cc1)N1CC[C@@H](Nc2ccc(C(F)(F)F)cn2)[C@@H](O)C1] | 548.2 | ++ |
| 104 | 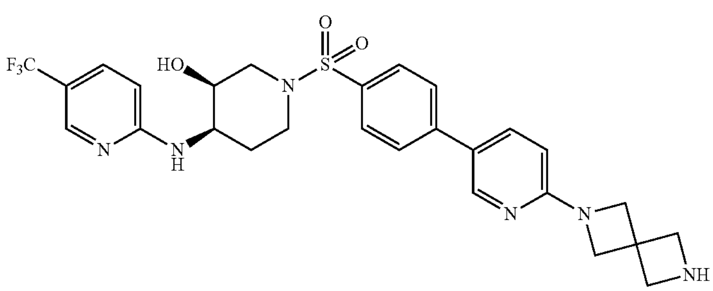 [SMILES: O=S(=O)(c1ccc(-c2ccc(N3CC4(CNC4)C3)nc2)cc1)N1CC[C@@H](Nc2ccc(C(F)(F)F)cn2)[C@@H](O)C1] | 575.2 | +++ |
| 105 | 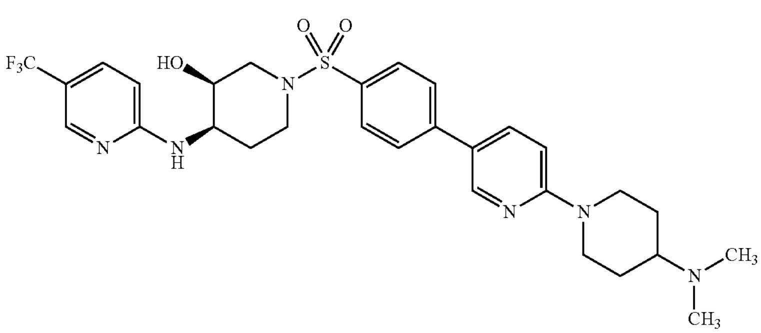 [SMILES: CN(C)C1CCN(c2ccc(-c3ccc(S(=O)(=O)N4CC[C@@H](Nc5ccc(C(F)(F)F)cn5)[C@@H](O)C4)cc3)cn2)CC1] | 605.3 | ++ |

TABLE 1-continued

| Compound | Structure | m/z | Potency |
|---|---|---|---|
| 106 | 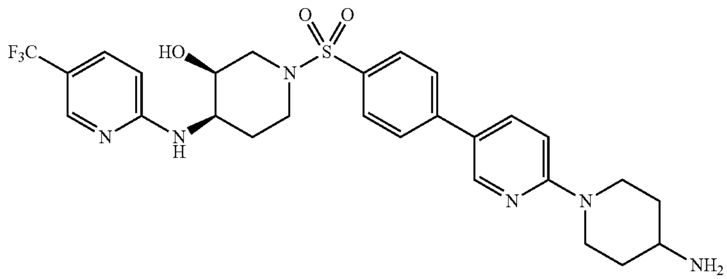 [SMILES: NC1CCN(c2ccc(-c3ccc(S(=O)(=O)N4CC[C@@H](Nc5ccc(C(F)(F)F)cn5)[C@@H](O)C4)cc3)cn2)CC1] | 577.2 | +++ |
| 107 | 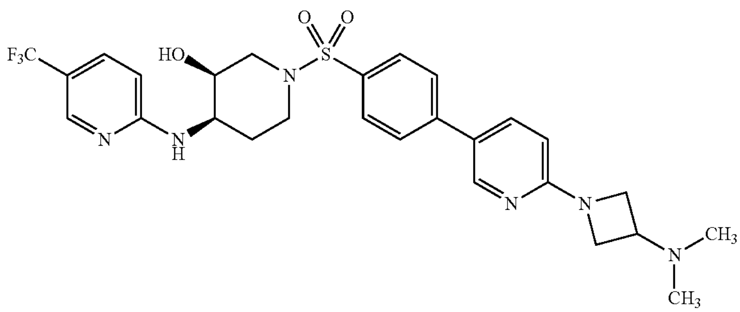 [SMILES: CN(C)C1CN(c2ccc(-c3ccc(S(=O)(=O)N4CC[C@@H](Nc5ccc(C(F)(F)F)cn5)[C@@H](O)C4)cc3)cn2)C1] | 577.2 | ++ |
| 108 | 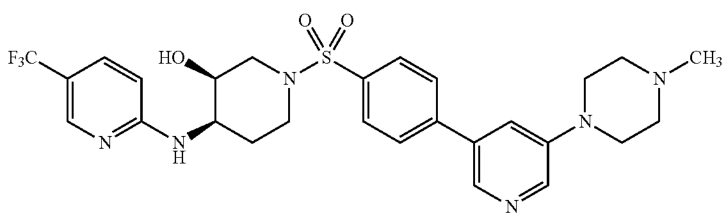 [SMILES: CN1CCN(c2cncc(-c3ccc(S(=O)(=O)N4CC[C@@H](Nc5ccc(C(F)(F)F)cn5)[C@@H](O)C4)cc3)c2)CC1] | 577.1 | +++ |
| 109 | 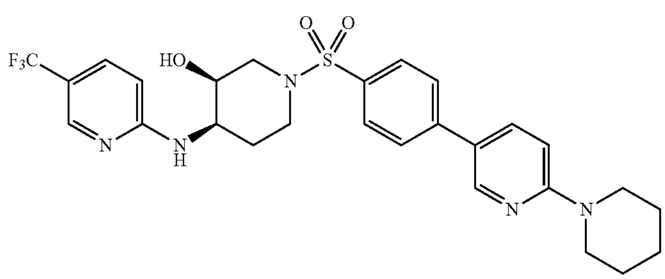 [SMILES: O=S(=O)(c1ccc(-c2ccc(N3CCCCC3)nc2)cc1)N1CC[C@@H](Nc2ccc(C(F)(F)F)cn2)[C@@H](O)C1] | 562.2 | ++ |
| 110 | 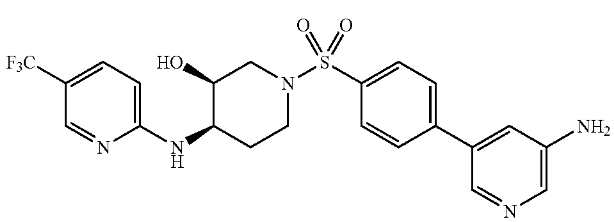 [SMILES: Nc1cncc(-c2ccc(S(=O)(=O)N3CC[C@@H](Nc4ccc(C(F)(F)F)cn4)[C@@H](O)C3)cc2)c1] | 494.1 | +++ |
| 111 | 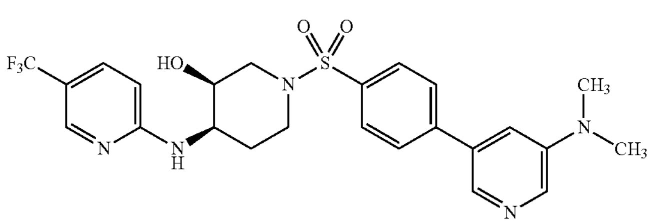 [SMILES: CN(C)c1cncc(-c2ccc(S(=O)(=O)N3CC[C@@H](Nc4ccc(C(F)(F)F)cn4)[C@@H](O)C3)cc2)c1] | 522.2 | +++ |

TABLE 1-continued

| Compound | Structure | m/z | Potency |
|---|---|---|---|
| 112 | 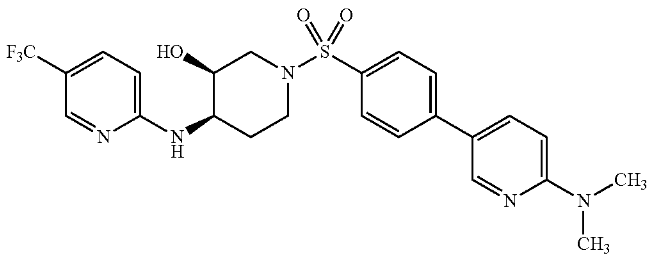 [SMILES: CN(C)c1ccc(-c2ccc(S(=O)(=O)N3CC[C@@H](Nc4ccc(C(F)(F)F)cn4)[C@@H](O)C3)cc2)cn1] | 522.1 | +++ |
| 113 | 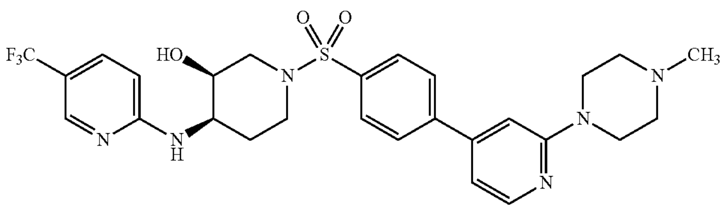 [SMILES: CN1CCN(c2cc(-c3ccc(S(=O)(=O)N4CC[C@@H](Nc5ccc(C(F)(F)F)cn5)[C@@H](O)C4)cc3)ccn2)CC1] | 577.2 | + |
| 114 | 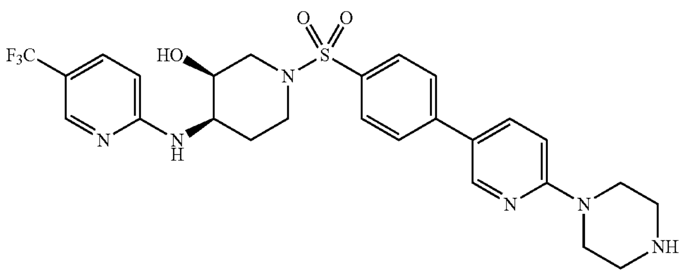 [SMILES: O=S(=O)(c1ccc(-c2ccc(N3CCNCC3)nc2)cc1)N1CC[C@@H](Nc2ccc(C(F)(F)F)cn2)[C@@H](O)C1] | 563.2 | ++ |
| 115 | 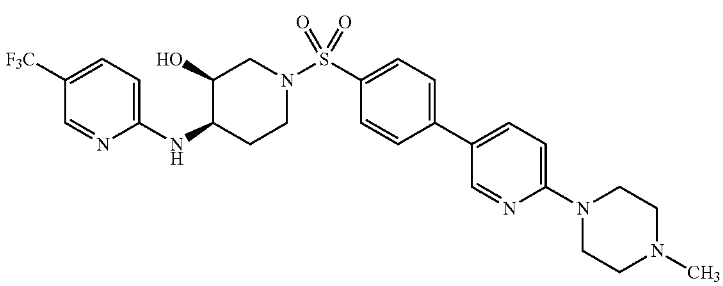 | 577.2 | +++ |
| 116 | 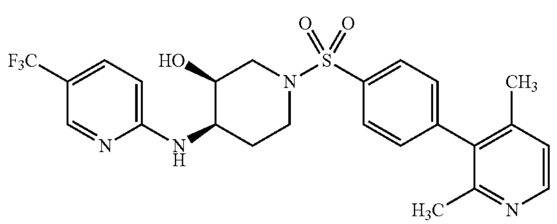 [SMILES: Cc1ccnc(C)c1-c1ccc(S(=O)(=O)N2CC[C@@H](Nc3ccc(C(F)(F)F)cn3)[C@@H](O)C2)cc1] | 507.1 | +++ |
| 117 | 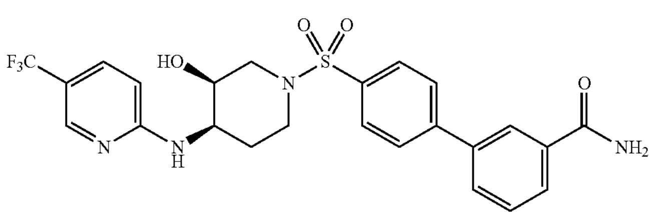 [SMILES: NC(=O)c1cccc(-c2ccc(S(=O)(=O)N3CC[C@@H](Nc4ccc(C(F)(F)F)cn4)[C@@H](O)C3)cc2)c1] | 521.1 | +++ |

TABLE 1-continued
| Compound | Structure | m/z | Potency |
|---|---|---|---|
| 118 | 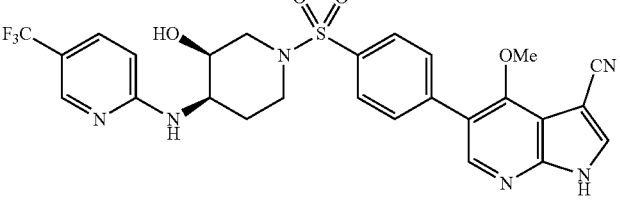 | 573.2 | +++ |
| 119 | 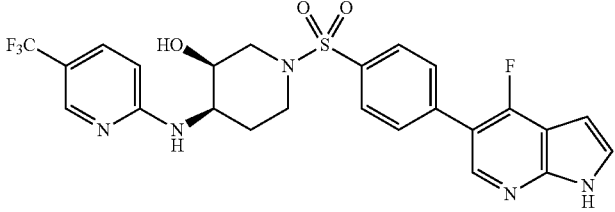 [SMILES: O=S(=O)(c1ccc(-c2cnc3[nH]ccc3c2F)cc1)N1CC[C@@H](Nc2ccc(C(F)(F)F)cn2)[C@@H](O)C1] | 536.1 | +++ |
| 120 | 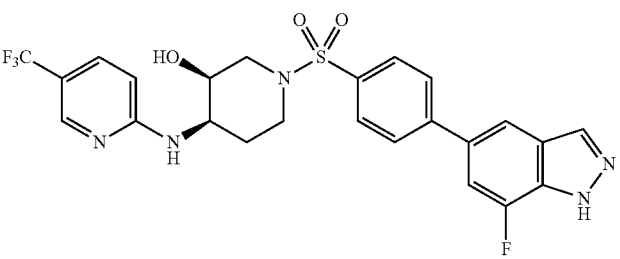 [SMILES: O=S(=O)(c1ccc(-c2cc(F)c3[nH]ncc3c2)cc1)N1CC[C@@H](Nc2ccc(C(F)(F)F)cn2)[C@@H](O)C1] | 536.1 | +++ |
| 121 | 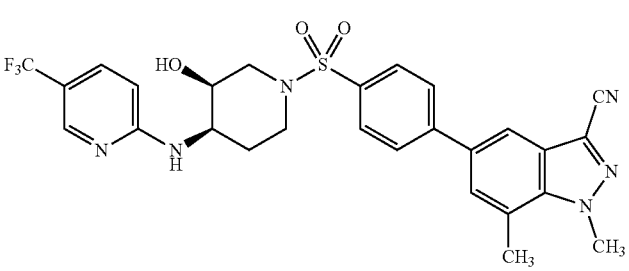 [SMILES: Cc1cc(-c2ccc(S(=O)(=O)N3CC[C@@H](Nc4ccc(C(F)(F)F)cn4)[C@@H](O)C3)cc2)cc2c(C#N)nn(C)c12] | 571.2 | +++ |
| 122 | 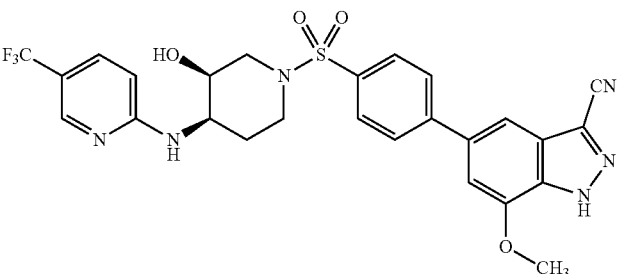 | 573.2 | +++ |
| 123 | 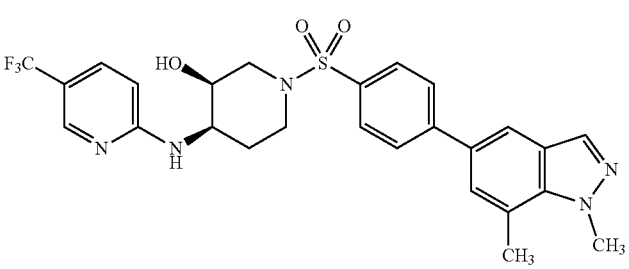 [SMILES: Cc1cc(-c2ccc(S(=O)(=O)N3CC[C@@H](Nc4ccc(C(F)(F)F)cn4)[C@@H](O)C3)cc2)cc2cnn(C)c12] | 546.1 | +++ |

TABLE 1-continued

| Compound | Structure | m/z | Potency |
|---|---|---|---|
| 124 | 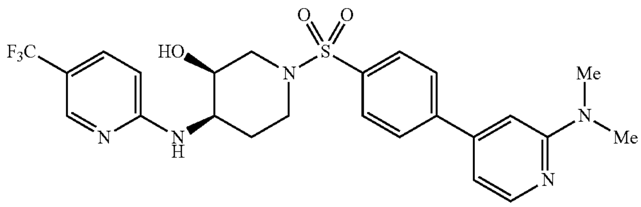 [SMILES: CN(C)c1cc(-c2ccc(S(=O)(=O)N3CC[C@@H](Nc4ccc(C(F)(F)F)cn4)[C@@H](O)C3)cc2)ccn1] | 522.0 | ++ |
| 125 | 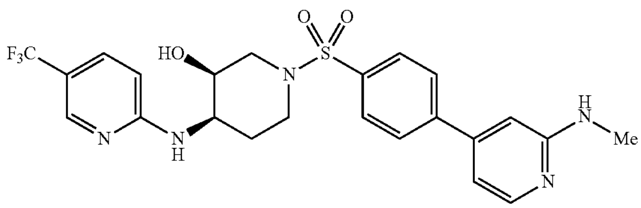 [SMILES: CNc1cc(-c2ccc(S(=O)(=O)N3CC[C@@H](Nc4ccc(C(F)(F)F)cn4)[C@@H](O)C3)cc2)ccn1] | 508.1 | ++ |
| 126 | 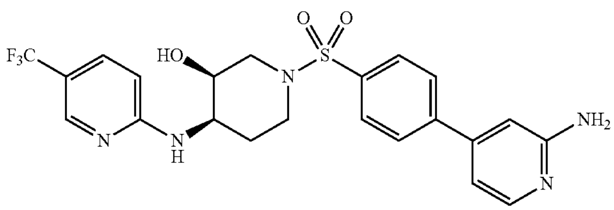 [SMILES: Nc1cc(-c2ccc(S(=O)(=O)N3CC[C@@H](Nc4ccc(C(F)(F)F)cn4)[C@@H](O)C3)cc2)ccn1] | 494.1 | ++ |
| 127 | 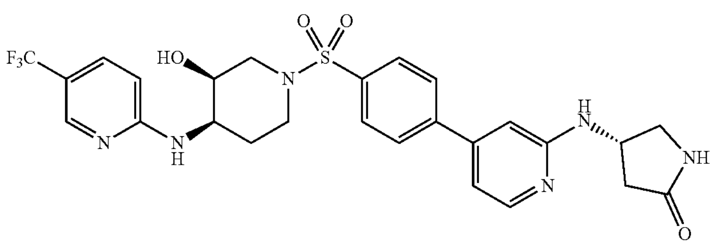 [SMILES: O=C1C[C@H](Nc2cc(-c3ccc(S(=O)(=O)N4CC[C@@H](Nc5ccc(C(F)(F)F)cn5)[C@@H](O)C4)cc3)ccn2)CN1] | 577.2 | ++ |
| 128 | 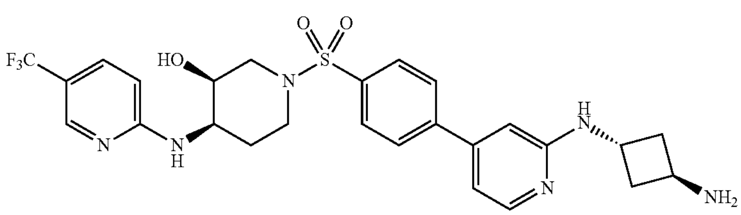 [SMILES: N[C@H]1C[C@H](Nc2cc(-c3ccc(S(=O)(=O)N4CC[C@@H](Nc5ccc(C(F)(F)F)cn5)[C@@H](O)C4)cc3)ccn2)C1] | 563.2 | +++ |
| 129 | 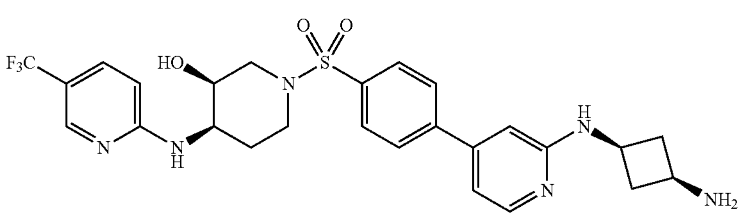 [SMILES: N[C@H]1C[C@@H](Nc2cc(-c3ccc(S(=O)(=O)N4CC[C@@H](Nc5ccc(C(F)(F)F)cn5)[C@@H](O)C4)cc3)ccn2)C1] | 563.1 | +++ |
| 130 | 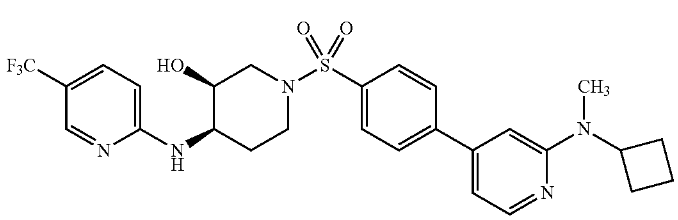 [SMILES: CN(c1cc(-c2ccc(S(=O)(=O)N3CC[C@@H](Nc4ccc(C(F)(F)F)cn4)[C@@H](O)C3)cc2)ccn1)C1CCC1] | 562.1 | +++ |

TABLE 1-continued

| Compound | Structure | m/z | Potency |
|---|---|---|---|
| 131 | 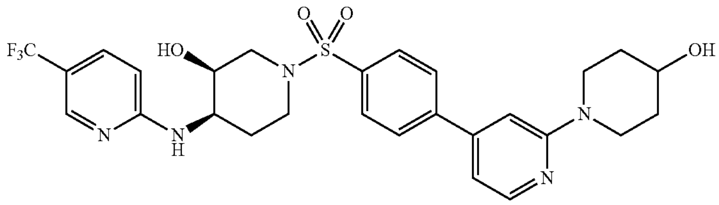 [SMILES: O=S(=O)(c1ccc(-c2ccnc(N3CCC(O)CC3)c2)cc1)N1CC[C@@H](Nc2ccc(C(F)(F)F)cn2)[C@@H](O)C1] | 578.1 | +++ |
| 132 | 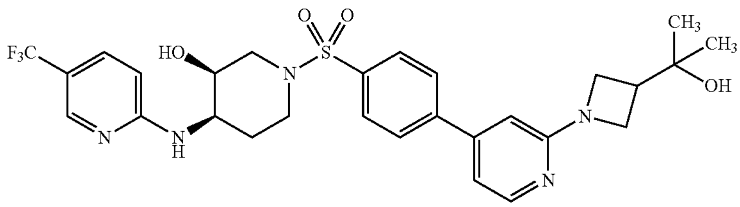 [SMILES: CC(C)(O)C1CN(c2cc(-c3ccc(S(=O)(=O)N4CC[C@@H](Nc5ccc(C(F)(F)F)cn5)[C@@H](O)C4)cc3)ccn2)C1] | 592.1 | +++ |
| 133 | 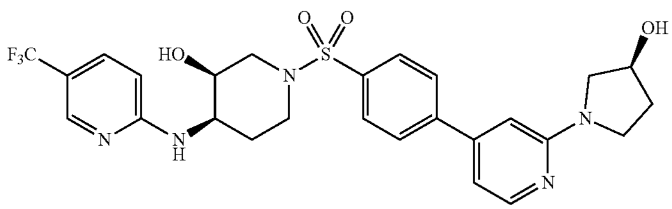 [SMILES: O=S(=O)(c1ccc(-c2ccnc(N3CC[C@H](O)C3)c2)cc1)N1CC[C@@H](Nc2ccc(C(F)(F)F)cn2)[C@@H](O)C1] | 564.0 | +++ |
| 134 | 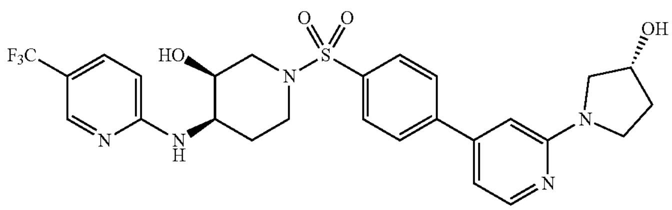 [SMILES: O=S(=O)(c1ccc(-c2ccnc(N3CC[C@@H](O)C3)c2)cc1)N1CC[C@@H](Nc2ccc(C(F)(F)F)cn2)[C@@H](O)C1] | 564.0 | +++ |
| 135 | 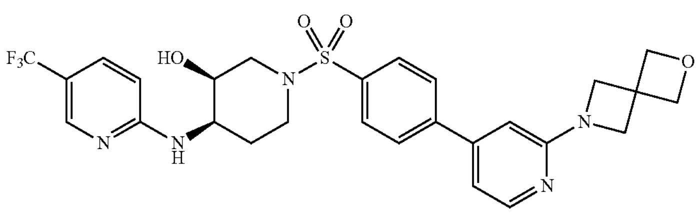 [SMILES: O=S(=O)(c1ccc(-c2ccnc(N3CC4(COC4)C3)c2)cc1)N1CC[C@@H](Nc2ccc(C(F)(F)F)cn2)[C@@H](O)C1] | 576.2 | +++ |
| 136 | 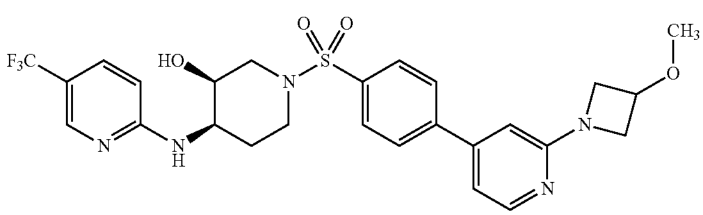 [SMILES: COC1CN(c2cc(-c3ccc(S(=O)(=O)N4CC[C@@H](Nc5ccc(C(F)(F)F)cn5)[C@@H](O)C4)cc3)ccn2)C1] | 564.2 | ++ |
| 137 | 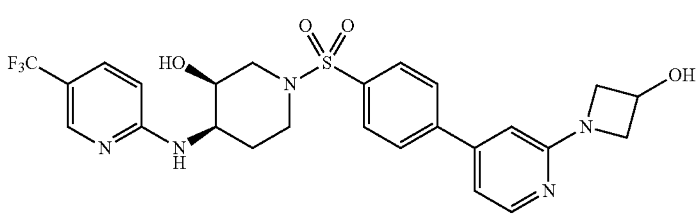 [SMILES: O=S(=O)(c1ccc(-c2ccnc(N3CC(O)C3)c2)cc1)N1CC[C@@H](Nc2ccc(C(F)(F)F)cn2)[C@@H](O)C1] | 550.1 | +++ |

TABLE 1-continued

| Compound | Structure | m/z | Potency |
|---|---|---|---|
| 138 | 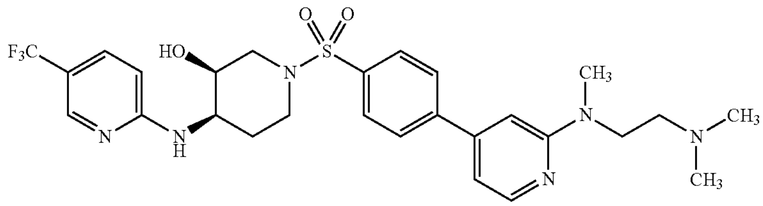 [SMILES: CN(C)CCN(C)c1cc(-c2ccc(S(=O)(=O)N3CC[C@@H](Nc4ccc(C(F)(F)F)cn4)[C@@H](O)C3)cc2)ccn1] | 579.1 | +++ |
| 139 | 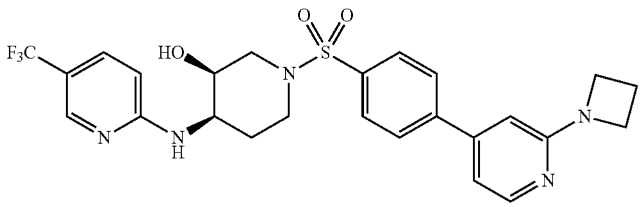 [SMILES: O=S(=O)(c1ccc(-c2ccnc(N3CCC3)c2)cc1)N1CC[C@@H](Nc2ccc(C(F)(F)F)cn2)[C@@H](O)C1] | 534.0 | +++ |
| 140 | 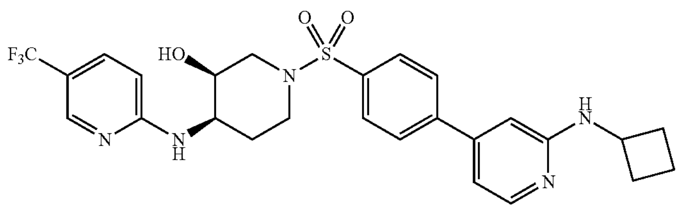 [SMILES: O=S(=O)(c1ccc(-c2ccnc(NC3CCC3)c2)cc1)N1CC[C@@H](Nc2ccc(C(F)(F)F)cn2)[C@@H](O)C1] | 548.1 | +++ |
| 141 | 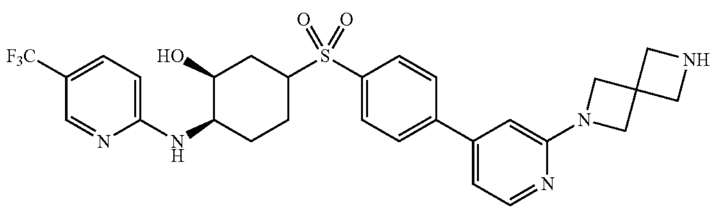 [SMILES: O=S(=O)(c1ccc(-c2ccnc(N3CC4(CNC4)C3)c2)cc1)C1CC[C@@H](Nc2ccc(C(F)(F)F)cn2)[C@@H](O)C1] | 575.1 | ++ |
| 142 | 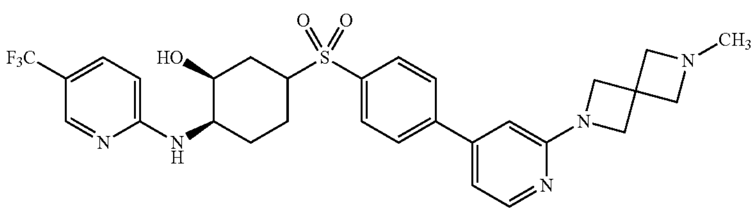 [SMILES: CN1CC2(C1)CN(c1cc(-c3ccc(S(=O)(=O)C4CC[C@@H](Nc5ccc(C(F)(F)F)cn5)[C@@H](O)C4)cc3)ccn1)C2] | 589.1 | ++ |
| 143 | 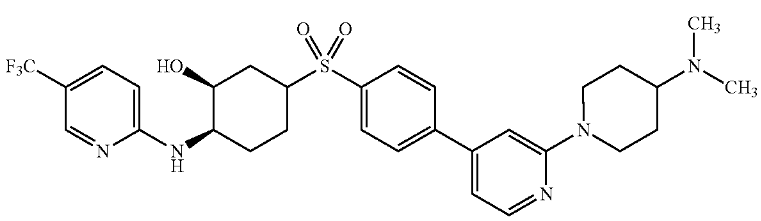 [SMILES: CN(C)C1CCN(c2cc(-c3ccc(S(=O)(=O)C4CC[C@@H](Nc5ccc(C(F)(F)F)cn5)[C@@H](O)C4)cc3)ccn2)CC1] | 605.2 | ++ |
| 144 | 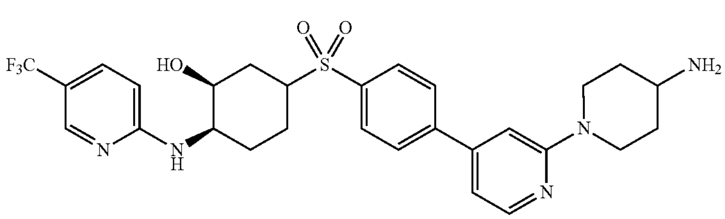 [SMILES: NC1CCN(c2cc(-c3ccc(S(=O)(=O)C4CC[C@@H](Nc5ccc(C(F)(F)F)cn5)[C@@H](O)C4)cc3)ccn2)CC1] | 577.2 | +++ |

TABLE 1-continued

| Compound | Structure | m/z | Potency |
|---|---|---|---|
| 145 | 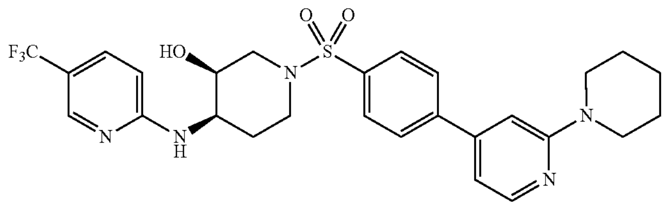 [SMILES: O=S(=O)(c1ccc(-c2ccnc(N3CCCCC3)c2)cc1)N1CC[C@@H](Nc2ccc(C(F)(F)F)cn2)[C@@H](O)C1] | 562.0 | +++ |
| 146 | 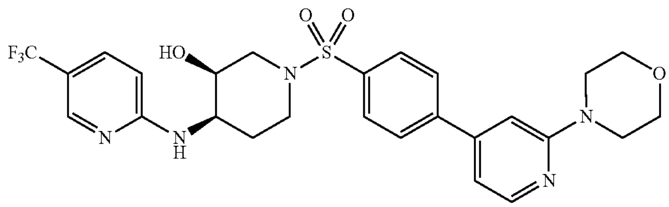 [SMILES: O=S(=O)(c1ccc(-c2ccnc(N3CCOCC3)c2)cc1)N1CC[C@@H](Nc2ccc(C(F)(F)F)cn2)[C@@H](O)C1] | 564.0 | +++ |
| 147 | 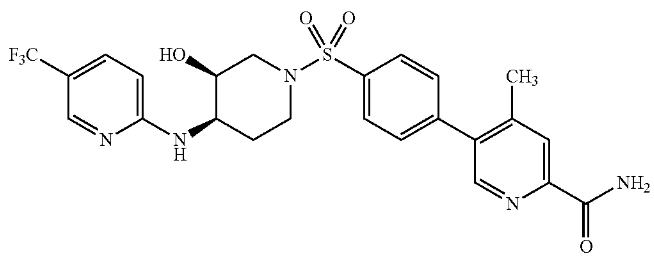 [SMILES: Cc1cc(C(N)=O)ncc1-c1ccc(S(=O)(=O)N2CC[C@@H](Nc3ccc(C(F)(F)F)cn3)[C@@H](O)C2)cc1] | 536.1 | +++ |
| 148 | 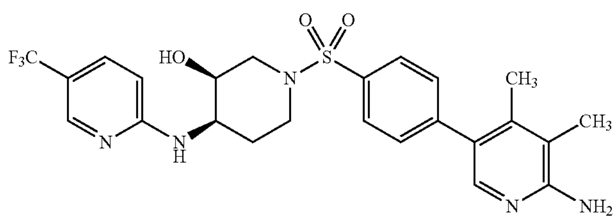 [SMILES: Cc1c(-c2ccc(S(=O)(=O)N3CC[C@@H](Nc4ccc(C(F)(F)F)cn4)[C@@H](O)C3)cc2)cnc(N)c1C] | 522.0 | +++ |
| 149 | 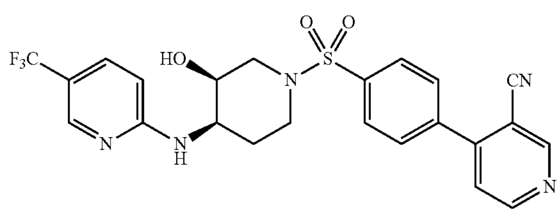 [SMILES: N#Cc1cnccc1-c1ccc(S(=O)(=O)N2CC[C@@H](Nc3ccc(C(F)(F)F)cn3)[C@@H](O)C2)cc1] | 504.1 | ++ |
| 150 | 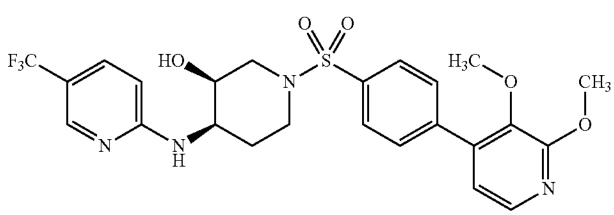 [SMILES: COc1nccc(-c2ccc(S(=O)(=O)N3CC[C@@H](Nc4ccc(C(F)(F)F)cn4)[C@@H](O)C3)cc2)c1OC] | 539.0 | +++ |
| 151 | 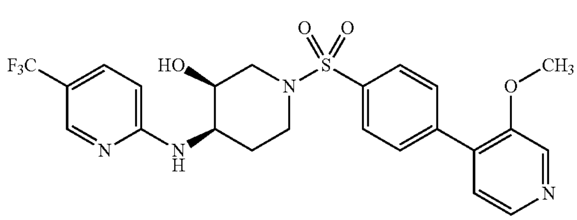 [SMILES: COc1cnccc1-c1ccc(S(=O)(=O)N2CC[C@@H](Nc3ccc(C(F)(F)F)cn3)[C@@H](O)C2)cc1] | 509.0 | ++ |

TABLE 1-continued

| Compound | Structure | m/z | Potency |
|---|---|---|---|
| 152 | 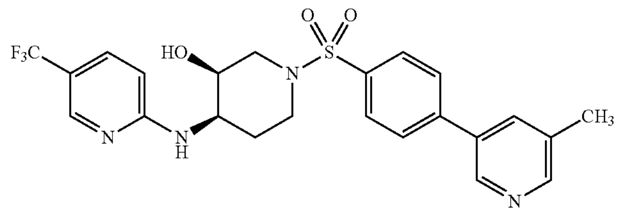 [SMILES: Cc1cncc(-c2ccc(S(=O)(=O)N3CC[C@@H](Nc4ccc(C(F)(F)F)cn4)[C@@H](O)C3)cc2)c1] | 493.1 | +++ |
| 153 | 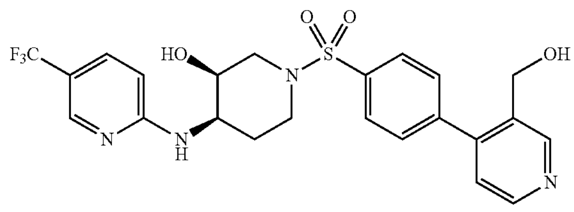 [SMILES: O=S(=O)(c1ccc(-c2ccncc2CO)cc1)N1CC[C@@H](Nc2ccc(C(F)(F)F)cn2)[C@@H](O)C1] | 509.1 | ++ |
| 154 | 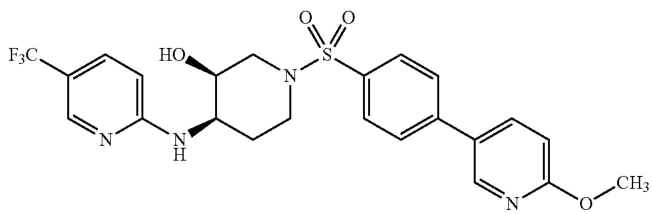 [SMILES: COc1ccc(-c2ccc(S(=O)(=O)N3CC[C@@H](Nc4ccc(C(F)(F)F)cn4)[C@@H](O)C3)cc2)cn1] | 509.1 | ++ |
| 155 | 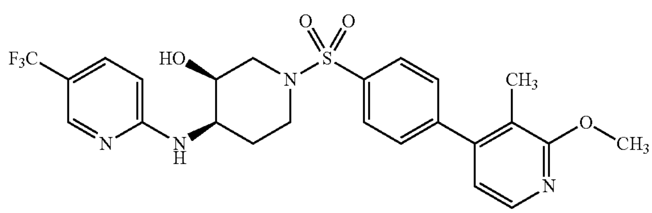 [SMILES: COc1nccc(-c2ccc(S(=O)(=O)N3CC[C@@H](Nc4ccc(C(F)(F)F)cn4)[C@@H](O)C3)cc2)c1C] | 523.1 | +++ |
| 156 | 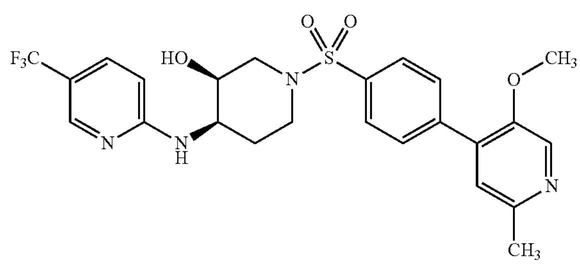 [SMILES: COc1cnc(C)cc1-c1ccc(S(=O)(=O)N2CC[C@@H](Nc3ccc(C(F)(F)F)cn3)[C@@H](O)C2)cc1] | 523.0 | +++ |
| 157 | 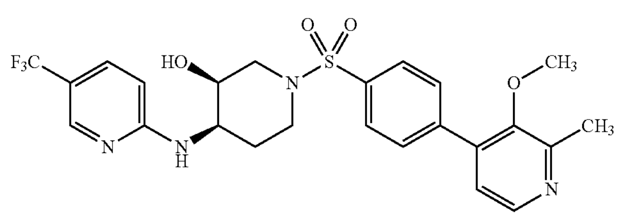 [SMILES: COc1c(-c2ccc(S(=O)(=O)N3CC[C@@H](Nc4ccc(C(F)(F)F)cn4)[C@@H](O)C3)cc2)ccnc1C] | 523.0 | +++ |
| 158 | 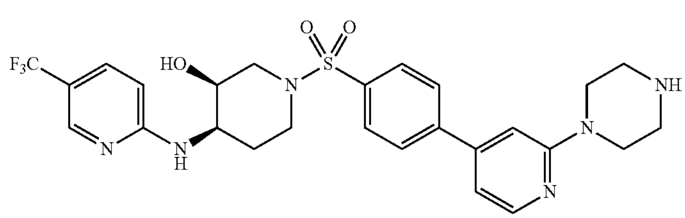 [SMILES: O=S(=O)(c1ccc(-c2ccnc(N3CCNCC3)c2)cc1)N1CC[C@@H](Nc2ccc(C(F)(F)F)cn2)[C@@H](O)C1] | 563.0 | ++ |

TABLE 1-continued

| Compound | Structure | m/z | Potency |
|---|---|---|---|
| 159 | 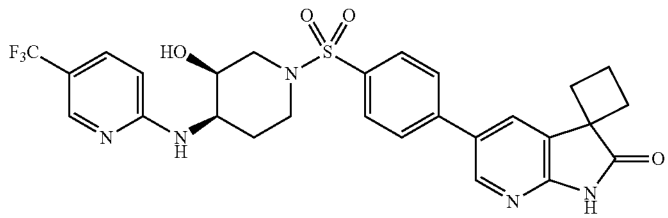 [SMILES: O=C1Nc2ncc(-c3ccc(S(=O)(=O)N4CC[C@@H](Nc5ccc(C(F)(F)F)cn5)[C@@H](O)C4)cc3)cc2C12CCC2] | 574.1 | +++ |
| 160 | 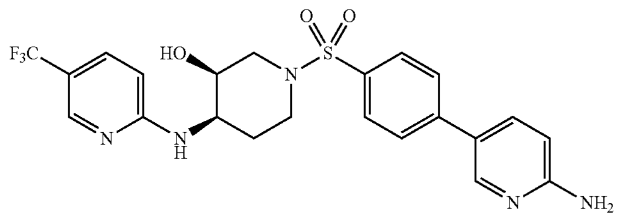 [SMILES: Nc1ccc(-c2ccc(S(=O)(=O)N3CC[C@@H](Nc4ccc(C(F)(F)F)cn4)[C@@H](O)C3)cc2)cn1] | 494.1 | +++ |
| 161 | 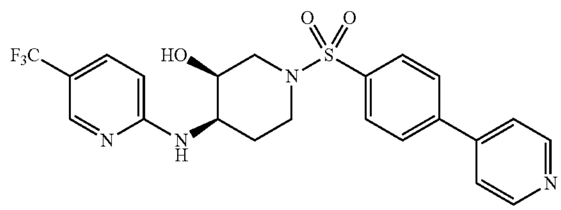 [SMILES: O=S(=O)(c1ccc(-c2ccncc2)cc1)N1CC[C@@H](Nc2ccc(C(F)(F)F)cn2)[C@@H](O)C1] | 479.0 | +++ |
| 162 | 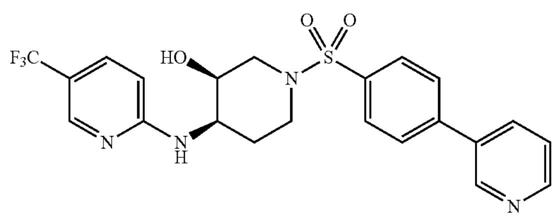 [SMILES: O=S(=O)(c1ccc(-c2cccnc2)cc1)N1CC[C@@H](Nc2ccc(C(F)(F)F)cn2)[C@@H](O)C1] | 479.0 | +++ |
| 163 | 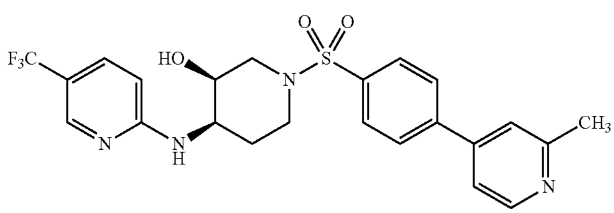 [SMILES: Cc1cc(-c2ccc(S(=O)(=O)N3CC[C@@H](Nc4ccc(C(F)(F)F)cn4)[C@@H](O)C3)cc2)ccn1] | 493.1 | +++ |
| 164 | 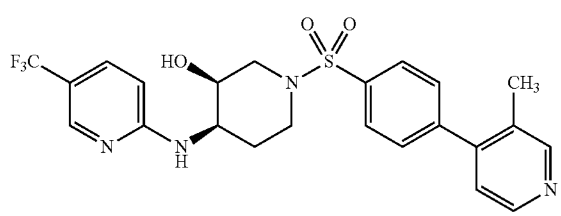 [SMILES: Cc1cnccc1-c1ccc(S(=O)(=O)N2CC[C@@H](Nc3ccc(C(F)(F)F)cn3)[C@@H](O)C2)cc1] | 493.0 | +++ |
| 165 | 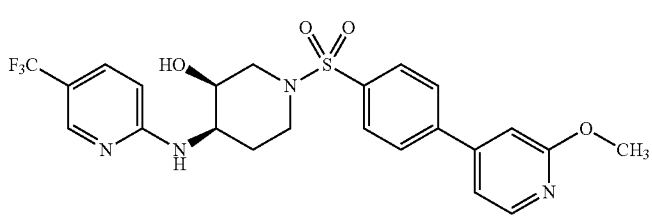 [SMILES: COc1cc(-c2ccc(S(=O)(=O)N3CC[C@@H](Nc4ccc(C(F)(F)F)cn4)[C@@H](O)C3)cc2)ccn1] | 509.1 | ++ |

TABLE 1-continued

| Compound | Structure | m/z | Potency |
|---|---|---|---|
| 166 | 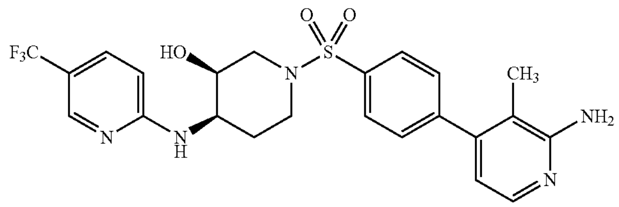 [SMILES: Cc1c(-c2ccc(S(=O)(=O)N3CC[C@@H](Nc4ccc(C(F)(F)F)cn4)[C@@H](O)C3)cc2)ccnc1N] | 508.0 | +++ |
| 167 | 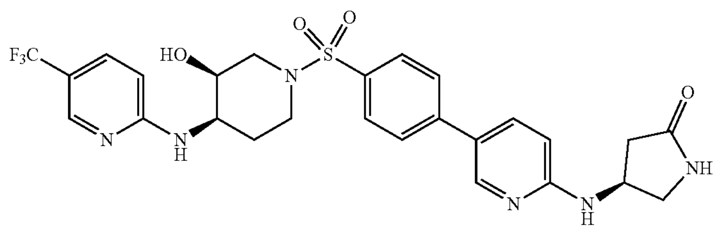 [SMILES: O=C1C[C@H](Nc2ccc(-c3ccc(S(=O)(=O)N4CC[C@@H](Nc5ccc(C(F)(F)F)cn5)[C@@H](O)C4)cc3)cn2)CN1] | 577.2 | +++ |
| 168 | 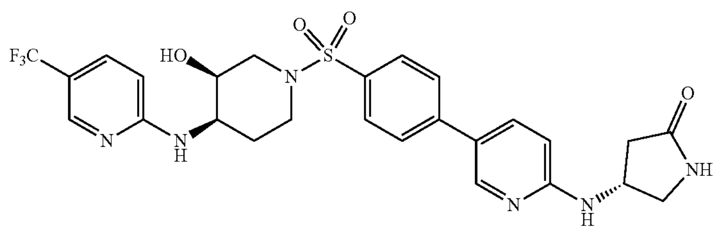 [SMILES: O=C1C[C@@H](Nc2ccc(-c3ccc(S(=O)(=O)N4CC[C@@H](Nc5ccc(C(F)(F)F)cn5)[C@@H](O)C4)cc3)cn2)CN1] | 577.2 | +++ |
| 169 | 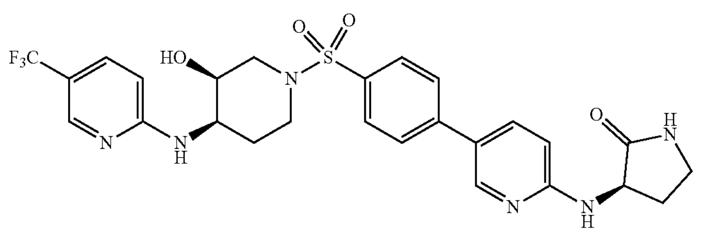 [SMILES: O=C1NCC[C@H]1Nc1ccc(-c2ccc(S(=O)(=O)N3CC[C@@H](Nc4ccc(C(F)(F)F)cn4)[C@@H](O)C3)cc2)cn1] | 577.2 | +++ |
| 170 | 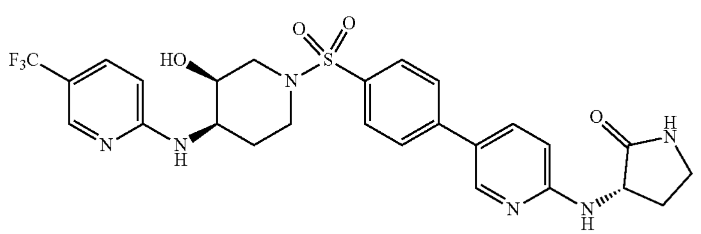 [SMILES: O=C1NCC[C@@H]1Nc1ccc(-c2ccc(S(=O)(=O)N3CC[C@@H](Nc4ccc(C(F)(F)F)cn4)[C@@H](O)C3)cc2)cn1] | 577.2 | +++ |
| 171 | 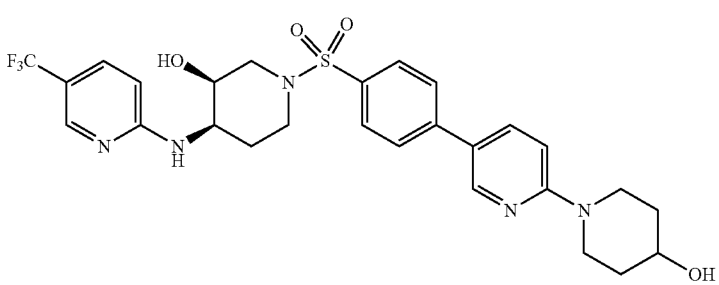 [SMILES: O=S(=O)(c1ccc(-c2ccc(N3CCC(O)CC3)nc2)cc1)N1CC[C@@H](Nc2ccc(C(F)(F)F)cn2)[C@@H](O)C1] | 578.3 | +++ |

TABLE 1-continued

| Compound | Structure | m/z | Potency |
|---|---|---|---|
| 172 | 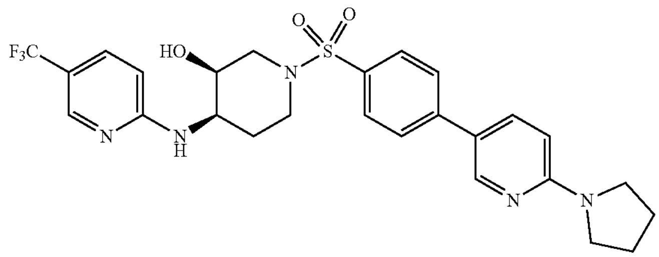 [SMILES: O=S(=O)(c1ccc(-c2ccc(N3CCCC3)nc2)cc1)N1CC[C@@H](Nc2ccc(C(F)(F)F)cn2)[C@@H](O)C1] | 548.2 | +++ |
| 173 | 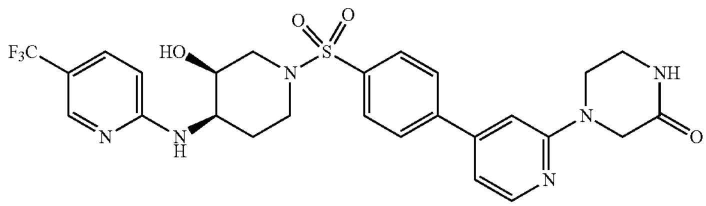 [SMILES: O=C1CN(c2cc(-c3ccc(S(=O)(=O)N4CC[C@@H](Nc5ccc(C(F)(F)F)cn5)[C@@H](O)C4)cc3)ccn2)CCN1] | 577.2 | +++ |
| 174 | 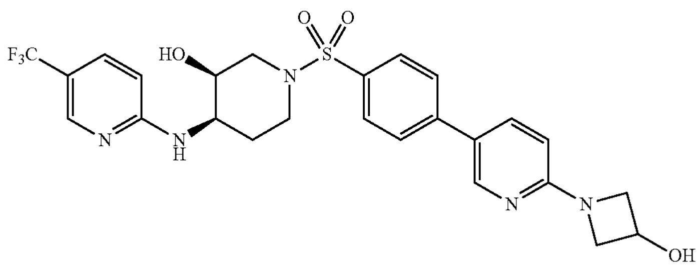 [SMILES: O=S(=O)(c1ccc(-c2ccc(N3CC(O)C3)nc2)cc1)N1CC[C@@H](Nc2ccc(C(F)(F)F)cn2)[C@@H](O)C1] | 550.2 | +++ |
| 175 | 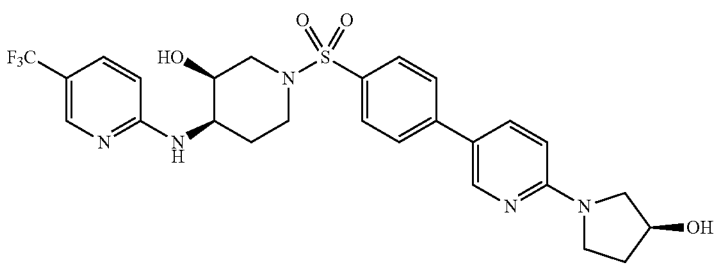 [SMILES: O=S(=O)(c1ccc(-c2ccc(N3CC[C@H](O)C3)nc2)cc1)N1CC[C@@H](Nc2ccc(C(F)(F)F)cn2)[C@@H](O)C1] | 564.1 | +++ |
| 176 | 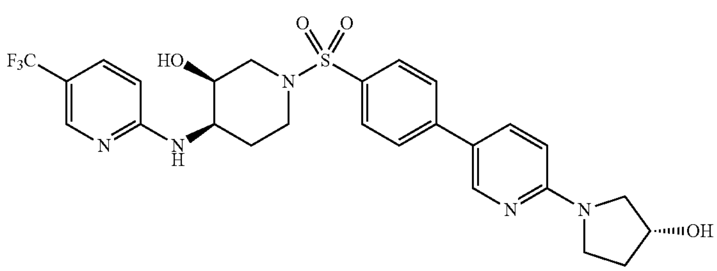 [SMILES: O=S(=O)(c1ccc(-c2ccc(N3CC[C@@H](O)C3)nc2)cc1)N1CC[C@@H](Nc2ccc(C(F)(F)F)cn2)[C@@H](O)C1] | 564.2 | +++ |
| 177 | 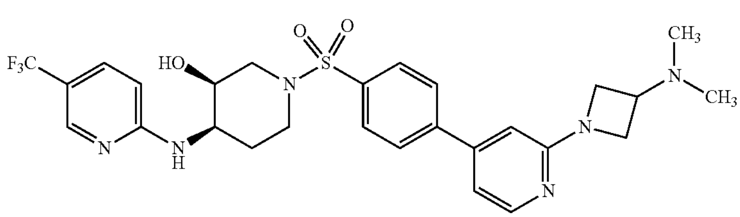 [SMILES: CN(C)C1CN(c2cc(-c3ccc(S(=O)(=O)N4CC[C@@H](Nc5ccc(C(F)(F)F)cn5)[C@@H](O)C4)cc3)ccn2)C1] | 577.2 | ++ |

TABLE 1-continued
| Compound | Structure | m/z | Potency |
|---|---|---|---|
| 178 | 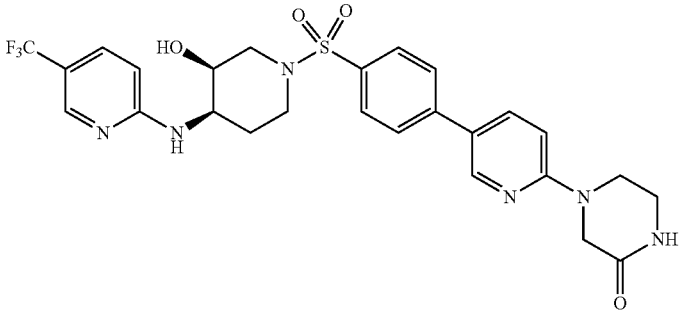 [SMILES: O=C1CN(c2ccc(-c3ccc(S(=O)(=O)N4CC[C@@H](Nc5ccc(C(F)(F)F)cn5)[C@@H](O)C4)cc3)cn2)CCN1] | 577.2 | +++ |
| 179 | 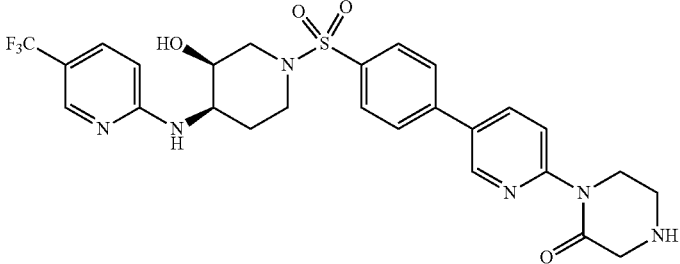 [SMILES: O=C1CNCCN1c1ccc(-c2ccc(S(=O)(=O)N3CC[C@@H](Nc4ccc(C(F)(F)F)cn4)[C@@H](O)C3)cc2)cn1] | 577.2 | +++ |
| 180 | 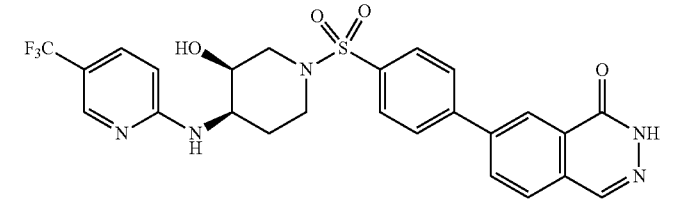 [SMILES: O=c1[nH]ncc2ccc(-c3ccc(S(=O)(=O)N4CC[C@@H](Nc5ccc(C(F)(F)F)cn5)[C@@H](O)C4)cc3)cc12] | 546.1 | +++ |
| 181 | 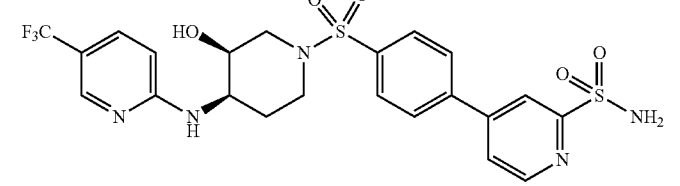 | 558.0 | +++ |
| 182 | 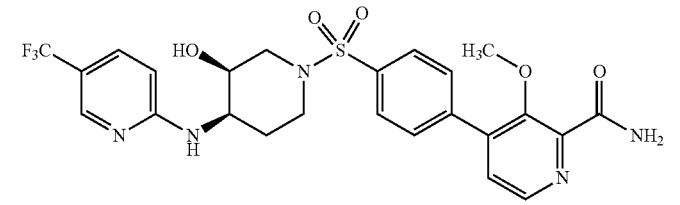 [SMILES: COc1c(-c2ccc(S(=O)(=O)N3CC[C@@H](Nc4ccc(C(F)(F)F)cn4)[C@@H](O)C3)cc2)ccnc1C(N)=O] | 552.1 | +++ |
| 183 | 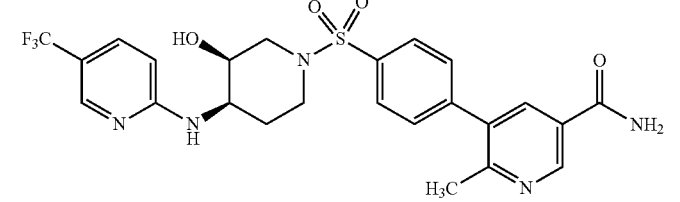 | 536.1 | +++ |

TABLE 1-continued

| Compound | Structure | m/z | Potency |
|---|---|---|---|
| 184 | 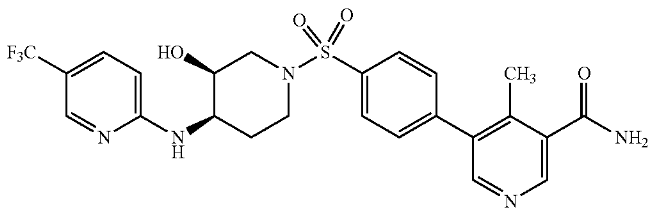 [SMILES: Cc1c(C(N)=O)cncc1-c1ccc(S(=O)(=O)N2CC[C@@H](Nc3ccc(C(F)(F)F)cn3)[C@@H](O)C2)cc1] | 536.1 | +++ |
| 185 | 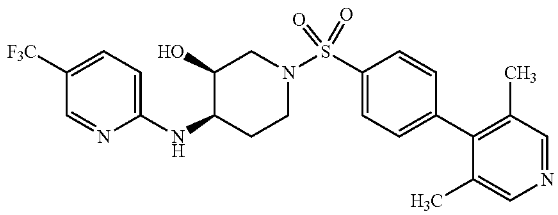 [SMILES: Cc1cncc(C)c1-c1ccc(S(=O)(=O)N2CC[C@@H](Nc3ccc(C(F)(F)F)cn3)[C@@H](O)C2)cc1] | 507.1 | +++ |
| 186 | 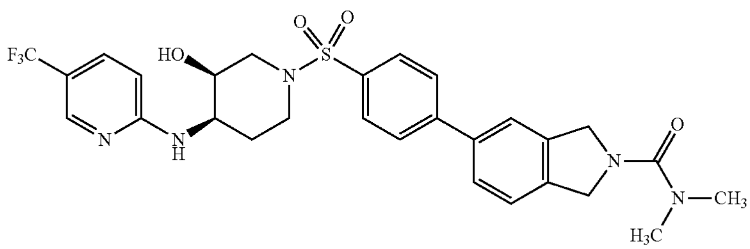 [SMILES: CN(C)C(=O)N1Cc2ccc(-c3ccc(S(=O)(=O)N4CC[C@@H](Nc5ccc(C(F)(F)F)cn5)[C@@H](O)C4)cc3)cc2C1] | 590.2 | +++ |
| 187 | 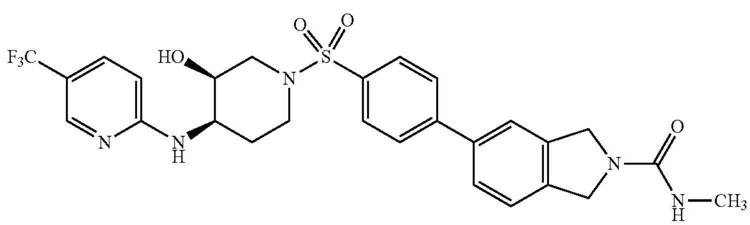 [SMILES: CNC(=O)N1Cc2ccc(-c3ccc(S(=O)(=O)N4CC[C@@H](Nc5ccc(C(F)(F)F)cn5)[C@@H](O)C4)cc3)cc2C1] | 576.2 | +++ |
| 188 | 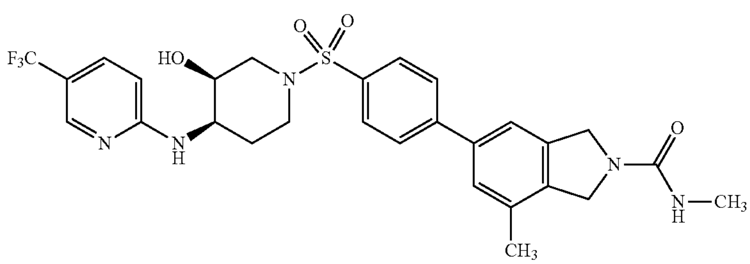 [SMILES: CNC(=O)N1Cc2cc(-c3ccc(S(=O)(=O)N4CC[C@@H](Nc5ccc(C(F)(F)F)cn5)[C@@H](O)C4)cc3)cc(C)c2C1] | 590.2 | +++ |
| 189 | 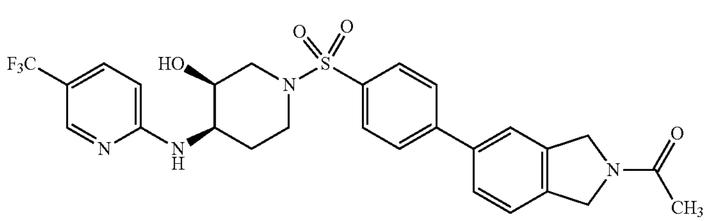 [SMILES: CC(=O)N1Cc2ccc(-c3ccc(S(=O)(=O)N4CC[C@@H](Nc5ccc(C(F)(F)F)cn5)[C@@H](O)C4)cc3)cc2C1] | 508.1 | ++ |

TABLE 1-continued

| Compound | Structure | m/z | Potency |
|---|---|---|---|
| 190 | 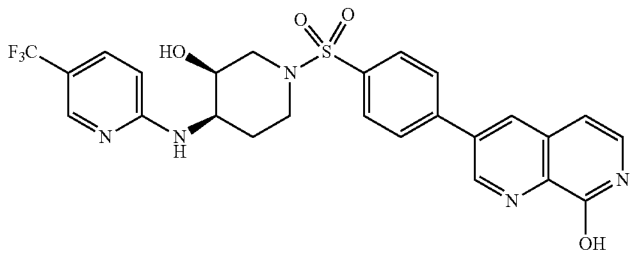 [SMILES: O=S(=O)(c1ccc(-c2cnc3c(O)nccc3c2)cc1)N1CC[C@@H](Nc2ccc(C(F)(F)F)cn2)[C@@H](O)C1] | 546.0 | +++ |
| 191 | 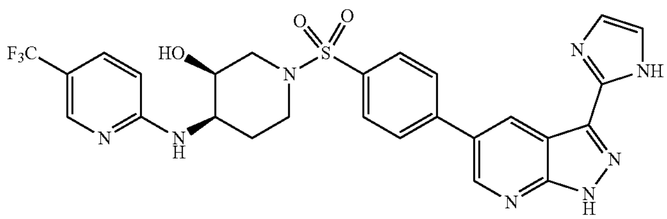 [SMILES: O=S(=O)(c1ccc(-c2cnc3[nH]nc(-c4ncc[nH]4)c3c2)cc1)N1CC[C@@H](Nc2ccc(C(F)(F)F)cn2)[C@@H](O)C1] | 585.0 | +++ |
| 192 | 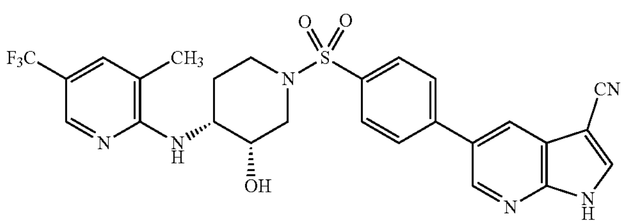 [SMILES: Cc1cc(C(F)(F)F)cnc1N[C@@H]1CCN(S(=O)(=O)c2ccc(-c3cnc4[nH]cc(C#N)c4c3)cc2)C[C@@H]1O] | 557.1 | +++ |
| 193 | 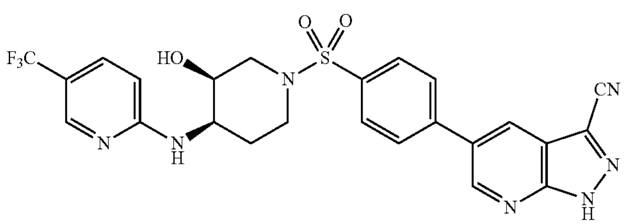 [SMILES: N#Cc1n[nH]c2ncc(-c3ccc(S(=O)(=O)N4CC[C@@H](Nc5ccc(C(F)(F)F)cn5)[C@@H](O)C4)cc3)cc12] | 544.0 | +++ |
| 194 | 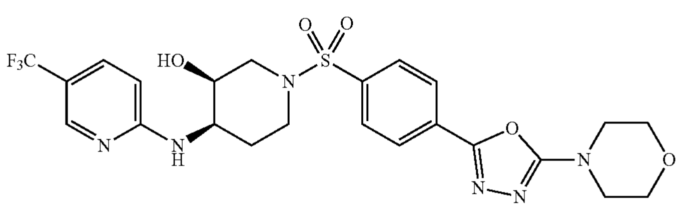 [SMILES: O=S(=O)(c1ccc(-c2nnc(N3CCOCC3)o2)cc1)N1CC[C@@H](Nc2ccc(C(F)(F)F)cn2)[C@@H](O)C1] | 555.2 | + |
| 195 | 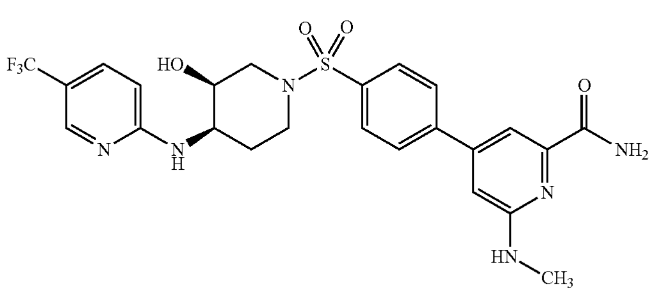 [SMILES: CNc1cc(-c2ccc(S(=O)(=O)N3CC[C@@H](Nc4ccc(C(F)(F)F)cn4)[C@@H](O)C3)cc2)cc(C(N)=O)n1] | 555.1 | +++ |

TABLE 1-continued

| Compound | Structure | m/z | Potency |
|---|---|---|---|
| 196 | 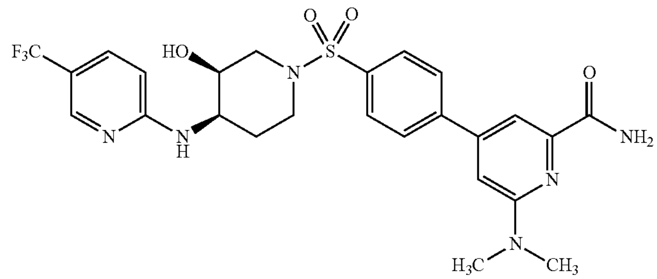 [SMILES: CN(C)c1cc(-c2ccc(S(=O)(=O)N3CC[C@@H](Nc4ccc(C(F)(F)F)cn4)[C@@H](O)C3)cc2)cc(C(N)=O)n1] | 565.2 | +++ |
| 197 | 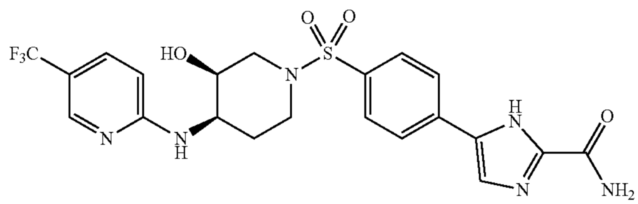 [SMILES: NC(=O)c1ncc(-c2ccc(S(=O)(=O)N3CC[C@@H](Nc4ccc(C(F)(F)F)cn4)[C@@H](O)C3)cc2)[nH]1] | 511.1 | ++ |
| 198 | 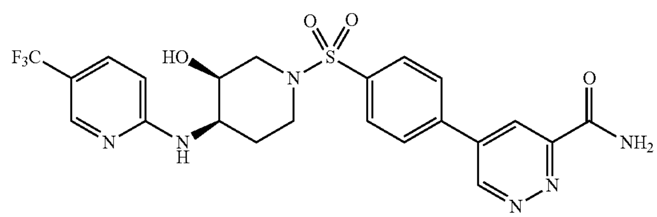 [SMILES: NC(=O)c1cc(-c2ccc(S(=O)(=O)N3CC[C@@H](Nc4ccc(C(F)(F)F)cn4)[C@@H](O)C3)cc2)cnn1] | 523.1 | +++ |
| 199 | 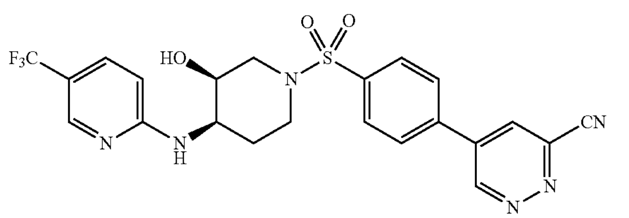 [SMILES: N#Cc1cc(-c2ccc(S(=O)(=O)N3CC[C@@H](Nc4ccc(C(F)(F)F)cn4)[C@@H](O)C3)cc2)cnn1] | 505.1 | ++ |
| 200 | 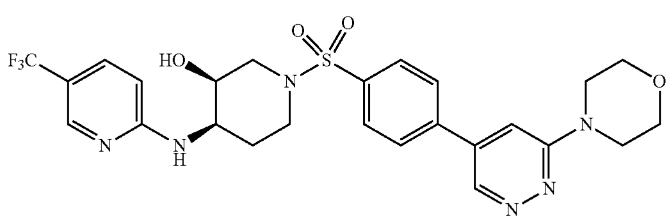 [SMILES: O=S(=O)(c1ccc(-c2cnnc(N3CCOCC3)c2)cc1)N1CC[C@@H](Nc2ccc(C(F)(F)F)cn2)[C@@H](O)C1] | 565.0 | +++ |
| 201 | 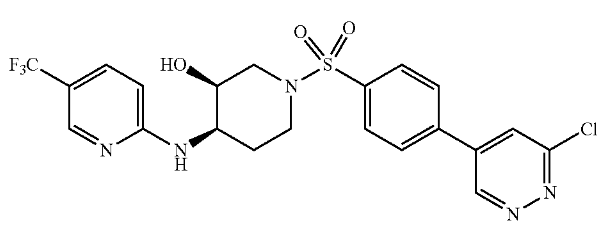 [SMILES: O=S(=O)(c1ccc(-c2cnnc(Cl)c2)cc1)N1CC[C@@H](Nc2ccc(C(F)(F)F)cn2)[C@@H](O)C1] | 514.0 | +++ |

TABLE 1-continued

| Compound | Structure | m/z | Potency |
|---|---|---|---|
| 202 | 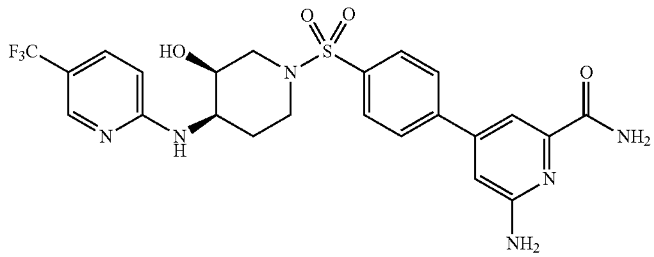 [SMILES: NC(=O)c1cc(-c2ccc(S(=O)(=O)N3CC[C@@H](Nc4ccc(C(F)(F)F)cn4)[C@@H](O)C3)cc2)cc(N)n1] | 537.0 | +++ |
| 203 | 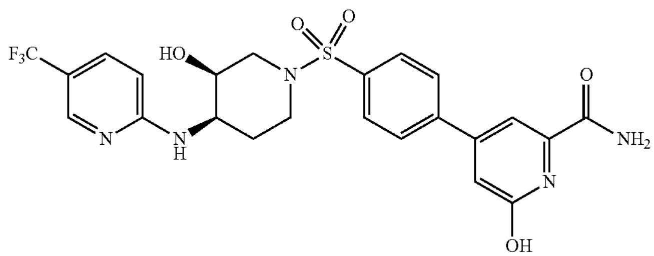 [SMILES: NC(=O)c1cc(-c2ccc(S(=O)(=O)N3CC[C@@H](Nc4ccc(C(F)(F)F)cn4)[C@@H](O)C3)cc2)cc(O)n1] | 538.0 | +++ |
| 204 | 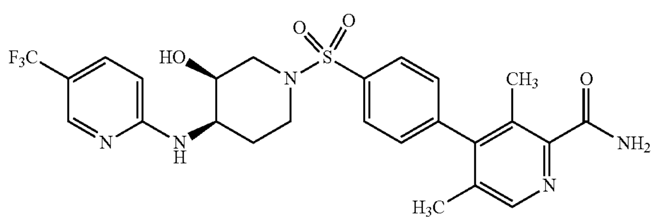 [SMILES: Cc1cnc(C(N)=O)c(C)c1-c1ccc(S(=O)(=O)N2CC[C@@H](Nc3ccc(C(F)(F)F)cn3)[C@@H](O)C2)cc1] | 550.2 | +++ |
| 205 | 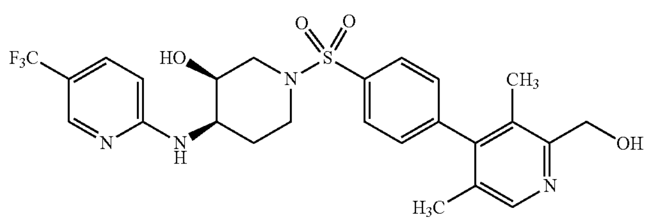 [SMILES: Cc1cnc(CO)c(C)c1-c1ccc(S(=O)(=O)N2CC[C@@H](Nc3ccc(C(F)(F)F)cn3)[C@@H](O)C2)cc1] | 537.2 | ++ |
| 206 | 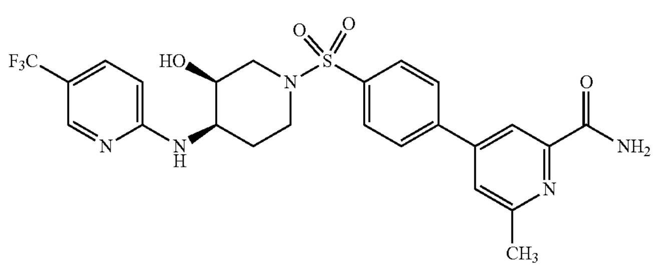 [SMILES: Cc1cc(-c2ccc(S(=O)(=O)N3CC[C@@H](Nc4ccc(C(F)(F)F)cn4)[C@@H](O)C3)cc2)cc(C(N)=O)n1] | 536.1 | +++ |
| 207 | 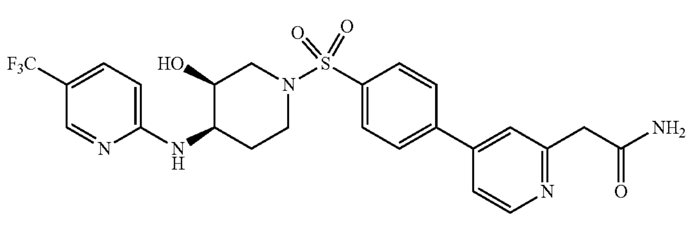 [SMILES: NC(=O)Cc1cc(-c2ccc(S(=O)(=O)N3CC[C@@H](Nc4ccc(C(F)(F)F)cn4)[C@@H](O)C3)cc2)ccn1] | 536.1 | ++ |

TABLE 1-continued

| Compound | Structure | m/z | Potency |
|---|---|---|---|
| 208 | 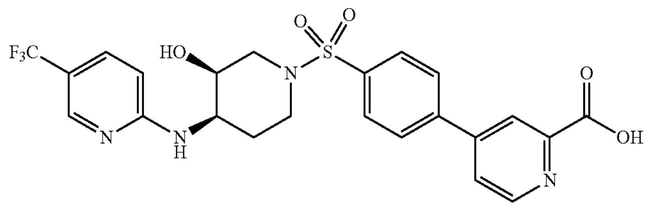 [SMILES: O=C(O)c1cc(-c2ccc(S(=O)(=O)N3CC[C@@H](Nc4ccc(C(F)(F)F)cn4)[C@@H](O)C3)cc2)ccn1] | 523.1 | + |
| 209 | 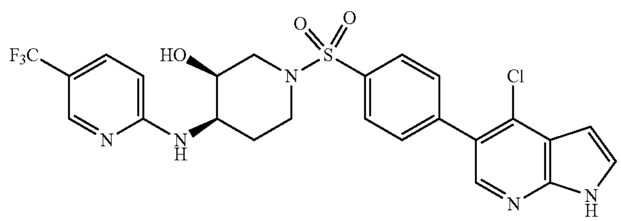 [SMILES: O=S(=O)(c1ccc(-c2cnc3[nH]ccc3c2Cl)cc1)N1CC[C@@H](Nc2ccc(C(F)(F)F)cn2)[C@@H](O)C1] | 551.8 | +++ |
| 210 | 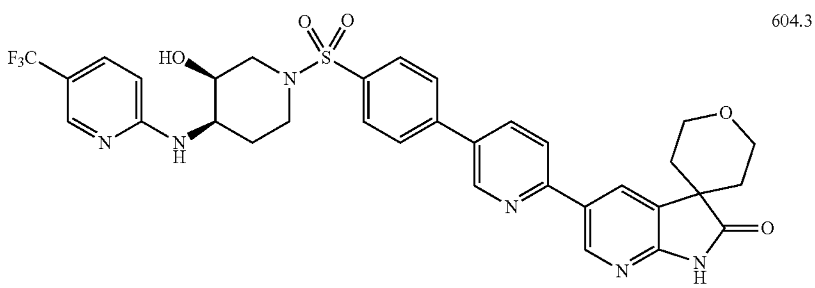 | 604.3 | +++ |
| 211 | 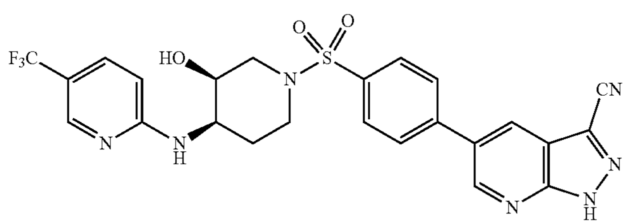 [SMILES: N#Cc1n[nH]c2ncc(-c3ccc(S(=O)(=O)N4CC[C@@H](Nc5ccc(C(F)(F)F)cn5)[C@@H](O)C4)cc3)cc12] | 543.3 | +++ |
| 212 | 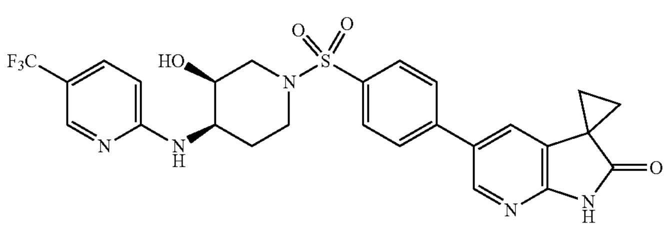 [SMILES: O=C1Nc2ncc(-c3ccc(S(=O)(=O)N4CC[C@@H](Nc5ccc(C(F)(F)F)cn5)[C@@H](O)C4)cc3)cc2C12CC2] | 560.4 | +++ |
| 213 | 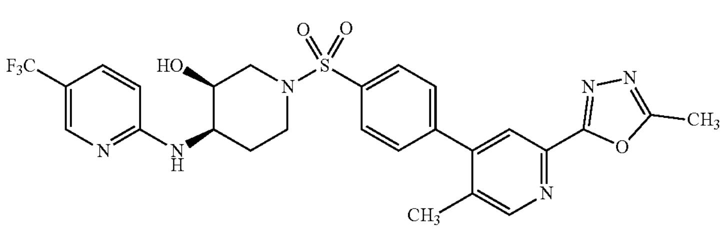 [SMILES: Cc1nnc(-c2cc(-c3ccc(S(=O)(=O)N4CC[C@@H](Nc5ccc(C(F)(F)F)cn5)[C@@H](O)C4)cc3)c(C)cn2)o1] | 575.3 | +++ |

TABLE 1-continued

| Compound | Structure | m/z | Potency |
|---|---|---|---|
| 214 | [structure: F₃C-pyridine-NH-piperidine(OH)-N-SO₂-phenyl-pyridine(OMe)-oxadiazole-CH₃] | 591.2 | +++ |
| 215 | [structure: F₃C-pyridine-NH-piperidine(OH)-N-SO₂-phenyl-pyridine-imidazole-CH₃] | 559.2 | ++ |

Biological Example 2: Comparison Activity

A comparison table is shown below to illustrate the benefit of an OH group on the piperidine ring, as shown.

| Structure | Potency Increase by changing H to OH X = OH is more active |
|---|---|
| [structure: F₃C-pyridine-NH-piperidine(X)-N-SO₂-phenyl-7-azaindole-CN] | >35x |
| [structure: F₃C-pyridine-NH-piperidine(X)-N-SO₂-phenyl-indazole-CN] | >8x |
| [structure: F₃C-pyridine-NH-piperidine(X)-N-SO₂-phenyl-phthalazinone] | >15x |

-continued
| Structure | Potency Increase by changing H to OH X = OH is more active |
|---|---|
| 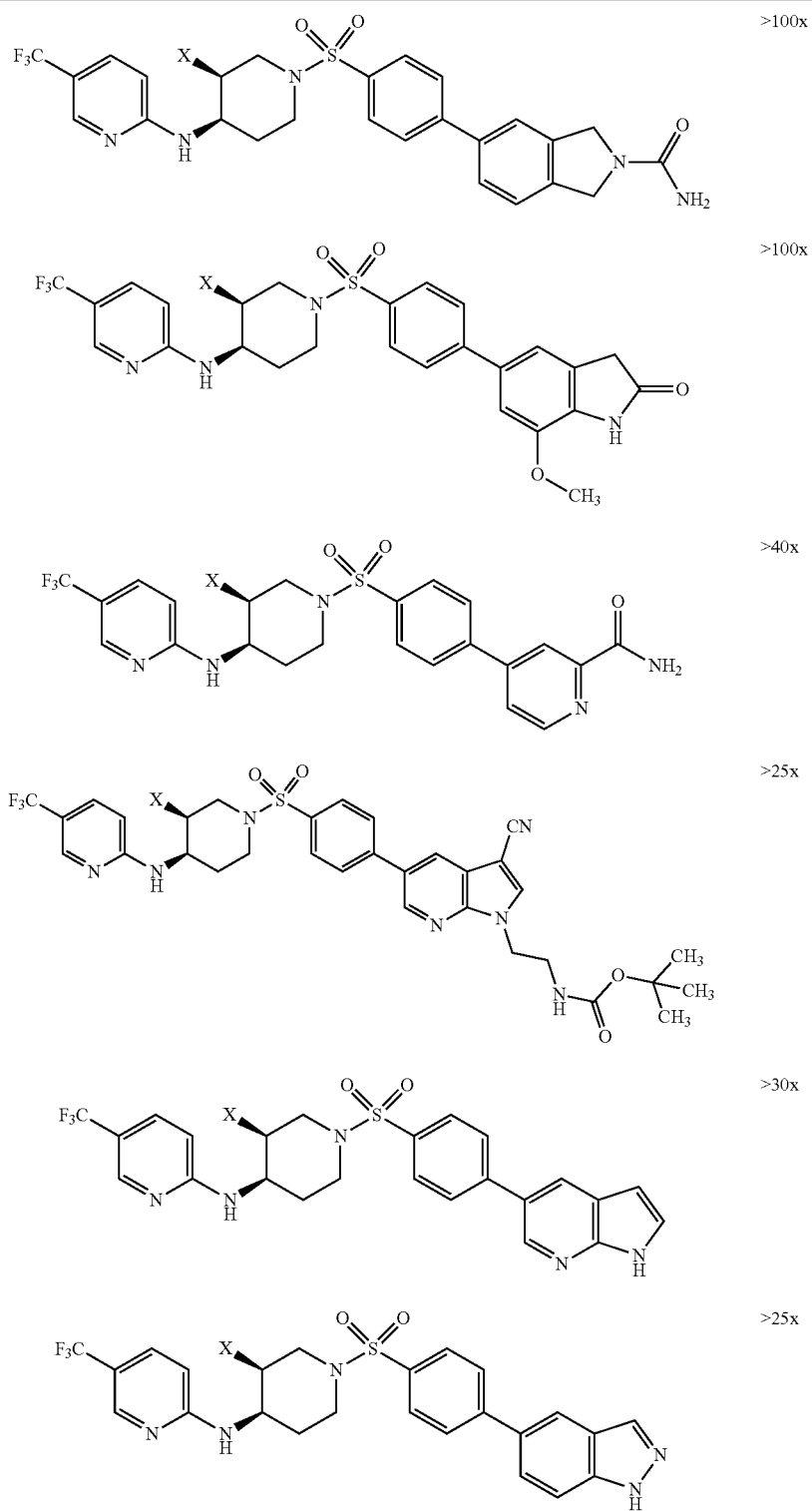 | >100x |
| | >100x |
| 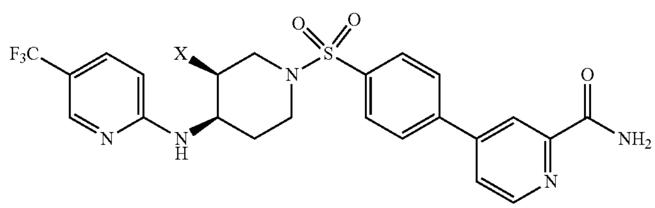 | >40x |
| | >25x |
| 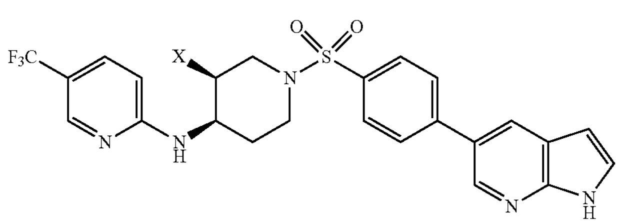 | >30x |
| | >25x |

-continued
| Structure | Potency Increase by changing H to OH X = OH is more active |
|---|---|
| 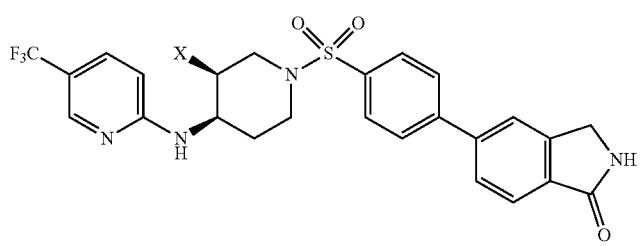 | >15x |
| 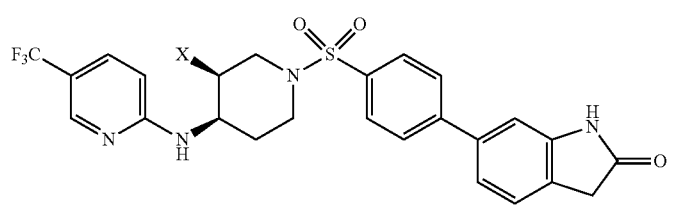 | >14x |
| 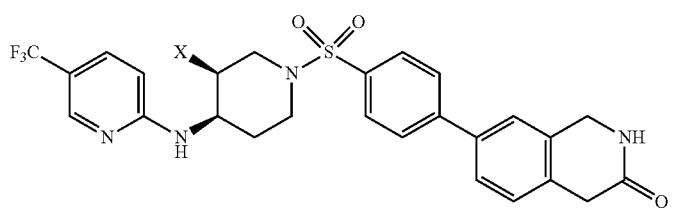 | >50x |
| 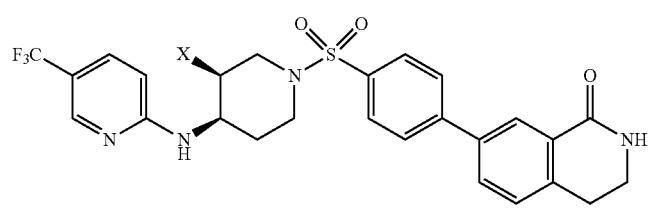 | >23x |
| 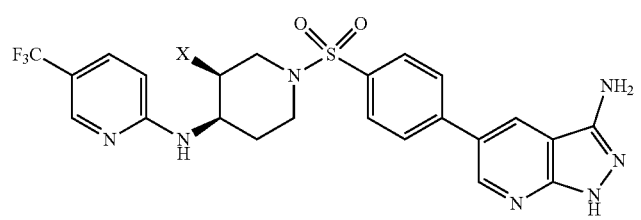 | >15x |
| 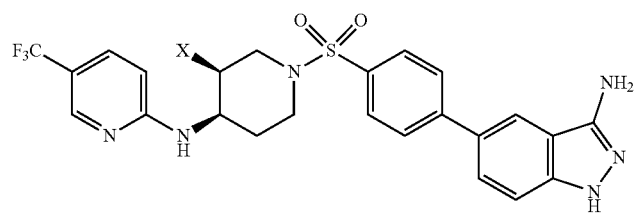 | >10x |

| Structure | Potency Increase by changing H to OH X = OH is more active |
|---|---|
| (structure 1) | >30x |
| (structure 2) | >40x |
| (structure 3) | >100x |

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A compound having formula (Ia):

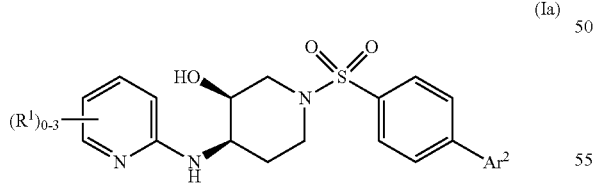

(Ia)

or a pharmaceutically acceptable salt, hydrate, solvate, N-oxide, optically enriched form, or rotamer thereof, wherein each $R^1$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, and —$NR^aR^b$;

each $R^a$ and $R^b$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl;

$Ar^2$ is selected from the group consisting of:
i) monocyclic 5- or 6-membered aromatic or heteroaromatic ring having 0 to 3 heteroatoms as ring vertices selected from N, O and S, and which is substituted with 0 to 5 $R^2$; and
ii) bicyclic 9- or 10-membered fused aromatic or heteroaromatic ring having 0 to 4 heteroatoms as ring vertices selected from N, O and S, and which is substituted with 0 to 5 $R^2$;

each $R^2$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^c$, —$SR^c$, —$COR^c$, —$CO_2R^c$, —$NR^cR^d$, —$CONR^cR^d$, —$CO(NR^c)_2COR^d$, —$SO_2R^c$, —$SO_2NR^cR^d$, —$X^2$—$CONR^cR^d$, —$X^2$—$NR^cSO_2R^d$, —$X^2$—$NR^cCO_2R^d$, —$X^2$—$P(=O)(OR^d)_2$, —$X^2$—$O$—$P(=O)(OR^d)_2$, —$N(R^c)$—$R^d$—$X^2$—$NR^cR^d$, oxo, 4- to 6-membered heterocyclyl, 7- to 10-membered spiroheterocyclyl and 5- or 6-membered heteroaryl; and wherein the heterocyclyl, spiroheterocyclyl and heteroaryl rings of $R^2$ have from 1 to 3 heteroatoms selected from N, O, and S, and are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl; and wherein two $R^2$ groups attached to the same carbon atom are optionally combined to form a 3- to 6-membered spirocyclic ring or a 3- to 6-membered spiroheterocyclic ring having from 1 to 3 heteroatoms selected from N, O, and S;

$R^c$ is independently selected from the group consisting of hydrogen, hydroxyl, $C_{1-4}$ alkyl, $C_{1-4}$ haloalkyl, and $C_{1-4}$ hydroxyalkyl;

$R^d$ is independently selected from the group consisting of hydrogen, hydroxyl, halogen, cyano, $C_{1-4}$ alkyl, $C_{1-4}$ haloalkyl, $C_{1-4}$ hydroxyalkyl, $C_{3-6}$ cycloalkyl, 4- to 6-membered heterocyclyl, and 5- or 6-membered heteroaryl; and wherein the $C_{3-6}$ cycloalkyl, 4- to 6-membered heterocyclyl, and 5- or 6-membered heteroaryl rings of $R^d$ have from 1 to 3 heteroatoms selected from N, O, and S, and are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl;

or $R^c$ and $R^d$, when attached to the same nitrogen atom are joined to form a 4- to 7-membered heterocyclic ring having from 0 to 2 additional heteroatoms as ring vertices selected from O, S, S(O), S(O)$_2$, NH, and N($C_{1-4}$ alkyl); and $X^2$ is $C_{1-4}$ alkylene.

2. A compound having formula (Ia):

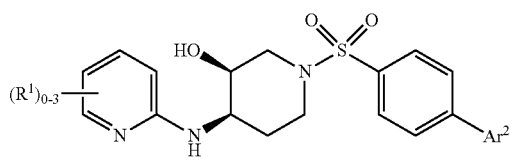

(Ia)

or a pharmaceutically acceptable salt, hydrate, solvate, N-oxide, optically enriched form, or rotamer thereof, wherein each $R^1$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR', and —NR$^a$R$^b$;

each $R^a$ and $R^b$ is independently selected from the group consisting of hydrogen, $C_{1-4}$ alkyl, $C_{1-4}$ haloalkyl, $C_{1-4}$ hydroxyalkyl, and $C_{3-6}$ cycloalkyl;

Ar$^2$ is selected from the group consisting of:
i) monocyclic 5- or 6-membered aromatic or heteroaromatic ring having 0 to 3 heteroatoms as ring vertices selected from N, O and S, and which is substituted with 0 to 5 $R^2$; and
ii) bicyclic 9- or 10-membered fused aromatic or heteroaromatic ring having 0 to 4 heteroatoms as ring vertices selected from N, O and S, and which is substituted with 0 to 5 $R^2$;

each $R^2$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR$^c$, —SR$^c$, —COR$^c$, —CO$_2$R$^c$, —NR$^c$R$^d$, —CONR$^c$R$^d$, —CO(NR$^c$)$_2$COR$^d$, —SO$_2$R$^c$, —SO$_2$NR$^c$R$^d$, —X$^2$—CONR$^c$R$^d$, —X$^2$—NR$^c$SO$_2$R$^d$, —X$^2$—NR$^c$CO$_2$R$^d$, —X$^2$—P(=O)(OR$^d$)$_2$, —X$^2$—O—P(=O)(OR$^d$)$_2$, —NR$^c$R$^d$—X$^2$—NR$^c$R$^d$, oxo, 4- to 6-membered heterocyclyl, 7- to 10-membered spiroheterocyclyl and 5- or 6-membered heteroaryl; and wherein the heterocyclyl, spiroheterocyclyl and heteroaryl rings of $R^2$ are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl; and wherein two $R^2$ groups attached to the same carbon atom are optionally combined to form a 3- to 6-membered spirocyclic ring;

$R^c$ is independently selected from the group consisting of hydrogen, hydroxyl, halogen, cyano, $C_{1-4}$ alkyl, $C_{1-4}$ haloalkyl, and $C_{1-4}$ hydroxyalkyl;

$R^d$ is independently selected from the group consisting of hydrogen, hydroxyl, halogen, cyano, $C_{1-4}$ alkyl, $C_{1-4}$ haloalkyl, $C_{1-4}$ hydroxyalkyl, $C_{3-6}$ cycloalkyl, 4- to 6-membered heterocyclyl, and 5- or 6-membered heteroaryl; and wherein the $C_{3-6}$ cycloalkyl, 4- to 6-membered heterocyclyl, and 5- or 6-membered heteroaryl rings of $R^d$ are each unsubstituted or substituted with one or two members independently selected from the group consisting of halogen, hydroxyl, oxo, $C_{1-4}$ alkyl, amino, $C_{1-4}$ alkylamino, di-$C_{1-4}$ alkylamino, $C_{1-4}$ alkoxy, $C_{1-4}$ hydroxyalkyl, and $C_{1-4}$ haloalkyl;

or $R^c$ and $R^d$, when attached to the same nitrogen atom are joined to form a 4- to 7-membered heterocyclic ring having from 0 to 2 additional heteroatoms as ring vertices selected from O, S, S(O), S(O)$_2$, NH, and N($C_{1-4}$ alkyl); and $X^2$ is $C_{1-4}$ alkylene.

3. The compound of claim 1, or a pharmaceutically acceptable salt, hydrate, solvate, N-oxide or rotamer thereof, wherein Ar$^2$ is a bicyclic 9- or 10-membered fused aromatic or heteroaromatic ring that is substituted with 0 to 5 $R^2$.

4. The compound of claim 1, or a pharmaceutically acceptable salt, hydrate, solvate, N-oxide or rotamer thereof, wherein Ar$^2$ is a monocyclic 5- or 6-membered aromatic or heteroaromatic ring that is substituted with 0 to 5 $R^2$.

5. The compound of claim 1, or a pharmaceutically acceptable salt thereof, wherein Ar$^2$ is selected from the group consisting of

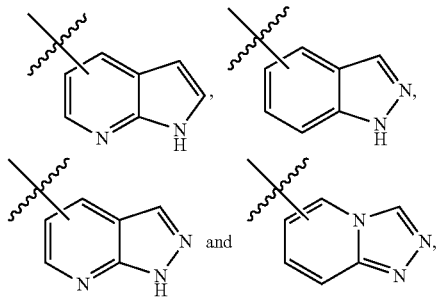

and each of which is substituted with from 0-3 $R^2$.

6. The compound of claim 1, or a pharmaceutically acceptable salt thereof, wherein Ar$^2$ is selected from the group consisting of

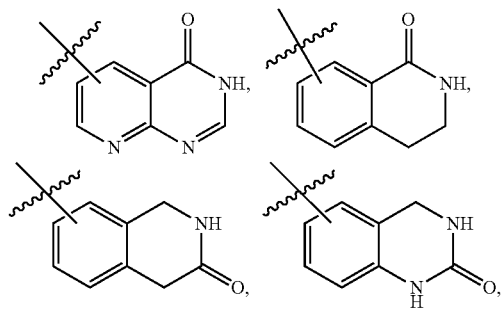

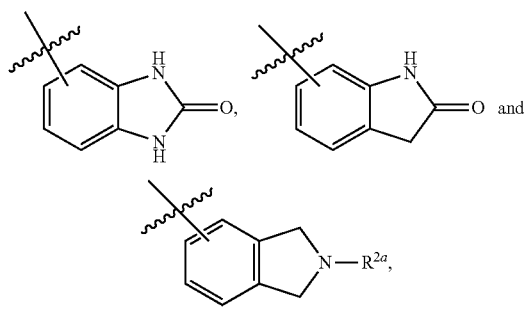

each of which is substituted with from 0-3 R², and wherein R²ᵃ is selected from the group consisting of hydrogen, $C_{1-4}$ alkyl, $C_{1-4}$ haloalkyl, $C_{1-4}$hydroxyalkyl, —C(O)NH₂, —C(O)N(H)$C_{1-4}$alkyl, —C(O)N($C_{1-4}$alkyl)₂, —S(O)₂$C_{1-4}$alkyl, —S(O)₂N(H)$C_{1-4}$alkyl, —C(O)O$C_{1-4}$alkyl, and —C(O)$C_{1-4}$alkyl.

7. The compound of claim 1, or a pharmaceutically acceptable salt thereof, wherein Ar² is selected from the group consisting of phenyl, pyridyl, thiazolyl, oxadiazolyl, imidazolyl, pyridazinyl, and oxazolyl, each of which is substituted with from 0-3 R².

8. The compound of claim 1, or a pharmaceutically acceptable salt thereof, wherein Ar² is pyridyl, which is substituted with from 0-3 R².

9. The compound of claim 1, or a pharmaceutically acceptable salt thereof, wherein Ar² is thiazolyl, which is substituted with from 0-2 R².

10. The compound of claim 1, or a pharmaceutically acceptable salt thereof, wherein Ar² is 1,3,4-oxadiazolyl, which is substituted with from 0-1 R².

11. The compound of claim 1, or a pharmaceutically acceptable salt thereof, wherein Ar² imidazolyl, which is substituted with from 0-2 R².

12. The compound of claim 1, having the formula:

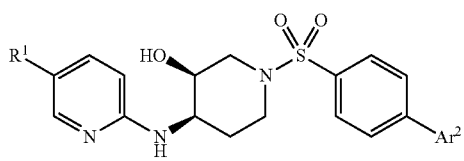

or a pharmaceutically acceptable salt thereof, wherein R¹ is —CN or —CF₃.

13. The compound of claim 1, having the formula:

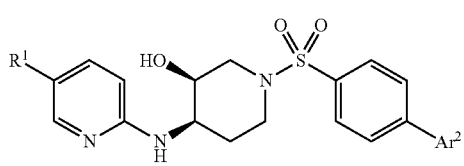

or a pharmaceutically acceptable salt thereof, wherein R¹ is —CN or —CF₃; and Ar² is selected from the group consisting of

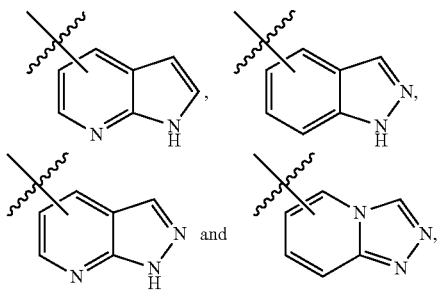

each of which is substituted with from 0-3 R².

14. The compound of claim 1, or a pharmaceutically acceptable salt thereof, wherein R¹ is —CN or —CF₃; and Ar² is selected from the group consisting of

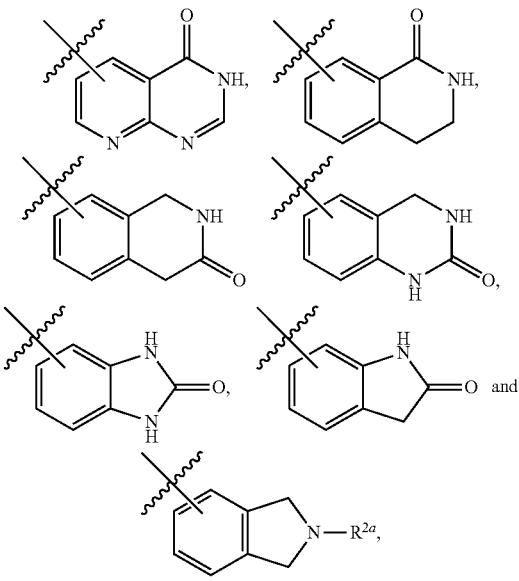

each of which is substituted with from 0-3 R², and wherein R²ᵃ is selected from the group consisting of hydrogen, $C_{1-4}$ alkyl, $C_{1-4}$ haloalkyl, $C_{1-4}$ hydroxyalkyl, —C(O)NH₂, —C(O)N(H)$C_{1-4}$alkyl, —C(O)N($C_{1-4}$alkyl)₂, —S(O)₂$C_{1-4}$alkyl, —S(O)₂N(H)$C_{1-4}$alkyl, —C(O)O$C_{1-4}$alkyl, and —C(O)$C_{1-4}$alkyl.

15. The compound of claim 1, or a pharmaceutically acceptable salt thereof, wherein R¹ is —CN or —CF₃; and Ar² is selected from the group consisting of phenyl, pyridyl, thiazolyl, oxadiazolyl, imidazolyl, pyridazinyl, and oxazolyl, each of which is substituted with from 0-2 R².

16. The compound of claim 12, or a pharmaceutically acceptable salt thereof, wherein Ar² is selected from the group consisting of

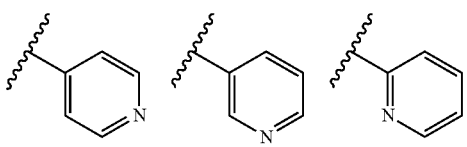

-continued

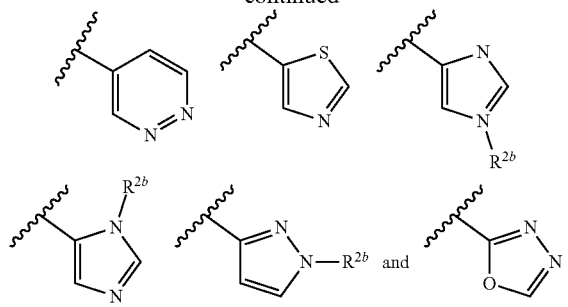

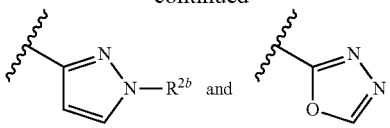

each of which is substituted with from 0-2 R², and wherein R²ᵇ is selected from the group consisting of hydrogen, $C_{1-4}$ alkyl, $C_{1-4}$ haloalkyl, and $C_{1-4}$ hydroxyalkyl.

17. The compound of claim 16, or a pharmaceutically acceptable salt thereof, wherein Ar² is selected from the group consisting of

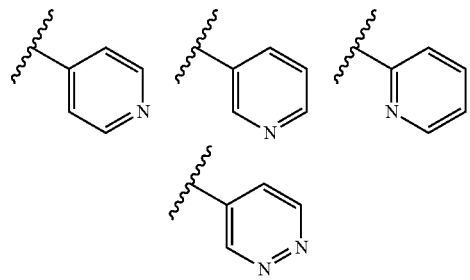

each of which is substituted with from 0-2 R².

18. The compound of claim 16, or a pharmaceutically acceptable salt thereof, wherein Ar² is selected from the group consisting of

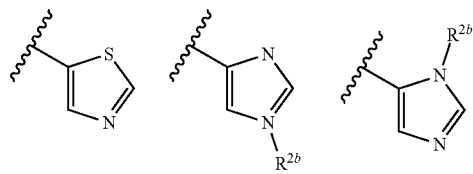

each of which is substituted with from 0-1 R²; and wherein R²ᵇ is selected from the group consisting of hydrogen, $C_{1-4}$ alkyl, $C_{1-4}$ haloalkyl, and $C_{1-4}$ hydroxyalkyl.

19. The compound of claim 1, or a pharmaceutically acceptable salt thereof, wherein R¹ is CF₃; and R² is CN, —CH₃, —OH, —NH₂, —N(CH₃)₂, —C(O)NH₂, —C(O)N(H)(CH₃), —C(O)N(CH₃)₂, —C(O)CH₃, —C(O)OCH₃, —S(O)₂NH₂, Cl, F, —N(CH₃)₂, —OCH₃, —CH₂OH, —N(H)Rᵈ, piperazinyl, piperidinyl, morpholinyl, triazolyl, 1,3,4-oxadiazolyl, pyrrolidinyl, or azetidinyl, wherein the piperazinyl, piperidinyl, morpholinyl, triazolyl, 1,3,4-oxadiazolyl, pyrrolidinyl and azetidinyl groups can be optionally substituted with 1 or 2 substituents selected from the group consisting of —CH₃, C(CH₃)₂OH, OH, —OCH₃, —NH₂, and —N(CH₃)₂.

20. The compound of claim 19, or a pharmaceutically acceptable salt thereof, wherein R² is CN, —CH₃, —OH, —NH₂, —N(CH₃)₂, —C(O)NH₂, —C(O)N(H)(CH₃), —C(O)N(CH₃)₂, —C(O)CH₃, —C(O)OCH₃, —S(O)₂NH₂, Cl, F, —N(CH₃)₂, —OCH₃, —N(H)Rᵈ, or —CH₂OH.

21. The compound of claim 19, or a pharmaceutically acceptable salt thereof, wherein R² is piperazinyl, piperidinyl, morpholinyl, triazolyl, 1,3,4-oxadiazolyl, pyrrolidinyl, or azetidinyl, wherein the the piperazinyl, piperidinyl, morpholinyl, triazolyl, 1,3,4-oxadiazolyl, pyrrolidinyl and azetidinyl groups can be optionally substituted with 1 or 2 substituents selected from the group consisting of —CH₃, C(CH₃)₂OH, OH, —OCH₃, —NH₂, and —N(CH₃)₂.

22. A compound selected from the group consisting of

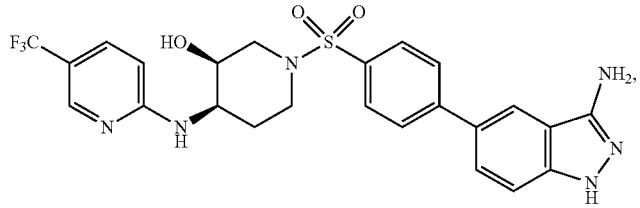

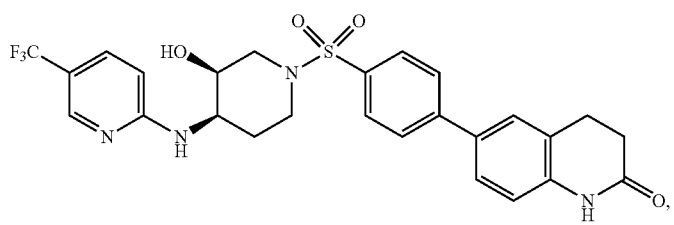

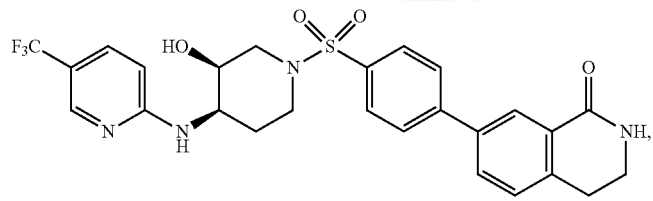
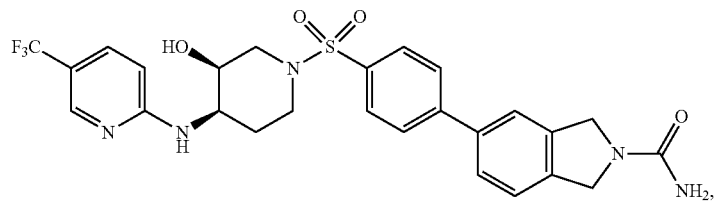
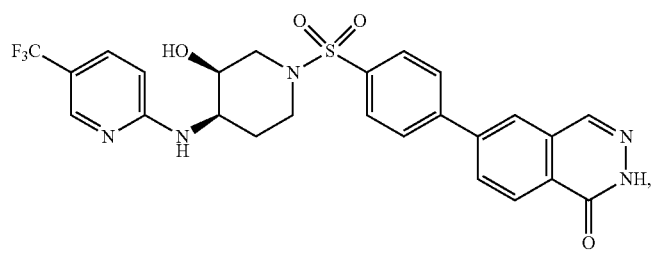
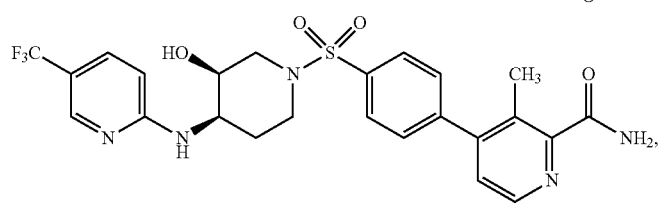
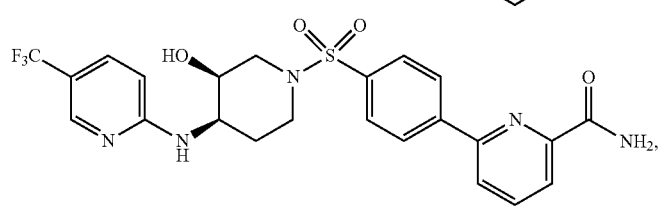
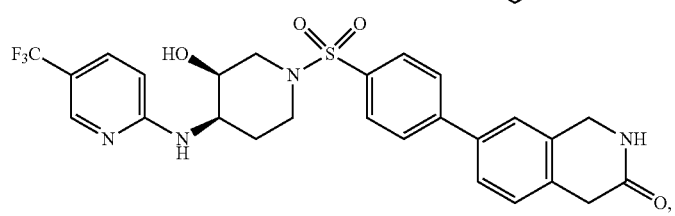
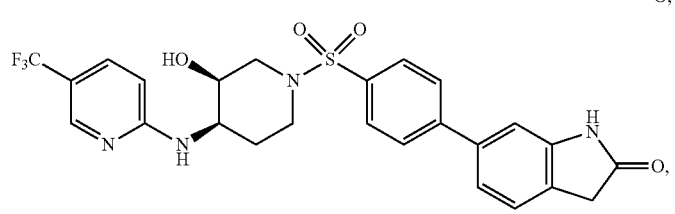
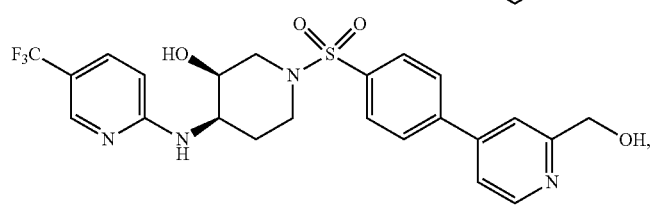

-continued
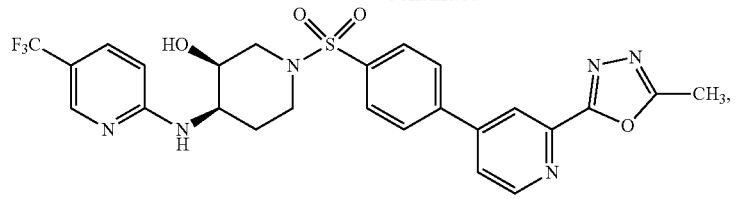
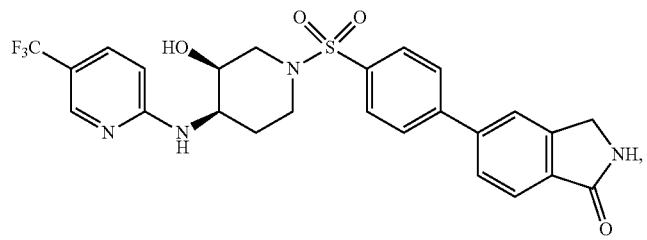
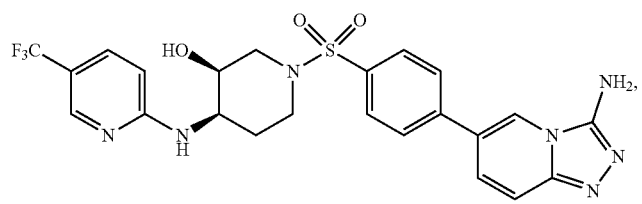
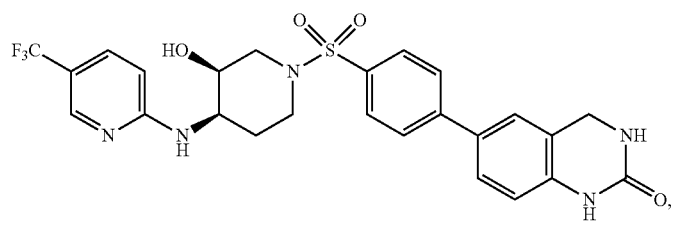
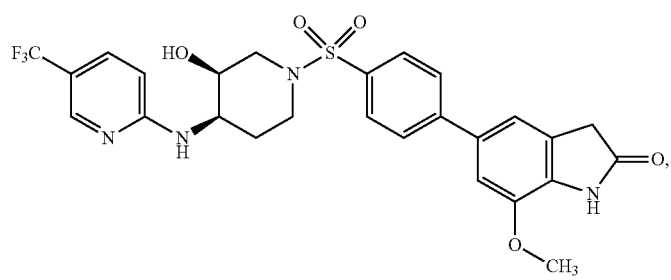
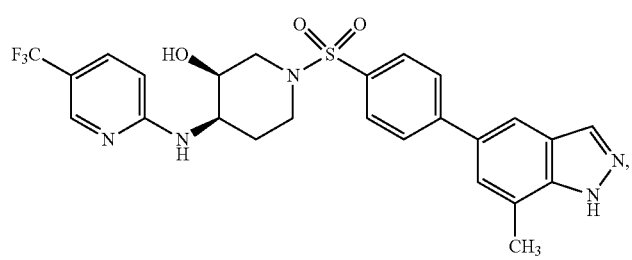
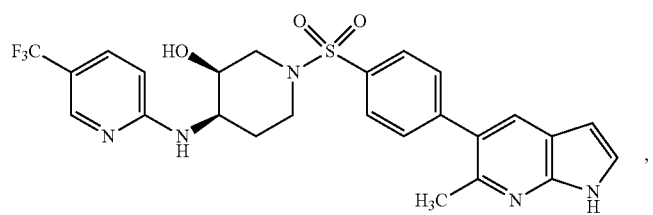

-continued
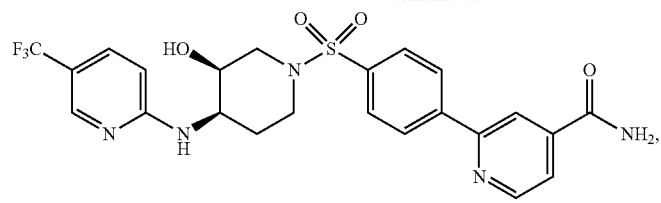
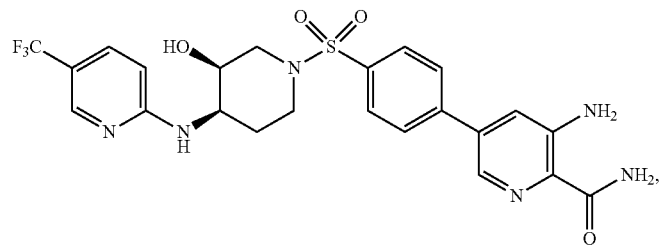
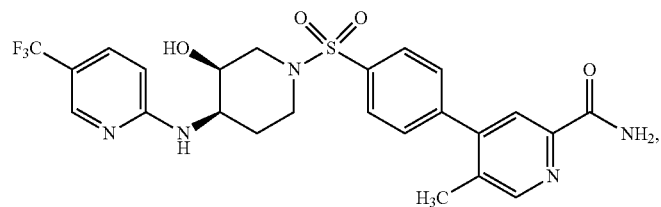
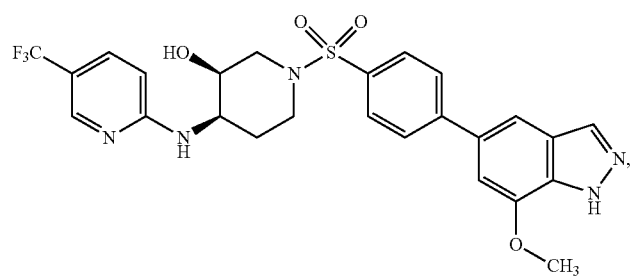
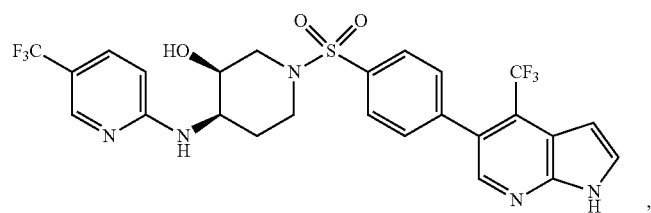
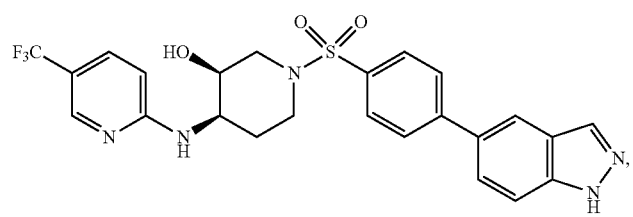
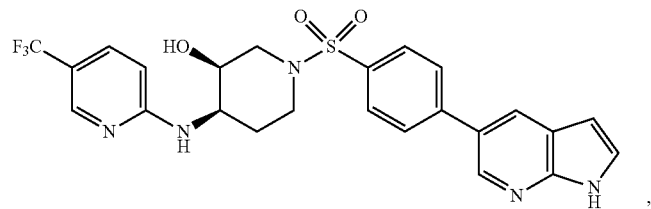

-continued
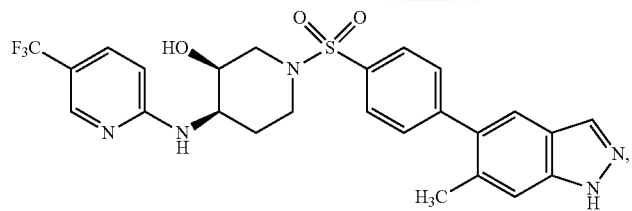
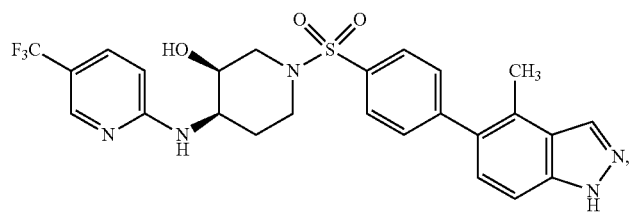
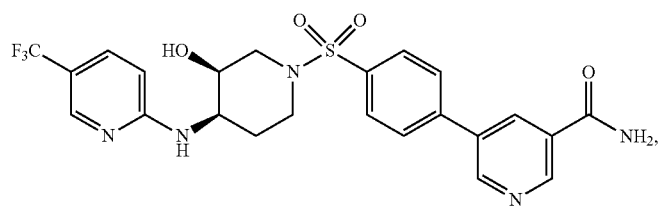
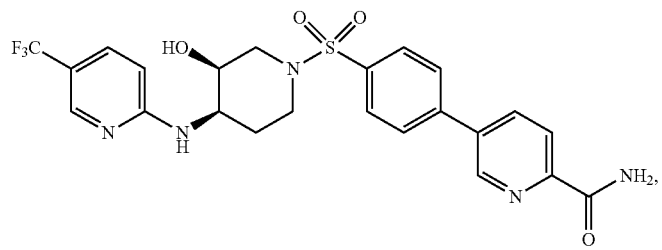
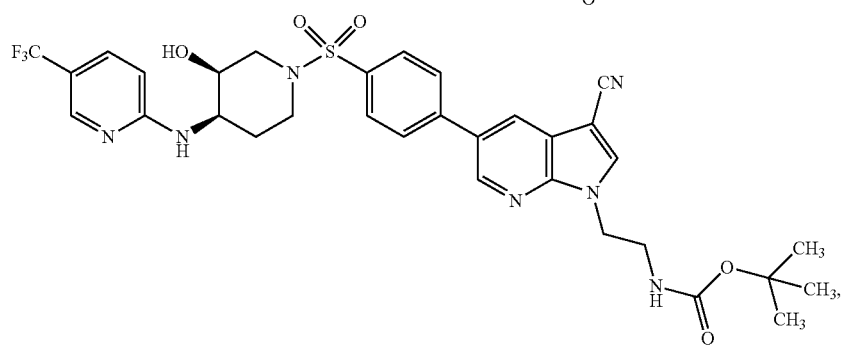
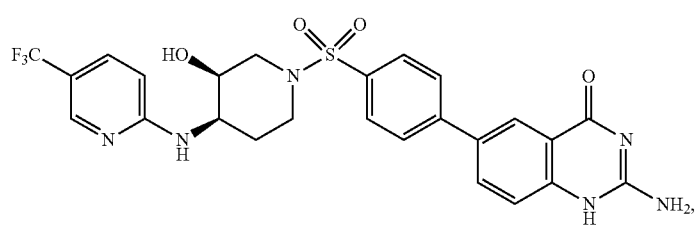
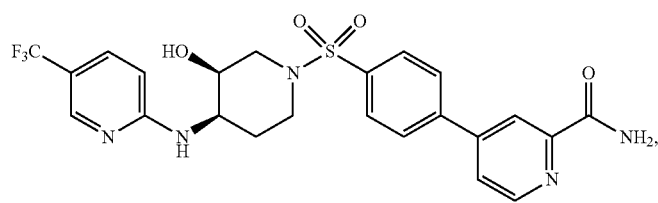

-continued
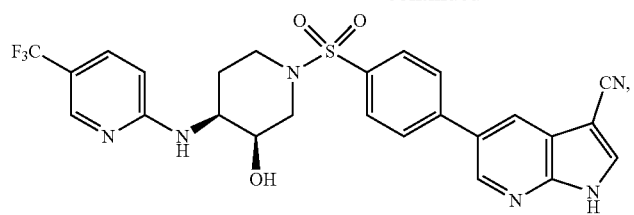
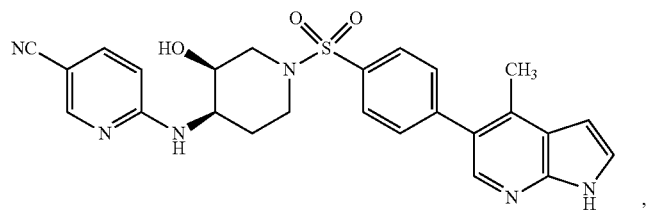
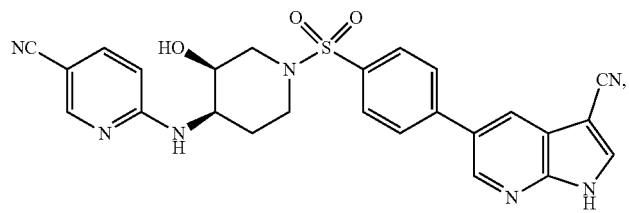
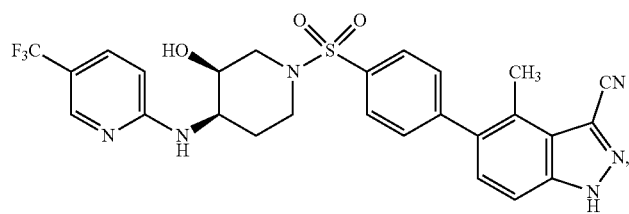
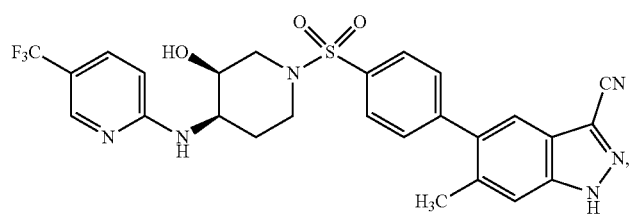
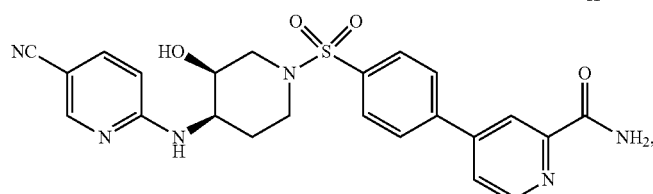
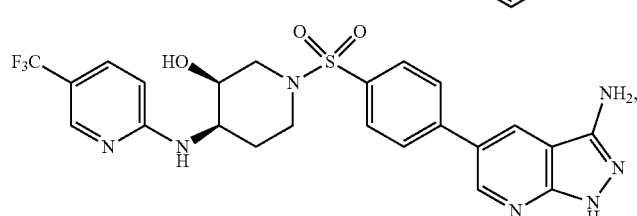
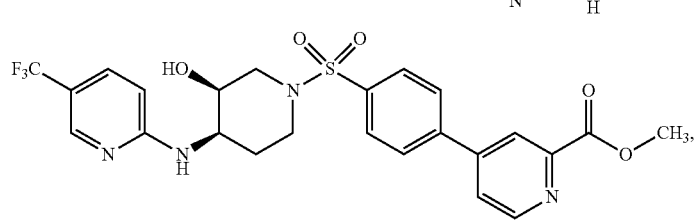

-continued
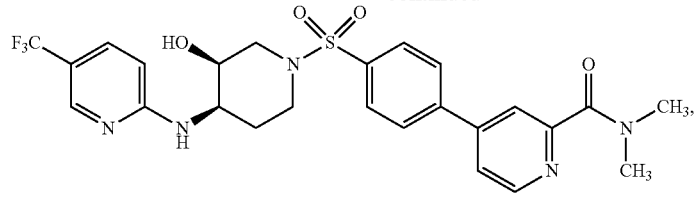
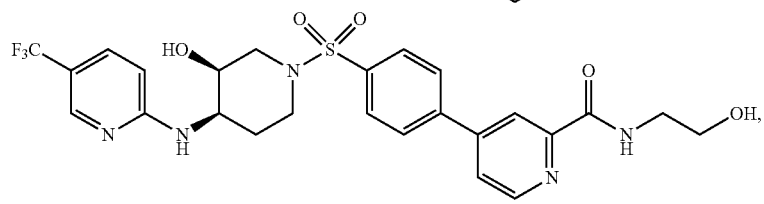
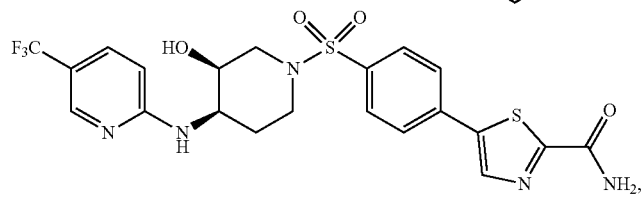
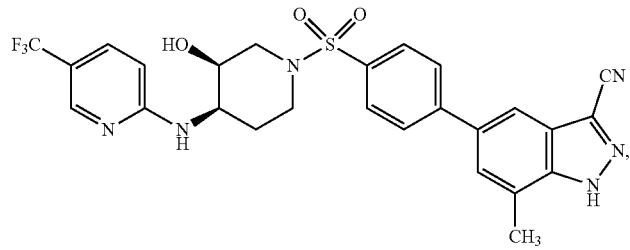
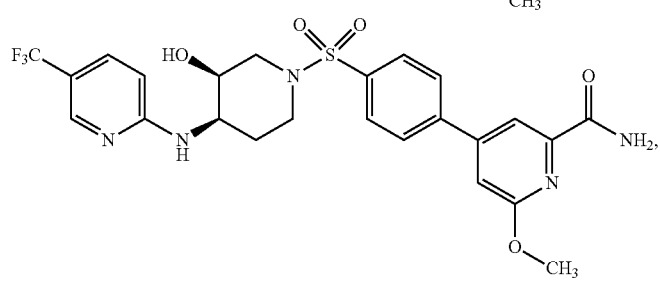
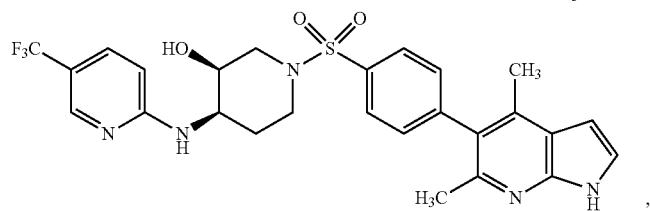
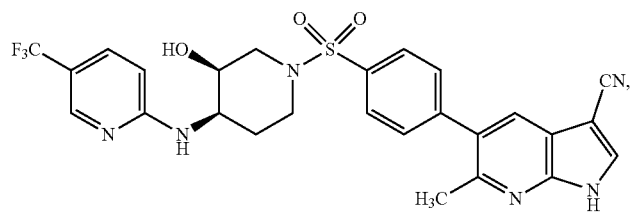
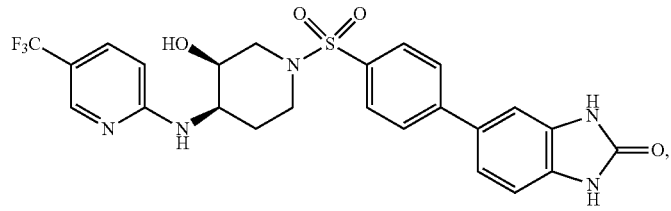

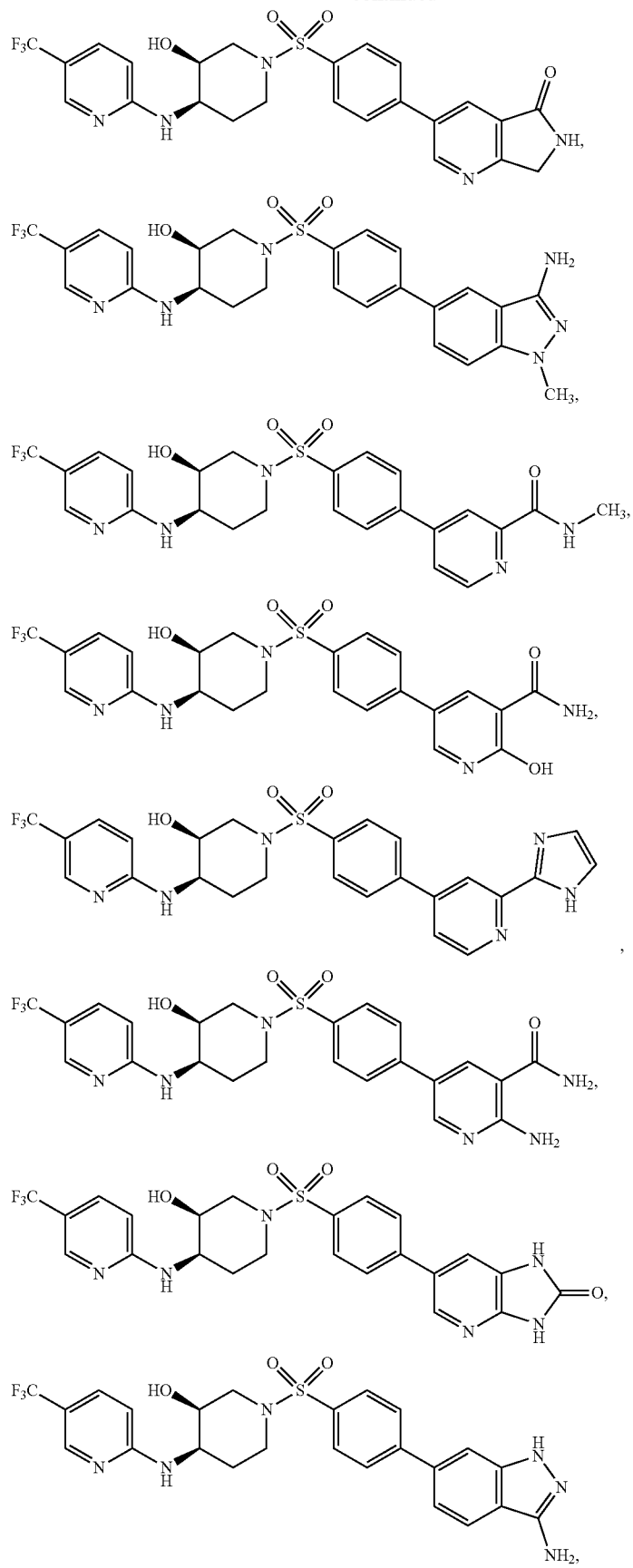

-continued
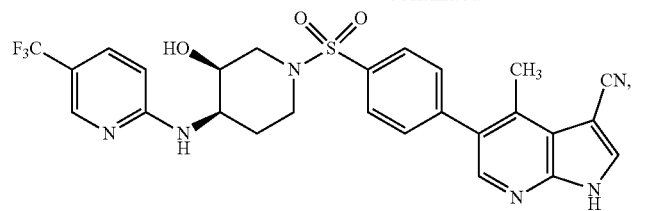
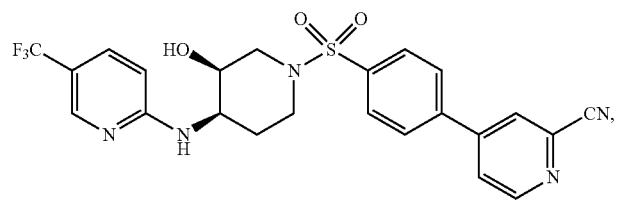
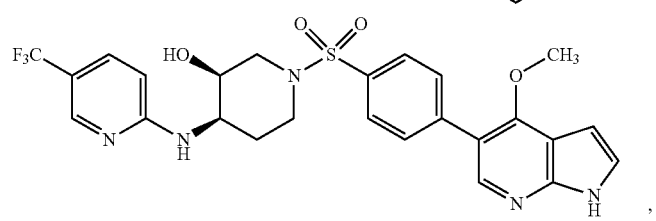,
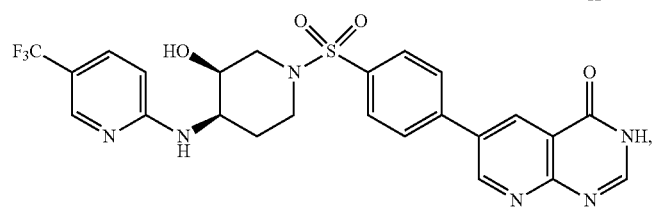
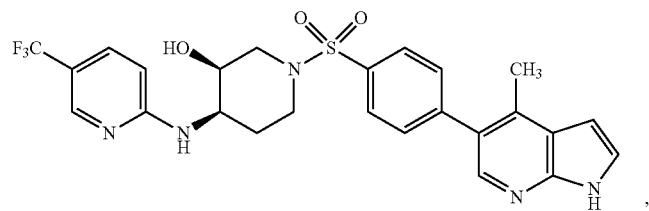,
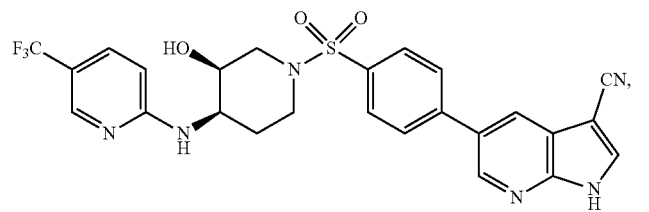
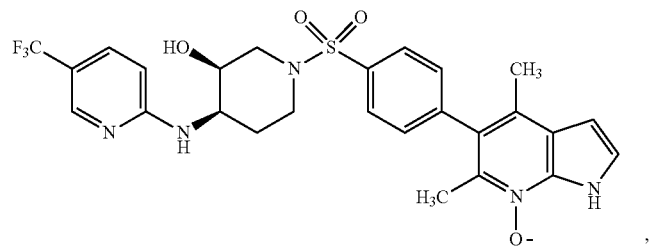,
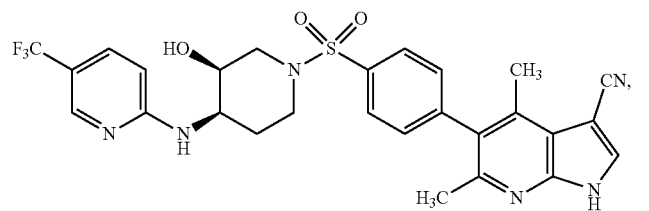

-continued
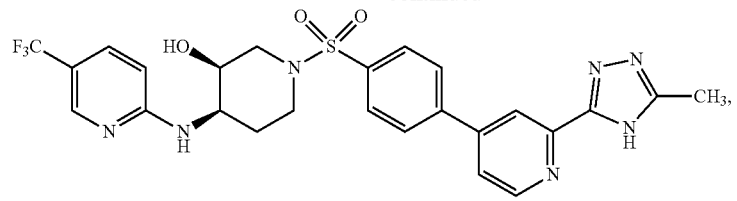
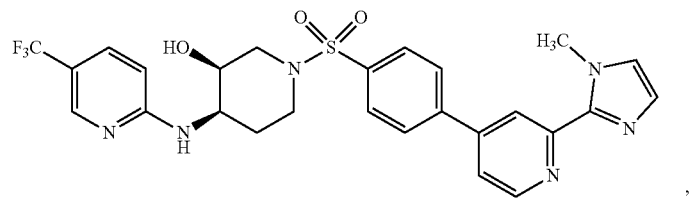
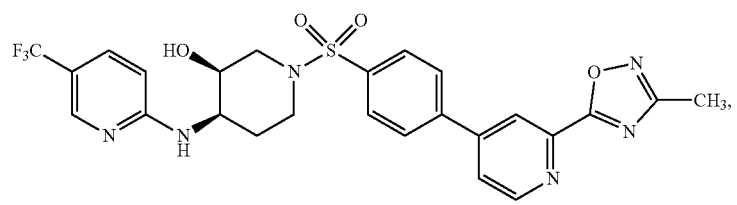
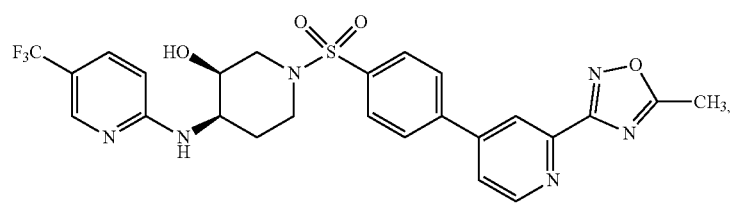
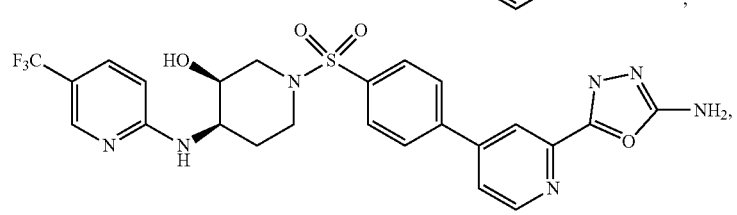
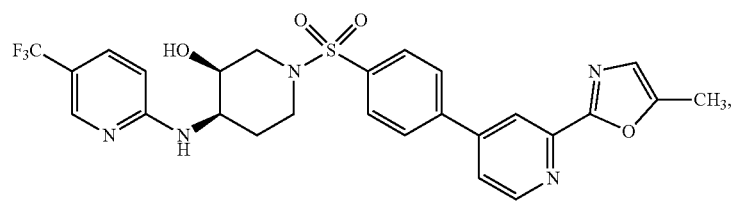
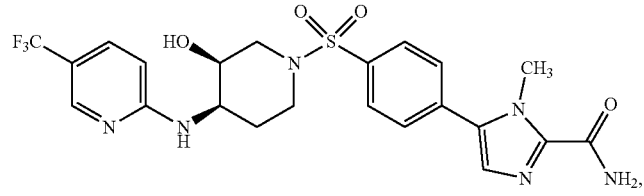

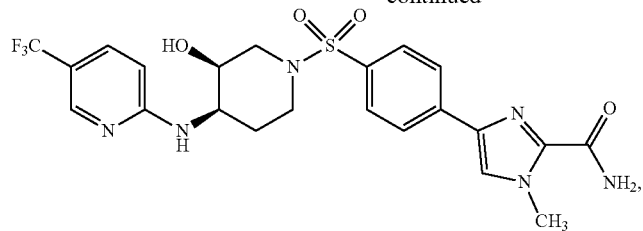
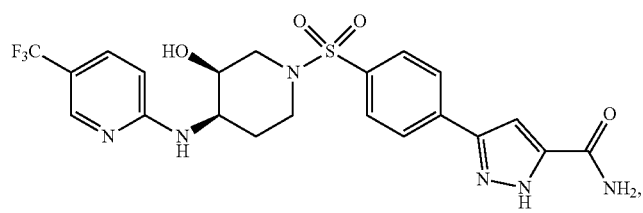
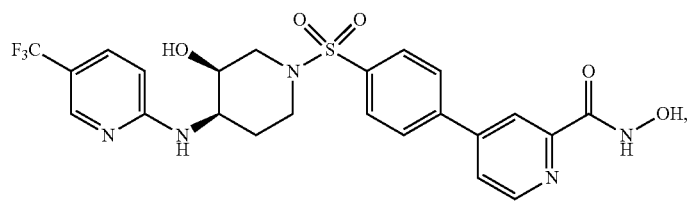
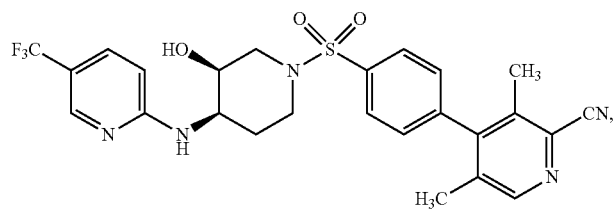
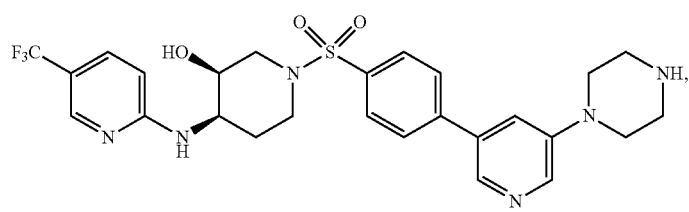
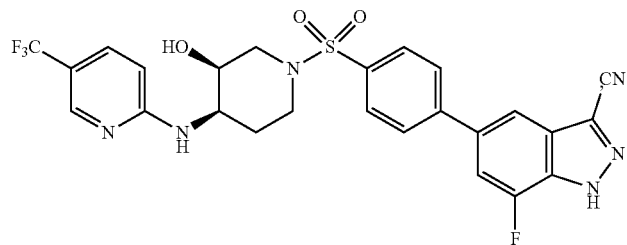
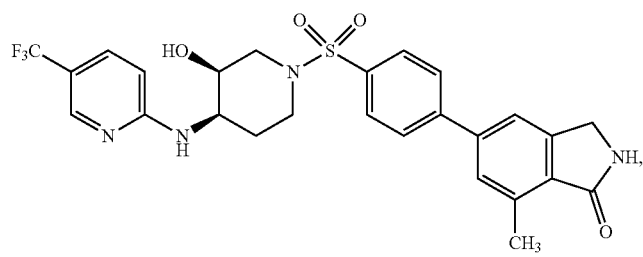

-continued
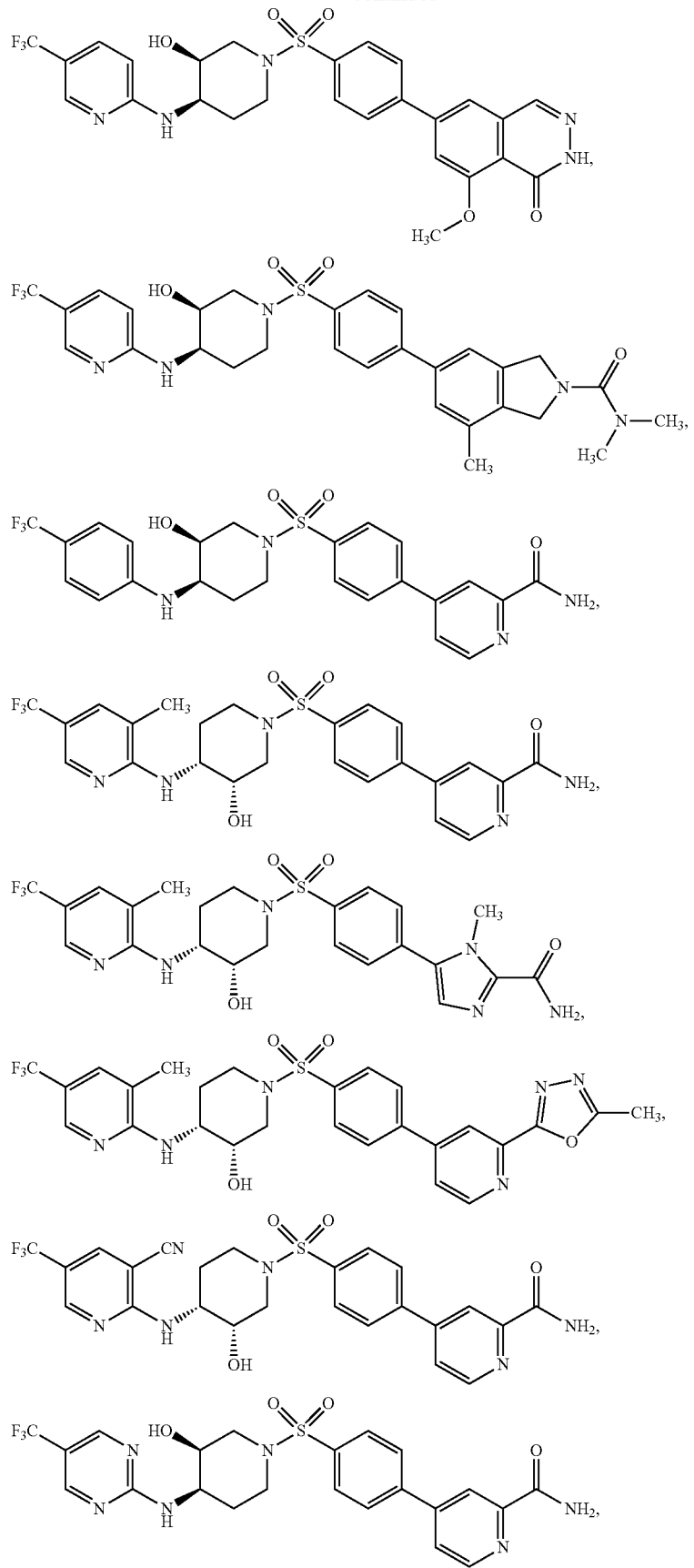

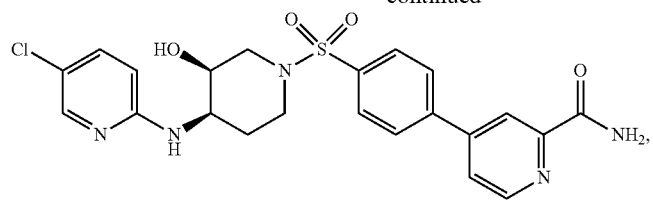
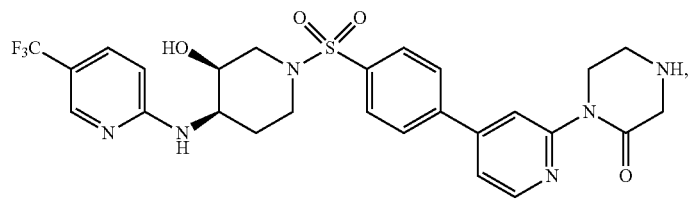
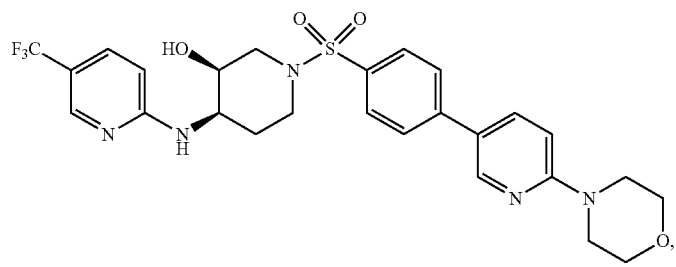
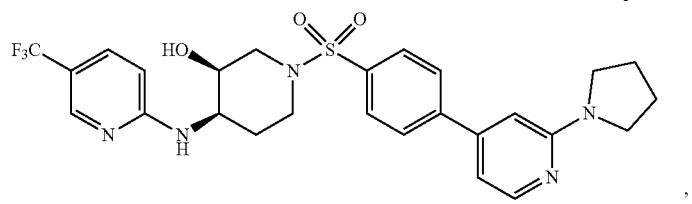
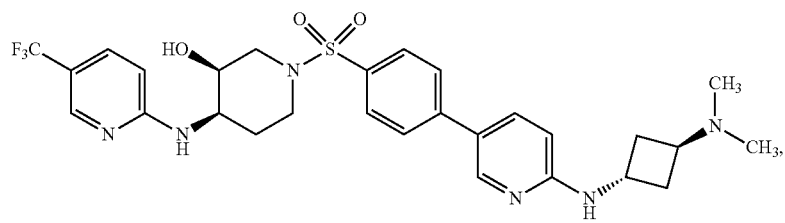
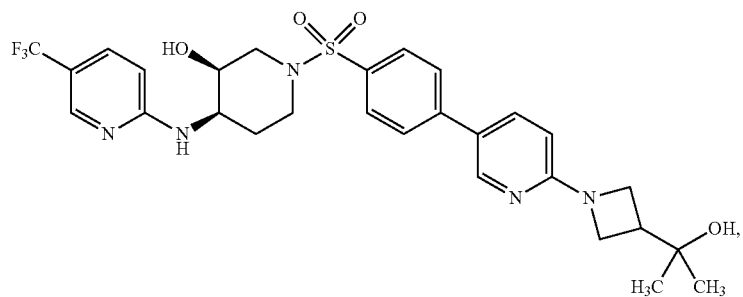
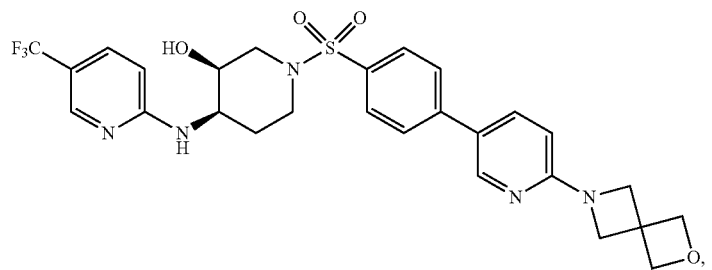

-continued
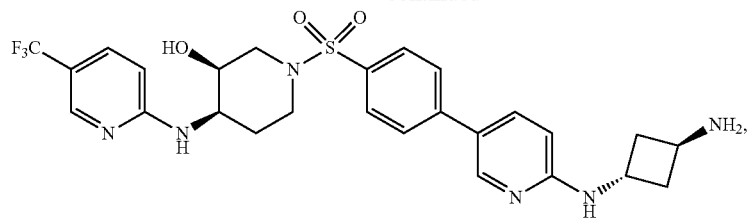
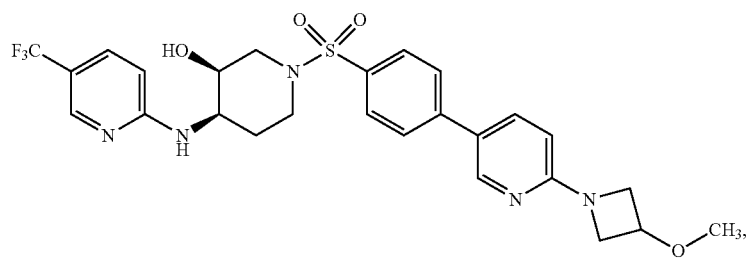
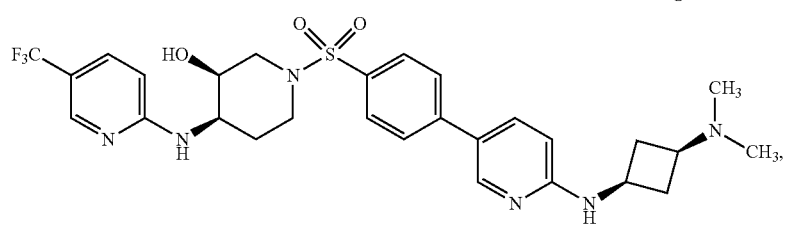
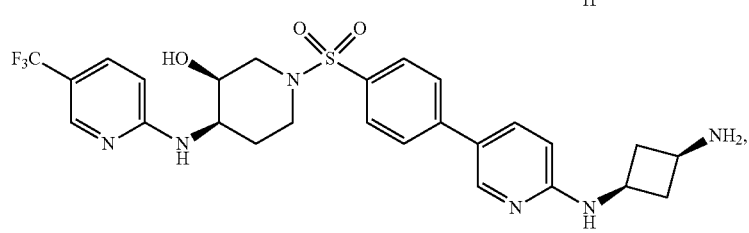
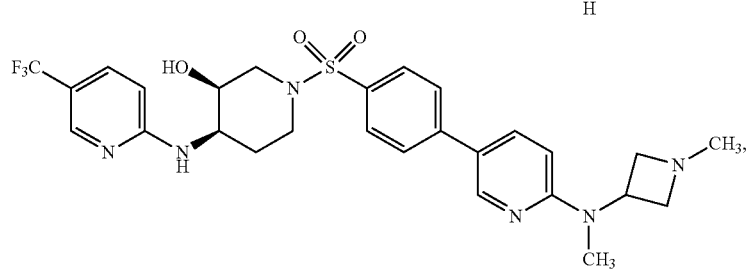
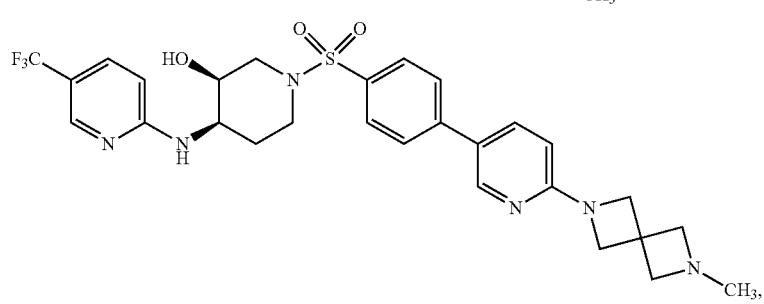
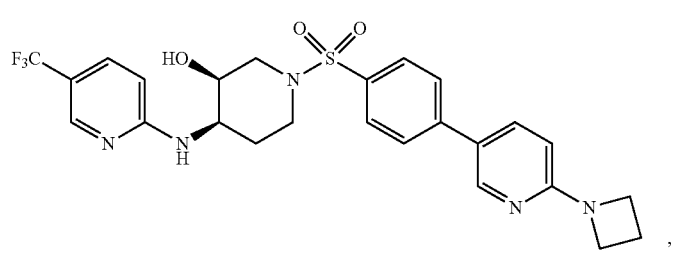

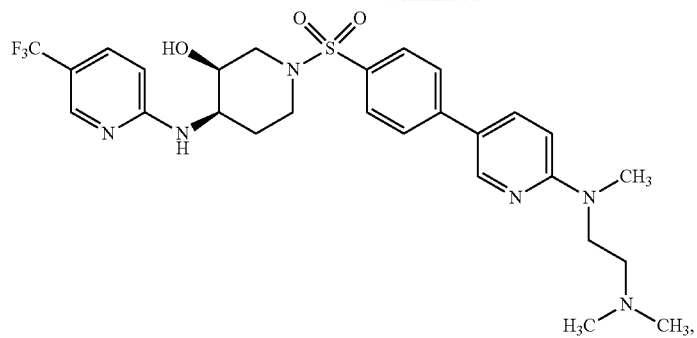
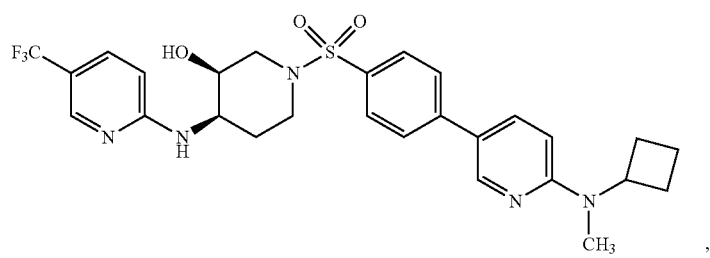
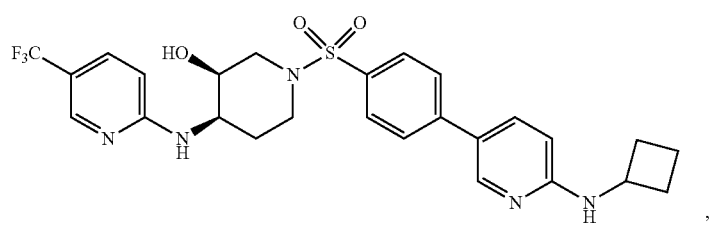
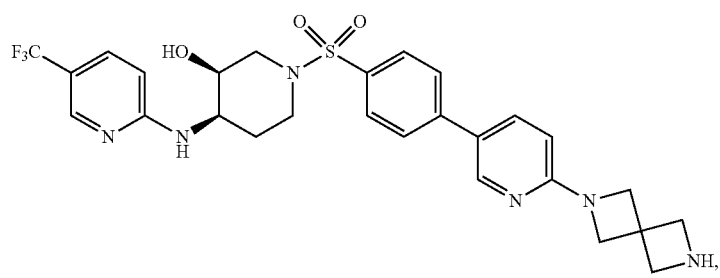
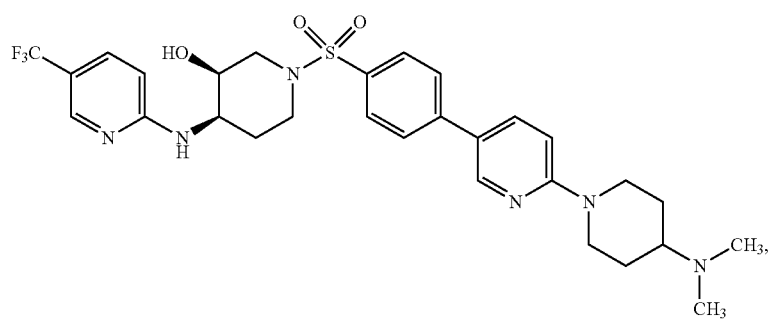
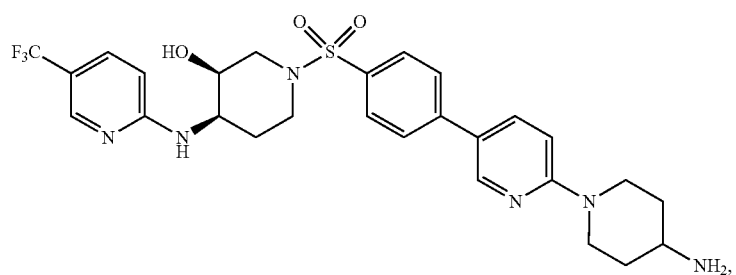

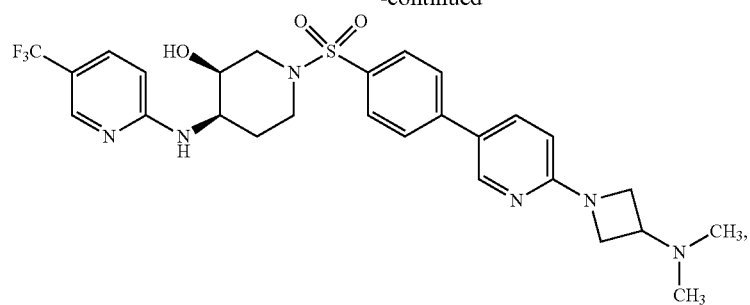
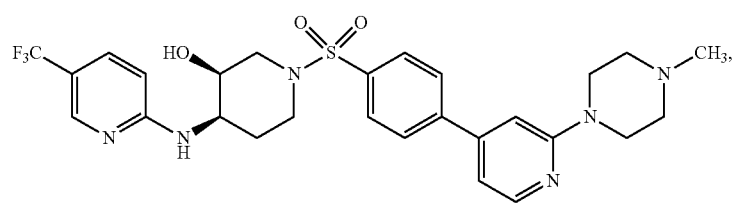
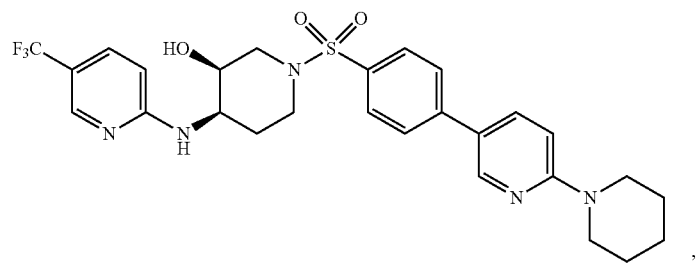
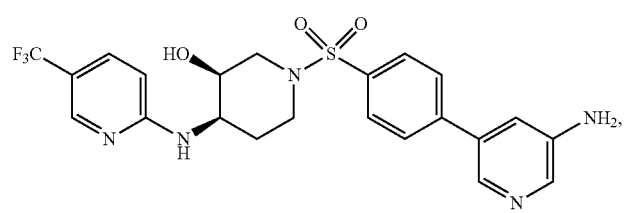
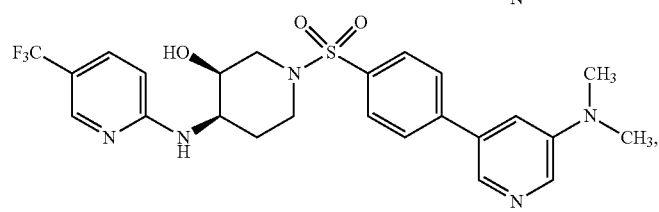
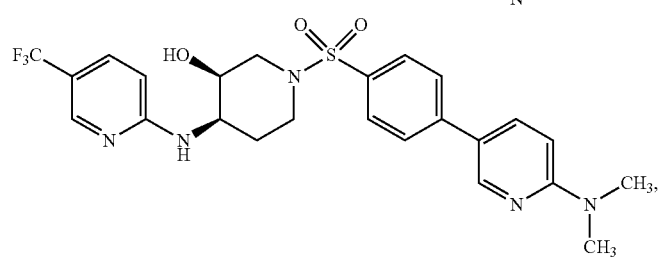
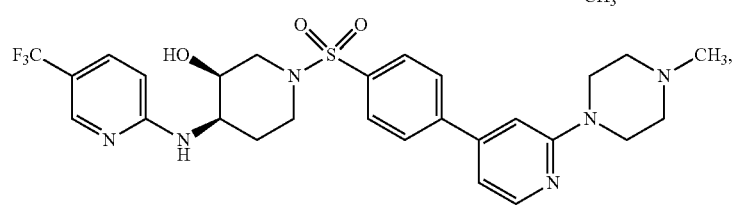

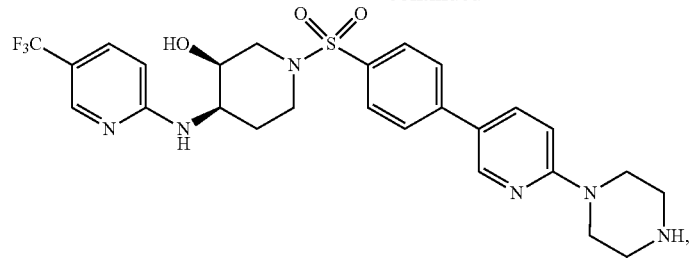
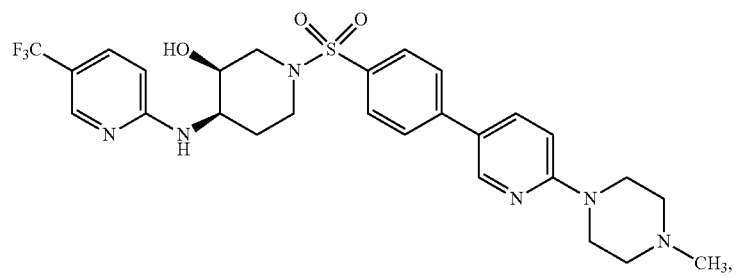
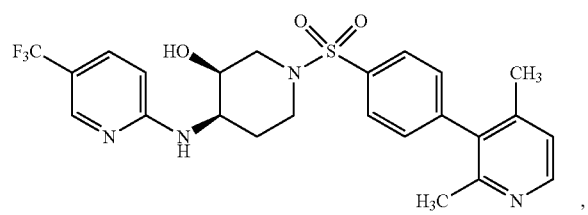
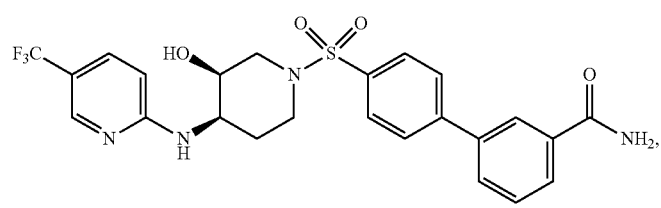
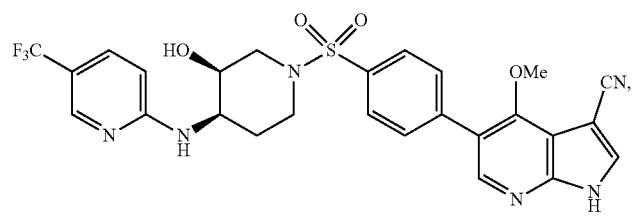
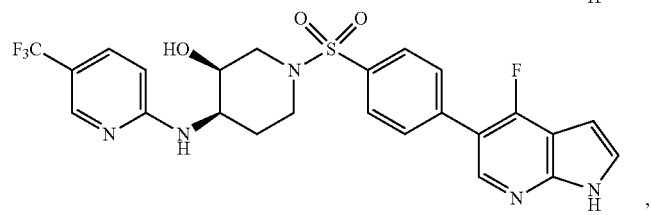
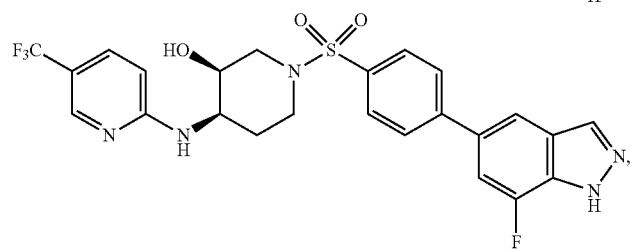

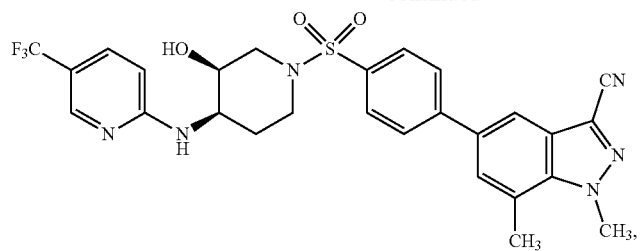
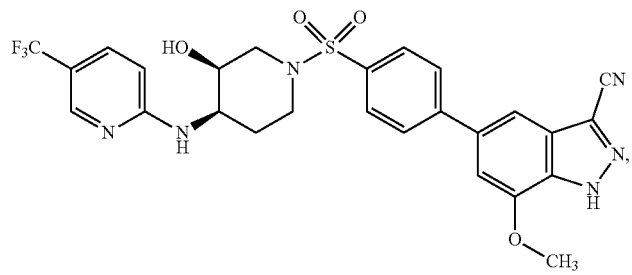
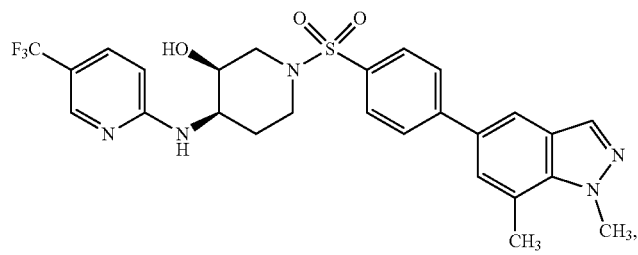
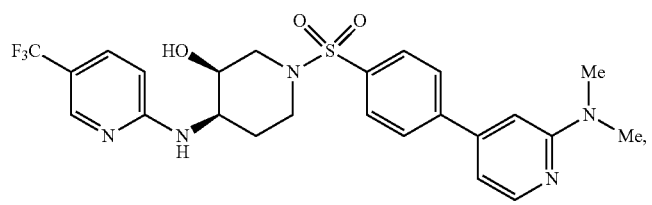
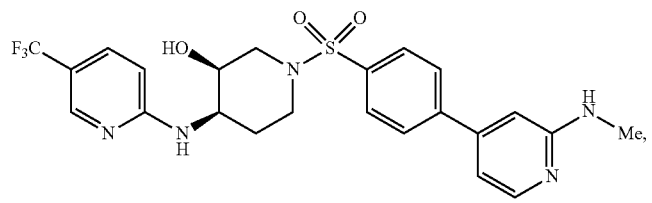
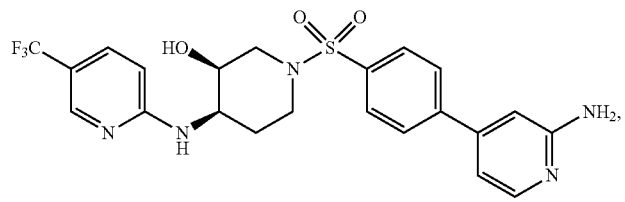
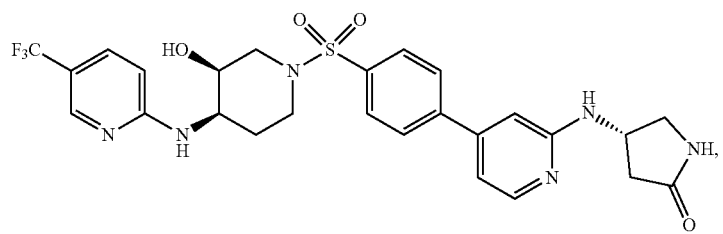

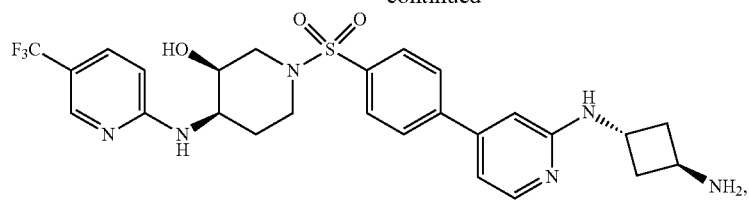
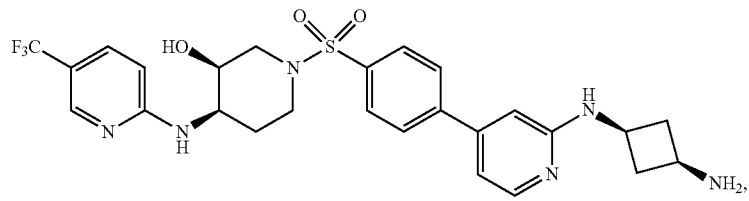
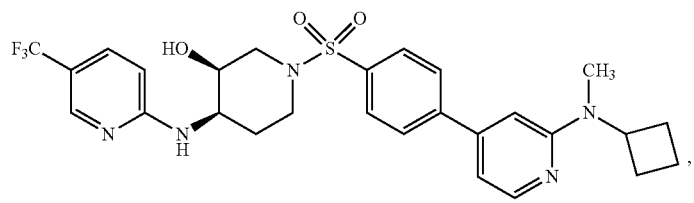
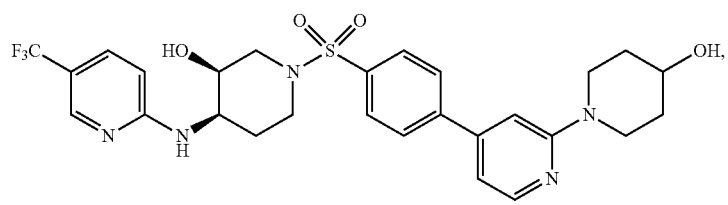
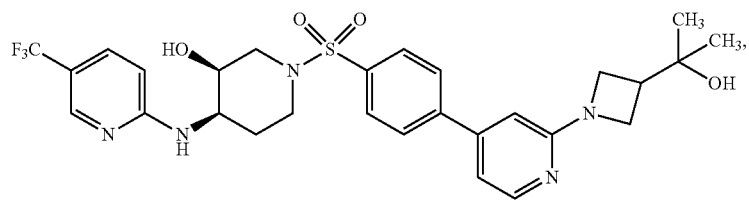
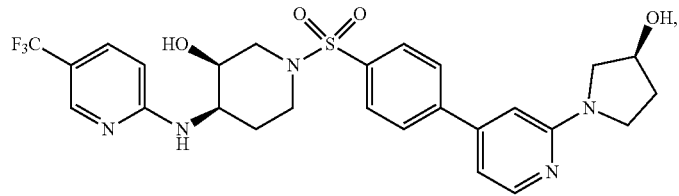
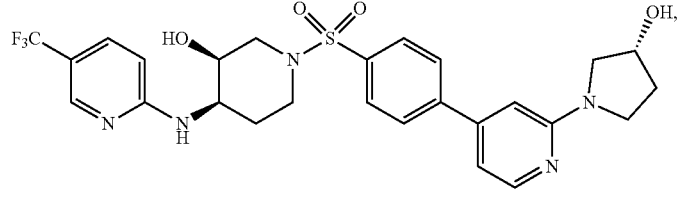
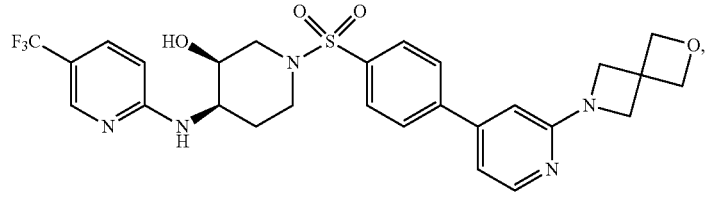

-continued
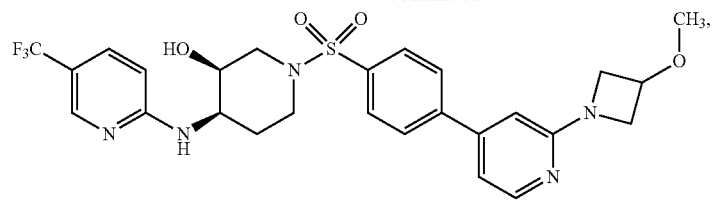
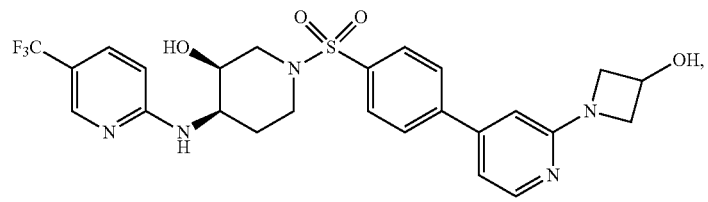
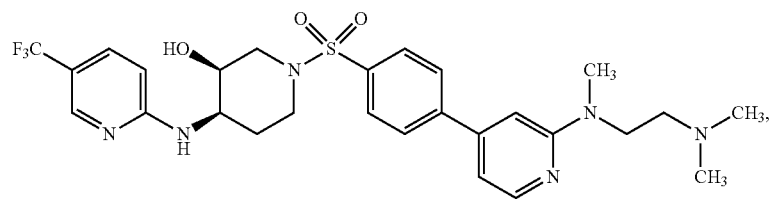
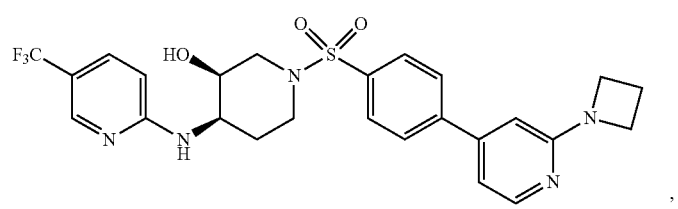
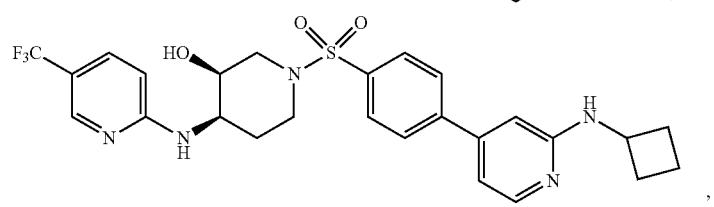
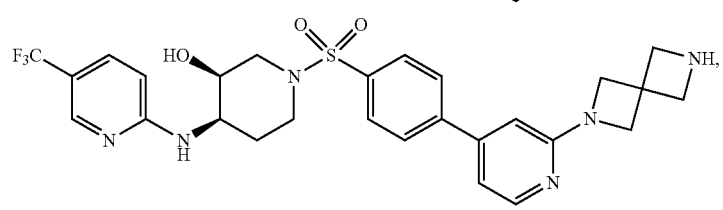
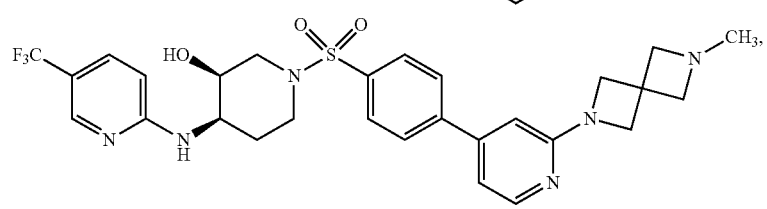
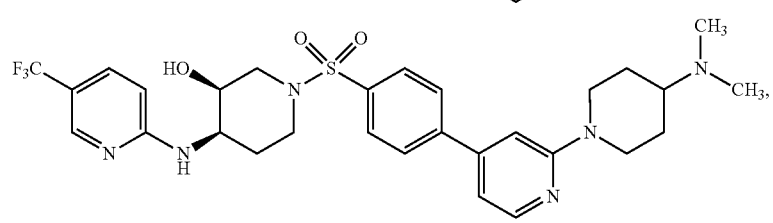

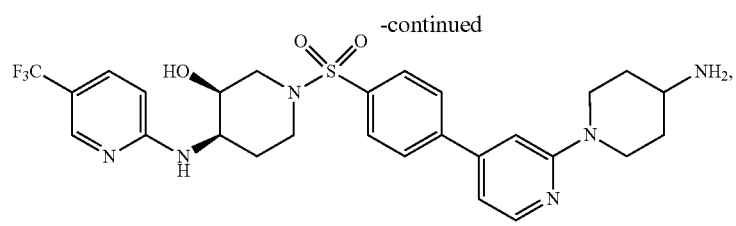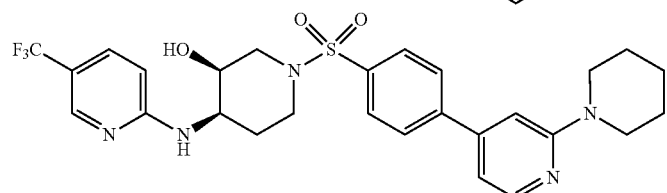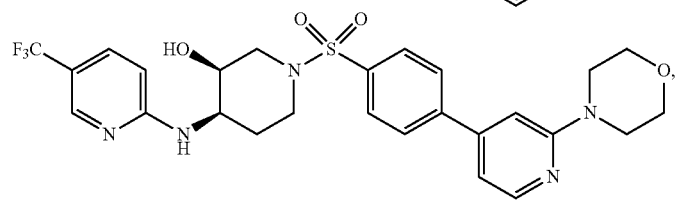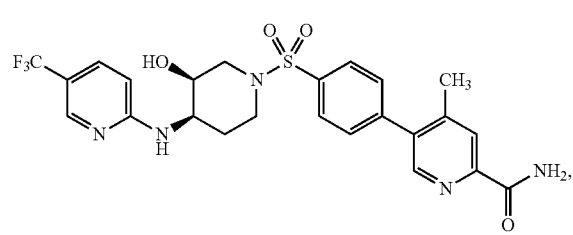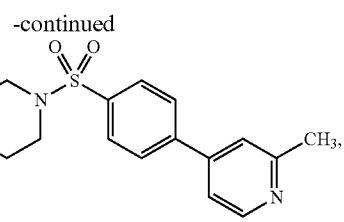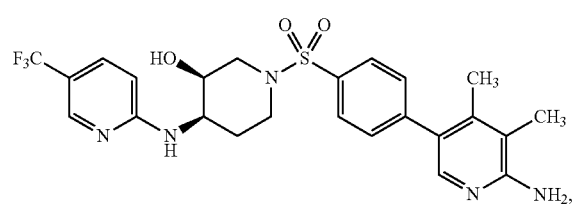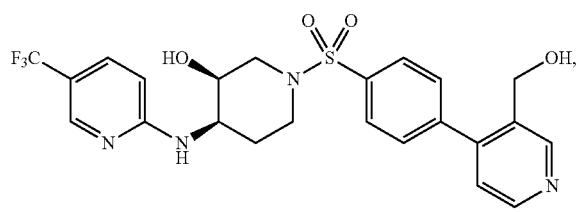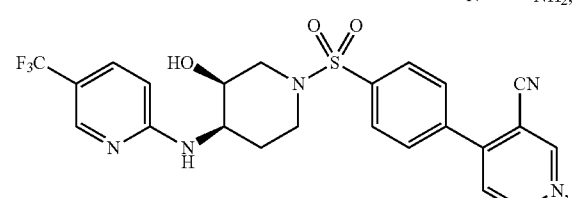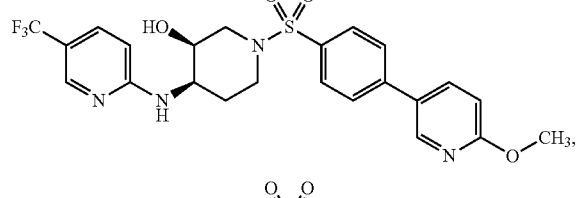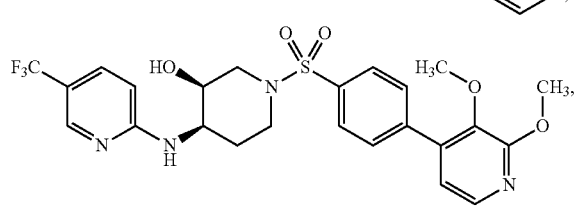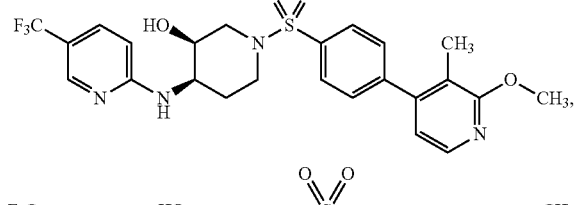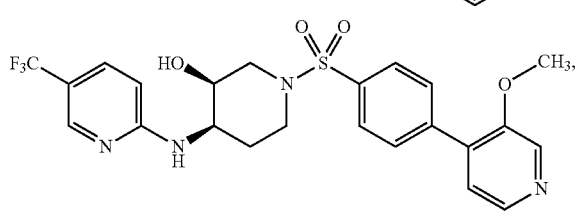

211
-continued

212
-continued

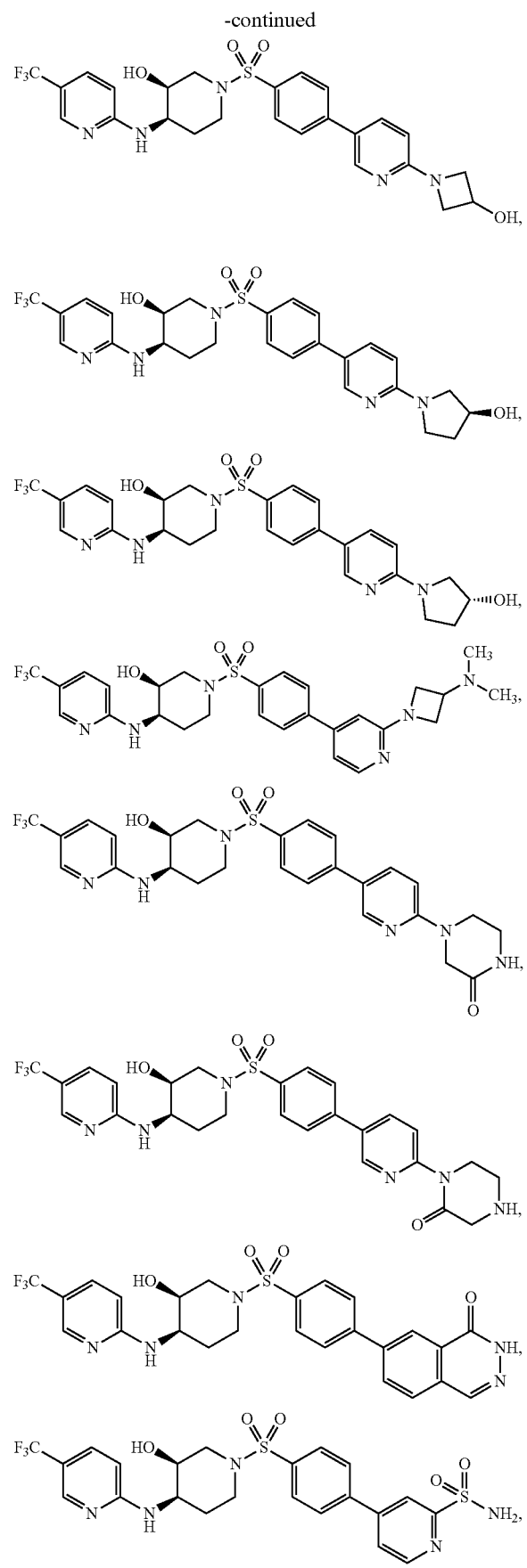
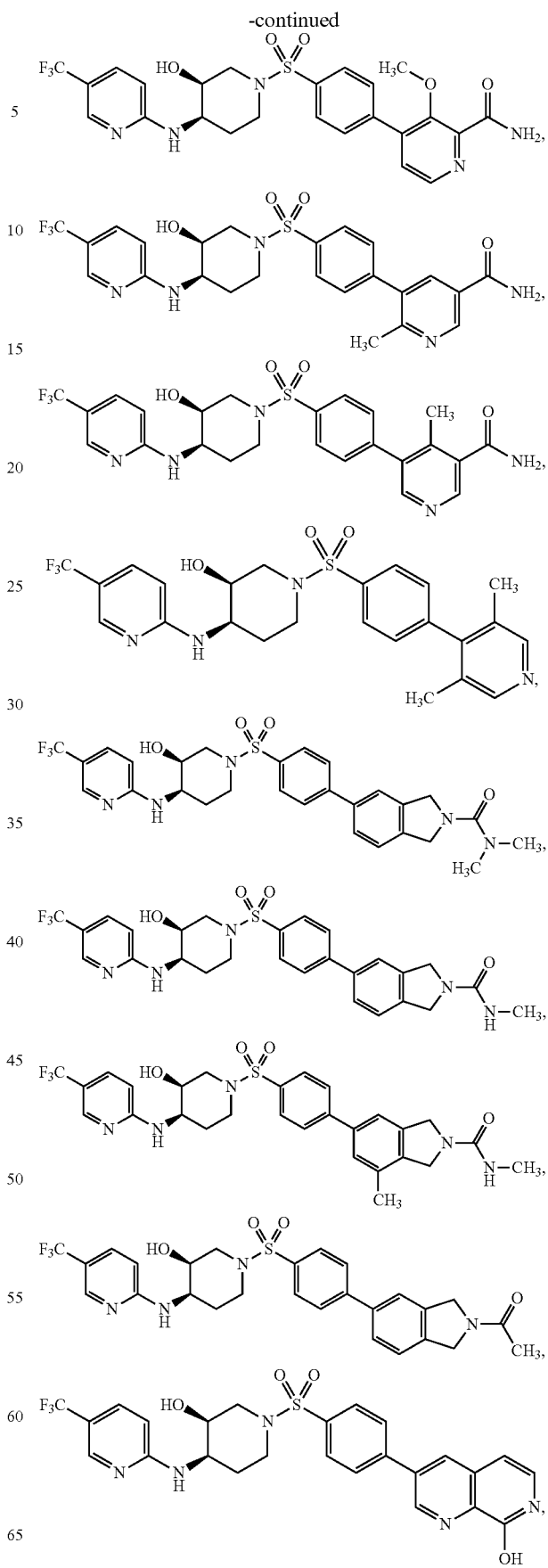

215
-continued
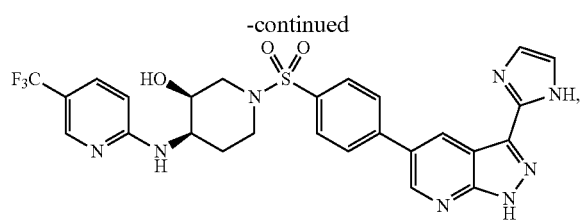
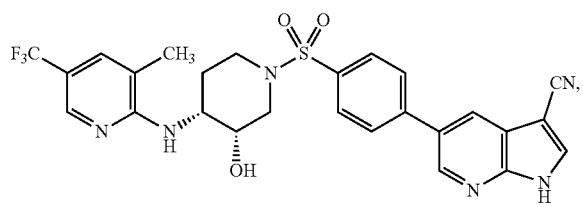
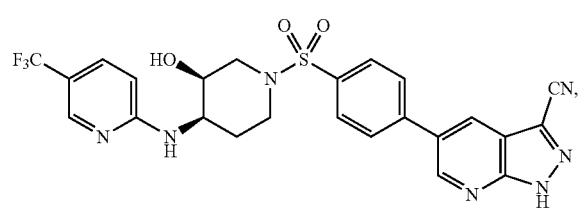
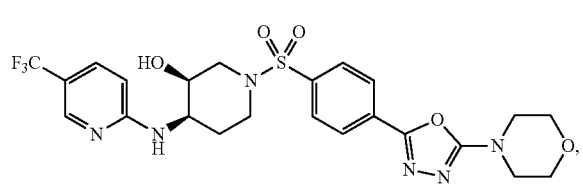
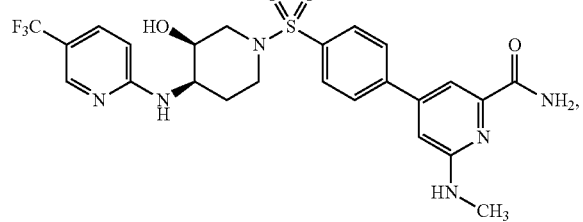
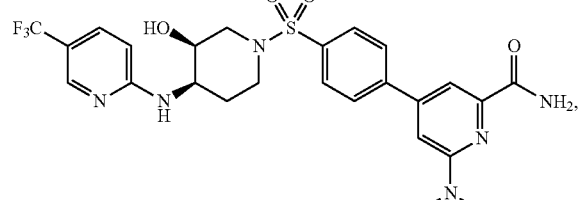
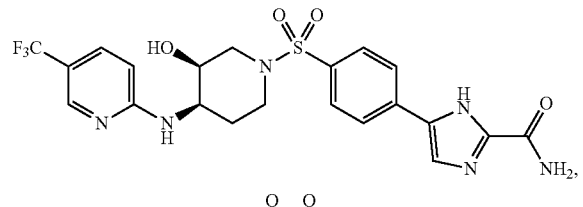
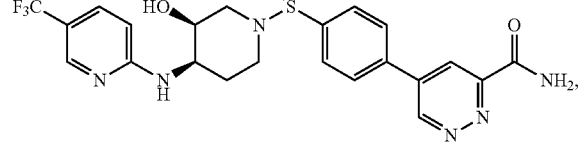
216
-continued
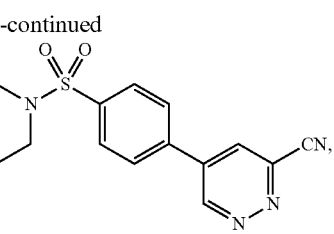
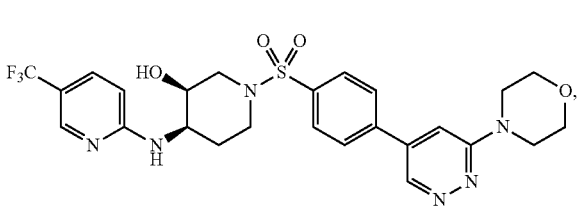
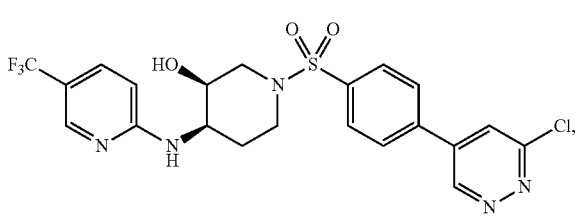
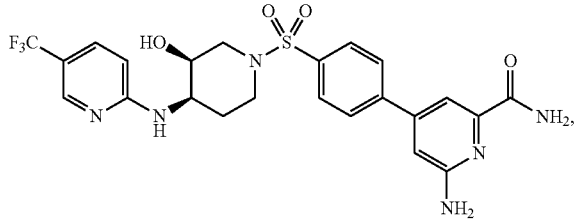
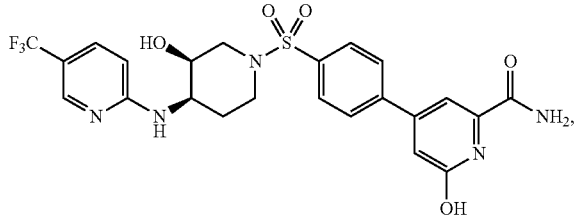
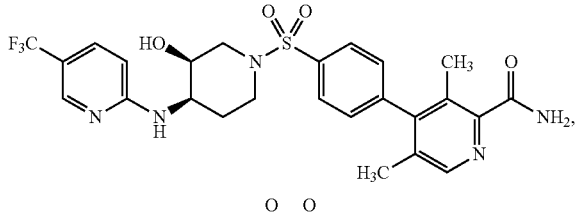
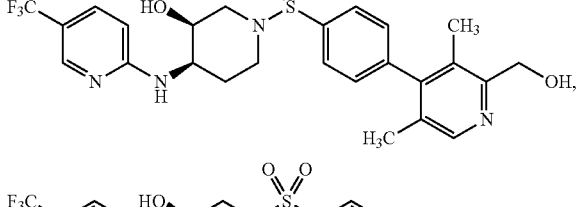
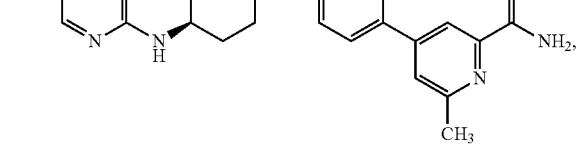

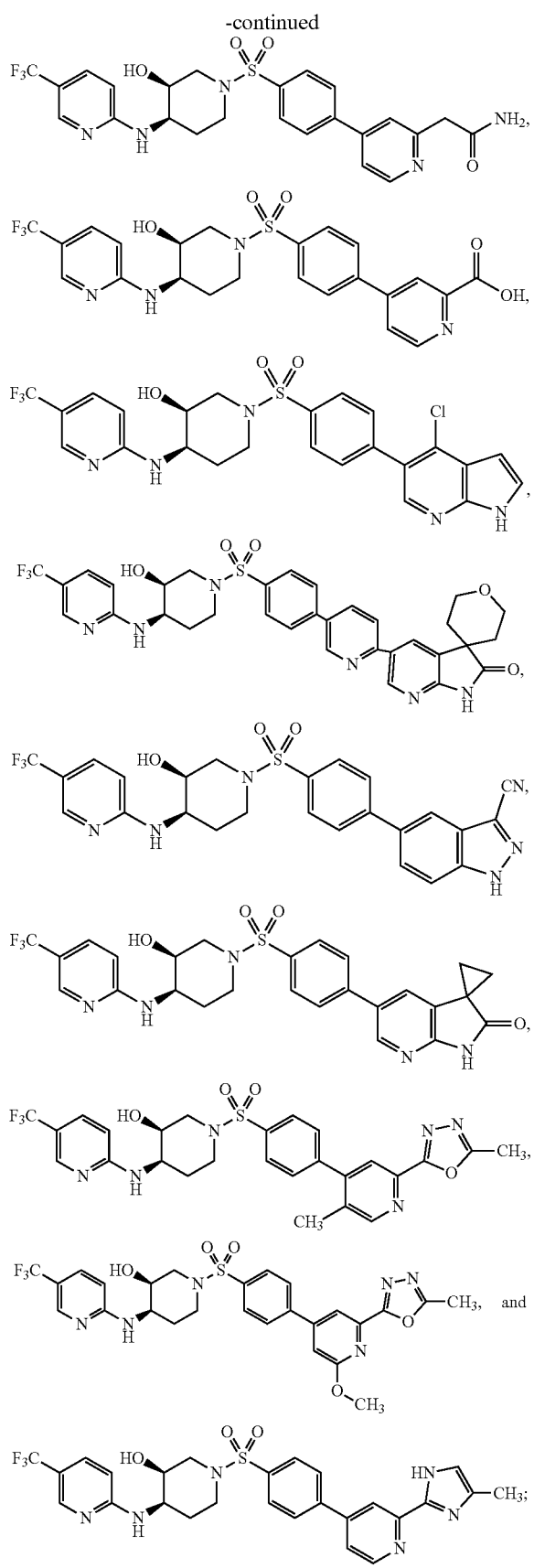

or a pharmaceutically acceptable salt thereof.

23. A pharmaceutical composition comprising a compound of claim 1, or a pharmaceutically acceptable salt, hydrate, solvate, N-oxide or rotamer thereof, with a pharmaceutically acceptable excipient.

24. A method of treating a disease or condition modulated at least in part by CCR6, comprising administering to a subject in need thereof, a compound of claim 1, or a pharmaceutically acceptable salt, hydrate, solvate, N-oxide or rotamer thereof.

25. The method in accordance with claim 24, wherein said disease or condition is an inflammatory disease or condition.

26. The method in accordance with claim 24, wherein said disease or condition is atopic dermatitis, scleroderma, lumbar disk disease, psoriasis, pustular psoriasis, rheumatoid arthritis, psoratic arthritis, arthritis associated with systemic lupus erythematosus, endometriosis, or periodontitis.

27. The method in accordance with claim 24, wherein said disease or condition is psoriasis, or pustular psoriasis.

28. A method of treating a disease or condition modulated at least in part by CCR6, comprising administering to a subject in need thereof, a compound of claim 22, or a pharmaceutically acceptable salt, hydrate, solvate, N-oxide or rotamer thereof.

29. The compound of claim 1, having the formula

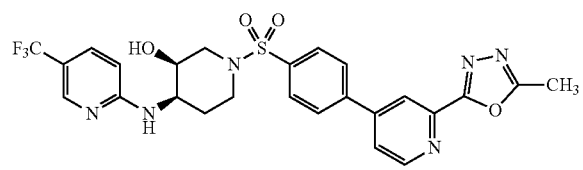 [SMILES: Cc1nnc(-c2cc(-c3ccc(S(=O)(=O)N4CC[C@@H](Nc5ccc(C(F)(F)F)cn5)[C@@H](O)C4)cc3)ccn2)o1]

or a pharmaceutically acceptable salt thereof.

30. The compound of claim 1, having the formula

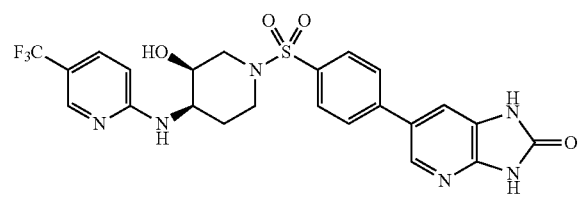 [SMILES: O=c1[nH]c2cc(-c3ccc(S(=O)(=O)N4CC[C@@H](Nc5ccc(C(F)(F)F)cn5)[C@@H](O)C4)cc3)cnc2[nH]1]

or a pharmaceutically acceptable salt thereof.

31. The compound of claim 1, having the formula

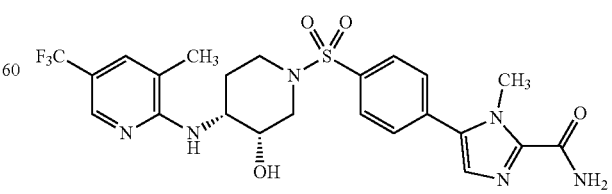

or a pharmaceutically acceptable salt thereof.

32. The compound of claim 1, having the formula

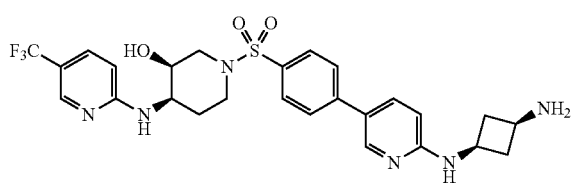 [SMILES: N[C@H]1C[C@@H](Nc2ccc(-c3ccc(S(=O)(=O)N4CC[C@@H](Nc5ccc(C(F)(F)F)cn5)[C@@H](O)C4)cc3)cn2)C1]

or a pharmaceutically acceptable salt thereof.

33. The compound of claim 1, having the formula

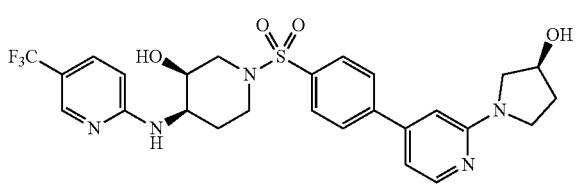 [SMILES: O=S(=O)(c1ccc(-c2ccnc(N3CC[C@H](O)C3)c2)cc1)N1CC[C@@H](Nc2ccc(C(F)(F)F)cn2)[C@@H](O)C1]

or a pharmaceutically acceptable salt thereof.

34. The compound of claim 1, having the formula

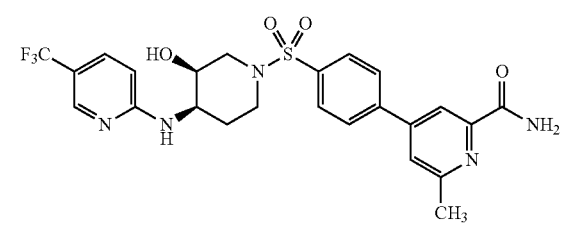 [SMILES: Cc1cc(-c2ccc(S(=O)(=O)N3CC[C@@H](Nc4ccc(C(F)(F)F)cn4)[C@@H](O)C3)cc2)cc(C(N)=O)n1]

or a pharmaceutically acceptable salt thereof.

35. The compound of claim 1, having the formula

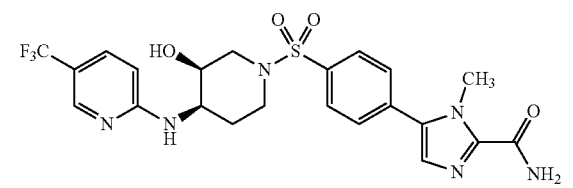 [SMILES: Cn1c(-c2ccc(S(=O)(=O)N3CC[C@@H](Nc4ccc(C(F)(F)F)cn4)[C@@H](O)C3)cc2)cnc1C(N)=O]

or a pharmaceutically acceptable salt thereof.

36. The compound of claim 1, having the formula

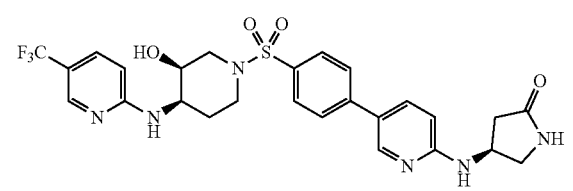 [SMILES: O=C1C[C@H](Nc2ccc(-c3ccc(S(=O)(=O)N4CC[C@@H](Nc5ccc(C(F)(F)F)cn5)[C@@H](O)C4)cc3)cn2)CN1]

or a pharmaceutically acceptable salt thereof.

37. The compound of claim 1, having the formula

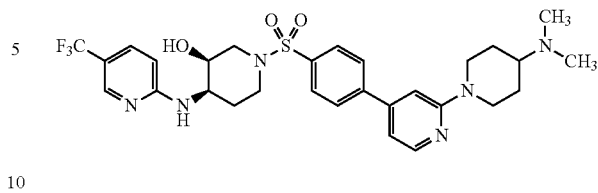

or a pharmaceutically acceptable salt thereof.

38. The compound of claim 1, having the formula

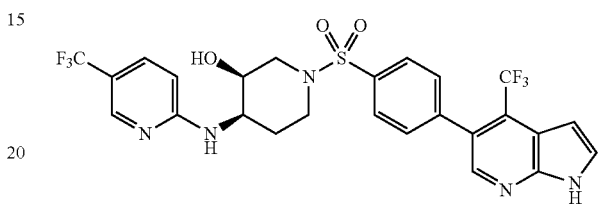

or a pharmaceutically acceptable salt thereof.

39. A pharmaceutical composition comprising a compound of claim 1; or a pharmaceutically acceptable salt thereof.

40. The pharmaceutical composition of claim 39, wherein the compound is:

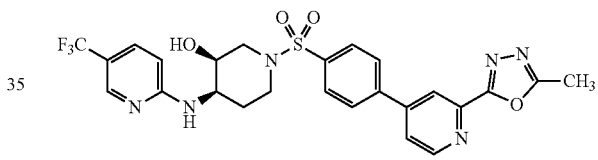

or a pharmaceutically acceptable salt thereof.

41. The pharmaceutical composition of claim 39, wherein the compound is:

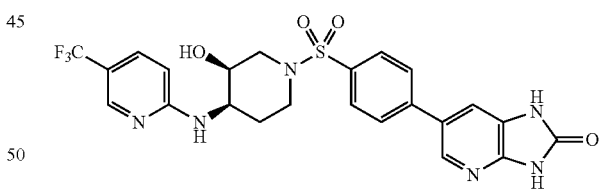

or a pharmaceutically acceptable salt thereof.

42. The pharmaceutical composition of claim 39, wherein the compound is:

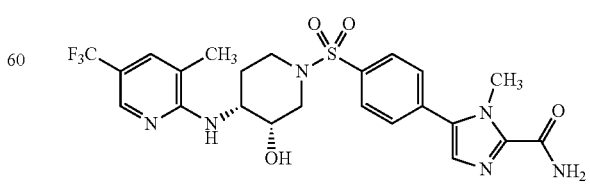

or a pharmaceutically acceptable salt thereof.

43. The pharmaceutical composition of claim 39, wherein the compound is:

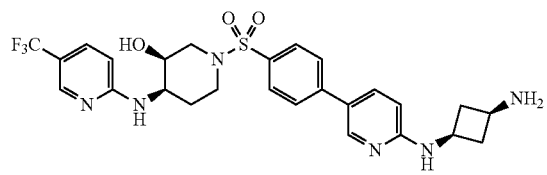 [SMILES: N[C@H]1C[C@@H](Nc2ccc(-c3ccc(S(=O)(=O)N4CC[C@@H](Nc5ccc(C(F)(F)F)cn5)[C@@H](O)C4)cc3)cn2)C1]

or a pharmaceutically acceptable salt thereof.

44. The pharmaceutical composition of claim 39, wherein the compound is:

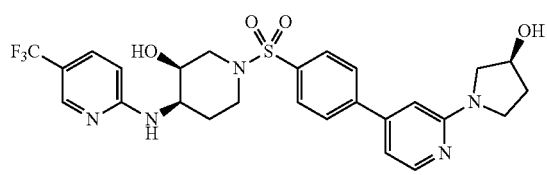 [SMILES: O=S(=O)(c1ccc(-c2ccnc(N3CC[C@H](O)C3)c2)cc1)N1CC[C@@H](Nc2ccc(C(F)(F)F)cn2)[C@@H](O)C1]

or a pharmaceutically acceptable salt thereof.

45. The pharmaceutical composition of claim 39, wherein the compound is:

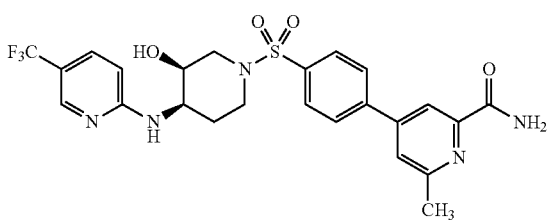 [SMILES: Cc1cc(-c2ccc(S(=O)(=O)N3CC[C@@H](Nc4ccc(C(F)(F)F)cn4)[C@@H](O)C3)cc2)cc(C(N)=O)n1]

or a pharmaceutically acceptable salt thereof.

46. The pharmaceutical composition of claim 39, wherein the compound is:

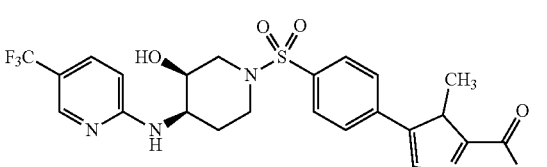

or a pharmaceutically acceptable salt thereof.

47. The pharmaceutical composition of claim 39, wherein the compound is:

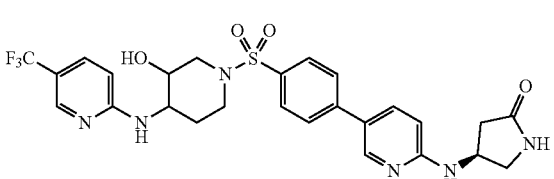

or a pharmaceutically acceptable salt thereof.

48. The pharmaceutical composition of claim 39, wherein the compound is:

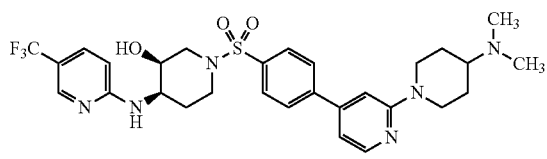 [SMILES: CN(C)C1CCN(c2cc(-c3ccc(S(=O)(=O)N4CC[C@@H](Nc5ccc(C(F)(F)F)cn5)[C@@H](O)C4)cc3)ccn2)CC1]

or a pharmaceutically acceptable salt thereof.

49. The pharmaceutical composition of claim 39, wherein the compound is:

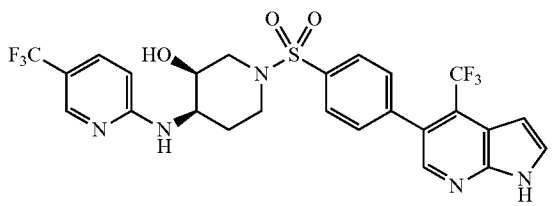 [SMILES: O=S(=O)(c1ccc(-c2cnc3[nH]ccc3c2C(F)(F)F)cc1)N1CC[C@@H](Nc2ccc(C(F)(F)F)cn2)[C@@H](O)C1]

or a pharmaceutically acceptable salt thereof.

50. The method of treating a disease or condition of claim 26, wherein the compound is:

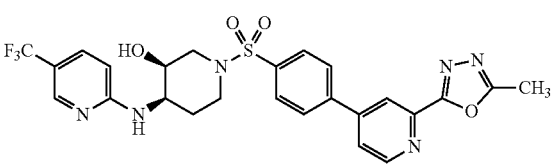 [SMILES: Cc1nnc(-c2cc(-c3ccc(S(=O)(=O)N4CC[C@@H](Nc5ccc(C(F)(F)F)cn5)[C@@H](O)C4)cc3)ccn2)o1]

or a pharmaceutically acceptable salt thereof.

51. The method of treating a disease or condition of claim 26, wherein the compound is:

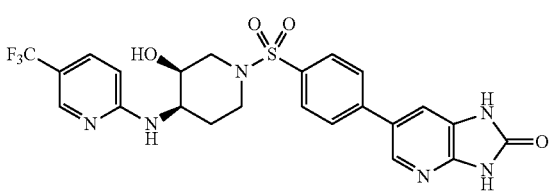 [SMILES: O=c1[nH]c2cc(-c3ccc(S(=O)(=O)N4CC[C@@H](Nc5ccc(C(F)(F)F)cn5)[C@@H](O)C4)cc3)cnc2[nH]1]

or a pharmaceutically acceptable salt thereof.

52. The method of treating a disease or condition of claim 26, wherein the compound is:

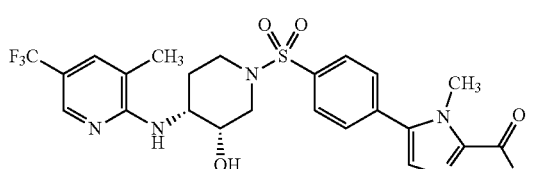

or a pharmaceutically acceptable salt thereof.

53. The method of treating a disease or condition of claim 26, wherein the compound is:

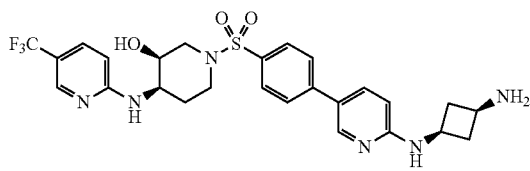 [SMILES: N[C@H]1C[C@@H](Nc2ccc(-c3ccc(S(=O)(=O)N4CC[C@@H](Nc5ccc(C(F)(F)F)cn5)[C@@H](O)C4)cc3)cn2)C1]

or a pharmaceutically acceptable salt thereof.

54. The method of treating a disease or condition of claim 26, wherein the compound is:

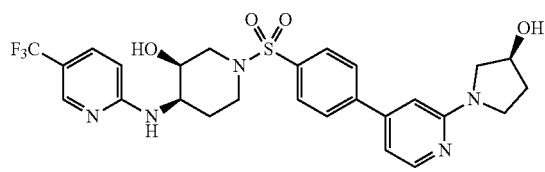 [SMILES: O=S(=O)(c1ccc(-c2ccnc(N3CC[C@H](O)C3)c2)cc1)N1CC[C@@H](Nc2ccc(C(F)(F)F)cn2)[C@@H](O)C1]

or a pharmaceutically acceptable salt thereof.

55. The method of treating a disease or condition of claim 26, wherein the compound is:

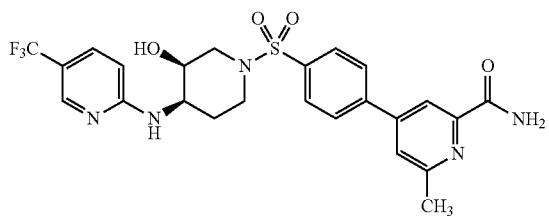 [SMILES: Cc1cc(-c2ccc(S(=O)(=O)N3CC[C@@H](Nc4ccc(C(F)(F)F)cn4)[C@@H](O)C3)cc2)cc(C(N)=O)n1]

or a pharmaceutically acceptable salt thereof.

56. The method of treating a disease or condition of claim 26, wherein the compound is:

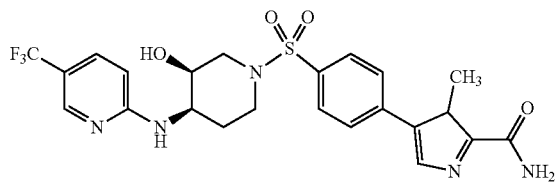 [SMILES: CC1C(c2ccc(S(=O)(=O)N3CC[C@@H](Nc4ccc(C(F)(F)F)cn4)[C@@H](O)C3)cc2)=CN=C1C(N)=O]

or a pharmaceutically acceptable salt thereof.

57. The method of treating a disease or condition of claim 26, wherein the compound is:

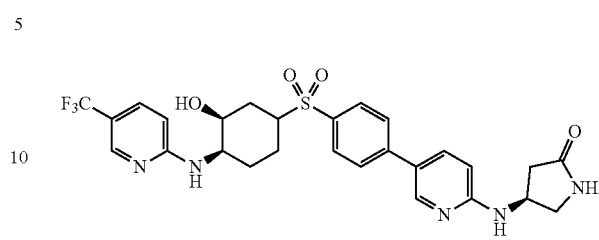

or a pharmaceutically acceptable salt thereof.

58. The method of treating a disease or condition of claim 26, wherein the compound is:

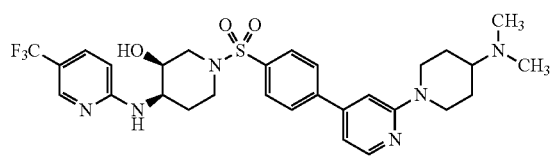 [SMILES: CN(C)C1CCN(c2cc(-c3ccc(S(=O)(=O)N4CC[C@@H](Nc5ccc(C(F)(F)F)cn5)[C@@H](O)C4)cc3)ccn2)CC1]

or a pharmaceutically acceptable salt thereof.

59. The method of treating a disease or condition of claim 26, wherein the compound is:

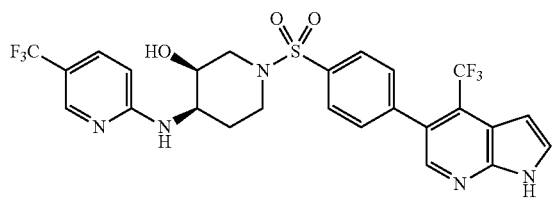 [SMILES: O=S(=O)(c1ccc(-c2cnc3[nH]ccc3c2C(F)(F)F)cc1)N1CC[C@@H](Nc2ccc(C(F)(F)F)cn2)[C@@H](O)C1]

or a pharmaceutically acceptable salt thereof.

* * * * *